(12) United States Patent
Allerson et al.

(10) Patent No.: US 11,078,485 B2
(45) Date of Patent: *Aug. 3, 2021

(54) COMPOSITIONS COMPRISING ALTERNATING 2'-MODIFIED NUCLEOSIDES FOR USE IN GENE MODULATION

(71) Applicant: Ionis Pharmaceuticals, Inc., Carlsbad, CA (US)

(72) Inventors: Charles Allerson, San Diego, CA (US); Balkrishen Bhat, Carlsbad, CA (US); Anne B. Eldrup, Newtown, CT (US); Muthiah Manoharan, Weston, MA (US); Richard H. Griffey, Vista, CA (US); Brenda F. Baker, Carlsbad, CA (US); Eric E. Swayze, Encinitas, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/286,075

(22) Filed: Feb. 26, 2019

(65) Prior Publication Data
US 2020/0017855 A1 Jan. 16, 2020

Related U.S. Application Data

(63) Continuation of application No. 15/623,193, filed on Jun. 14, 2017, now Pat. No. 10,266,825, which is a continuation of application No. 14/834,224, filed on Aug. 24, 2015, now Pat. No. 9,708,610, which is a continuation of application No. 10/860,265, filed on Jun. 3, 2004, now Pat. No. 9,150,605, which is a continuation-in-part of application No. 10/701,007, filed on Nov. 4, 2003, now Pat. No. 8,604,183.

(60) Provisional application No. 60/423,760, filed on Nov. 5, 2002, provisional application No. 60/555,521, filed on Mar. 22, 2004.

(51) Int. Cl.
*C12N 15/113* (2010.01)
*C07H 21/00* (2006.01)
*C07H 21/04* (2006.01)
*C12N 15/11* (2006.01)
*A61K 48/00* (2006.01)
*C07H 21/02* (2006.01)

(52) U.S. Cl.
CPC .......... *C12N 15/113* (2013.01); *A61K 48/005* (2013.01); *C07H 21/00* (2013.01); *C07H 21/02* (2013.01); *C07H 21/04* (2013.01); *C12N 15/111* (2013.01); *C12N 2310/14* (2013.01); *C12N 2310/321* (2013.01); *C12N 2310/322* (2013.01); *C12N 2310/323* (2013.01); *C12N 2320/30* (2013.01); *C12N 2320/51* (2013.01)

(58) Field of Classification Search
CPC .............. C12N 15/11; C12N 2310/321; C12N 2310/322; C12N 2310/344; C12N 2310/345; C12N 2320/51; A61K 31/713
USPC ....... 435/6.1, 91.1, 91.31, 455, 458; 514/44; 536/23.1, 24.5
See application file for complete search history.

(56) References Cited

U.S. PATENT DOCUMENTS

| | | | | |
|---|---|---|---|---|
| 8,604,183 B2* | 12/2013 | Allerson | ................ | C07H 21/00 435/6.1 |
| 9,150,605 B2* | 10/2015 | Allerson | ................ | C07H 21/00 |
| 9,708,610 B2* | 7/2017 | Allerson | ................ | C07H 21/02 |
| 10,266,825 B2* | 4/2019 | Allerson | .............. | A61K 48/005 |

* cited by examiner

*Primary Examiner* — Jane J Zara
(74) *Attorney, Agent, or Firm* — McNeill Baur PLLC

(57) ABSTRACT

The present invention provides compositions comprising at least one oligomeric compound comprising an alternating motif and further include a region that is complementary to a nucleic acid target. The compositions are useful for targeting selected nucleic acid molecules and modulating the expression of one or more genes. In preferred embodiments the compositions of the present invention hybridize to a portion of a target RNA resulting in loss of normal function of the target RNA. The present invention also provides methods for modulating gene expression.

7 Claims, No Drawings
Specification includes a Sequence Listing.

SEQUENCE LISTING

<160> NUMBER OF SEQ ID NOS: 157

<210> SEQ ID NO 1
<211> LENGTH: 19
<212> TYPE: RNA
<213> ORGANISM: Artificial
<220> FEATURE:
<223> OTHER INFORMATION: Synthetic Construct

<400> SEQUENCE: 1
cgagaggcgg acgggaccg                                                    19

<210> SEQ ID NO 2
<211> LENGTH: 21
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (20)..(21)
<223> OTHER INFORMATION: deoxythymidine(dT)

<400> SEQUENCE: 2
cgagaggcgg acgggaccgt t                                                 21

<210> SEQ ID NO 3
<211> LENGTH: 21
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (20)..(21)
<223> OTHER INFORMATION: deoxythymidine(dT)

<400> SEQUENCE: 3
cggtcccgtc cgcctctcgt t                                                 21

<210> SEQ ID NO 4
<211> LENGTH: 19
<212> TYPE: DNA
<213> ORGANISM: Artificial
<220> FEATURE:
<223> OTHER INFORMATION: Synthetic Construct

<400> SEQUENCE: 4
gctctccgcc tgccctggc                                                    19

<210> SEQ ID NO 5
<211> LENGTH: 22
<212> TYPE: DNA
<213> ORGANISM: Artificial
<220> FEATURE:
<223> OTHER INFORMATION: Reverse primer
<220> FEATURE:
<221> NAME/KEY: misc_feature
<222> LOCATION: (1)..(3)
<223> OTHER INFORMATION: 2'-O-methoxyethyl
<220> FEATURE:
<221> NAME/KEY: misc_feature
<222> LOCATION: (13)..(20)
<223> OTHER INFORMATION: 2'-O-methoxyethyl

<400> SEQUENCE: 5
ccaagtctgg ctcgttctca gt                                                22

-continued

```
<210> SEQ ID NO 6
<211> LENGTH: 23
<212> TYPE: DNA
<213> ORGANISM: Artificial
<220> FEATURE:
<223> OTHER INFORMATION: PCR probe
<220> FEATURE:
<221> NAME/KEY: misc_feature
<222> LOCATION: (1)..(5)
<223> OTHER INFORMATION: 2'-O-methoxyethyl
<220> FEATURE:
<221> NAME/KEY: misc_feature
<222> LOCATION: (16)..(20)
<223> OTHER INFORMATION: 2'-O-methoxyethyl

<400> SEQUENCE: 6
cgaggctggc ttcatccact gcc                                              23

<210> SEQ ID NO 7
<211> LENGTH: 19
<212> TYPE: DNA
<213> ORGANISM: Artificial
<220> FEATURE:
<223> OTHER INFORMATION: Forward primer

<400> SEQUENCE: 7
gaaggtgaag gtcggagtc                                                   19

<210> SEQ ID NO 8
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (1)..(20)
<223> OTHER INFORMATION: phosphorothioate linkages
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (17)..(17)
<223> OTHER INFORMATION: 2'-O-methyl
<220> FEATURE:
```

```
<221> NAME/KEY: misc_feature
<222> LOCATION: (19)..(19)
<223> OTHER INFORMATION: 2'-O-methyl

<400> SEQUENCE: 8
uuugucucug guccuuacuu                                                        20

<210> SEQ ID NO 9
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphorothioate linkages
<220> FEATURE:
<221> NAME/KEY: misc_feature
<222> LOCATION: (2)..(2)
<223> OTHER INFORMATION: 2'-O-methyl
<220> FEATURE:
<221> NAME/KEY: misc_feature
<222> LOCATION: (4)..(4)
<223> OTHER INFORMATION: 2'-O-methyl
<220> FEATURE:
<221> NAME/KEY: misc_feature
<222> LOCATION: (6)..(6)
<223> OTHER INFORMATION: 2'-O-methyl
<220> FEATURE:
<221> NAME/KEY: misc_feature
<222> LOCATION: (8)..(8)
<223> OTHER INFORMATION: 2'-O-methyl
<220> FEATURE:
<221> NAME/KEY: misc_feature
<222> LOCATION: (10)..(10)
<223> OTHER INFORMATION: 2'-O-methyl
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (14)..(14)
<223> OTHER INFORMATION: 2'-O-methyl
<220> FEATURE:
<221> NAME/KEY: misc_feature
<222> LOCATION: (16)..(16)
<223> OTHER INFORMATION: 2'-O-methyl
<220> FEATURE:
<221> NAME/KEY: misc_feature
<222> LOCATION: (18)..(18)
<223> OTHER INFORMATION: 2'-O-methyl
<220> FEATURE:
<221> NAME/KEY: misc_feature
<222> LOCATION: (20)..(20)
<223> OTHER INFORMATION: 2'-O-methyl

<400> SEQUENCE: 9
uuugucucug guccuuacuu                                                        20

<210> SEQ ID NO 10
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (1)..(20)
<223> OTHER INFORMATION: phosphodiester linkages
```

```
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (19)..(19)
<223> OTHER INFORMATION: 2'-O-methyl

<400> SEQUENCE: 10
uuugucucug guccuuacuu                                                     20

<210> SEQ ID NO 11
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphodiester linkages
<220> FEATURE:
<221> NAME/KEY: misc_feature
<222> LOCATION: (2)..(2)
<223> OTHER INFORMATION: 2'-O-methyl
<220> FEATURE:
<221> NAME/KEY: misc_feature
<222> LOCATION: (4)..(4)
<223> OTHER INFORMATION: 2'-O-methyl
<220> FEATURE:
<221> NAME/KEY: misc_feature
<222> LOCATION: (6)..(6)
<223> OTHER INFORMATION: 2'-O-methyl
<220> FEATURE:
<221> NAME/KEY: misc_feature
<222> LOCATION: (8)..(8)
<223> OTHER INFORMATION: 2'-O-methyl
<220> FEATURE:
<221> NAME/KEY: misc_feature
<222> LOCATION: (10)..(10)
<223> OTHER INFORMATION: 2'-O-methyl
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (14)..(14)
```

```
<223> OTHER INFORMATION: 2'-O-methyl
<220> FEATURE:
<221> NAME/KEY: misc_feature
<222> LOCATION: (16)..(16)
<223> OTHER INFORMATION: 2'-O-methyl
<220> FEATURE:
<221> NAME/KEY: misc_feature
<222> LOCATION: (18)..(18)
<223> OTHER INFORMATION: 2'-O-methyl
<220> FEATURE:
<221> NAME/KEY: misc_feature
<222> LOCATION: (20)..(20)
<223> OTHER INFORMATION: 2'-O-methyl

<400> SEQUENCE: 11
uuugucucug guccuuacuu                                              20

<210> SEQ ID NO 12
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphorothioate linkages

<400> SEQUENCE: 12
uuugucucug guccuuacuu                                              20

<210> SEQ ID NO 13
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphodiester linkages

<400> SEQUENCE: 13
aaguaaggac cagagacaaa                                              20

<210> SEQ ID NO 14
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (1)..(20)
<223> OTHER INFORMATION: phosphodiester linkages
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
```

```
<222> LOCATION: (9)..(9)
<223> OTHER INFORMATION: 2'-O-methyl
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (19)..(19)
<223> OTHER INFORMATION: 2'-O-methyl

<400> SEQUENCE: 14
aaguaaggac cagagacaaa                                                    20

<210> SEQ ID NO 15
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphodiester linkages
<220> FEATURE:
<221> NAME/KEY: misc_feature
<222> LOCATION: (2)..(2)
<223> OTHER INFORMATION: 2'-O-methyl
<220> FEATURE:
<221> NAME/KEY: misc_feature
<222> LOCATION: (4)..(4)
<223> OTHER INFORMATION: 2'-O-methyl
<220> FEATURE:
<221> NAME/KEY: misc_feature
<222> LOCATION: (6)..(6)
<223> OTHER INFORMATION: 2'-O-methyl
<220> FEATURE:
<221> NAME/KEY: misc_feature
<222> LOCATION: (8)..(8)
<223> OTHER INFORMATION: 2'-O-methyl
<220> FEATURE:
<221> NAME/KEY: misc_feature
<222> LOCATION: (10)..(10)
<223> OTHER INFORMATION: 2'-O-methyl
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (14)..(14)
<223> OTHER INFORMATION: 2'-O-methyl
<220> FEATURE:
<221> NAME/KEY: misc_feature
<222> LOCATION: (16)..(16)
<223> OTHER INFORMATION: 2'-O-methyl
<220> FEATURE:
<221> NAME/KEY: misc_feature
<222> LOCATION: (18)..(18)
<223> OTHER INFORMATION: 2'-O-methyl
<220> FEATURE:
<221> NAME/KEY: misc_feature
<222> LOCATION: (20)..(20)
<223> OTHER INFORMATION: 2'-O-methyl
```

<400> SEQUENCE: 15
aaguaaggac cagagacaaa                                              20

<210> SEQ ID NO 16
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphodiester linkages
<220> FEATURE:
<221> NAME/KEY: misc_feature
<222> LOCATION: (1)..(1)
<223> OTHER INFORMATION: 2'-F modified nucleoside
<220> FEATURE:
<221> NAME/KEY: misc_feature
<222> LOCATION: (2)..(2)
<223> OTHER INFORMATION: 2'deoxyribonucleoside
<220> FEATURE:
<221> NAME/KEY: misc_feature
<222> LOCATION: (3)..(3)
<223> OTHER INFORMATION: 2'-F modified nucleoside
<220> FEATURE:
<221> NAME/KEY: misc_feature
<222> LOCATION: (4)..(4)
<223> OTHER INFORMATION: 2'deoxyribonucleoside
<220> FEATURE:
<221> NAME/KEY: misc_feature
<222> LOCATION: (5)..(5)
<223> OTHER INFORMATION: 2'-F modified nucleoside
<220> FEATURE:
<221> NAME/KEY: misc_feature
<222> LOCATION: (6)..(6)
<223> OTHER INFORMATION: 2'deoxyribonucleoside
<220> FEATURE:
<221> NAME/KEY: misc_feature
<222> LOCATION: (7)..(7)
<223> OTHER INFORMATION: 2'-F modified nucleoside
<220> FEATURE:
<221> NAME/KEY: misc_feature
<222> LOCATION: (8)..(8)
<223> OTHER INFORMATION: 2'deoxyribonucleoside
<220> FEATURE:
<221> NAME/KEY: misc_feature
<222> LOCATION: (9)..(9)
<223> OTHER INFORMATION: 2'-F modified nucleoside
<220> FEATURE:
<221> NAME/KEY: misc_feature
<222> LOCATION: (10)..(10)
<223> OTHER INFORMATION: 2'deoxyribonucleoside
<220> FEATURE:
<221> NAME/KEY: misc_feature
<222> LOCATION: (11)..(11)
<223> OTHER INFORMATION: 2'-F modified nucleoside
<220> FEATURE:
<221> NAME/KEY: misc_feature
<222> LOCATION: (12)..(12)
<223> OTHER INFORMATION: 2'deoxyribonucleoside
<220> FEATURE:
<221> NAME/KEY: misc_feature
<222> LOCATION: (13)..(13)
<223> OTHER INFORMATION: 2'-F modified nucleoside
<220> FEATURE:
<221> NAME/KEY: misc_feature
<222> LOCATION: (14)..(14)
<223> OTHER INFORMATION: 2'deoxyribonucleoside
<220> FEATURE:
<221> NAME/KEY: misc_feature
<222> LOCATION: (15)..(15)
<223> OTHER INFORMATION: 2'-F modified nucleoside
<220> FEATURE:
<221> NAME/KEY: misc_feature
<222> LOCATION: (16)..(16)
<223> OTHER INFORMATION: 2'deoxyribonucleoside -continued

```
<220> FEATURE:
<221> NAME/KEY: misc_feature
<222> LOCATION: (17)..(17)
<223> OTHER INFORMATION: 2'-F modified nucleoside
<220> FEATURE:
<221> NAME/KEY: misc_feature
<222> LOCATION: (18)..(18)
<223> OTHER INFORMATION: 2'deoxyribonucleoside
<220> FEATURE:
<221> NAME/KEY: misc_feature
<222> LOCATION: (19)..(19)
<223> OTHER INFORMATION: 2'-F modified nucleoside
<220> FEATURE:
<221> NAME/KEY: misc_feature
<222> LOCATION: (20)..(20)
<223> OTHER INFORMATION: 2'deoxyribonucleoside

<400> SEQUENCE: 16
aaguaaggac cagagacaaa                                               20

<210> SEQ ID NO 17
<211> LENGTH: 20
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphodiester linkages
<220> FEATURE:
<221> NAME/KEY: misc_feature
<222> LOCATION: (1)..(1)
<223> OTHER INFORMATION: 2'deoxyribonucleoside
<220> FEATURE:
<221> NAME/KEY: misc_feature
<222> LOCATION: (2)..(2)
<223> OTHER INFORMATION: 2'-F modified nucleoside
<220> FEATURE:
<221> NAME/KEY: misc_feature
<222> LOCATION: (3)..(3)
<223> OTHER INFORMATION: 2'deoxyribonucleoside
<220> FEATURE:
<221> NAME/KEY: misc_feature
<222> LOCATION: (4)..(4)
<223> OTHER INFORMATION: 2'-F modified nucleoside
<220> FEATURE:
<221> NAME/KEY: misc_feature
<222> LOCATION: (5)..(5)
<223> OTHER INFORMATION: 2'deoxyribonucleoside
<220> FEATURE:
<221> NAME/KEY: misc_feature
<222> LOCATION: (6)..(6)
<223> OTHER INFORMATION: 2'-F modified nucleoside
<220> FEATURE:
<221> NAME/KEY: misc_feature
<222> LOCATION: (7)..(7)
<223> OTHER INFORMATION: 2'deoxyribonucleoside
<220> FEATURE:
<221> NAME/KEY: misc_feature
<222> LOCATION: (8)..(8)
<223> OTHER INFORMATION: 2'-F modified nucleoside
<220> FEATURE:
<221> NAME/KEY: misc_feature
<222> LOCATION: (9)..(9)
<223> OTHER INFORMATION: 2'deoxyribonucleoside
<220> FEATURE:
<221> NAME/KEY: misc_feature
<222> LOCATION: (10)..(10)
<223> OTHER INFORMATION: 2'-F modified nucleoside
<220> FEATURE:
<221> NAME/KEY: misc_feature
<222> LOCATION: (11)..(11)
<223> OTHER INFORMATION: 2'deoxyribonucleoside
<220> FEATURE:
<221> NAME/KEY: misc_feature
<222> LOCATION: (12)..(12)
```

```
<223> OTHER INFORMATION: 2'-F modified nucleoside
<220> FEATURE:
<221> NAME/KEY: misc_feature
<222> LOCATION: (13)..(13)
<223> OTHER INFORMATION: 5-methyl cytidine
<220> FEATURE:
<221> NAME/KEY: misc_feature
<222> LOCATION: (14)..(14)
<223> OTHER INFORMATION: 2'-F modified nucleoside
<220> FEATURE:
<221> NAME/KEY: misc_feature
<222> LOCATION: (15)..(15)
<223> OTHER INFORMATION: 2'deoxyribonucleoside
<220> FEATURE:
<221> NAME/KEY: misc_feature
<222> LOCATION: (16)..(16)
<223> OTHER INFORMATION: 2'-F modified nucleoside
<220> FEATURE:
<221> NAME/KEY: misc_feature
<222> LOCATION: (17)..(17)
<223> OTHER INFORMATION: 2'deoxyribonucleoside
<220> FEATURE:
<221> NAME/KEY: misc_feature
<222> LOCATION: (18)..(18)
<223> OTHER INFORMATION: 2'-F modified nucleoside
<220> FEATURE:
<221> NAME/KEY: misc_feature
<222> LOCATION: (19)..(19)
<223> OTHER INFORMATION: 2'deoxyribonucleoside
<220> FEATURE:
<221> NAME/KEY: misc_feature
<222> LOCATION: (20)..(20)
<223> OTHER INFORMATION: 2'-F modified nucleoside

<400> SEQUENCE: 17
tutgtctctg gucctuactu                                              20

<210> SEQ ID NO 18
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphodiester linkages
<220> FEATURE:
<221> NAME/KEY: misc_feature
<222> LOCATION: (1)..(1)
<223> OTHER INFORMATION: 2'deoxyribonucleoside
<220> FEATURE:
<221> NAME/KEY: misc_feature
<222> LOCATION: (2)..(2)
<223> OTHER INFORMATION: 2'-F modified nucleoside
<220> FEATURE:
<221> NAME/KEY: misc_feature
<222> LOCATION: (3)..(3)
<223> OTHER INFORMATION: 2'deoxyribonucleoside
<220> FEATURE:
<221> NAME/KEY: misc_feature
<222> LOCATION: (4)..(4)
<223> OTHER INFORMATION: 2'-F modified nucleoside
<220> FEATURE:
<221> NAME/KEY: misc_feature
<222> LOCATION: (5)..(5)
<223> OTHER INFORMATION: 2'deoxyribonucleoside
<220> FEATURE:
<221> NAME/KEY: misc_feature
<222> LOCATION: (6)..(6)
<223> OTHER INFORMATION: 2'-F modified nucleoside
<220> FEATURE:
<221> NAME/KEY: misc_feature
<222> LOCATION: (7)..(7)
<223> OTHER INFORMATION: 2'deoxyribonucleoside
<220> FEATURE:
<221> NAME/KEY: misc_feature
```

```
<222> LOCATION: (8)..(8)
<223> OTHER INFORMATION: 2'-F modified nucleoside
<220> FEATURE:
<221> NAME/KEY: misc_feature
<222> LOCATION: (9)..(9)
<223> OTHER INFORMATION: 2'deoxyribonucleoside
<220> FEATURE:
<221> NAME/KEY: misc_feature
<222> LOCATION: (10)..(10)
<223> OTHER INFORMATION: 5-methyl cytidine
<220> FEATURE:
<221> NAME/KEY: misc_feature
<222> LOCATION: (10)..(10)
<223> OTHER INFORMATION: 2'-F modified nucleoside
<220> FEATURE:
<221> NAME/KEY: misc_feature
<222> LOCATION: (11)..(11)
<223> OTHER INFORMATION: 2'deoxyribonucleoside
<220> FEATURE:
<221> NAME/KEY: misc_feature
<222> LOCATION: (12)..(12)
<223> OTHER INFORMATION: 2'-F modified nucleoside
<220> FEATURE:
<221> NAME/KEY: misc_feature
<222> LOCATION: (13)..(13)
<223> OTHER INFORMATION: 2'deoxyribonucleoside
<220> FEATURE:
<221> NAME/KEY: misc_feature
<222> LOCATION: (14)..(14)
<223> OTHER INFORMATION: 2'-F modified nucleoside
<220> FEATURE:
<221> NAME/KEY: misc_feature
<222> LOCATION: (15)..(15)
<223> OTHER INFORMATION: 2'deoxyribonucleoside
<220> FEATURE:
<221> NAME/KEY: misc_feature
<222> LOCATION: (16)..(16)
<223> OTHER INFORMATION: 2'-F modified nucleoside
<220> FEATURE:
<221> NAME/KEY: misc_feature
<222> LOCATION: (17)..(17)
<223> OTHER INFORMATION: 2'deoxyribonucleoside
<220> FEATURE:
<221> NAME/KEY: misc_feature
<222> LOCATION: (18)..(18)
<223> OTHER INFORMATION: 2'-F modified nucleoside
<220> FEATURE:
<221> NAME/KEY: misc_feature
<222> LOCATION: (19)..(19)
<223> OTHER INFORMATION: 2'deoxyribonucleoside
<220> FEATURE:
<221> NAME/KEY: misc_feature
<222> LOCATION: (20)..(20)
<223> OTHER INFORMATION: 2'-F modified nucleoside

<400> SEQUENCE: 18
aaguaaggac cagagacaaa                                                   20

<210> SEQ ID NO 19
<211> LENGTH: 20
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphorothioate linkages
<220> FEATURE:
<221> NAME/KEY: misc_feature
<222> LOCATION: (1)..(1)
<223> OTHER INFORMATION: 2'deoxyribonucleoside
<220> FEATURE:
<221> NAME/KEY: misc_feature
<222> LOCATION: (2)..(2)
<223> OTHER INFORMATION: 2'-F modified nucleoside
<220> FEATURE:
```

```
<221> NAME/KEY: misc_feature
<222> LOCATION: (3)..(3)
<223> OTHER INFORMATION: 2'deoxyribonucleoside
<220> FEATURE:
<221> NAME/KEY: misc_feature
<222> LOCATION: (4)..(4)
<223> OTHER INFORMATION: 2'-F modified nucleoside
<220> FEATURE:
<221> NAME/KEY: misc_feature
<222> LOCATION: (5)..(5)
<223> OTHER INFORMATION: 2'deoxyribonucleoside
<220> FEATURE:
<221> NAME/KEY: misc_feature
<222> LOCATION: (6)..(6)
<223> OTHER INFORMATION: 2'-F modified nucleoside
<220> FEATURE:
<221> NAME/KEY: misc_feature
<222> LOCATION: (7)..(7)
<223> OTHER INFORMATION: 2'deoxyribonucleoside
<220> FEATURE:
<221> NAME/KEY: misc_feature
<222> LOCATION: (8)..(8)
<223> OTHER INFORMATION: 2'-F modified nucleoside
<220> FEATURE:
<221> NAME/KEY: misc_feature
<222> LOCATION: (9)..(9)
<223> OTHER INFORMATION: 2'deoxyribonucleoside
<220> FEATURE:
<221> NAME/KEY: misc_feature
<222> LOCATION: (10)..(10)
<223> OTHER INFORMATION: 2'-F modified nucleoside
<220> FEATURE:
<221> NAME/KEY: misc_feature
<222> LOCATION: (11)..(11)
<223> OTHER INFORMATION: 2'deoxyribonucleoside
<220> FEATURE:
<221> NAME/KEY: misc_feature
<222> LOCATION: (12)..(12)
<223> OTHER INFORMATION: 2'-F modified nucleoside
<220> FEATURE:
<221> NAME/KEY: misc_feature
<222> LOCATION: (13)..(13)
<223> OTHER INFORMATION: 5-methyl cytidine
<220> FEATURE:
<221> NAME/KEY: misc_feature
<222> LOCATION: (14)..(14)
<223> OTHER INFORMATION: 2'-F modified nucleoside
<220> FEATURE:
<221> NAME/KEY: misc_feature
<222> LOCATION: (15)..(15)
<223> OTHER INFORMATION: 2'deoxyribonucleoside
<220> FEATURE:
<221> NAME/KEY: misc_feature
<222> LOCATION: (16)..(16)
<223> OTHER INFORMATION: 2'-F modified nucleoside
<220> FEATURE:
<221> NAME/KEY: misc_feature
<222> LOCATION: (17)..(17)
<223> OTHER INFORMATION: 2'deoxyribonucleoside
<220> FEATURE:
<221> NAME/KEY: misc_feature
<222> LOCATION: (18)..(18)
<223> OTHER INFORMATION: 2'-F modified nucleoside
<220> FEATURE:
<221> NAME/KEY: misc_feature
<222> LOCATION: (19)..(19)
<223> OTHER INFORMATION: 2'deoxyribonucleoside
<220> FEATURE:
<221> NAME/KEY: misc_feature
<222> LOCATION: (20)..(20)
<223> OTHER INFORMATION: 2'-F modified nucleoside

<400> SEQUENCE: 19
tutgtctctg gucctuactu                                                   20

<210> SEQ ID NO 20
<211> LENGTH: 20
```

```
<212> TYPE: DNA
<213> ORGANISM: Artificial
<220> FEATURE:
<223> OTHER INFORMATION: Synthetic Construct

<400> SEQUENCE: 20
tutgtctctg gucctuactu                                                    20

<210> SEQ ID NO 21
<211> LENGTH: 20
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphodiester linkages
<220> FEATURE:
<221> NAME/KEY: misc_feature
<222> LOCATION: (1)..(1)
<223> OTHER INFORMATION: 2'-F modified nucleoside
<220> FEATURE:
<221> NAME/KEY: misc_feature
<222> LOCATION: (2)..(2)
<223> OTHER INFORMATION: 2'deoxyribonucleoside
<220> FEATURE:
<221> NAME/KEY: misc_feature
<222> LOCATION: (3)..(3)
<223> OTHER INFORMATION: 2'-F modified nucleoside
<220> FEATURE:
<221> NAME/KEY: misc_feature
<222> LOCATION: (4)..(4)
<223> OTHER INFORMATION: 2'deoxyribonucleoside
<220> FEATURE:
<221> NAME/KEY: misc_feature
<222> LOCATION: (5)..(5)
<223> OTHER INFORMATION: 2'-F modified nucleoside
<220> FEATURE:
<221> NAME/KEY: misc_feature
<222> LOCATION: (6)..(6)
<223> OTHER INFORMATION: 5-methyl cytidine
<220> FEATURE:
<221> NAME/KEY: misc_feature
<222> LOCATION: (7)..(7)
<223> OTHER INFORMATION: 2'-F modified nucleoside
<220> FEATURE:
<221> NAME/KEY: misc_feature
<222> LOCATION: (8)..(8)
<223> OTHER INFORMATION: 5-methyl cytidine
<220> FEATURE:
<221> NAME/KEY: misc_feature
<222> LOCATION: (9)..(9)
<223> OTHER INFORMATION: 2'-F modified nucleoside
<220> FEATURE:
<221> NAME/KEY: misc_feature
<222> LOCATION: (10)..(10)
<223> OTHER INFORMATION: 2'deoxyribonucleoside
<220> FEATURE:
<221> NAME/KEY: misc_feature
<222> LOCATION: (11)..(11)
<223> OTHER INFORMATION: 2'-F modified nucleoside
<220> FEATURE:
<221> NAME/KEY: misc_feature
<222> LOCATION: (12)..(12)
<223> OTHER INFORMATION: 2'deoxyribonucleoside
<220> FEATURE:
<221> NAME/KEY: misc_feature
<222> LOCATION: (13)..(13)
<223> OTHER INFORMATION: 2'-F modified nucleoside
<220> FEATURE:
<221> NAME/KEY: misc_feature
<222> LOCATION: (14)..(14)
<223> OTHER INFORMATION: 5-methyl cytidine
<220> FEATURE:
<221> NAME/KEY: misc_feature
<222> LOCATION: (15)..(15)
```

```
<223> OTHER INFORMATION: 2'-F modified nucleoside
<220> FEATURE:
<221> NAME/KEY: misc_feature
<222> LOCATION: (16)..(16)
<223> OTHER INFORMATION: 2'deoxyribonucleoside
<220> FEATURE:
<221> NAME/KEY: misc_feature
<222> LOCATION: (17)..(17)
<223> OTHER INFORMATION: 2'-F modified nucleoside
<220> FEATURE:
<221> NAME/KEY: misc_feature
<222> LOCATION: (18)..(18)
<223> OTHER INFORMATION: 5-methyl cytidine
<220> FEATURE:
<221> NAME/KEY: misc_feature
<222> LOCATION: (19)..(19)
<223> OTHER INFORMATION: 2'-F modified nucleoside
<220> FEATURE:
<221> NAME/KEY: misc_feature
<222> LOCATION: (20)..(20)
<223> OTHER INFORMATION: 2'deoxyribonucleoside

<400> SEQUENCE: 21
utugucucug gtccutacut                                              20

<210> SEQ ID NO 22
<211> LENGTH: 20
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphorothioate linkages
<220> FEATURE:
<221> NAME/KEY: misc_feature
<222> LOCATION: (1)..(1)
<223> OTHER INFORMATION: 2'-F modified nucleoside
<220> FEATURE:
<221> NAME/KEY: misc_feature
<222> LOCATION: (2)..(2)
<223> OTHER INFORMATION: 2'deoxyribonucleoside
<220> FEATURE:
<221> NAME/KEY: misc_feature
<222> LOCATION: (3)..(3)
<223> OTHER INFORMATION: 2'-F modified nucleoside
<220> FEATURE:
<221> NAME/KEY: misc_feature
<222> LOCATION: (4)..(4)
<223> OTHER INFORMATION: 2'deoxyribonucleoside
<220> FEATURE:
<221> NAME/KEY: misc_feature
<222> LOCATION: (5)..(5)
<223> OTHER INFORMATION: 2'-F modified nucleoside
<220> FEATURE:
<221> NAME/KEY: misc_feature
<222> LOCATION: (6)..(6)
<223> OTHER INFORMATION: 5-methyl cytidine
<220> FEATURE:
<221> NAME/KEY: misc_feature
<222> LOCATION: (7)..(7)
<223> OTHER INFORMATION: 2'-F modified nucleoside
<220> FEATURE:
<221> NAME/KEY: misc_feature
<222> LOCATION: (8)..(8)
<223> OTHER INFORMATION: 5-methyl cytidine
<220> FEATURE:
<221> NAME/KEY: misc_feature
<222> LOCATION: (9)..(9)
<223> OTHER INFORMATION: 2'-F modified nucleoside
<220> FEATURE:
<221> NAME/KEY: misc_feature
<222> LOCATION: (10)..(10)
<223> OTHER INFORMATION: 2'deoxyribonucleoside
<220> FEATURE:
<221> NAME/KEY: misc_feature
```

```
<222> LOCATION: (11)..(11)
<223> OTHER INFORMATION: 2'-F modified nucleoside
<220> FEATURE:
<221> NAME/KEY: misc_feature
<222> LOCATION: (12)..(12)
<223> OTHER INFORMATION: 2'deoxyribonucleoside
<220> FEATURE:
<221> NAME/KEY: misc_feature
<222> LOCATION: (13)..(13)
<223> OTHER INFORMATION: 2'-F modified nucleoside
<220> FEATURE:
<221> NAME/KEY: misc_feature
<222> LOCATION: (14)..(14)
<223> OTHER INFORMATION: 5-methyl cytidine
<220> FEATURE:
<221> NAME/KEY: misc_feature
<222> LOCATION: (15)..(15)
<223> OTHER INFORMATION: 2'-F modified nucleoside
<220> FEATURE:
<221> NAME/KEY: misc_feature
<222> LOCATION: (16)..(16)
<223> OTHER INFORMATION: 2'deoxyribonucleoside
<220> FEATURE:
<221> NAME/KEY: misc_feature
<222> LOCATION: (17)..(17)
<223> OTHER INFORMATION: 2'-F modified nucleoside
<220> FEATURE:
<221> NAME/KEY: misc_feature
<222> LOCATION: (18)..(18)
<223> OTHER INFORMATION: 5-methyl cytidine
<220> FEATURE:
<221> NAME/KEY: misc_feature
<222> LOCATION: (19)..(19)
<223> OTHER INFORMATION: 2'-F modified nucleoside
<220> FEATURE:
<221> NAME/KEY: misc_feature
<222> LOCATION: (20)..(20)
<223> OTHER INFORMATION: 2'deoxyribonucleoside

<400> SEQUENCE: 22
utugucucug gtccutacut                                                    20

<210> SEQ ID NO 23
<211> LENGTH: 20
<212> TYPE: DNA
<213> ORGANISM: Artificial
<220> FEATURE:
<223> OTHER INFORMATION: Synthetic Construct

<400> SEQUENCE: 23
utugucucug gtccutacut                                                    20

<210> SEQ ID NO 24
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphodiester linkages
<220> FEATURE:
<221> NAME/KEY: misc_feature
<222> LOCATION: (1)..(1)
<223> OTHER INFORMATION: 2'-F modified nucleoside
<220> FEATURE:
<221> NAME/KEY: misc_feature
<222> LOCATION: (2)..(2)
<223> OTHER INFORMATION: 2'-OCH3 modified nucleoside
<220> FEATURE:
<221> NAME/KEY: misc_feature
<222> LOCATION: (3)..(3)
<223> OTHER INFORMATION: 2'-F modified nucleoside
<220> FEATURE:
```

<221> NAME/KEY: misc_feature
<222> LOCATION: (4)..(4)
<223> OTHER INFORMATION: 2'-OCH3 modified nucleoside
<220> FEATURE:
<221> NAME/KEY: misc_feature
<222> LOCATION: (5)..(5)
<223> OTHER INFORMATION: 2'-F modified nucleoside
<220> FEATURE:
<221> NAME/KEY: misc_feature
<222> LOCATION: (6)..(6)
<223> OTHER INFORMATION: 2'-OCH3 modified nucleoside
<220> FEATURE:
<221> NAME/KEY: misc_feature
<222> LOCATION: (7)..(7)
<223> OTHER INFORMATION: 2'-F modified nucleoside
<220> FEATURE:
<221> NAME/KEY: misc_feature
<222> LOCATION: (8)..(8)
<223> OTHER INFORMATION: 2'-OCH3 modified nucleoside
<220> FEATURE:
<221> NAME/KEY: misc_feature
<222> LOCATION: (9)..(9)
<223> OTHER INFORMATION: 2'-F modified nucleoside
<220> FEATURE:
<221> NAME/KEY: misc_feature
<222> LOCATION: (10)..(10)
<223> OTHER INFORMATION: 2'-OCH3 modified nucleoside
<220> FEATURE:
<221> NAME/KEY: misc_feature
<222> LOCATION: (11)..(11)
<223> OTHER INFORMATION: 2'-F modified nucleoside
<220> FEATURE:
<221> NAME/KEY: misc_feature
<222> LOCATION: (12)..(12)
<223> OTHER INFORMATION: 2'-OCH3 modified nucleoside
<220> FEATURE:
<221> NAME/KEY: misc_feature
<222> LOCATION: (13)..(13)
<223> OTHER INFORMATION: 2'-F modified nucleoside
<220> FEATURE:
<221> NAME/KEY: misc_feature
<222> LOCATION: (14)..(14)
<223> OTHER INFORMATION: 2'-OCH3 modified nucleoside
<220> FEATURE:
<221> NAME/KEY: misc_feature
<222> LOCATION: (15)..(15)
<223> OTHER INFORMATION: 2'-F modified nucleoside
<220> FEATURE:
<221> NAME/KEY: misc_feature
<222> LOCATION: (16)..(16)
<223> OTHER INFORMATION: 2'-OCH3 modified nucleoside
<220> FEATURE:
<221> NAME/KEY: misc_feature
<222> LOCATION: (17)..(17)
<223> OTHER INFORMATION: 2'-F modified nucleoside
<220> FEATURE:
<221> NAME/KEY: misc_feature
<222> LOCATION: (18)..(18)
<223> OTHER INFORMATION: 2'-OCH3 modified nucleoside
<220> FEATURE:
<221> NAME/KEY: misc_feature
<222> LOCATION: (19)..(19)
<223> OTHER INFORMATION: 2'-F modified nucleoside
<220> FEATURE:
<221> NAME/KEY: misc_feature
<222> LOCATION: (20)..(20)
<223> OTHER INFORMATION: 2'-OCH3 modified nucleoside

<400> SEQUENCE: 24
aaguaaggac cagagacaaa                                              20

<210> SEQ ID NO 25
<211> LENGTH: 20
<212> TYPE: RNA
<213> ORGANISM: Artificial
<220> FEATURE:
<223> OTHER INFORMATION: Synthetic Construct -continued

```
<220> FEATURE:
<221> NAME/KEY: misc_feature
<222> LOCATION: (1)..(20)
<223> OTHER INFORMATION: phosphodiester linkages
<220> FEATURE:
<221> NAME/KEY: misc_feature
<222> LOCATION: (1)..(1)
<223> OTHER INFORMATION: 2'-F modified nucleoside
<220> FEATURE:
<221> NAME/KEY: misc_feature
<222> LOCATION: (2)..(2)
<223> OTHER INFORMATION: 2'-OCH3 modified nucleoside
<220> FEATURE:
<221> NAME/KEY: misc_feature
<222> LOCATION: (3)..(3)
<223> OTHER INFORMATION: 2'-F modified nucleoside
<220> FEATURE:
<221> NAME/KEY: misc_feature
<222> LOCATION: (4)..(4)
<223> OTHER INFORMATION: 2'-OCH3 modified nucleoside
<220> FEATURE:
<221> NAME/KEY: misc_feature
<222> LOCATION: (5)..(5)
<223> OTHER INFORMATION: 2'-F modified nucleoside
<220> FEATURE:
<221> NAME/KEY: misc_feature
<222> LOCATION: (6)..(6)
<223> OTHER INFORMATION: 2'-OCH3 modified nucleoside
<220> FEATURE:
<221> NAME/KEY: misc_feature
<222> LOCATION: (7)..(7)
<223> OTHER INFORMATION: 2'-F modified nucleoside
<220> FEATURE:
<221> NAME/KEY: misc_feature
<222> LOCATION: (8)..(8)
<223> OTHER INFORMATION: 2'-OCH3 modified nucleoside
<220> FEATURE:
<221> NAME/KEY: misc_feature
<222> LOCATION: (9)..(9)
<223> OTHER INFORMATION: 2'-F modified nucleoside
<220> FEATURE:
<221> NAME/KEY: misc_feature
<222> LOCATION: (10)..(10)
<223> OTHER INFORMATION: 2'-OCH3 modified nucleoside
<220> FEATURE:
<221> NAME/KEY: misc_feature
<222> LOCATION: (11)..(11)
<223> OTHER INFORMATION: 2'-F modified nucleoside
<220> FEATURE:
<221> NAME/KEY: misc_feature
<222> LOCATION: (12)..(12)
<223> OTHER INFORMATION: 2'-OCH3 modified nucleoside
<220> FEATURE:
<221> NAME/KEY: misc_feature
<222> LOCATION: (13)..(13)
<223> OTHER INFORMATION: 2'-F modified nucleoside
<220> FEATURE:
<221> NAME/KEY: misc_feature
<222> LOCATION: (14)..(14)
<223> OTHER INFORMATION: 2'-OCH3 modified nucleoside
<220> FEATURE:
<221> NAME/KEY: misc_feature
<222> LOCATION: (15)..(15)
<223> OTHER INFORMATION: 2'-F modified nucleoside
<220> FEATURE:
<221> NAME/KEY: misc_feature
<222> LOCATION: (16)..(16)
<223> OTHER INFORMATION: 2'-OCH3 modified nucleoside
<220> FEATURE:
<221> NAME/KEY: misc_feature
<222> LOCATION: (17)..(17)
<223> OTHER INFORMATION: 2'-F modified nucleoside
<220> FEATURE:
<221> NAME/KEY: misc_feature
<222> LOCATION: (18)..(18)
<223> OTHER INFORMATION: 2'-OCH3 modified nucleoside
<220> FEATURE:
<221> NAME/KEY: misc_feature
<222> LOCATION: (19)..(19)
```

<223> OTHER INFORMATION: 2'-F modified nucleoside
<220> FEATURE:
<221> NAME/KEY: misc_feature
<222> LOCATION: (20)..(20)
<223> OTHER INFORMATION: 2'-OCH3 modified nucleoside

<400> SEQUENCE: 25
uuugucucug guccuuacuu                                               20

<210> SEQ ID NO 26
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphodiester linkages
<220> FEATURE:
<221> NAME/KEY: misc_feature
<222> LOCATION: (1)..(1)
<223> OTHER INFORMATION: 2'-OCH3
<220> FEATURE:
<221> NAME/KEY: misc_feature
<222> LOCATION: (2)..(2)
<223> OTHER INFORMATION: 2'-F modified nucleoside
<220> FEATURE:
<221> NAME/KEY: misc_feature
<222> LOCATION: (3)..(3)
<223> OTHER INFORMATION: 2'-OCH3
<220> FEATURE:
<221> NAME/KEY: misc_feature
<222> LOCATION: (4)..(4)
<223> OTHER INFORMATION: 2'-F modified nucleoside
<220> FEATURE:
<221> NAME/KEY: misc_feature
<222> LOCATION: (5)..(5)
<223> OTHER INFORMATION: 2'-OCH3
<220> FEATURE:
<221> NAME/KEY: misc_feature
<222> LOCATION: (6)..(6)
<223> OTHER INFORMATION: 2'-F modified nucleoside
<220> FEATURE:
<221> NAME/KEY: misc_feature
<222> LOCATION: (7)..(7)
<223> OTHER INFORMATION: 2'-OCH3
<220> FEATURE:
<221> NAME/KEY: misc_feature
<222> LOCATION: (8)..(8)
<223> OTHER INFORMATION: 2'-F modified nucleoside
<220> FEATURE:
<221> NAME/KEY: misc_feature
<222> LOCATION: (9)..(9)
<223> OTHER INFORMATION: 2'-OCH3
<220> FEATURE:
<221> NAME/KEY: misc_feature
<222> LOCATION: (10)..(10)
<223> OTHER INFORMATION: 2'-F modified nucleoside
<220> FEATURE:
<221> NAME/KEY: misc_feature
<222> LOCATION: (11)..(11)
<223> OTHER INFORMATION: 2'-OCH3
<220> FEATURE:
<221> NAME/KEY: misc_feature
<222> LOCATION: (12)..(12)
<223> OTHER INFORMATION: 2'-F modified nucleoside
<220> FEATURE:
<221> NAME/KEY: misc_feature
<222> LOCATION: (13)..(13)
<223> OTHER INFORMATION: 2'-OCH3
<220> FEATURE:
<221> NAME/KEY: misc_feature
<222> LOCATION: (14)..(14)
<223> OTHER INFORMATION: 2'-F
<220> FEATURE:
<221> NAME/KEY: misc_feature

```
<222> LOCATION: (15)..(15)
<223> OTHER INFORMATION: 2'-OCH3
<220> FEATURE:
<221> NAME/KEY: misc_feature
<222> LOCATION: (16)..(16)
<223> OTHER INFORMATION: 2'-F
<220> FEATURE:
<221> NAME/KEY: misc_feature
<222> LOCATION: (17)..(17)
<223> OTHER INFORMATION: 2'-OCH3
<220> FEATURE:
<221> NAME/KEY: misc_feature
<222> LOCATION: (18)..(18)
<223> OTHER INFORMATION: 2'-F modified nucleoside
<220> FEATURE:
<221> NAME/KEY: misc_feature
<222> LOCATION: (19)..(19)
<223> OTHER INFORMATION: 2'-OCH3
<220> FEATURE:
<221> NAME/KEY: misc_feature
<222> LOCATION: (20)..(20)
<223> OTHER INFORMATION: 2'-F

<400> SEQUENCE: 26
aaguaaggac cagagacaaa                                                  20

<210> SEQ ID NO 27
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphorothioate linkages
<220> FEATURE:
<221> NAME/KEY: misc_feature
<222> LOCATION: (1)..(1)
<223> OTHER INFORMATION: 2'-F modified nucleoside
<220> FEATURE:
<221> NAME/KEY: misc_feature
<222> LOCATION: (2)..(2)
<223> OTHER INFORMATION: 2'-OCH3 modified nucleoside
<220> FEATURE:
<221> NAME/KEY: misc_feature
<222> LOCATION: (3)..(3)
<223> OTHER INFORMATION: 2'-F modified nucleoside
<220> FEATURE:
<221> NAME/KEY: misc_feature
<222> LOCATION: (4)..(4)
<223> OTHER INFORMATION: 2'-OCH3 modified nucleoside
<220> FEATURE:
<221> NAME/KEY: misc_feature
<222> LOCATION: (5)..(5)
<223> OTHER INFORMATION: 2'-F modified nucleoside
<220> FEATURE:
<221> NAME/KEY: misc_feature
<222> LOCATION: (6)..(6)
<223> OTHER INFORMATION: 2'-OCH3 modified nucleoside
<220> FEATURE:
<221> NAME/KEY: misc_feature
<222> LOCATION: (7)..(7)
<223> OTHER INFORMATION: 2'-F modified nucleoside
<220> FEATURE:
<221> NAME/KEY: misc_feature
<222> LOCATION: (8)..(8)
<223> OTHER INFORMATION: 2'-OCH3 modified nucleoside
<220> FEATURE:
<221> NAME/KEY: misc_feature
<222> LOCATION: (9)..(9)
<223> OTHER INFORMATION: 2'-F modified nucleoside
<220> FEATURE:
<221> NAME/KEY: misc_feature
<222> LOCATION: (10)..(10)
<223> OTHER INFORMATION: 2'-OCH3 modified nucleoside
<220> FEATURE:
```

```
<221> NAME/KEY: misc_feature
<222> LOCATION: (11)..(11)
<223> OTHER INFORMATION: 2'-F modified nucleoside
<220> FEATURE:
<221> NAME/KEY: misc_feature
<222> LOCATION: (12)..(12)
<223> OTHER INFORMATION: 2'-OCH3 modified nucleoside
<220> FEATURE:
<221> NAME/KEY: misc_feature
<222> LOCATION: (13)..(13)
<223> OTHER INFORMATION: 2'-F modified nucleoside
<220> FEATURE:
<221> NAME/KEY: misc_feature
<222> LOCATION: (14)..(14)
<223> OTHER INFORMATION: 2'-OCH3 modified nucleoside
<220> FEATURE:
<221> NAME/KEY: misc_feature
<222> LOCATION: (15)..(15)
<223> OTHER INFORMATION: 2'-F modified nucleoside
<220> FEATURE:
<221> NAME/KEY: misc_feature
<222> LOCATION: (16)..(16)
<223> OTHER INFORMATION: 2'-OCH3 modified nucleoside
<220> FEATURE:
<221> NAME/KEY: misc_feature
<222> LOCATION: (17)..(17)
<223> OTHER INFORMATION: 2'-F modified nucleoside
<220> FEATURE:
<221> NAME/KEY: misc_feature
<222> LOCATION: (18)..(18)
<223> OTHER INFORMATION: 2'-OCH3 modified nucleoside
<220> FEATURE:
<221> NAME/KEY: misc_feature
<222> LOCATION: (19)..(19)
<223> OTHER INFORMATION: 2'-F modified nucleoside
<220> FEATURE:
<221> NAME/KEY: misc_feature
<222> LOCATION: (20)..(20)
<223> OTHER INFORMATION: 2'-OCH3 modified nucleoside

<400> SEQUENCE: 27
uuugucucug guccuuacuu                                                   20

<210> SEQ ID NO 28
<211> LENGTH: 18
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(18)
<223> OTHER INFORMATION: phosphodiester linkages
<220> FEATURE:
<221> NAME/KEY: misc_feature
<222> LOCATION: (1)..(1)
<223> OTHER INFORMATION: 2'-OCH3 modified nucleoside
<220> FEATURE:
<221> NAME/KEY: misc_feature
<222> LOCATION: (2)..(2)
<223> OTHER INFORMATION: 2'-F modified nucleoside
<220> FEATURE:
<221> NAME/KEY: misc_feature
<222> LOCATION: (3)..(3)
<223> OTHER INFORMATION: 2'-OCH3 modified nucleoside
<220> FEATURE:
<221> NAME/KEY: misc_feature
<222> LOCATION: (4)..(4)
<223> OTHER INFORMATION: 2'-F modified nucleoside
<220> FEATURE:
<221> NAME/KEY: misc_feature
<222> LOCATION: (5)..(5)
<223> OTHER INFORMATION: 2'-OCH3 modified nucleoside
<220> FEATURE:
<221> NAME/KEY: misc_feature
<222> LOCATION: (6)..(6)
<223> OTHER INFORMATION: 2'-F modified nucleoside
```

```
<220> FEATURE:
<221> NAME/KEY: misc_feature
<222> LOCATION: (7)..(7)
<223> OTHER INFORMATION: 2'-OCH3 modified nucleoside
<220> FEATURE:
<221> NAME/KEY: misc_feature
<222> LOCATION: (8)..(8)
<223> OTHER INFORMATION: 2'-F modified nucleoside
<220> FEATURE:
<221> NAME/KEY: misc_feature
<222> LOCATION: (9)..(9)
<223> OTHER INFORMATION: 2'-OCH3 modified nucleoside
<220> FEATURE:
<221> NAME/KEY: misc_feature
<222> LOCATION: (10)..(10)
<223> OTHER INFORMATION: 2'-F modified nucleoside
<220> FEATURE:
<221> NAME/KEY: misc_feature
<222> LOCATION: (11)..(11)
<223> OTHER INFORMATION: 2'-OCH3 modified nucleoside
<220> FEATURE:
<221> NAME/KEY: misc_feature
<222> LOCATION: (12)..(12)
<223> OTHER INFORMATION: 2'-F modified nucleoside
<220> FEATURE:
<221> NAME/KEY: misc_feature
<222> LOCATION: (13)..(13)
<223> OTHER INFORMATION: 2'-OCH3 modified nucleoside
<220> FEATURE:
<221> NAME/KEY: misc_feature
<222> LOCATION: (14)..(14)
<223> OTHER INFORMATION: 2'-F modified nucleoside
<220> FEATURE:
<221> NAME/KEY: misc_feature
<222> LOCATION: (15)..(15)
<223> OTHER INFORMATION: 2'-OCH3 modified nucleoside
<220> FEATURE:
<221> NAME/KEY: misc_feature
<222> LOCATION: (16)..(16)
<223> OTHER INFORMATION: 2'-F modified nucleoside
<220> FEATURE:
<221> NAME/KEY: misc_feature
<222> LOCATION: (17)..(17)
<223> OTHER INFORMATION: 2'-OCH3 modified nucleoside
<220> FEATURE:
<221> NAME/KEY: misc_feature
<222> LOCATION: (18)..(18)
<223> OTHER INFORMATION: 2'-F modified nucleoside

<400> SEQUENCE: 28
uuugucuggu ccuuacuu                                                   18

<210> SEQ ID NO 29
<211> LENGTH: 18
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(18)
<223> OTHER INFORMATION: phosphorothioate linkages
<220> FEATURE:
<221> NAME/KEY: misc_feature
<222> LOCATION: (1)..(1)
<223> OTHER INFORMATION: 2'-OCH3 modified nucleoside
<220> FEATURE:
<221> NAME/KEY: misc_feature
<222> LOCATION: (2)..(2)
<223> OTHER INFORMATION: 2'-F modified nucleoside
<220> FEATURE:
<221> NAME/KEY: misc_feature
<222> LOCATION: (3)..(3)
<223> OTHER INFORMATION: 2'-OCH3 modified nucleoside
<220> FEATURE:
<221> NAME/KEY: misc_feature
<222> LOCATION: (4)..(4)
```

```
<223> OTHER INFORMATION: 2'-F modified nucleoside
<220> FEATURE:
<221> NAME/KEY: misc_feature
<222> LOCATION: (5)..(5)
<223> OTHER INFORMATION: 2'-OCH3 modified nucleoside
<220> FEATURE:
<221> NAME/KEY: misc_feature
<222> LOCATION: (6)..(6)
<223> OTHER INFORMATION: 2'-F modified nucleoside
<220> FEATURE:
<221> NAME/KEY: misc_feature
<222> LOCATION: (7)..(7)
<223> OTHER INFORMATION: 2'-OCH3 modified nucleoside
<220> FEATURE:
<221> NAME/KEY: misc_feature
<222> LOCATION: (8)..(8)
<223> OTHER INFORMATION: 2'-F modified nucleoside
<220> FEATURE:
<221> NAME/KEY: misc_feature
<222> LOCATION: (9)..(9)
<223> OTHER INFORMATION: 2'-OCH3 modified nucleoside
<220> FEATURE:
<221> NAME/KEY: misc_feature
<222> LOCATION: (10)..(10)
<223> OTHER INFORMATION: 2'-F modified nucleoside
<220> FEATURE:
<221> NAME/KEY: misc_feature
<222> LOCATION: (11)..(11)
<223> OTHER INFORMATION: 2'-OCH3 modified nucleoside
<220> FEATURE:
<221> NAME/KEY: misc_feature
<222> LOCATION: (12)..(12)
<223> OTHER INFORMATION: 2'-F modified nucleoside
<220> FEATURE:
<221> NAME/KEY: misc_feature
<222> LOCATION: (13)..(13)
<223> OTHER INFORMATION: 2'-OCH3 modified nucleoside
<220> FEATURE:
<221> NAME/KEY: misc_feature
<222> LOCATION: (14)..(14)
<223> OTHER INFORMATION: 2'-F modified nucleoside
<220> FEATURE:
<221> NAME/KEY: misc_feature
<222> LOCATION: (15)..(15)
<223> OTHER INFORMATION: 2'-OCH3 modified nucleoside
<220> FEATURE:
<221> NAME/KEY: misc_feature
<222> LOCATION: (16)..(16)
<223> OTHER INFORMATION: 2'-F modified nucleoside
<220> FEATURE:
<221> NAME/KEY: misc_feature
<222> LOCATION: (17)..(17)
<223> OTHER INFORMATION: 2'-OCH3 modified nucleoside
<220> FEATURE:
<221> NAME/KEY: misc_feature
<222> LOCATION: (18)..(18)
<223> OTHER INFORMATION: 2'-F modified nucleoside

<400> SEQUENCE: 29
uuugucuggu ccuuacuu                                                   18

<210> SEQ ID NO 30
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphodiester linkages
<220> FEATURE:
<221> NAME/KEY: misc_feature
<222> LOCATION: (2)..(2)
<223> OTHER INFORMATION: 2'-F modified nucleoside
<220> FEATURE:
<221> NAME/KEY: misc_feature
```

<222> LOCATION: (4)..(4)
<223> OTHER INFORMATION: 2'-F modified nucleoside
<220> FEATURE:
<221> NAME/KEY: misc_feature
<222> LOCATION: (6)..(6)
<223> OTHER INFORMATION: 2'-F modified nucleoside
<220> FEATURE:
<221> NAME/KEY: misc_feature
<222> LOCATION: (8)..(8)
<223> OTHER INFORMATION: 2'-F modified nucleoside
<220> FEATURE:
<221> NAME/KEY: misc_feature
<222> LOCATION: (10)..(10)
<223> OTHER INFORMATION: 2'-F modified nucleoside
<220> FEATURE:
<221> NAME/KEY: misc_feature
<222> LOCATION: (12)..(12)
<223> OTHER INFORMATION: 2'-F modified nucleoside
<220> FEATURE:
<221> NAME/KEY: misc_feature
<222> LOCATION: (14)..(14)
<223> OTHER INFORMATION: 2'-F modified nucleoside
<220> FEATURE:
<221> NAME/KEY: misc_feature
<222> LOCATION: (16)..(16)
<223> OTHER INFORMATION: 2'-F modified nucleoside
<220> FEATURE:
<221> NAME/KEY: misc_feature
<222> LOCATION: (18)..(18)
<223> OTHER INFORMATION: 2'-F modified nucleoside
<220> FEATURE:
<221> NAME/KEY: misc_feature
<222> LOCATION: (20)..(20)
<223> OTHER INFORMATION: 2'-F modified nucleoside

<400> SEQUENCE: 30
uuugucucug guccuuacuu                                               20

<210> SEQ ID NO 31
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphorothioate linkages
<220> FEATURE:
<221> NAME/KEY: misc_feature
<222> LOCATION: (2)..(2)
<223> OTHER INFORMATION: 2'-F modified nucleoside
<220> FEATURE:
<221> NAME/KEY: misc_feature
<222> LOCATION: (4)..(4)
<223> OTHER INFORMATION: 2'-F modified nucleoside
<220> FEATURE:
<221> NAME/KEY: misc_feature
<222> LOCATION: (6)..(6)
<223> OTHER INFORMATION: 2'-F modified nucleoside
<220> FEATURE:
<221> NAME/KEY: misc_feature
<222> LOCATION: (8)..(8)
<223> OTHER INFORMATION: 2'-F modified nucleoside
<220> FEATURE:
<221> NAME/KEY: misc_feature
<222> LOCATION: (10)..(10)
<223> OTHER INFORMATION: 2'-F modified nucleoside
<220> FEATURE:
<221> NAME/KEY: misc_feature
<222> LOCATION: (12)..(12)
<223> OTHER INFORMATION: 2'-F modified nucleoside
<220> FEATURE:
<221> NAME/KEY: misc_feature
<222> LOCATION: (14)..(14)
<223> OTHER INFORMATION: 2'-F modified nucleoside
<220> FEATURE:

```
<221> NAME/KEY: misc_feature
<222> LOCATION: (16)..(16)
<223> OTHER INFORMATION: 2'-F modified nucleoside
<220> FEATURE:
<221> NAME/KEY: misc_feature
<222> LOCATION: (18)..(18)
<223> OTHER INFORMATION: 2'-F modified nucleoside
<220> FEATURE:
<221> NAME/KEY: misc_feature
<222> LOCATION: (20)..(20)
<223> OTHER INFORMATION: 2'-F modified nucleoside

<400> SEQUENCE: 31
uuugucucug guccuuacuu                                                  20

<210> SEQ ID NO 32
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphodiester linkages
<220> FEATURE:
<221> NAME/KEY: misc_feature
<222> LOCATION: (1)..(1)
<223> OTHER INFORMATION: 2'-F modified nucleoside
<220> FEATURE:
<221> NAME/KEY: misc_feature
<222> LOCATION: (3)..(3)
<223> OTHER INFORMATION: 2'-F modified nucleoside
<220> FEATURE:
<221> NAME/KEY: misc_feature
<222> LOCATION: (5)..(5)
<223> OTHER INFORMATION: 2'-F modified nucleoside
<220> FEATURE:
<221> NAME/KEY: misc_feature
<222> LOCATION: (7)..(7)
<223> OTHER INFORMATION: 2'-F modified nucleoside
<220> FEATURE:
<221> NAME/KEY: misc_feature
<222> LOCATION: (9)..(9)
<223> OTHER INFORMATION: 2'-F modified nucleoside
<220> FEATURE:
<221> NAME/KEY: misc_feature
<222> LOCATION: (11)..(11)
<223> OTHER INFORMATION: 2'-F modified nucleoside
<220> FEATURE:
<221> NAME/KEY: misc_feature
<222> LOCATION: (13)..(13)
<223> OTHER INFORMATION: 2'-F modified nucleoside
<220> FEATURE:
<221> NAME/KEY: misc_feature
<222> LOCATION: (15)..(15)
<223> OTHER INFORMATION: 2'-F modified nucleoside
<220> FEATURE:
<221> NAME/KEY: misc_feature
<222> LOCATION: (17)..(17)
<223> OTHER INFORMATION: 2'-F modified nucleoside
<220> FEATURE:
<221> NAME/KEY: misc_feature
<222> LOCATION: (19)..(19)
<223> OTHER INFORMATION: 2'-F modified nucleoside

<400> SEQUENCE: 32
uuugucucug guccuuacuu                                                  20

<210> SEQ ID NO 33
<211> LENGTH: 20
<212> TYPE: RNA
<213> ORGANISM: Artificial
<220> FEATURE:
<223> OTHER INFORMATION: Synthetic Construct
```

```
<220> FEATURE:
<221> NAME/KEY: misc_feature
<222> LOCATION: (1)..(20)
<223> OTHER INFORMATION: phosphorothioate linkages
<220> FEATURE:
<221> NAME/KEY: misc_feature
<222> LOCATION: (1)..(1)
<223> OTHER INFORMATION: 2'-F modified nucleoside
<220> FEATURE:
<221> NAME/KEY: misc_feature
<222> LOCATION: (3)..(3)
<223> OTHER INFORMATION: 2'-F modified nucleoside
<220> FEATURE:
<221> NAME/KEY: misc_feature
<222> LOCATION: (5)..(5)
<223> OTHER INFORMATION: 2'-F modified nucleoside
<220> FEATURE:
<221> NAME/KEY: misc_feature
<222> LOCATION: (7)..(7)
<223> OTHER INFORMATION: 2'-F modified nucleoside
<220> FEATURE:
<221> NAME/KEY: misc_feature
<222> LOCATION: (9)..(9)
<223> OTHER INFORMATION: 2'-F modified nucleoside
<220> FEATURE:
<221> NAME/KEY: misc_feature
<222> LOCATION: (11)..(11)
<223> OTHER INFORMATION: 2'-F modified nucleoside
<220> FEATURE:
<221> NAME/KEY: misc_feature
<222> LOCATION: (13)..(13)
<223> OTHER INFORMATION: 2'-F modified nucleoside
<220> FEATURE:
<221> NAME/KEY: misc_feature
<222> LOCATION: (15)..(15)
<223> OTHER INFORMATION: 2'-F modified nucleoside
<220> FEATURE:
<221> NAME/KEY: misc_feature
<222> LOCATION: (17)..(17)
<223> OTHER INFORMATION: 2'-F modified nucleoside
<220> FEATURE:
<221> NAME/KEY: misc_feature
<222> LOCATION: (19)..(19)
<223> OTHER INFORMATION: 2'-F modified nucleoside

<400> SEQUENCE: 33
uuugucucug guccuuacuu                                                    20

<210> SEQ ID NO 34
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphodiester linkages
<220> FEATURE:
<221> NAME/KEY: misc_feature
<222> LOCATION: (1)..(1)
<223> OTHER INFORMATION: 2'-F modified nucleoside
<220> FEATURE:
<221> NAME/KEY: misc_feature
<222> LOCATION: (3)..(3)
<223> OTHER INFORMATION: 2'-F modified nucleoside
<220> FEATURE:
<221> NAME/KEY: misc_feature
<222> LOCATION: (5)..(5)
<223> OTHER INFORMATION: 2'-F modified nucleoside
<220> FEATURE:
<221> NAME/KEY: misc_feature
<222> LOCATION: (7)..(7)
<223> OTHER INFORMATION: 2'-F modified nucleoside
<220> FEATURE:
<221> NAME/KEY: misc_feature
<222> LOCATION: (9)..(9)
```

```
<223> OTHER INFORMATION: 2'-F modified nucleoside
<220> FEATURE:
<221> NAME/KEY: misc_feature
<222> LOCATION: (11)..(11)
<223> OTHER INFORMATION: 2'-F modified nucleoside
<220> FEATURE:
<221> NAME/KEY: misc_feature
<222> LOCATION: (13)..(13)
<223> OTHER INFORMATION: 2'-F modified nucleoside
<220> FEATURE:
<221> NAME/KEY: misc_feature
<222> LOCATION: (15)..(15)
<223> OTHER INFORMATION: 2'-F modified nucleoside
<220> FEATURE:
<221> NAME/KEY: misc_feature
<222> LOCATION: (17)..(17)
<223> OTHER INFORMATION: 2'-F modified nucleoside
<220> FEATURE:
<221> NAME/KEY: misc_feature
<222> LOCATION: (19)..(19)
<223> OTHER INFORMATION: 2'-F modified nucleoside

<400> SEQUENCE: 34
aaguaaggac cagagacaaa                                              20

<210> SEQ ID NO 35
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphodiester linkages
<220> FEATURE:
<221> NAME/KEY: misc_feature
<222> LOCATION: (2)..(2)
<223> OTHER INFORMATION: 2'-F modified nucleoside
<220> FEATURE:
<221> NAME/KEY: misc_feature
<222> LOCATION: (4)..(4)
<223> OTHER INFORMATION: 2'-F modified nucleoside
<220> FEATURE:
<221> NAME/KEY: misc_feature
<222> LOCATION: (6)..(6)
<223> OTHER INFORMATION: 2'-F modified nucleoside
<220> FEATURE:
<221> NAME/KEY: misc_feature
<222> LOCATION: (8)..(8)
<223> OTHER INFORMATION: 2'-F modified nucleoside
<220> FEATURE:
<221> NAME/KEY: misc_feature
<222> LOCATION: (10)..(10)
<223> OTHER INFORMATION: 2'-F modified nucleoside
<220> FEATURE:
<221> NAME/KEY: misc_feature
<222> LOCATION: (12)..(12)
<223> OTHER INFORMATION: 2'-F modified nucleoside
<220> FEATURE:
<221> NAME/KEY: misc_feature
<222> LOCATION: (14)..(14)
<223> OTHER INFORMATION: 2'-F modified nucleoside
<220> FEATURE:
<221> NAME/KEY: misc_feature
<222> LOCATION: (16)..(16)
<223> OTHER INFORMATION: 2'-F modified nucleoside
<220> FEATURE:
<221> NAME/KEY: misc_feature
<222> LOCATION: (18)..(18)
<223> OTHER INFORMATION: 2'-F modified nucleoside
<220> FEATURE:
<221> NAME/KEY: misc_feature
<222> LOCATION: (20)..(20)
<223> OTHER INFORMATION: 2'-F modified nucleoside

<400> SEQUENCE: 35
```
aaguaaggac cagagacaaa                                             20

<210> SEQ ID NO 36
<211> LENGTH: 20
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphorothioate linkages
<220> FEATURE:
<221> NAME/KEY: misc_feature
<222> LOCATION: (1)..(1)
<223> OTHER INFORMATION: 2'-H
<220> FEATURE:
<221> NAME/KEY: misc_feature
<222> LOCATION: (2)..(2)
<223> OTHER INFORMATION: 2'-O-methoxyethyl
<220> FEATURE:
<221> NAME/KEY: misc_feature
<222> LOCATION: (3)..(3)
<223> OTHER INFORMATION: 2'-H
<220> FEATURE:
<221> NAME/KEY: misc_feature
<222> LOCATION: (4)..(4)
<223> OTHER INFORMATION: 2'-O-methoxyethyl
<220> FEATURE:
<221> NAME/KEY: misc_feature
<222> LOCATION: (5)..(5)
<223> OTHER INFORMATION: 2'-H
<220> FEATURE:
<221> NAME/KEY: misc_feature
<222> LOCATION: (6)..(6)
<223> OTHER INFORMATION: 5'-methyl cytidine
<220> FEATURE:
<221> NAME/KEY: misc_feature
<222> LOCATION: (6)..(6)
<223> OTHER INFORMATION: 2'-O-methoxyethyl
<220> FEATURE:
<221> NAME/KEY: misc_feature
<222> LOCATION: (7)..(7)
<223> OTHER INFORMATION: 2'-H
<220> FEATURE:
<221> NAME/KEY: misc_feature
<222> LOCATION: (8)..(8)
<223> OTHER INFORMATION: 5'-methyl cytidine
<220> FEATURE:
<221> NAME/KEY: misc_feature
<222> LOCATION: (8)..(8)
<223> OTHER INFORMATION: 2'-O-methoxyethyl
<220> FEATURE:
<221> NAME/KEY: misc_feature
<222> LOCATION: (9)..(9)
<223> OTHER INFORMATION: 2'-H
<220> FEATURE:
<221> NAME/KEY: misc_feature
<222> LOCATION: (10)..(10)
<223> OTHER INFORMATION: 2'-O-methoxyethyl
<220> FEATURE:
<221> NAME/KEY: misc_feature
<222> LOCATION: (11)..(11)
<223> OTHER INFORMATION: 2'-H
<220> FEATURE:
<221> NAME/KEY: misc_feature
<222> LOCATION: (12)..(12)
<223> OTHER INFORMATION: 2'-O-methoxyethyl
<220> FEATURE:
<221> NAME/KEY: misc_feature
<222> LOCATION: (13)..(14)
<223> OTHER INFORMATION: 5'-methyl cytidine
<220> FEATURE:
<221> NAME/KEY: misc_feature
<222> LOCATION: (13)..(13)
<223> OTHER INFORMATION: 2'-H
<220> FEATURE:

```
<221> NAME/KEY: misc_feature
<222> LOCATION: (14)..(14)
<223> OTHER INFORMATION: 2'-O-methoxyethyl
<220> FEATURE:
<221> NAME/KEY: misc_feature
<222> LOCATION: (15)..(15)
<223> OTHER INFORMATION: 2'-H
<220> FEATURE:
<221> NAME/KEY: misc_feature
<222> LOCATION: (16)..(16)
<223> OTHER INFORMATION: 2'-O-methoxyethyl
<220> FEATURE:
<221> NAME/KEY: misc_feature
<222> LOCATION: (17)..(17)
<223> OTHER INFORMATION: 2'-H
<220> FEATURE:
<221> NAME/KEY: misc_feature
<222> LOCATION: (18)..(18)
<223> OTHER INFORMATION: 5'-methyl cytidine
<220> FEATURE:
<221> NAME/KEY: misc_feature
<222> LOCATION: (18)..(18)
<223> OTHER INFORMATION: 2'-O-methoxyethyl
<220> FEATURE:
<221> NAME/KEY: misc_feature
<222> LOCATION: (19)..(19)
<223> OTHER INFORMATION: 2'-H
<220> FEATURE:
<221> NAME/KEY: misc_feature
<222> LOCATION: (20)..(20)
<223> OTHER INFORMATION: 2'-O-methoxyethyl

<400> SEQUENCE: 36
tttgtctctg gtccttactt                                               20

<210> SEQ ID NO 37
<211> LENGTH: 20
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphorothioate linkages
<220> FEATURE:
<221> NAME/KEY: misc_feature
<222> LOCATION: (1)..(1)
<223> OTHER INFORMATION: 2'-O-methoxyethyl
<220> FEATURE:
<221> NAME/KEY: misc_feature
<222> LOCATION: (2)..(2)
<223> OTHER INFORMATION: 2'-H
<220> FEATURE:
<221> NAME/KEY: misc_feature
<222> LOCATION: (3)..(3)
<223> OTHER INFORMATION: 2'-O-methoxyethyl
<220> FEATURE:
<221> NAME/KEY: misc_feature
<222> LOCATION: (4)..(4)
<223> OTHER INFORMATION: 2'-H
<220> FEATURE:
<221> NAME/KEY: misc_feature
<222> LOCATION: (5)..(5)
<223> OTHER INFORMATION: 2'-O-methoxyethyl
<220> FEATURE:
<221> NAME/KEY: misc_feature
<222> LOCATION: (6)..(6)
<223> OTHER INFORMATION: 5'-methyl cytidine
<220> FEATURE:
<221> NAME/KEY: misc_feature
<222> LOCATION: (6)..(6)
<223> OTHER INFORMATION: 2'-H
<220> FEATURE:
<221> NAME/KEY: misc_feature
<222> LOCATION: (7)..(7)
<223> OTHER INFORMATION: 2'-O-methoxyethyl
```

```
<220> FEATURE:
<221> NAME/KEY: misc_feature
<222> LOCATION: (8)..(8)
<223> OTHER INFORMATION: 5'-methyl cytidine
<220> FEATURE:
<221> NAME/KEY: misc_feature
<222> LOCATION: (8)..(8)
<223> OTHER INFORMATION: 2'-H
<220> FEATURE:
<221> NAME/KEY: misc_feature
<222> LOCATION: (9)..(9)
<223> OTHER INFORMATION: 2'-O-methoxyethyl
<220> FEATURE:
<221> NAME/KEY: misc_feature
<222> LOCATION: (10)..(10)
<223> OTHER INFORMATION: 2'-H
<220> FEATURE:
<221> NAME/KEY: misc_feature
<222> LOCATION: (11)..(11)
<223> OTHER INFORMATION: 2'-O-methoxyethyl
<220> FEATURE:
<221> NAME/KEY: misc_feature
<222> LOCATION: (12)..(12)
<223> OTHER INFORMATION: 2'-H
<220> FEATURE:
<221> NAME/KEY: misc_feature
<222> LOCATION: (13)..(14)
<223> OTHER INFORMATION: 5'-methyl cytidine
<220> FEATURE:
<221> NAME/KEY: misc_feature
<222> LOCATION: (13)..(13)
<223> OTHER INFORMATION: 2'-O-methoxyethyl
<220> FEATURE:
<221> NAME/KEY: misc_feature
<222> LOCATION: (14)..(14)
<223> OTHER INFORMATION: 2'-H
<220> FEATURE:
<221> NAME/KEY: misc_feature
<222> LOCATION: (15)..(15)
<223> OTHER INFORMATION: 2'-O-methoxyethyl
<220> FEATURE:
<221> NAME/KEY: misc_feature
<222> LOCATION: (16)..(16)
<223> OTHER INFORMATION: 2'-H
<220> FEATURE:
<221> NAME/KEY: misc_feature
<222> LOCATION: (17)..(17)
<223> OTHER INFORMATION: 2'-O-methoxyethyl
<220> FEATURE:
<221> NAME/KEY: misc_feature
<222> LOCATION: (18)..(18)
<223> OTHER INFORMATION: 5'-methyl cytidine
<220> FEATURE:
<221> NAME/KEY: misc_feature
<222> LOCATION: (18)..(18)
<223> OTHER INFORMATION: 2'-H
<220> FEATURE:
<221> NAME/KEY: misc_feature
<222> LOCATION: (19)..(19)
<223> OTHER INFORMATION: 2'-O-methoxyethyl
<220> FEATURE:
<221> NAME/KEY: misc_feature
<222> LOCATION: (20)..(20)
<223> OTHER INFORMATION: 2'-H

<400> SEQUENCE: 37
tttgtctctg gtccttactt                                               20

<210> SEQ ID NO 38
<211> LENGTH: 20
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
```

-continued

```
<223> OTHER INFORMATION: phosphodiester linkages
<220> FEATURE:
<221> NAME/KEY: misc_feature
<222> LOCATION: (1)..(1)
<223> OTHER INFORMATION: 2'-H
<220> FEATURE:
<221> NAME/KEY: misc_feature
<222> LOCATION: (2)..(2)
<223> OTHER INFORMATION: 2'-O-methoxyethyl
<220> FEATURE:
<221> NAME/KEY: misc_feature
<222> LOCATION: (3)..(3)
<223> OTHER INFORMATION: 2'-H
<220> FEATURE:
<221> NAME/KEY: misc_feature
<222> LOCATION: (4)..(4)
<223> OTHER INFORMATION: 2'-O-methoxyethyl
<220> FEATURE:
<221> NAME/KEY: misc_feature
<222> LOCATION: (5)..(5)
<223> OTHER INFORMATION: 2'-H
<220> FEATURE:
<221> NAME/KEY: misc_feature
<222> LOCATION: (6)..(6)
<223> OTHER INFORMATION: 5'-methyl cytidine
<220> FEATURE:
<221> NAME/KEY: misc_feature
<222> LOCATION: (6)..(6)
<223> OTHER INFORMATION: 2'-O-methoxyethyl
<220> FEATURE:
<221> NAME/KEY: misc_feature
<222> LOCATION: (7)..(7)
<223> OTHER INFORMATION: 2'-H
<220> FEATURE:
<221> NAME/KEY: misc_feature
<222> LOCATION: (8)..(8)
<223> OTHER INFORMATION: 5'-methyl cytidine
<220> FEATURE:
<221> NAME/KEY: misc_feature
<222> LOCATION: (8)..(8)
<223> OTHER INFORMATION: 2'-O-methoxyethyl
<220> FEATURE:
<221> NAME/KEY: misc_feature
<222> LOCATION: (9)..(9)
<223> OTHER INFORMATION: 2'-H
<220> FEATURE:
<221> NAME/KEY: misc_feature
<222> LOCATION: (10)..(10)
<223> OTHER INFORMATION: 2'-O-methoxyethyl
<220> FEATURE:
<221> NAME/KEY: misc_feature
<222> LOCATION: (11)..(11)
<223> OTHER INFORMATION: 2'-H
<220> FEATURE:
<221> NAME/KEY: misc_feature
<222> LOCATION: (12)..(12)
<223> OTHER INFORMATION: 2'-O-methoxyethyl
<220> FEATURE:
<221> NAME/KEY: misc_feature
<222> LOCATION: (13)..(14)
<223> OTHER INFORMATION: 5'-methyl cytidine
<220> FEATURE:
<221> NAME/KEY: misc_feature
<222> LOCATION: (13)..(13)
<223> OTHER INFORMATION: 2'-H
<220> FEATURE:
<221> NAME/KEY: misc_feature
<222> LOCATION: (14)..(14)
<223> OTHER INFORMATION: 2'-O-methoxyethyl
<220> FEATURE:
<221> NAME/KEY: misc_feature
<222> LOCATION: (15)..(15)
<223> OTHER INFORMATION: 2'-H
<220> FEATURE:
<221> NAME/KEY: misc_feature
<222> LOCATION: (16)..(16)
<223> OTHER INFORMATION: 2'-O-methoxyethyl
<220> FEATURE:
<221> NAME/KEY: misc_feature
```

```
<222> LOCATION: (17)..(17)
<223> OTHER INFORMATION: 2'-H
<220> FEATURE:
<221> NAME/KEY: misc_feature
<222> LOCATION: (18)..(18)
<223> OTHER INFORMATION: 5'-methyl cytidine
<220> FEATURE:
<221> NAME/KEY: misc_feature
<222> LOCATION: (18)..(18)
<223> OTHER INFORMATION: 2'-O-methoxyethyl
<220> FEATURE:
<221> NAME/KEY: misc_feature
<222> LOCATION: (19)..(19)
<223> OTHER INFORMATION: 2'-H
<220> FEATURE:
<221> NAME/KEY: misc_feature
<222> LOCATION: (20)..(20)
<223> OTHER INFORMATION: 2'-O-methoxyethyl

<400> SEQUENCE: 38
tttgtctctg gtccttactt                                                   20

<210> SEQ ID NO 39
<211> LENGTH: 20
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphodiester linkages
<220> FEATURE:
<221> NAME/KEY: misc_feature
<222> LOCATION: (1)..(1)
<223> OTHER INFORMATION: 2'-O-methoxyethyl
<220> FEATURE:
<221> NAME/KEY: misc_feature
<222> LOCATION: (2)..(2)
<223> OTHER INFORMATION: 2'-H
<220> FEATURE:
<221> NAME/KEY: misc_feature
<222> LOCATION: (3)..(3)
<223> OTHER INFORMATION: 2'-O-methoxyethyl
<220> FEATURE:
<221> NAME/KEY: misc_feature
<222> LOCATION: (4)..(4)
<223> OTHER INFORMATION: 2'-H
<220> FEATURE:
<221> NAME/KEY: misc_feature
<222> LOCATION: (5)..(5)
<223> OTHER INFORMATION: 2'-O-methoxyethyl
<220> FEATURE:
<221> NAME/KEY: misc_feature
<222> LOCATION: (6)..(6)
<223> OTHER INFORMATION: 5'-methyl cytidine
<220> FEATURE:
<221> NAME/KEY: misc_feature
<222> LOCATION: (6)..(6)
<223> OTHER INFORMATION: 2'-H
<220> FEATURE:
<221> NAME/KEY: misc_feature
<222> LOCATION: (7)..(7)
<223> OTHER INFORMATION: 2'-O-methoxyethyl
<220> FEATURE:
<221> NAME/KEY: misc_feature
<222> LOCATION: (8)..(8)
<223> OTHER INFORMATION: 5'-methyl cytidine
<220> FEATURE:
<221> NAME/KEY: misc_feature
<222> LOCATION: (8)..(8)
<223> OTHER INFORMATION: 2'-H
<220> FEATURE:
<221> NAME/KEY: misc_feature
<222> LOCATION: (9)..(9)
<223> OTHER INFORMATION: 2'-O-methoxyethyl
<220> FEATURE:
```

```
<221> NAME/KEY: misc_feature
<222> LOCATION: (10)..(10)
<223> OTHER INFORMATION: 2'-H
<220> FEATURE:
<221> NAME/KEY: misc_feature
<222> LOCATION: (11)..(11)
<223> OTHER INFORMATION: 2'-O-methoxyethyl
<220> FEATURE:
<221> NAME/KEY: misc_feature
<222> LOCATION: (12)..(12)
<223> OTHER INFORMATION: 2'-H
<220> FEATURE:
<221> NAME/KEY: misc_feature
<222> LOCATION: (13)..(14)
<223> OTHER INFORMATION: 5'-methyl cytidine
<220> FEATURE:
<221> NAME/KEY: misc_feature
<222> LOCATION: (13)..(13)
<223> OTHER INFORMATION: 2'-O-methoxyethyl
<220> FEATURE:
<221> NAME/KEY: misc_feature
<222> LOCATION: (14)..(14)
<223> OTHER INFORMATION: 2'-H
<220> FEATURE:
<221> NAME/KEY: misc_feature
<222> LOCATION: (15)..(15)
<223> OTHER INFORMATION: 2'-O-methoxyethyl
<220> FEATURE:
<221> NAME/KEY: misc_feature
<222> LOCATION: (16)..(16)
<223> OTHER INFORMATION: 2'-H
<220> FEATURE:
<221> NAME/KEY: misc_feature
<222> LOCATION: (17)..(17)
<223> OTHER INFORMATION: 2'-O-methoxyethyl
<220> FEATURE:
<221> NAME/KEY: misc_feature
<222> LOCATION: (18)..(18)
<223> OTHER INFORMATION: 5'-methyl cytidine
<220> FEATURE:
<221> NAME/KEY: misc_feature
<222> LOCATION: (18)..(18)
<223> OTHER INFORMATION: 2'-H
<220> FEATURE:
<221> NAME/KEY: misc_feature
<222> LOCATION: (19)..(19)
<223> OTHER INFORMATION: 2'-O-methoxyethyl
<220> FEATURE:
<221> NAME/KEY: misc_feature
<222> LOCATION: (20)..(20)
<223> OTHER INFORMATION: 2'-H

<400> SEQUENCE: 39
tttgtctctg gtccttactt                                              20

<210> SEQ ID NO 40
<211> LENGTH: 20
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphorothioate linkages
<220> FEATURE:
<221> NAME/KEY: misc_feature
<222> LOCATION: (1)..(1)
<223> OTHER INFORMATION: 2'-H
<220> FEATURE:
<221> NAME/KEY: misc_feature
<222> LOCATION: (2)..(2)
<223> OTHER INFORMATION: 2'-O-methoxyethyl
<220> FEATURE:
<221> NAME/KEY: misc_feature
<222> LOCATION: (3)..(3)
<223> OTHER INFORMATION: 2'-H
```

-continued

```
<220> FEATURE:
<221> NAME/KEY: misc_feature
<222> LOCATION: (4)..(4)
<223> OTHER INFORMATION: 2'-O-methoxyethyl
<220> FEATURE:
<221> NAME/KEY: misc_feature
<222> LOCATION: (5)..(5)
<223> OTHER INFORMATION: 2'-H
<220> FEATURE:
<221> NAME/KEY: misc_feature
<222> LOCATION: (6)..(6)
<223> OTHER INFORMATION: 5'-methyl cytidine
<220> FEATURE:
<221> NAME/KEY: misc_feature
<222> LOCATION: (6)..(6)
<223> OTHER INFORMATION: 2'-O-methoxyethyl
<220> FEATURE:
<221> NAME/KEY: misc_feature
<222> LOCATION: (7)..(7)
<223> OTHER INFORMATION: 2'-H
<220> FEATURE:
<221> NAME/KEY: misc_feature
<222> LOCATION: (8)..(8)
<223> OTHER INFORMATION: 5'-methyl cytidine
<220> FEATURE:
<221> NAME/KEY: misc_feature
<222> LOCATION: (8)..(8)
<223> OTHER INFORMATION: 2'-O-methoxyethyl
<220> FEATURE:
<221> NAME/KEY: misc_feature
<222> LOCATION: (9)..(9)
<223> OTHER INFORMATION: 2'-H
<220> FEATURE:
<221> NAME/KEY: misc_feature
<222> LOCATION: (10)..(10)
<223> OTHER INFORMATION: 2'-O-methoxyethyl
<220> FEATURE:
<221> NAME/KEY: misc_feature
<222> LOCATION: (11)..(11)
<223> OTHER INFORMATION: 2'-H
<220> FEATURE:
<221> NAME/KEY: misc_feature
<222> LOCATION: (12)..(12)
<223> OTHER INFORMATION: 2'-O-methoxyethyl
<220> FEATURE:
<221> NAME/KEY: misc_feature
<222> LOCATION: (13)..(14)
<223> OTHER INFORMATION: 5'-methyl cytidine
<220> FEATURE:
<221> NAME/KEY: misc_feature
<222> LOCATION: (13)..(13)
<223> OTHER INFORMATION: 2'-H
<220> FEATURE:
<221> NAME/KEY: misc_feature
<222> LOCATION: (14)..(14)
<223> OTHER INFORMATION: 2'-O-methoxyethyl
<220> FEATURE:
<221> NAME/KEY: misc_feature
<222> LOCATION: (15)..(15)
<223> OTHER INFORMATION: 2'-H
<220> FEATURE:
<221> NAME/KEY: misc_feature
<222> LOCATION: (16)..(16)
<223> OTHER INFORMATION: 2'-O-methoxyethyl
<220> FEATURE:
<221> NAME/KEY: misc_feature
<222> LOCATION: (17)..(17)
<223> OTHER INFORMATION: 2'-H
<220> FEATURE:
<221> NAME/KEY: misc_feature
<222> LOCATION: (18)..(18)
<223> OTHER INFORMATION: 5'-methyl cytidine
<220> FEATURE:
<221> NAME/KEY: misc_feature
<222> LOCATION: (18)..(18)
<223> OTHER INFORMATION: 2'-O-methoxyethyl
<220> FEATURE:
<221> NAME/KEY: misc_feature
<222> LOCATION: (19)..(19)
```

```
<223> OTHER INFORMATION: 2'-H
<220> FEATURE:
<221> NAME/KEY: misc_feature
<222> LOCATION: (20)..(20)
<223> OTHER INFORMATION: 2'-O-methoxyethyl

<400> SEQUENCE: 40
utugucucug gtccutacut                                              20

<210> SEQ ID NO 41
<211> LENGTH: 20
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphorothioate linkages
<220> FEATURE:
<221> NAME/KEY: misc_feature
<222> LOCATION: (1)..(1)
<223> OTHER INFORMATION: 2'-O-methoxyethyl
<220> FEATURE:
<221> NAME/KEY: misc_feature
<222> LOCATION: (2)..(2)
<223> OTHER INFORMATION: 2'-H
<220> FEATURE:
<221> NAME/KEY: misc_feature
<222> LOCATION: (3)..(3)
<223> OTHER INFORMATION: 2'-O-methoxyethyl
<220> FEATURE:
<221> NAME/KEY: misc_feature
<222> LOCATION: (4)..(4)
<223> OTHER INFORMATION: 2'-H
<220> FEATURE:
<221> NAME/KEY: misc_feature
<222> LOCATION: (5)..(5)
<223> OTHER INFORMATION: 2'-O-methoxyethyl
<220> FEATURE:
<221> NAME/KEY: misc_feature
<222> LOCATION: (6)..(6)
<223> OTHER INFORMATION: 5'-methyl cytidine
<220> FEATURE:
<221> NAME/KEY: misc_feature
<222> LOCATION: (6)..(6)
<223> OTHER INFORMATION: 2'-H
<220> FEATURE:
<221> NAME/KEY: misc_feature
<222> LOCATION: (7)..(7)
<223> OTHER INFORMATION: 2'-O-methoxyethyl
<220> FEATURE:
<221> NAME/KEY: misc_feature
<222> LOCATION: (8)..(8)
<223> OTHER INFORMATION: 5'-methyl cytidine
<220> FEATURE:
<221> NAME/KEY: misc_feature
<222> LOCATION: (8)..(8)
<223> OTHER INFORMATION: 2'-H
<220> FEATURE:
<221> NAME/KEY: misc_feature
<222> LOCATION: (9)..(9)
<223> OTHER INFORMATION: 2'-O-methoxyethyl
<220> FEATURE:
<221> NAME/KEY: misc_feature
<222> LOCATION: (10)..(10)
<223> OTHER INFORMATION: 2'-H
<220> FEATURE:
<221> NAME/KEY: misc_feature
<222> LOCATION: (11)..(11)
<223> OTHER INFORMATION: 2'-O-methoxyethyl
<220> FEATURE:
<221> NAME/KEY: misc_feature
<222> LOCATION: (12)..(12)
<223> OTHER INFORMATION: 2'-H
<220> FEATURE:
<221> NAME/KEY: misc_feature
```

```
<222> LOCATION: (13)..(14)
<223> OTHER INFORMATION: 5'-methyl cytidine
<220> FEATURE:
<221> NAME/KEY: misc_feature
<222> LOCATION: (13)..(13)
<223> OTHER INFORMATION: 2'-O-methoxyethyl
<220> FEATURE:
<221> NAME/KEY: misc_feature
<222> LOCATION: (14)..(14)
<223> OTHER INFORMATION: 2'-H
<220> FEATURE:
<221> NAME/KEY: misc_feature
<222> LOCATION: (15)..(15)
<223> OTHER INFORMATION: 2'-O-methoxyethyl
<220> FEATURE:
<221> NAME/KEY: misc_feature
<222> LOCATION: (16)..(16)
<223> OTHER INFORMATION: 2'-H
<220> FEATURE:
<221> NAME/KEY: misc_feature
<222> LOCATION: (17)..(17)
<223> OTHER INFORMATION: 2'-O-methoxyethyl
<220> FEATURE:
<221> NAME/KEY: misc_feature
<222> LOCATION: (18)..(18)
<223> OTHER INFORMATION: 5'-methyl cytidine
<220> FEATURE:
<221> NAME/KEY: misc_feature
<222> LOCATION: (18)..(18)
<223> OTHER INFORMATION: 2'-H
<220> FEATURE:
<221> NAME/KEY: misc_feature
<222> LOCATION: (19)..(19)
<223> OTHER INFORMATION: 2'-O-methoxyethyl
<220> FEATURE:
<221> NAME/KEY: misc_feature
<222> LOCATION: (20)..(20)
<223> OTHER INFORMATION: 2'-H

<400> SEQUENCE: 41
tutgtctctg gucctuactu                                          20

<210> SEQ ID NO 42
<211> LENGTH: 20
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphodiester linkages
<220> FEATURE:
<221> NAME/KEY: misc_feature
<222> LOCATION: (1)..(1)
<223> OTHER INFORMATION: 2'-H
<220> FEATURE:
<221> NAME/KEY: misc_feature
<222> LOCATION: (2)..(2)
<223> OTHER INFORMATION: 2'-O-methoxyethyl
<220> FEATURE:
<221> NAME/KEY: misc_feature
<222> LOCATION: (3)..(3)
<223> OTHER INFORMATION: 2'-H
<220> FEATURE:
<221> NAME/KEY: misc_feature
<222> LOCATION: (4)..(4)
<223> OTHER INFORMATION: 2'-O-methoxyethyl
<220> FEATURE:
<221> NAME/KEY: misc_feature
<222> LOCATION: (5)..(5)
<223> OTHER INFORMATION: 2'-H
<220> FEATURE:
<221> NAME/KEY: misc_feature
<222> LOCATION: (6)..(6)
<223> OTHER INFORMATION: 5'-methyl cytidine
<220> FEATURE:
```

```
<221> NAME/KEY: misc_feature
<222> LOCATION: (6)..(6)
<223> OTHER INFORMATION: 2'-O-methoxyethyl
<220> FEATURE:
<221> NAME/KEY: misc_feature
<222> LOCATION: (7)..(7)
<223> OTHER INFORMATION: 2'-H
<220> FEATURE:
<221> NAME/KEY: misc_feature
<222> LOCATION: (8)..(8)
<223> OTHER INFORMATION: 5'-methyl cytidine
<220> FEATURE:
<221> NAME/KEY: misc_feature
<222> LOCATION: (8)..(8)
<223> OTHER INFORMATION: 2'-O-methoxyethyl
<220> FEATURE:
<221> NAME/KEY: misc_feature
<222> LOCATION: (9)..(9)
<223> OTHER INFORMATION: 2'-H
<220> FEATURE:
<221> NAME/KEY: misc_feature
<222> LOCATION: (10)..(10)
<223> OTHER INFORMATION: 2'-O-methoxyethyl
<220> FEATURE:
<221> NAME/KEY: misc_feature
<222> LOCATION: (11)..(11)
<223> OTHER INFORMATION: 2'-H
<220> FEATURE:
<221> NAME/KEY: misc_feature
<222> LOCATION: (12)..(12)
<223> OTHER INFORMATION: 2'-O-methoxyethyl
<220> FEATURE:
<221> NAME/KEY: misc_feature
<222> LOCATION: (13)..(14)
<223> OTHER INFORMATION: 5'-methyl cytidine
<220> FEATURE:
<221> NAME/KEY: misc_feature
<222> LOCATION: (13)..(13)
<223> OTHER INFORMATION: 2'-H
<220> FEATURE:
<221> NAME/KEY: misc_feature
<222> LOCATION: (14)..(14)
<223> OTHER INFORMATION: 2'-O-methoxyethyl
<220> FEATURE:
<221> NAME/KEY: misc_feature
<222> LOCATION: (15)..(15)
<223> OTHER INFORMATION: 2'-H
<220> FEATURE:
<221> NAME/KEY: misc_feature
<222> LOCATION: (16)..(16)
<223> OTHER INFORMATION: 2'-O-methoxyethyl
<220> FEATURE:
<221> NAME/KEY: misc_feature
<222> LOCATION: (17)..(17)
<223> OTHER INFORMATION: 2'-H
<220> FEATURE:
<221> NAME/KEY: misc_feature
<222> LOCATION: (18)..(18)
<223> OTHER INFORMATION: 5'-methyl cytidine
<220> FEATURE:
<221> NAME/KEY: misc_feature
<222> LOCATION: (18)..(18)
<223> OTHER INFORMATION: 2'-O-methoxyethyl
<220> FEATURE:
<221> NAME/KEY: misc_feature
<222> LOCATION: (19)..(19)
<223> OTHER INFORMATION: 2'-H
<220> FEATURE:
<221> NAME/KEY: misc_feature
<222> LOCATION: (20)..(20)
<223> OTHER INFORMATION: 2'-O-methoxyethyl

<400> SEQUENCE: 42
utugucucug gtccutacut                                              20

<210> SEQ ID NO 43
<211> LENGTH: 20
```

```
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphodiester linkages
<220> FEATURE:
<221> NAME/KEY: misc_feature
<222> LOCATION: (1)..(1)
<223> OTHER INFORMATION: 2'-O-methoxyethyl
<220> FEATURE:
<221> NAME/KEY: misc_feature
<222> LOCATION: (2)..(2)
<223> OTHER INFORMATION: 2'-H
<220> FEATURE:
<221> NAME/KEY: misc_feature
<222> LOCATION: (3)..(3)
<223> OTHER INFORMATION: 2'-O-methoxyethyl
<220> FEATURE:
<221> NAME/KEY: misc_feature
<222> LOCATION: (4)..(4)
<223> OTHER INFORMATION: 2'-H
<220> FEATURE:
<221> NAME/KEY: misc_feature
<222> LOCATION: (5)..(5)
<223> OTHER INFORMATION: 2'-O-methoxyethyl
<220> FEATURE:
<221> NAME/KEY: misc_feature
<222> LOCATION: (6)..(6)
<223> OTHER INFORMATION: 5'-methyl cytidine
<220> FEATURE:
<221> NAME/KEY: misc_feature
<222> LOCATION: (6)..(6)
<223> OTHER INFORMATION: 2'-H
<220> FEATURE:
<221> NAME/KEY: misc_feature
<222> LOCATION: (7)..(7)
<223> OTHER INFORMATION: 2'-O-methoxyethyl
<220> FEATURE:
<221> NAME/KEY: misc_feature
<222> LOCATION: (8)..(8)
<223> OTHER INFORMATION: 5'-methyl cytidine
<220> FEATURE:
<221> NAME/KEY: misc_feature
<222> LOCATION: (8)..(8)
<223> OTHER INFORMATION: 2'-H
<220> FEATURE:
<221> NAME/KEY: misc_feature
<222> LOCATION: (9)..(9)
<223> OTHER INFORMATION: 2'-O-methoxyethyl
<220> FEATURE:
<221> NAME/KEY: misc_feature
<222> LOCATION: (10)..(10)
<223> OTHER INFORMATION: 2'-H
<220> FEATURE:
<221> NAME/KEY: misc_feature
<222> LOCATION: (11)..(11)
<223> OTHER INFORMATION: 2'-O-methoxyethyl
<220> FEATURE:
<221> NAME/KEY: misc_feature
<222> LOCATION: (12)..(12)
<223> OTHER INFORMATION: 2'-H
<220> FEATURE:
<221> NAME/KEY: misc_feature
<222> LOCATION: (13)..(14)
<223> OTHER INFORMATION: 5'-methyl cytidine
<220> FEATURE:
<221> NAME/KEY: misc_feature
<222> LOCATION: (13)..(13)
<223> OTHER INFORMATION: 2'-O-methoxyethyl
<220> FEATURE:
<221> NAME/KEY: misc_feature
<222> LOCATION: (14)..(14)
<223> OTHER INFORMATION: 2'-H
<220> FEATURE:
<221> NAME/KEY: misc_feature
<222> LOCATION: (15)..(15)
```

```
<223> OTHER INFORMATION: 2'-O-methoxyethyl
<220> FEATURE:
<221> NAME/KEY: misc_feature
<222> LOCATION: (16)..(16)
<223> OTHER INFORMATION: 2'-H
<220> FEATURE:
<221> NAME/KEY: misc_feature
<222> LOCATION: (17)..(17)
<223> OTHER INFORMATION: 2'-O-methoxyethyl
<220> FEATURE:
<221> NAME/KEY: misc_feature
<222> LOCATION: (18)..(18)
<223> OTHER INFORMATION: 5'-methyl cytidine
<220> FEATURE:
<221> NAME/KEY: misc_feature
<222> LOCATION: (18)..(18)
<223> OTHER INFORMATION: 2'-H
<220> FEATURE:
<221> NAME/KEY: misc_feature
<222> LOCATION: (19)..(19)
<223> OTHER INFORMATION: 2'-O-methoxyethyl
<220> FEATURE:
<221> NAME/KEY: misc_feature
<222> LOCATION: (20)..(20)
<223> OTHER INFORMATION: 2'-H

<400> SEQUENCE: 43
tutgtctctg gucctuactu                                                     20

<210> SEQ ID NO 44
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphodiester linkages
<220> FEATURE:
<221> NAME/KEY: misc_feature
<222> LOCATION: (1)..(1)
<223> OTHER INFORMATION: 2'-OH
<220> FEATURE:
<221> NAME/KEY: misc_feature
<222> LOCATION: (2)..(2)
<223> OTHER INFORMATION: 2'-O-methoxyethyl
<220> FEATURE:
<221> NAME/KEY: misc_feature
<222> LOCATION: (3)..(3)
<223> OTHER INFORMATION: 2'-OH
<220> FEATURE:
<221> NAME/KEY: misc_feature
<222> LOCATION: (4)..(4)
<223> OTHER INFORMATION: 2'-O-methoxyethyl
<220> FEATURE:
<221> NAME/KEY: misc_feature
<222> LOCATION: (5)..(5)
<223> OTHER INFORMATION: 2'-OH
<220> FEATURE:
<221> NAME/KEY: misc_feature
<222> LOCATION: (6)..(6)
<223> OTHER INFORMATION: 2'-O-methoxyethyl
<220> FEATURE:
<221> NAME/KEY: misc_feature
<222> LOCATION: (7)..(7)
<223> OTHER INFORMATION: 2'-OH
<220> FEATURE:
<221> NAME/KEY: misc_feature
<222> LOCATION: (8)..(8)
<223> OTHER INFORMATION: 2'-O-methoxyethyl
<220> FEATURE:
<221> NAME/KEY: misc_feature
<222> LOCATION: (9)..(9)
<223> OTHER INFORMATION: 2'-OH
<220> FEATURE:
<221> NAME/KEY: misc_feature
```

```
<222> LOCATION: (10)..(10)
<223> OTHER INFORMATION: 2'-O-methoxyethyl
<220> FEATURE:
<221> NAME/KEY: misc_feature
<222> LOCATION: (10)..(11)
<223> OTHER INFORMATION: 5'-methyl cytidine
<220> FEATURE:
<221> NAME/KEY: misc_feature
<222> LOCATION: (11)..(11)
<223> OTHER INFORMATION: 2'-OH
<220> FEATURE:
<221> NAME/KEY: misc_feature
<222> LOCATION: (12)..(12)
<223> OTHER INFORMATION: 2'-O-methoxyethyl
<220> FEATURE:
<221> NAME/KEY: misc_feature
<222> LOCATION: (13)..(13)
<223> OTHER INFORMATION: 2'-OH
<220> FEATURE:
<221> NAME/KEY: misc_feature
<222> LOCATION: (14)..(14)
<223> OTHER INFORMATION: 2'-O-methoxyethyl
<220> FEATURE:
<221> NAME/KEY: misc_feature
<222> LOCATION: (15)..(15)
<223> OTHER INFORMATION: 2'-OH
<220> FEATURE:
<221> NAME/KEY: misc_feature
<222> LOCATION: (16)..(16)
<223> OTHER INFORMATION: 2'-O-methoxyethyl
<220> FEATURE:
<221> NAME/KEY: misc_feature
<222> LOCATION: (17)..(17)
<223> OTHER INFORMATION: 2'-OH
<220> FEATURE:
<221> NAME/KEY: misc_feature
<222> LOCATION: (17)..(17)
<223> OTHER INFORMATION: 5'-methyl cytidine
<220> FEATURE:
<221> NAME/KEY: misc_feature
<222> LOCATION: (18)..(18)
<223> OTHER INFORMATION: 2'-O-methoxyethyl
<220> FEATURE:
<221> NAME/KEY: misc_feature
<222> LOCATION: (19)..(19)
<223> OTHER INFORMATION: 2'-OH
<220> FEATURE:
<221> NAME/KEY: misc_feature
<222> LOCATION: (20)..(20)
<223> OTHER INFORMATION: 2'-O-methoxyethyl

<400> SEQUENCE: 44
aaguaaggac cagagacaaa                                            20

<210> SEQ ID NO 45
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphodiester linkages
<220> FEATURE:
<221> NAME/KEY: misc_feature
<222> LOCATION: (1)..(1)
<223> OTHER INFORMATION: 2'-O-methoxyethyl
<220> FEATURE:
<221> NAME/KEY: misc_feature
<222> LOCATION: (2)..(2)
<223> OTHER INFORMATION: 2'-OH
<220> FEATURE:
<221> NAME/KEY: misc_feature
<222> LOCATION: (3)..(3)
<223> OTHER INFORMATION: 2'-O-methoxyethyl
<220> FEATURE:
```

```
<221> NAME/KEY: misc_feature
<222> LOCATION: (4)..(4)
<223> OTHER INFORMATION: 2'-OH
<220> FEATURE:
<221> NAME/KEY: misc_feature
<222> LOCATION: (5)..(5)
<223> OTHER INFORMATION: 2'-O-methoxyethyl
<220> FEATURE:
<221> NAME/KEY: misc_feature
<222> LOCATION: (6)..(6)
<223> OTHER INFORMATION: 2'-OH
<220> FEATURE:
<221> NAME/KEY: misc_feature
<222> LOCATION: (7)..(7)
<223> OTHER INFORMATION: 2'-O-methoxyethyl
<220> FEATURE:
<221> NAME/KEY: misc_feature
<222> LOCATION: (8)..(8)
<223> OTHER INFORMATION: 2'-OH
<220> FEATURE:
<221> NAME/KEY: misc_feature
<222> LOCATION: (9)..(9)
<223> OTHER INFORMATION: 2'-O-methoxyethyl
<220> FEATURE:
<221> NAME/KEY: misc_feature
<222> LOCATION: (10)..(10)
<223> OTHER INFORMATION: 2'-OH
<220> FEATURE:
<221> NAME/KEY: misc_feature
<222> LOCATION: (10)..(11)
<223> OTHER INFORMATION: 5'-methyl cytidine
<220> FEATURE:
<221> NAME/KEY: misc_feature
<222> LOCATION: (11)..(11)
<223> OTHER INFORMATION: 2'-O-methoxyethyl
<220> FEATURE:
<221> NAME/KEY: misc_feature
<222> LOCATION: (12)..(12)
<223> OTHER INFORMATION: 2'-OH
<220> FEATURE:
<221> NAME/KEY: misc_feature
<222> LOCATION: (13)..(13)
<223> OTHER INFORMATION: 2'-O-methoxyethyl
<220> FEATURE:
<221> NAME/KEY: misc_feature
<222> LOCATION: (14)..(14)
<223> OTHER INFORMATION: 2'-OH
<220> FEATURE:
<221> NAME/KEY: misc_feature
<222> LOCATION: (15)..(15)
<223> OTHER INFORMATION: 2'-O-methoxyethyl
<220> FEATURE:
<221> NAME/KEY: misc_feature
<222> LOCATION: (16)..(16)
<223> OTHER INFORMATION: 2'-OH
<220> FEATURE:
<221> NAME/KEY: misc_feature
<222> LOCATION: (17)..(17)
<223> OTHER INFORMATION: 2'-O-methoxyethyl
<220> FEATURE:
<221> NAME/KEY: misc_feature
<222> LOCATION: (17)..(17)
<223> OTHER INFORMATION: 5'-methyl cytidine
<220> FEATURE:
<221> NAME/KEY: misc_feature
<222> LOCATION: (18)..(18)
<223> OTHER INFORMATION: 2'-OH
<220> FEATURE:
<221> NAME/KEY: misc_feature
<222> LOCATION: (19)..(19)
<223> OTHER INFORMATION: 2'-O-methoxyethyl
<220> FEATURE:
<221> NAME/KEY: misc_feature
<222> LOCATION: (20)..(20)
<223> OTHER INFORMATION: 2'-OH

<400> SEQUENCE: 45
aaguaaggac cagagacaaa                                           20
```

```
<210> SEQ ID NO 46
<211> LENGTH: 20
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphorothioate linkages
<220> FEATURE:
<221> NAME/KEY: misc_feature
<222> LOCATION: (1)..(1)
<223> OTHER INFORMATION: 2'-OH
<220> FEATURE:
<221> NAME/KEY: misc_feature
<222> LOCATION: (2)..(2)
<223> OTHER INFORMATION: 2'-O-methoxyethyl
<220> FEATURE:
<221> NAME/KEY: misc_feature
<222> LOCATION: (3)..(3)
<223> OTHER INFORMATION: 2'-OH
<220> FEATURE:
<221> NAME/KEY: misc_feature
<222> LOCATION: (4)..(4)
<223> OTHER INFORMATION: 2'-O-methoxyethyl
<220> FEATURE:
<221> NAME/KEY: misc_feature
<222> LOCATION: (5)..(5)
<223> OTHER INFORMATION: 2'-OH
<220> FEATURE:
<221> NAME/KEY: misc_feature
<222> LOCATION: (6)..(6)
<223> OTHER INFORMATION: 5'-methyl cytidine
<220> FEATURE:
<221> NAME/KEY: misc_feature
<222> LOCATION: (6)..(6)
<223> OTHER INFORMATION: 2'-O-methoxyethyl
<220> FEATURE:
<221> NAME/KEY: misc_feature
<222> LOCATION: (7)..(7)
<223> OTHER INFORMATION: 2'-OH
<220> FEATURE:
<221> NAME/KEY: misc_feature
<222> LOCATION: (8)..(8)
<223> OTHER INFORMATION: 5'-methyl cytidine
<220> FEATURE:
<221> NAME/KEY: misc_feature
<222> LOCATION: (8)..(8)
<223> OTHER INFORMATION: 2'-O-methoxyethyl
<220> FEATURE:
<221> NAME/KEY: misc_feature
<222> LOCATION: (9)..(9)
<223> OTHER INFORMATION: 2'-OH
<220> FEATURE:
<221> NAME/KEY: misc_feature
<222> LOCATION: (10)..(10)
<223> OTHER INFORMATION: 2'-O-methoxyethyl
<220> FEATURE:
<221> NAME/KEY: misc_feature
<222> LOCATION: (11)..(11)
<223> OTHER INFORMATION: 2'-OH
<220> FEATURE:
<221> NAME/KEY: misc_feature
<222> LOCATION: (12)..(12)
<223> OTHER INFORMATION: 2'-O-methoxyethyl
<220> FEATURE:
<221> NAME/KEY: misc_feature
<222> LOCATION: (13)..(14)
<223> OTHER INFORMATION: 5'-methyl cytidine
<220> FEATURE:
<221> NAME/KEY: misc_feature
<222> LOCATION: (13)..(13)
<223> OTHER INFORMATION: 2'-OH
<220> FEATURE:
<221> NAME/KEY: misc_feature
<222> LOCATION: (14)..(14)
```

```
<223> OTHER INFORMATION: 2'-O-methoxyethyl
<220> FEATURE:
<221> NAME/KEY: misc_feature
<222> LOCATION: (15)..(15)
<223> OTHER INFORMATION: 2'-OH
<220> FEATURE:
<221> NAME/KEY: misc_feature
<222> LOCATION: (16)..(16)
<223> OTHER INFORMATION: 2'-O-methoxyethyl
<220> FEATURE:
<221> NAME/KEY: misc_feature
<222> LOCATION: (17)..(17)
<223> OTHER INFORMATION: 2'-OH
<220> FEATURE:
<221> NAME/KEY: misc_feature
<222> LOCATION: (18)..(18)
<223> OTHER INFORMATION: 5'-methyl cytidine
<220> FEATURE:
<221> NAME/KEY: misc_feature
<222> LOCATION: (18)..(18)
<223> OTHER INFORMATION: 2'-O-methoxyethyl
<220> FEATURE:
<221> NAME/KEY: misc_feature
<222> LOCATION: (19)..(19)
<223> OTHER INFORMATION: 2'-H
<220> FEATURE:
<221> NAME/KEY: misc_feature
<222> LOCATION: (19)..(19)
<223> OTHER INFORMATION: 2'-OH
<220> FEATURE:
<221> NAME/KEY: misc_feature
<222> LOCATION: (20)..(20)
<223> OTHER INFORMATION: 2'-O-methoxyethyl

<400> SEQUENCE: 46
utugucucug gtccutacut                                              20

<210> SEQ ID NO 47
<211> LENGTH: 20
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphorothioate linkages
<220> FEATURE:
<221> NAME/KEY: misc_feature
<222> LOCATION: (1)..(1)
<223> OTHER INFORMATION: 2'-O-methoxyethyl
<220> FEATURE:
<221> NAME/KEY: misc_feature
<222> LOCATION: (2)..(2)
<223> OTHER INFORMATION: 2'-OH
<220> FEATURE:
<221> NAME/KEY: misc_feature
<222> LOCATION: (3)..(3)
<223> OTHER INFORMATION: 2'-O-methoxyethyl
<220> FEATURE:
<221> NAME/KEY: misc_feature
<222> LOCATION: (4)..(4)
<223> OTHER INFORMATION: 2'-OH
<220> FEATURE:
<221> NAME/KEY: misc_feature
<222> LOCATION: (5)..(5)
<223> OTHER INFORMATION: 2'-O-methoxyethyl
<220> FEATURE:
<221> NAME/KEY: misc_feature
<222> LOCATION: (6)..(6)
<223> OTHER INFORMATION: 5'-methyl cytidine
<220> FEATURE:
<221> NAME/KEY: misc_feature
<222> LOCATION: (6)..(6)
<223> OTHER INFORMATION: 2'-OH
<220> FEATURE:
<221> NAME/KEY: misc_feature
```

```
<222> LOCATION: (7)..(7)
<223> OTHER INFORMATION: 2'-O-methoxyethyl
<220> FEATURE:
<221> NAME/KEY: misc_feature
<222> LOCATION: (8)..(8)
<223> OTHER INFORMATION: 5'-methyl cytidine
<220> FEATURE:
<221> NAME/KEY: misc_feature
<222> LOCATION: (8)..(8)
<223> OTHER INFORMATION: 2'-OH
<220> FEATURE:
<221> NAME/KEY: misc_feature
<222> LOCATION: (9)..(9)
<223> OTHER INFORMATION: 2'-O-methoxyethyl
<220> FEATURE:
<221> NAME/KEY: misc_feature
<222> LOCATION: (10)..(10)
<223> OTHER INFORMATION: 2'-OH
<220> FEATURE:
<221> NAME/KEY: misc_feature
<222> LOCATION: (11)..(11)
<223> OTHER INFORMATION: 2'-O-methoxyethyl
<220> FEATURE:
<221> NAME/KEY: misc_feature
<222> LOCATION: (12)..(12)
<223> OTHER INFORMATION: 2'-OH
<220> FEATURE:
<221> NAME/KEY: misc_feature
<222> LOCATION: (13)..(14)
<223> OTHER INFORMATION: 5'-methyl cytidine
<220> FEATURE:
<221> NAME/KEY: misc_feature
<222> LOCATION: (13)..(13)
<223> OTHER INFORMATION: 2'-O-methoxyethyl
<220> FEATURE:
<221> NAME/KEY: misc_feature
<222> LOCATION: (14)..(14)
<223> OTHER INFORMATION: 2'-OH
<220> FEATURE:
<221> NAME/KEY: misc_feature
<222> LOCATION: (15)..(15)
<223> OTHER INFORMATION: 2'-O-methoxyethyl
<220> FEATURE:
<221> NAME/KEY: misc_feature
<222> LOCATION: (16)..(16)
<223> OTHER INFORMATION: 2'-OH
<220> FEATURE:
<221> NAME/KEY: misc_feature
<222> LOCATION: (17)..(17)
<223> OTHER INFORMATION: 2'-O-methoxyethyl
<220> FEATURE:
<221> NAME/KEY: misc_feature
<222> LOCATION: (18)..(18)
<223> OTHER INFORMATION: 5'-methyl cytidine
<220> FEATURE:
<221> NAME/KEY: misc_feature
<222> LOCATION: (18)..(18)
<223> OTHER INFORMATION: 2'-OH
<220> FEATURE:
<221> NAME/KEY: misc_feature
<222> LOCATION: (19)..(19)
<223> OTHER INFORMATION: 2'-O-methoxyethyl
<220> FEATURE:
<221> NAME/KEY: misc_feature
<222> LOCATION: (20)..(20)
<223> OTHER INFORMATION: 2'-OH

<400> SEQUENCE: 47
tutgtctctg gucctuactu                                              20

<210> SEQ ID NO 48
<211> LENGTH: 20
<212> TYPE: DNA
<213> ORGANISM: Artificial
<220> FEATURE:
<223> OTHER INFORMATION: Synthetic Construct
<220> FEATURE:
```

```
<221> NAME/KEY: misc_feature
<222> LOCATION: (1)..(20)
<223> OTHER INFORMATION: phosphodiester linkages
<220> FEATURE:
<221> NAME/KEY: misc_feature
<222> LOCATION: (1)..(1)
<223> OTHER INFORMATION: 2'-OH
<220> FEATURE:
<221> NAME/KEY: misc_feature
<222> LOCATION: (2)..(2)
<223> OTHER INFORMATION: 2'-O-methoxyethyl
<220> FEATURE:
<221> NAME/KEY: misc_feature
<222> LOCATION: (3)..(3)
<223> OTHER INFORMATION: 2'-OH
<220> FEATURE:
<221> NAME/KEY: misc_feature
<222> LOCATION: (4)..(4)
<223> OTHER INFORMATION: 2'-O-methoxyethyl
<220> FEATURE:
<221> NAME/KEY: misc_feature
<222> LOCATION: (5)..(5)
<223> OTHER INFORMATION: 2'-OH
<220> FEATURE:
<221> NAME/KEY: misc_feature
<222> LOCATION: (6)..(6)
<223> OTHER INFORMATION: 5'-methyl cytidine
<220> FEATURE:
<221> NAME/KEY: misc_feature
<222> LOCATION: (6)..(6)
<223> OTHER INFORMATION: 2'-O-methoxyethyl
<220> FEATURE:
<221> NAME/KEY: misc_feature
<222> LOCATION: (7)..(7)
<223> OTHER INFORMATION: 2'-OH
<220> FEATURE:
<221> NAME/KEY: misc_feature
<222> LOCATION: (8)..(8)
<223> OTHER INFORMATION: 5'-methyl cytidine
<220> FEATURE:
<221> NAME/KEY: misc_feature
<222> LOCATION: (8)..(8)
<223> OTHER INFORMATION: 2'-O-methoxyethyl
<220> FEATURE:
<221> NAME/KEY: misc_feature
<222> LOCATION: (9)..(9)
<223> OTHER INFORMATION: 2'-OH
<220> FEATURE:
<221> NAME/KEY: misc_feature
<222> LOCATION: (10)..(10)
<223> OTHER INFORMATION: 2'-O-methoxyethyl
<220> FEATURE:
<221> NAME/KEY: misc_feature
<222> LOCATION: (11)..(11)
<223> OTHER INFORMATION: 2'-OH
<220> FEATURE:
<221> NAME/KEY: misc_feature
<222> LOCATION: (12)..(12)
<223> OTHER INFORMATION: 2'-O-methoxyethyl
<220> FEATURE:
<221> NAME/KEY: misc_feature
<222> LOCATION: (13)..(14)
<223> OTHER INFORMATION: 5'-methyl cytidine
<220> FEATURE:
<221> NAME/KEY: misc_feature
<222> LOCATION: (13)..(13)
<223> OTHER INFORMATION: 2'-OH
<220> FEATURE:
<221> NAME/KEY: misc_feature
<222> LOCATION: (14)..(14)
<223> OTHER INFORMATION: 2'-O-methoxyethyl
<220> FEATURE:
<221> NAME/KEY: misc_feature
<222> LOCATION: (15)..(15)
<223> OTHER INFORMATION: 2'-OH
<220> FEATURE:
<221> NAME/KEY: misc_feature
<222> LOCATION: (16)..(16)
<223> OTHER INFORMATION: 2'-O-methoxyethyl
```

```
<220> FEATURE:
<221> NAME/KEY: misc_feature
<222> LOCATION: (17)..(17)
<223> OTHER INFORMATION: 2'-OH
<220> FEATURE:
<221> NAME/KEY: misc_feature
<222> LOCATION: (18)..(18)
<223> OTHER INFORMATION: 5'-methyl cytidine
<220> FEATURE:
<221> NAME/KEY: misc_feature
<222> LOCATION: (18)..(18)
<223> OTHER INFORMATION: 2'-O-methoxyethyl
<220> FEATURE:
<221> NAME/KEY: misc_feature
<222> LOCATION: (19)..(19)
<223> OTHER INFORMATION: 2'-OH
<220> FEATURE:
<221> NAME/KEY: misc_feature
<222> LOCATION: (20)..(20)
<223> OTHER INFORMATION: 2'-O-methoxyethyl

<400> SEQUENCE: 48
utugucucug gtccutacut                                                    20

<210> SEQ ID NO 49
<211> LENGTH: 20
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphodiester linkages
<220> FEATURE:
<221> NAME/KEY: misc_feature
<222> LOCATION: (1)..(1)
<223> OTHER INFORMATION: 2'-O-methoxyethyl
<220> FEATURE:
<221> NAME/KEY: misc_feature
<222> LOCATION: (2)..(2)
<223> OTHER INFORMATION: 2'-OH
<220> FEATURE:
<221> NAME/KEY: misc_feature
<222> LOCATION: (3)..(3)
<223> OTHER INFORMATION: 2'-O-methoxyethyl
<220> FEATURE:
<221> NAME/KEY: misc_feature
<222> LOCATION: (4)..(4)
<223> OTHER INFORMATION: 2'-OH
<220> FEATURE:
<221> NAME/KEY: misc_feature
<222> LOCATION: (5)..(5)
<223> OTHER INFORMATION: 2'-O-methoxyethyl
<220> FEATURE:
<221> NAME/KEY: misc_feature
<222> LOCATION: (6)..(6)
<223> OTHER INFORMATION: 5'-methyl cytidine
<220> FEATURE:
<221> NAME/KEY: misc_feature
<222> LOCATION: (6)..(6)
<223> OTHER INFORMATION: 2'-OH
<220> FEATURE:
<221> NAME/KEY: misc_feature
<222> LOCATION: (7)..(7)
<223> OTHER INFORMATION: 2'-O-methoxyethyl
<220> FEATURE:
<221> NAME/KEY: misc_feature
<222> LOCATION: (8)..(8)
<223> OTHER INFORMATION: 5'-methyl cytidine
<220> FEATURE:
<221> NAME/KEY: misc_feature
<222> LOCATION: (8)..(8)
<223> OTHER INFORMATION: 2'-OH
<220> FEATURE:
<221> NAME/KEY: misc_feature
<222> LOCATION: (9)..(9)
```

```
<223> OTHER INFORMATION: 2'-O-methoxyethyl
<220> FEATURE:
<221> NAME/KEY: misc_feature
<222> LOCATION: (10)..(10)
<223> OTHER INFORMATION: 2'-OH
<220> FEATURE:
<221> NAME/KEY: misc_feature
<222> LOCATION: (11)..(11)
<223> OTHER INFORMATION: 2'-O-methoxyethyl
<220> FEATURE:
<221> NAME/KEY: misc_feature
<222> LOCATION: (12)..(12)
<223> OTHER INFORMATION: 2'-OH
<220> FEATURE:
<221> NAME/KEY: misc_feature
<222> LOCATION: (13)..(14)
<223> OTHER INFORMATION: 5'-methyl cytidine
<220> FEATURE:
<221> NAME/KEY: misc_feature
<222> LOCATION: (13)..(13)
<223> OTHER INFORMATION: 2'-O-methoxyethyl
<220> FEATURE:
<221> NAME/KEY: misc_feature
<222> LOCATION: (14)..(14)
<223> OTHER INFORMATION: 2'-OH
<220> FEATURE:
<221> NAME/KEY: misc_feature
<222> LOCATION: (15)..(15)
<223> OTHER INFORMATION: 2'-O-methoxyethyl
<220> FEATURE:
<221> NAME/KEY: misc_feature
<222> LOCATION: (16)..(16)
<223> OTHER INFORMATION: 2'-OH
<220> FEATURE:
<221> NAME/KEY: misc_feature
<222> LOCATION: (17)..(17)
<223> OTHER INFORMATION: 2'-O-methoxyethyl
<220> FEATURE:
<221> NAME/KEY: misc_feature
<222> LOCATION: (18)..(18)
<223> OTHER INFORMATION: 5'-methyl cytidine
<220> FEATURE:
<221> NAME/KEY: misc_feature
<222> LOCATION: (18)..(18)
<223> OTHER INFORMATION: 2'-OH
<220> FEATURE:
<221> NAME/KEY: misc_feature
<222> LOCATION: (19)..(19)
<223> OTHER INFORMATION: 2'-O-methoxyethyl
<220> FEATURE:
<221> NAME/KEY: misc_feature
<222> LOCATION: (20)..(20)
<223> OTHER INFORMATION: 2'-OH

<400> SEQUENCE: 49
tutgtctctg guccuactu                                          20

<210> SEQ ID NO 50
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphorothioate linkages
<220> FEATURE:
<221> NAME/KEY: misc_feature
<222> LOCATION: (1)..(1)
<223> OTHER INFORMATION: 2'-H
<220> FEATURE:
<221> NAME/KEY: misc_feature
<222> LOCATION: (2)..(2)
<223> OTHER INFORMATION: 2'-O-methyl
<220> FEATURE:
<221> NAME/KEY: misc_feature
```

```
<222> LOCATION: (3)..(3)
<223> OTHER INFORMATION: 2'-H
<220> FEATURE:
<221> NAME/KEY: misc_feature
<222> LOCATION: (4)..(4)
<223> OTHER INFORMATION: 2'-O-methyl
<220> FEATURE:
<221> NAME/KEY: misc_feature
<222> LOCATION: (5)..(5)
<223> OTHER INFORMATION: 2'-H
<220> FEATURE:
<221> NAME/KEY: misc_feature
<222> LOCATION: (6)..(6)
<223> OTHER INFORMATION: 2'-O-methyl
<220> FEATURE:
<221> NAME/KEY: misc_feature
<222> LOCATION: (6)..(6)
<223> OTHER INFORMATION: 5'-methyl cytidine
<220> FEATURE:
<221> NAME/KEY: misc_feature
<222> LOCATION: (7)..(7)
<223> OTHER INFORMATION: 2'-H
<220> FEATURE:
<221> NAME/KEY: misc_feature
<222> LOCATION: (8)..(8)
<223> OTHER INFORMATION: 2'-O-methyl
<220> FEATURE:
<221> NAME/KEY: misc_feature
<222> LOCATION: (8)..(8)
<223> OTHER INFORMATION: 5'-methyl cytidine
<220> FEATURE:
<221> NAME/KEY: misc_feature
<222> LOCATION: (9)..(9)
<223> OTHER INFORMATION: 2'-H
<220> FEATURE:
<221> NAME/KEY: misc_feature
<222> LOCATION: (10)..(10)
<223> OTHER INFORMATION: 2'-O-methyl
<220> FEATURE:
<221> NAME/KEY: misc_feature
<222> LOCATION: (11)..(11)
<223> OTHER INFORMATION: 2'-H
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (13)..(13)
<223> OTHER INFORMATION: 2'-H
<220> FEATURE:
<221> NAME/KEY: misc_feature
<222> LOCATION: (13)..(14)
<223> OTHER INFORMATION: 5'-methyl cytidine
<220> FEATURE:
<221> NAME/KEY: misc_feature
<222> LOCATION: (14)..(14)
<223> OTHER INFORMATION: 2'-O-methyl
<220> FEATURE:
<221> NAME/KEY: misc_feature
<222> LOCATION: (15)..(15)
<223> OTHER INFORMATION: 2'-H
<220> FEATURE:
<221> NAME/KEY: misc_feature
<222> LOCATION: (16)..(16)
<223> OTHER INFORMATION: 2'-O-methyl
<220> FEATURE:
<221> NAME/KEY: misc_feature
<222> LOCATION: (17)..(17)
<223> OTHER INFORMATION: 2'-H
<220> FEATURE:
<221> NAME/KEY: misc_feature
<222> LOCATION: (18)..(18)
<223> OTHER INFORMATION: 2'-O-methyl
<220> FEATURE:
<221> NAME/KEY: misc_feature
<222> LOCATION: (18)..(18)
<223> OTHER INFORMATION: 5'-methyl cytidine
<220> FEATURE:
```

<221> NAME/KEY: misc_feature
<222> LOCATION: (19)..(19)
<223> OTHER INFORMATION: 2'-H
<220> FEATURE:
<221> NAME/KEY: misc_feature
<222> LOCATION: (20)..(20)
<223> OTHER INFORMATION: 2'-O-methyl

<400> SEQUENCE: 50
uuugucucug guccuuacuu                                                         20

<210> SEQ ID NO 51
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphodiester linkages
<220> FEATURE:
<221> NAME/KEY: misc_feature
<222> LOCATION: (1)..(1)
<223> OTHER INFORMATION: 2'-H
<220> FEATURE:
<221> NAME/KEY: misc_feature
<222> LOCATION: (2)..(2)
<223> OTHER INFORMATION: 2'-O-methyl
<220> FEATURE:
<221> NAME/KEY: misc_feature
<222> LOCATION: (3)..(3)
<223> OTHER INFORMATION: 2'-H
<220> FEATURE:
<221> NAME/KEY: misc_feature
<222> LOCATION: (4)..(4)
<223> OTHER INFORMATION: 2'-O-methyl
<220> FEATURE:
<221> NAME/KEY: misc_feature
<222> LOCATION: (5)..(5)
<223> OTHER INFORMATION: 2'-H
<220> FEATURE:
<221> NAME/KEY: misc_feature
<222> LOCATION: (6)..(6)
<223> OTHER INFORMATION: 2'-O-methyl
<220> FEATURE:
<221> NAME/KEY: misc_feature
<222> LOCATION: (6)..(6)
<223> OTHER INFORMATION: 5'-methyl cytidine
<220> FEATURE:
<221> NAME/KEY: misc_feature
<222> LOCATION: (7)..(7)
<223> OTHER INFORMATION: 2'-H
<220> FEATURE:
<221> NAME/KEY: misc_feature
<222> LOCATION: (8)..(8)
<223> OTHER INFORMATION: 2'-O-methyl
<220> FEATURE:
<221> NAME/KEY: misc_feature
<222> LOCATION: (8)..(8)
<223> OTHER INFORMATION: 5'-methyl cytidine
<220> FEATURE:
<221> NAME/KEY: misc_feature
<222> LOCATION: (9)..(9)
<223> OTHER INFORMATION: 2'-H
<220> FEATURE:
<221> NAME/KEY: misc_feature
<222> LOCATION: (10)..(10)
<223> OTHER INFORMATION: 2'-O-methyl
<220> FEATURE:
<221> NAME/KEY: misc_feature
<222> LOCATION: (11)..(11)
<223> OTHER INFORMATION: 2'-H
<220> FEATURE:
<221> NAME/KEY: misc_feature
<222> LOCATION: (12)..(12)
<223> OTHER INFORMATION: 2'-O-methyl

```
<220> FEATURE:
<221> NAME/KEY: misc_feature
<222> LOCATION: (13)..(13)
<223> OTHER INFORMATION: 2'-H
<220> FEATURE:
<221> NAME/KEY: misc_feature
<222> LOCATION: (13)..(14)
<223> OTHER INFORMATION: 5'-methyl cytidine
<220> FEATURE:
<221> NAME/KEY: misc_feature
<222> LOCATION: (14)..(14)
<223> OTHER INFORMATION: 2'-O-methyl
<220> FEATURE:
<221> NAME/KEY: misc_feature
<222> LOCATION: (15)..(15)
<223> OTHER INFORMATION: 2'-H
<220> FEATURE:
<221> NAME/KEY: misc_feature
<222> LOCATION: (16)..(16)
<223> OTHER INFORMATION: 2'-O-methyl
<220> FEATURE:
<221> NAME/KEY: misc_feature
<222> LOCATION: (17)..(17)
<223> OTHER INFORMATION: 2'-H
<220> FEATURE:
<221> NAME/KEY: misc_feature
<222> LOCATION: (18)..(18)
<223> OTHER INFORMATION: 2'-O-methyl
<220> FEATURE:
<221> NAME/KEY: misc_feature
<222> LOCATION: (18)..(18)
<223> OTHER INFORMATION: 5'-methyl cytidine
<220> FEATURE:
<221> NAME/KEY: misc_feature
<222> LOCATION: (19)..(19)
<223> OTHER INFORMATION: 2'-H
<220> FEATURE:
<221> NAME/KEY: misc_feature
<222> LOCATION: (20)..(20)
<223> OTHER INFORMATION: 2'-O-methyl

<400> SEQUENCE: 51
uuugucucug guccuuacuu                                               20

<210> SEQ ID NO 52
<211> LENGTH: 20
<212> TYPE: DNA
<213> ORGANISM: Artificial
<220> FEATURE:
<223> OTHER INFORMATION: Synthetic Construct

<400> SEQUENCE: 52
tttgtctctg gtccttactt                                               20

<210> SEQ ID NO 53
<211> LENGTH: 20
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: n is a, c, g, t or u

<400> SEQUENCE: 53
nnnnnnnnnn nnnnnnnnnn                                               20

<210> SEQ ID NO 54
<211> LENGTH: 12
<212> TYPE: RNA
<213> ORGANISM: Artificial
<220> FEATURE:
```

```
<223> OTHER INFORMATION: Dodecamer oligonucleotide

<400> SEQUENCE: 54
cgcgaauucg cg                                                              12

<210> SEQ ID NO 55
<211> LENGTH: 12
<212> TYPE: RNA
<213> ORGANISM: Artificial
<220> FEATURE:
<223> OTHER INFORMATION: Dodecamer oligonucleotide

<400> SEQUENCE: 55
gcgcuuaagc gc                                                              12

<210> SEQ ID NO 56
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphodiester linkages
<220> FEATURE:
<221> NAME/KEY: misc_feature
<222> LOCATION: (1)..(20)
<223> OTHER INFORMATION: 2'-OH

<400> SEQUENCE: 56
uuugucucug guccuuacuu                                                      20

<210> SEQ ID NO 57
<211> LENGTH: 19
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(19)
<223> OTHER INFORMATION: 2'-OH
<220> FEATURE:
<221> NAME/KEY: misc_feature
<222> LOCATION: (1)..(19)
<223> OTHER INFORMATION: Phosphoediester linkages

<400> SEQUENCE: 57
aaguaaccac cagagacaa                                                       19

<210> SEQ ID NO 58
<211> LENGTH: 19
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(19)
<223> OTHER INFORMATION: phosphodiester linkages

<400> SEQUENCE: 58
uugucucugg uccuuacuu                                                       19

<210> SEQ ID NO 59
<211> LENGTH: 19
<212> TYPE: RNA
<213> ORGANISM: Artificial
```

```
<220> FEATURE:
<223> OTHER INFORMATION: Synthetic Construct
<220> FEATURE:
<221> NAME/KEY: misc_feature
<222> LOCATION: (1)..(19)
<223> OTHER INFORMATION: phosphodiester linkages
<220> FEATURE:
<221> NAME/KEY: misc_feature
<222> LOCATION: (1)..(1)
<223> OTHER INFORMATION: 2'-OH
<220> FEATURE:
<221> NAME/KEY: misc_feature
<222> LOCATION: (2)..(2)
<223> OTHER INFORMATION: 2'-OMe
<220> FEATURE:
<221> NAME/KEY: misc_feature
<222> LOCATION: (3)..(3)
<223> OTHER INFORMATION: 2'-OH
<220> FEATURE:
<221> NAME/KEY: misc_feature
<222> LOCATION: (4)..(4)
<223> OTHER INFORMATION: 2'-OMe
<220> FEATURE:
<221> NAME/KEY: misc_feature
<222> LOCATION: (5)..(5)
<223> OTHER INFORMATION: 2'-OH
<220> FEATURE:
<221> NAME/KEY: misc_feature
<222> LOCATION: (6)..(6)
<223> OTHER INFORMATION: 2'-OMe
<220> FEATURE:
<221> NAME/KEY: misc_feature
<222> LOCATION: (7)..(7)
<223> OTHER INFORMATION: 2'-OH
<220> FEATURE:
<221> NAME/KEY: misc_feature
<222> LOCATION: (8)..(8)
<223> OTHER INFORMATION: 2'-OMe
<220> FEATURE:
<221> NAME/KEY: misc_feature
<222> LOCATION: (9)..(9)
<223> OTHER INFORMATION: 2'-OH
<220> FEATURE:
<221> NAME/KEY: misc_feature
<222> LOCATION: (10)..(10)
<223> OTHER INFORMATION: 2'-OMe
<220> FEATURE:
<221> NAME/KEY: misc_feature
<222> LOCATION: (11)..(11)
<223> OTHER INFORMATION: 2'-OH
<220> FEATURE:
<221> NAME/KEY: misc_feature
<222> LOCATION: (12)..(12)
<223> OTHER INFORMATION: 2'-OMe
<220> FEATURE:
<221> NAME/KEY: misc_feature
<222> LOCATION: (13)..(13)
<223> OTHER INFORMATION: 2'-OH
<220> FEATURE:
<221> NAME/KEY: misc_feature
<222> LOCATION: (14)..(14)
<223> OTHER INFORMATION: 2'-OMe
<220> FEATURE:
<221> NAME/KEY: misc_feature
<222> LOCATION: (15)..(15)
<223> OTHER INFORMATION: 2'-OH
<220> FEATURE:
<221> NAME/KEY: misc_feature
<222> LOCATION: (16)..(16)
<223> OTHER INFORMATION: 2'-OMe
<220> FEATURE:
<221> NAME/KEY: misc_feature
<222> LOCATION: (17)..(17)
<223> OTHER INFORMATION: 2'-OH
<220> FEATURE:
<221> NAME/KEY: misc_feature
<222> LOCATION: (18)..(18)
<223> OTHER INFORMATION: 2'-OMe
<220> FEATURE:
```

<221> NAME/KEY: misc_feature
<222> LOCATION: (19)..(19)
<223> OTHER INFORMATION: 2'-OH

<400> SEQUENCE: 59
aaguaaggac cagagacaa                                                  19

<210> SEQ ID NO 60
<211> LENGTH: 19
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(19)
<223> OTHER INFORMATION: phosphodiester linkages
<220> FEATURE:
<221> NAME/KEY: misc_feature
<222> LOCATION: (1)..(1)
<223> OTHER INFORMATION: 2'-OMe
<220> FEATURE:
<221> NAME/KEY: misc_feature
<222> LOCATION: (2)..(2)
<223> OTHER INFORMATION: 2'-OH
<220> FEATURE:
<221> NAME/KEY: misc_feature
<222> LOCATION: (3)..(3)
<223> OTHER INFORMATION: 2'-OMe
<220> FEATURE:
<221> NAME/KEY: misc_feature
<222> LOCATION: (4)..(4)
<223> OTHER INFORMATION: 2'-OH
<220> FEATURE:
<221> NAME/KEY: misc_feature
<222> LOCATION: (5)..(5)
<223> OTHER INFORMATION: 2'-OMe
<220> FEATURE:
<221> NAME/KEY: misc_feature
<222> LOCATION: (6)..(6)
<223> OTHER INFORMATION: 2'-OH
<220> FEATURE:
<221> NAME/KEY: misc_feature
<222> LOCATION: (7)..(7)
<223> OTHER INFORMATION: 2'-OMe
<220> FEATURE:
<221> NAME/KEY: misc_feature
<222> LOCATION: (8)..(8)
<223> OTHER INFORMATION: 2'-OH
<220> FEATURE:
<221> NAME/KEY: misc_feature
<222> LOCATION: (9)..(9)
<223> OTHER INFORMATION: 2'-OMe
<220> FEATURE:
<221> NAME/KEY: misc_feature
<222> LOCATION: (10)..(10)
<223> OTHER INFORMATION: 2'-OH
<220> FEATURE:
<221> NAME/KEY: misc_feature
<222> LOCATION: (11)..(11)
<223> OTHER INFORMATION: 2'-OMe
<220> FEATURE:
<221> NAME/KEY: misc_feature
<222> LOCATION: (12)..(12)
<223> OTHER INFORMATION: 2'-OH
<220> FEATURE:
<221> NAME/KEY: misc_feature
<222> LOCATION: (13)..(13)
<223> OTHER INFORMATION: 2'-OMe
<220> FEATURE:
<221> NAME/KEY: misc_feature
<222> LOCATION: (14)..(14)
<223> OTHER INFORMATION: 2'-OH
<220> FEATURE:
<221> NAME/KEY: misc_feature
<222> LOCATION: (15)..(15)
<223> OTHER INFORMATION: 2'-OMe -continued

```
<220> FEATURE:
<221> NAME/KEY: misc_feature
<222> LOCATION: (16)..(16)
<223> OTHER INFORMATION: 2'-OH
<220> FEATURE:
<221> NAME/KEY: misc_feature
<222> LOCATION: (17)..(17)
<223> OTHER INFORMATION: 2'-OMe
<220> FEATURE:
<221> NAME/KEY: misc_feature
<222> LOCATION: (18)..(18)
<223> OTHER INFORMATION: 2'-OH
<220> FEATURE:
<221> NAME/KEY: misc_feature
<222> LOCATION: (19)..(19)
<223> OTHER INFORMATION: 2'-OMe

<400> SEQUENCE: 60
uugucucugg uccuuacuu                                                    19

<210> SEQ ID NO 61
<211> LENGTH: 19
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(19)
<223> OTHER INFORMATION: phosphodiester linkages
<220> FEATURE:
<221> NAME/KEY: misc_feature
<222> LOCATION: (1)..(19)
<223> OTHER INFORMATION: 2'-OH

<400> SEQUENCE: 61
ggguaaauac auucuacau                                                    19

<210> SEQ ID NO 62
<211> LENGTH: 19
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(19)
<223> OTHER INFORMATION: phosphodiester linkages
<220> FEATURE:
<221> NAME/KEY: misc_feature
<222> LOCATION: (1)..(19)
<223> OTHER INFORMATION: 2'-OH

<400> SEQUENCE: 62
auguagaaug uauuuaccc                                                    19

<210> SEQ ID NO 63
<211> LENGTH: 19
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 2'-OH
<220> FEATURE:
<221> NAME/KEY: misc_feature
<222> LOCATION: (1)..(19)
<223> OTHER INFORMATION: phosphodiester linkages
<220> FEATURE:
<221> NAME/KEY: misc_feature
<222> LOCATION: (2)..(2)
```

```
<223> OTHER INFORMATION: 2'-OMe
<220> FEATURE:
<221> NAME/KEY: misc_feature
<222> LOCATION: (3)..(3)
<223> OTHER INFORMATION: 2'-OH
<220> FEATURE:
<221> NAME/KEY: misc_feature
<222> LOCATION: (4)..(4)
<223> OTHER INFORMATION: 2'-OMe
<220> FEATURE:
<221> NAME/KEY: misc_feature
<222> LOCATION: (5)..(5)
<223> OTHER INFORMATION: 2'-OH
<220> FEATURE:
<221> NAME/KEY: misc_feature
<222> LOCATION: (6)..(6)
<223> OTHER INFORMATION: 2'-OMe
<220> FEATURE:
<221> NAME/KEY: misc_feature
<222> LOCATION: (7)..(7)
<223> OTHER INFORMATION: 2'-OH
<220> FEATURE:
<221> NAME/KEY: misc_feature
<222> LOCATION: (8)..(8)
<223> OTHER INFORMATION: 2'-OMe
<220> FEATURE:
<221> NAME/KEY: misc_feature
<222> LOCATION: (9)..(9)
<223> OTHER INFORMATION: 2'-OH
<220> FEATURE:
<221> NAME/KEY: misc_feature
<222> LOCATION: (10)..(10)
<223> OTHER INFORMATION: 2'-OMe
<220> FEATURE:
<221> NAME/KEY: misc_feature
<222> LOCATION: (11)..(11)
<223> OTHER INFORMATION: 2'-OH
<220> FEATURE:
<221> NAME/KEY: misc_feature
<222> LOCATION: (12)..(12)
<223> OTHER INFORMATION: 2'-OMe
<220> FEATURE:
<221> NAME/KEY: misc_feature
<222> LOCATION: (13)..(13)
<223> OTHER INFORMATION: 2'-OH
<220> FEATURE:
<221> NAME/KEY: misc_feature
<222> LOCATION: (14)..(14)
<223> OTHER INFORMATION: 2'-OMe
<220> FEATURE:
<221> NAME/KEY: misc_feature
<222> LOCATION: (15)..(15)
<223> OTHER INFORMATION: 2'-OH
<220> FEATURE:
<221> NAME/KEY: misc_feature
<222> LOCATION: (16)..(16)
<223> OTHER INFORMATION: 2'-OMe
<220> FEATURE:
<221> NAME/KEY: misc_feature
<222> LOCATION: (17)..(17)
<223> OTHER INFORMATION: 2'-OH
<220> FEATURE:
<221> NAME/KEY: misc_feature
<222> LOCATION: (18)..(18)
<223> OTHER INFORMATION: 2'-OMe
<220> FEATURE:
<221> NAME/KEY: misc_feature
<222> LOCATION: (19)..(19)
<223> OTHER INFORMATION: 2'-OH

<400> SEQUENCE: 63
gggauuauac auucuacau                                               19

<210> SEQ ID NO 64
<211> LENGTH: 19
<212> TYPE: RNA
<213> ORGANISM: Artificial
```

```
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 2'-OMe
<220> FEATURE:
<221> NAME/KEY: misc_feature
<222> LOCATION: (1)..(19)
<223> OTHER INFORMATION: phosphodiester linkages
<220> FEATURE:
<221> NAME/KEY: misc_feature
<222> LOCATION: (2)..(2)
<223> OTHER INFORMATION: 2'-OH
<220> FEATURE:
<221> NAME/KEY: misc_feature
<222> LOCATION: (3)..(3)
<223> OTHER INFORMATION: 2'-OMe
<220> FEATURE:
<221> NAME/KEY: misc_feature
<222> LOCATION: (4)..(4)
<223> OTHER INFORMATION: 2'-OH
<220> FEATURE:
<221> NAME/KEY: misc_feature
<222> LOCATION: (5)..(5)
<223> OTHER INFORMATION: 2'-OMe
<220> FEATURE:
<221> NAME/KEY: misc_feature
<222> LOCATION: (6)..(6)
<223> OTHER INFORMATION: 2'-OH
<220> FEATURE:
<221> NAME/KEY: misc_feature
<222> LOCATION: (7)..(7)
<223> OTHER INFORMATION: 2'-OMe
<220> FEATURE:
<221> NAME/KEY: misc_feature
<222> LOCATION: (8)..(8)
<223> OTHER INFORMATION: 2'-OH
<220> FEATURE:
<221> NAME/KEY: misc_feature
<222> LOCATION: (9)..(9)
<223> OTHER INFORMATION: 2'-OMe
<220> FEATURE:
<221> NAME/KEY: misc_feature
<222> LOCATION: (10)..(10)
<223> OTHER INFORMATION: 2'-OH
<220> FEATURE:
<221> NAME/KEY: misc_feature
<222> LOCATION: (11)..(11)
<223> OTHER INFORMATION: 2'-OMe
<220> FEATURE:
<221> NAME/KEY: misc_feature
<222> LOCATION: (12)..(12)
<223> OTHER INFORMATION: 2'-OH
<220> FEATURE:
<221> NAME/KEY: misc_feature
<222> LOCATION: (13)..(13)
<223> OTHER INFORMATION: 2'-OMe
<220> FEATURE:
<221> NAME/KEY: misc_feature
<222> LOCATION: (14)..(14)
<223> OTHER INFORMATION: 2'-OH
<220> FEATURE:
<221> NAME/KEY: misc_feature
<222> LOCATION: (15)..(15)
<223> OTHER INFORMATION: 2'-OMe
<220> FEATURE:
<221> NAME/KEY: misc_feature
<222> LOCATION: (16)..(16)
<223> OTHER INFORMATION: 2'-OH
<220> FEATURE:
<221> NAME/KEY: misc_feature
<222> LOCATION: (17)..(17)
<223> OTHER INFORMATION: 2'-OMe
<220> FEATURE:
<221> NAME/KEY: misc_feature
<222> LOCATION: (18)..(18)
<223> OTHER INFORMATION: 2'-OH
<220> FEATURE:
```

<221> NAME/KEY: misc_feature
<222> LOCATION: (19)..(19)
<223> OTHER INFORMATION: 2'-OMe

<400> SEQUENCE: 64
auguagaaug uauuuaccc                                                19

<210> SEQ ID NO 65
<211> LENGTH: 19
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(19)
<223> OTHER INFORMATION: 2'-OH
<220> FEATURE:
<221> NAME/KEY: misc_feature
<222> LOCATION: (1)..(19)
<223> OTHER INFORMATION: phosphodiester linkages

<400> SEQUENCE: 65
ucaaauccag aggcuagca                                                19

<210> SEQ ID NO 66
<211> LENGTH: 19
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(19)
<223> OTHER INFORMATION: 2'-OH
<220> FEATURE:
<221> NAME/KEY: misc_feature
<222> LOCATION: (1)..(19)
<223> OTHER INFORMATION: phosphodiester linkages

<400> SEQUENCE: 66
ugcuagccuc uggauuuga                                                19

<210> SEQ ID NO 67
<211> LENGTH: 19
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 2'-OH
<220> FEATURE:
<221> NAME/KEY: misc_feature
<222> LOCATION: (1)..(19)
<223> OTHER INFORMATION: phosphodiester linkages
<220> FEATURE:
<221> NAME/KEY: misc_feature
<222> LOCATION: (2)..(2)
<223> OTHER INFORMATION: 2'-OMe
<220> FEATURE:
<221> NAME/KEY: misc_feature
<222> LOCATION: (3)..(3)
<223> OTHER INFORMATION: 2'-OH
<220> FEATURE:
<221> NAME/KEY: misc_feature
<222> LOCATION: (4)..(4)
<223> OTHER INFORMATION: 2'-OMe
<220> FEATURE:
<221> NAME/KEY: misc_feature
<222> LOCATION: (5)..(5)
<223> OTHER INFORMATION: 2'-OH -continued

```
<220> FEATURE:
<221> NAME/KEY: misc_feature
<222> LOCATION: (6)..(6)
<223> OTHER INFORMATION: 2'-OMe
<220> FEATURE:
<221> NAME/KEY: misc_feature
<222> LOCATION: (7)..(7)
<223> OTHER INFORMATION: 2'-OH
<220> FEATURE:
<221> NAME/KEY: misc_feature
<222> LOCATION: (8)..(8)
<223> OTHER INFORMATION: 2'-OMe
<220> FEATURE:
<221> NAME/KEY: misc_feature
<222> LOCATION: (9)..(9)
<223> OTHER INFORMATION: 2'-OH
<220> FEATURE:
<221> NAME/KEY: misc_feature
<222> LOCATION: (10)..(10)
<223> OTHER INFORMATION: 2'-OMe
<220> FEATURE:
<221> NAME/KEY: misc_feature
<222> LOCATION: (11)..(11)
<223> OTHER INFORMATION: 2'-OH
<220> FEATURE:
<221> NAME/KEY: misc_feature
<222> LOCATION: (12)..(12)
<223> OTHER INFORMATION: 2'-OMe
<220> FEATURE:
<221> NAME/KEY: misc_feature
<222> LOCATION: (13)..(13)
<223> OTHER INFORMATION: 2'-OH
<220> FEATURE:
<221> NAME/KEY: misc_feature
<222> LOCATION: (14)..(14)
<223> OTHER INFORMATION: 2'-OMe
<220> FEATURE:
<221> NAME/KEY: misc_feature
<222> LOCATION: (15)..(15)
<223> OTHER INFORMATION: 2'-OH
<220> FEATURE:
<221> NAME/KEY: misc_feature
<222> LOCATION: (16)..(16)
<223> OTHER INFORMATION: 2'-OMe
<220> FEATURE:
<221> NAME/KEY: misc_feature
<222> LOCATION: (17)..(17)
<223> OTHER INFORMATION: 2'-OH
<220> FEATURE:
<221> NAME/KEY: misc_feature
<222> LOCATION: (18)..(18)
<223> OTHER INFORMATION: 2'-OMe
<220> FEATURE:
<221> NAME/KEY: misc_feature
<222> LOCATION: (19)..(19)
<223> OTHER INFORMATION: 2'-OH

<400> SEQUENCE: 67
ucaaauccag aggcuagca                                                19

<210> SEQ ID NO 68
<211> LENGTH: 19
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 2'-OMe
<220> FEATURE:
<221> NAME/KEY: misc_feature
<222> LOCATION: (1)..(19)
<223> OTHER INFORMATION: phosphodiester linkages
<220> FEATURE:
<221> NAME/KEY: misc_feature
<222> LOCATION: (2)..(2)
```

<223> OTHER INFORMATION: 2'-OH
<220> FEATURE:
<221> NAME/KEY: misc_feature
<222> LOCATION: (3)..(3)
<223> OTHER INFORMATION: 2'-OMe
<220> FEATURE:
<221> NAME/KEY: misc_feature
<222> LOCATION: (4)..(4)
<223> OTHER INFORMATION: 2'-OH
<220> FEATURE:
<221> NAME/KEY: misc_feature
<222> LOCATION: (5)..(5)
<223> OTHER INFORMATION: 2'-OMe
<220> FEATURE:
<221> NAME/KEY: misc_feature
<222> LOCATION: (6)..(6)
<223> OTHER INFORMATION: 2'-OH
<220> FEATURE:
<221> NAME/KEY: misc_feature
<222> LOCATION: (8)..(8)
<223> OTHER INFORMATION: 2'-OH
<220> FEATURE:
<221> NAME/KEY: misc_feature
<222> LOCATION: (9)..(9)
<223> OTHER INFORMATION: 2'-OMe
<220> FEATURE:
<221> NAME/KEY: misc_feature
<222> LOCATION: (10)..(10)
<223> OTHER INFORMATION: 2'-OH
<220> FEATURE:
<221> NAME/KEY: misc_feature
<222> LOCATION: (11)..(11)
<223> OTHER INFORMATION: 2'-OMe
<220> FEATURE:
<221> NAME/KEY: misc_feature
<222> LOCATION: (12)..(12)
<223> OTHER INFORMATION: 2'-OH
<220> FEATURE:
<221> NAME/KEY: misc_feature
<222> LOCATION: (13)..(13)
<223> OTHER INFORMATION: 2'-OMe
<220> FEATURE:
<221> NAME/KEY: misc_feature
<222> LOCATION: (14)..(14)
<223> OTHER INFORMATION: 2'-OH
<220> FEATURE:
<221> NAME/KEY: misc_feature
<222> LOCATION: (15)..(15)
<223> OTHER INFORMATION: 2'-OMe
<220> FEATURE:
<221> NAME/KEY: misc_feature
<222> LOCATION: (16)..(16)
<223> OTHER INFORMATION: 2'-OH
<220> FEATURE:
<221> NAME/KEY: misc_feature
<222> LOCATION: (17)..(17)
<223> OTHER INFORMATION: 2'-OMe
<220> FEATURE:
<221> NAME/KEY: misc_feature
<222> LOCATION: (18)..(18)
<223> OTHER INFORMATION: 2'-OH
<220> FEATURE:
<221> NAME/KEY: misc_feature
<222> LOCATION: (19)..(19)
<223> OTHER INFORMATION: 2'-OMe

<400> SEQUENCE: 68
ugcuagccuc uggauuuga                                              19

<210> SEQ ID NO 69
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature

```
<222> LOCATION: (1)..(1)
<223> OTHER INFORMATION: 2'-OMe
<220> FEATURE:
<221> NAME/KEY: misc_feature
<222> LOCATION: (1)..(20)
<223> OTHER INFORMATION: phosphorthioate linkages
<220> FEATURE:
<221> NAME/KEY: misc_feature
<222> LOCATION: (2)..(2)
<223> OTHER INFORMATION: 2'-OH
<220> FEATURE:
<221> NAME/KEY: misc_feature
<222> LOCATION: (3)..(3)
<223> OTHER INFORMATION: 2'-OMe
<220> FEATURE:
<221> NAME/KEY: misc_feature
<222> LOCATION: (4)..(4)
<223> OTHER INFORMATION: 2'-OH
<220> FEATURE:
<221> NAME/KEY: misc_feature
<222> LOCATION: (5)..(5)
<223> OTHER INFORMATION: 2'-OMe
<220> FEATURE:
<221> NAME/KEY: misc_feature
<222> LOCATION: (6)..(6)
<223> OTHER INFORMATION: 2'-OH
<220> FEATURE:
<221> NAME/KEY: misc_feature
<222> LOCATION: (7)..(7)
<223> OTHER INFORMATION: 2'-OMe
<220> FEATURE:
<221> NAME/KEY: misc_feature
<222> LOCATION: (8)..(8)
<223> OTHER INFORMATION: 2'-OH
<220> FEATURE:
<221> NAME/KEY: misc_feature
<222> LOCATION: (9)..(9)
<223> OTHER INFORMATION: 2'-OMe
<220> FEATURE:
<221> NAME/KEY: misc_feature
<222> LOCATION: (11)..(11)
<223> OTHER INFORMATION: 2'-OMe
<220> FEATURE:
<221> NAME/KEY: misc_feature
<222> LOCATION: (12)..(12)
<223> OTHER INFORMATION: 2'-OH
<220> FEATURE:
<221> NAME/KEY: misc_feature
<222> LOCATION: (13)..(13)
<223> OTHER INFORMATION: 2'-OMe
<220> FEATURE:
<221> NAME/KEY: misc_feature
<222> LOCATION: (14)..(14)
<223> OTHER INFORMATION: 2'-OH
<220> FEATURE:
<221> NAME/KEY: misc_feature
<222> LOCATION: (15)..(15)
<223> OTHER INFORMATION: 2'-OMe
<220> FEATURE:
<221> NAME/KEY: misc_feature
<222> LOCATION: (16)..(16)
<223> OTHER INFORMATION: 2'-OH
<220> FEATURE:
<221> NAME/KEY: misc_feature
<222> LOCATION: (17)..(17)
<223> OTHER INFORMATION: 2'-OMe
<220> FEATURE:
<221> NAME/KEY: misc_feature
<222> LOCATION: (18)..(18)
<223> OTHER INFORMATION: 2'-OH
<220> FEATURE:
<221> NAME/KEY: misc_feature
<222> LOCATION: (19)..(19)
<223> OTHER INFORMATION: 2'-OMe
<220> FEATURE:
<221> NAME/KEY: misc_feature
<222> LOCATION: (20)..(20)
<223> OTHER INFORMATION: 2'-OH
```

<400> SEQUENCE: 69
uuugucucug guccuuacuu                                               20

<210> SEQ ID NO 70
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphodiester linkages
<220> FEATURE:
<221> NAME/KEY: misc_feature
<222> LOCATION: (1)..(1)
<223> OTHER INFORMATION: 2'-OH
<220> FEATURE:
<221> NAME/KEY: misc_feature
<222> LOCATION: (2)..(2)
<223> OTHER INFORMATION: 2'-OMe
<220> FEATURE:
<221> NAME/KEY: misc_feature
<222> LOCATION: (3)..(3)
<223> OTHER INFORMATION: 2'-OH
<220> FEATURE:
<221> NAME/KEY: misc_feature
<222> LOCATION: (4)..(4)
<223> OTHER INFORMATION: 2'-OMe
<220> FEATURE:
<221> NAME/KEY: misc_feature
<222> LOCATION: (5)..(5)
<223> OTHER INFORMATION: 2'-OH
<220> FEATURE:
<221> NAME/KEY: misc_feature
<222> LOCATION: (6)..(6)
<223> OTHER INFORMATION: 2'-OMe
<220> FEATURE:
<221> NAME/KEY: misc_feature
<222> LOCATION: (7)..(7)
<223> OTHER INFORMATION: 2'-OH
<220> FEATURE:
<221> NAME/KEY: misc_feature
<222> LOCATION: (8)..(8)
<223> OTHER INFORMATION: 2'-OMe
<220> FEATURE:
<221> NAME/KEY: misc_feature
<222> LOCATION: (9)..(9)
<223> OTHER INFORMATION: 2'-OH
<220> FEATURE:
<221> NAME/KEY: misc_feature
<222> LOCATION: (10)..(10)
<223> OTHER INFORMATION: 2'-OMe
<220> FEATURE:
<221> NAME/KEY: misc_feature
<222> LOCATION: (11)..(11)
<223> OTHER INFORMATION: 2'-OH
<220> FEATURE:
<221> NAME/KEY: misc_feature
<222> LOCATION: (12)..(12)
<223> OTHER INFORMATION: 2'-OMe
<220> FEATURE:
<221> NAME/KEY: misc_feature
<222> LOCATION: (13)..(13)
<223> OTHER INFORMATION: 2'-OH
<220> FEATURE:
<221> NAME/KEY: misc_feature
<222> LOCATION: (14)..(14)
<223> OTHER INFORMATION: 2'-OMe
<220> FEATURE:
<221> NAME/KEY: misc_feature
<222> LOCATION: (15)..(15)
<223> OTHER INFORMATION: 2'-OH
<220> FEATURE:
<221> NAME/KEY: misc_feature
<222> LOCATION: (16)..(16)
<223> OTHER INFORMATION: 2'-OMe

```
<220> FEATURE:
<221> NAME/KEY: misc_feature
<222> LOCATION: (17)..(17)
<223> OTHER INFORMATION: 2'-OH
<220> FEATURE:
<221> NAME/KEY: misc_feature
<222> LOCATION: (18)..(18)
<223> OTHER INFORMATION: 2'-OMe
<220> FEATURE:
<221> NAME/KEY: misc_feature
<222> LOCATION: (19)..(19)
<223> OTHER INFORMATION: 2'-OH
<220> FEATURE:
<221> NAME/KEY: misc_feature
<222> LOCATION: (20)..(20)
<223> OTHER INFORMATION: 2'-OMe

<400> SEQUENCE: 70
aaguaaggac cagagacaaa                                              20

<210> SEQ ID NO 71
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphodiester linkages
<220> FEATURE:
<221> NAME/KEY: misc_feature
<222> LOCATION: (1)..(1)
<223> OTHER INFORMATION: 2'-OH
<220> FEATURE:
<221> NAME/KEY: misc_feature
<222> LOCATION: (2)..(2)
<223> OTHER INFORMATION: 2'-OMe
<220> FEATURE:
<221> NAME/KEY: misc_feature
<222> LOCATION: (3)..(3)
<223> OTHER INFORMATION: 2'-OH
<220> FEATURE:
<221> NAME/KEY: misc_feature
<222> LOCATION: (4)..(4)
<223> OTHER INFORMATION: 2'-OMe
<220> FEATURE:
<221> NAME/KEY: misc_feature
<222> LOCATION: (5)..(5)
<223> OTHER INFORMATION: 2'-OH
<220> FEATURE:
<221> NAME/KEY: misc_feature
<222> LOCATION: (6)..(6)
<223> OTHER INFORMATION: 2'-OMe
<220> FEATURE:
<221> NAME/KEY: misc_feature
<222> LOCATION: (7)..(7)
<223> OTHER INFORMATION: 2'-OH
<220> FEATURE:
<221> NAME/KEY: misc_feature
<222> LOCATION: (8)..(8)
<223> OTHER INFORMATION: 2'-OMe
<220> FEATURE:
<221> NAME/KEY: misc_feature
<222> LOCATION: (9)..(9)
<223> OTHER INFORMATION: 2'-OH
<220> FEATURE:
<221> NAME/KEY: misc_feature
<222> LOCATION: (10)..(10)
<223> OTHER INFORMATION: 2'-OMe
<220> FEATURE:
<221> NAME/KEY: misc_feature
<222> LOCATION: (11)..(11)
<223> OTHER INFORMATION: 2'-OH
<220> FEATURE:
<221> NAME/KEY: misc_feature
<222> LOCATION: (12)..(12)
```

```
<223> OTHER INFORMATION: 2'-OMe
<220> FEATURE:
<221> NAME/KEY: misc_feature
<222> LOCATION: (13)..(13)
<223> OTHER INFORMATION: 2'-OH
<220> FEATURE:
<221> NAME/KEY: misc_feature
<222> LOCATION: (14)..(14)
<223> OTHER INFORMATION: 2'-OMe
<220> FEATURE:
<221> NAME/KEY: misc_feature
<222> LOCATION: (15)..(15)
<223> OTHER INFORMATION: 2'-OH
<220> FEATURE:
<221> NAME/KEY: misc_feature
<222> LOCATION: (16)..(16)
<223> OTHER INFORMATION: 2'-OMe
<220> FEATURE:
<221> NAME/KEY: misc_feature
<222> LOCATION: (17)..(17)
<223> OTHER INFORMATION: 2'-OH
<220> FEATURE:
<221> NAME/KEY: misc_feature
<222> LOCATION: (18)..(18)
<223> OTHER INFORMATION: 2'-OMe
<220> FEATURE:
<221> NAME/KEY: misc_feature
<222> LOCATION: (19)..(19)
<223> OTHER INFORMATION: 2'-OH
<220> FEATURE:
<221> NAME/KEY: misc_feature
<222> LOCATION: (20)..(20)
<223> OTHER INFORMATION: 2'-OMe

<400> SEQUENCE: 71
uuugucucug guccuuacuu                                              20

<210> SEQ ID NO 72
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 2'-OH
<220> FEATURE:
<221> NAME/KEY: misc_feature
<222> LOCATION: (2)..(20)
<223> OTHER INFORMATION: phosphorthioate linkages
<220> FEATURE:
<221> NAME/KEY: misc_feature
<222> LOCATION: (3)..(3)
<223> OTHER INFORMATION: 2'-OH
<220> FEATURE:
<221> NAME/KEY: misc_feature
<222> LOCATION: (5)..(5)
<223> OTHER INFORMATION: 2'-OH
<220> FEATURE:
<221> NAME/KEY: misc_feature
<222> LOCATION: (7)..(7)
<223> OTHER INFORMATION: 2'-OH
<220> FEATURE:
<221> NAME/KEY: misc_feature
<222> LOCATION: (9)..(9)
<223> OTHER INFORMATION: 2'-OH
<220> FEATURE:
<221> NAME/KEY: misc_feature
<222> LOCATION: (11)..(11)
<223> OTHER INFORMATION: 2'-OH
<220> FEATURE:
<221> NAME/KEY: misc_feature
<222> LOCATION: (13)..(13)
<223> OTHER INFORMATION: 2'-OH
<220> FEATURE:
<221> NAME/KEY: misc_feature
```

```
<222> LOCATION: (15)..(15)
<223> OTHER INFORMATION: 2'-OH
<220> FEATURE:
<221> NAME/KEY: misc_feature
<222> LOCATION: (17)..(17)
<223> OTHER INFORMATION: 2'-OH
<220> FEATURE:
<221> NAME/KEY: misc_feature
<222> LOCATION: (19)..(19)
<223> OTHER INFORMATION: 2'-OH

<400> SEQUENCE: 72
uuugucucug guccuuacuu                                               20

<210> SEQ ID NO 73
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphodiester linkages
<220> FEATURE:
<221> NAME/KEY: misc_feature
<222> LOCATION: (1)..(1)
<223> OTHER INFORMATION: 2'-OH
<220> FEATURE:
<221> NAME/KEY: misc_feature
<222> LOCATION: (2)..(2)
<223> OTHER INFORMATION: 2'-F
<220> FEATURE:
<221> NAME/KEY: misc_feature
<222> LOCATION: (3)..(3)
<223> OTHER INFORMATION: 2'-OH
<220> FEATURE:
<221> NAME/KEY: misc_feature
<222> LOCATION: (4)..(4)
<223> OTHER INFORMATION: 2'-F
<220> FEATURE:
<221> NAME/KEY: misc_feature
<222> LOCATION: (5)..(5)
<223> OTHER INFORMATION: 2'-OH
<220> FEATURE:
<221> NAME/KEY: misc_feature
<222> LOCATION: (6)..(6)
<223> OTHER INFORMATION: 2'-F
<220> FEATURE:
<221> NAME/KEY: misc_feature
<222> LOCATION: (7)..(7)
<223> OTHER INFORMATION: 2'-OH
<220> FEATURE:
<221> NAME/KEY: misc_feature
<222> LOCATION: (8)..(8)
<223> OTHER INFORMATION: 2'-F
<220> FEATURE:
<221> NAME/KEY: misc_feature
<222> LOCATION: (9)..(9)
<223> OTHER INFORMATION: 2'-OH
<220> FEATURE:
<221> NAME/KEY: misc_feature
<222> LOCATION: (10)..(10)
<223> OTHER INFORMATION: 2'-F
<220> FEATURE:
<221> NAME/KEY: misc_feature
<222> LOCATION: (11)..(11)
<223> OTHER INFORMATION: 2'-OH
<220> FEATURE:
<221> NAME/KEY: misc_feature
<222> LOCATION: (12)..(12)
<223> OTHER INFORMATION: 2'-F
<220> FEATURE:
<221> NAME/KEY: misc_feature
<222> LOCATION: (13)..(13)
<223> OTHER INFORMATION: 2'-OH
<220> FEATURE:
```

```
<221> NAME/KEY: misc_feature
<222> LOCATION: (14)..(14)
<223> OTHER INFORMATION: 2'-F
<220> FEATURE:
<221> NAME/KEY: misc_feature
<222> LOCATION: (15)..(15)
<223> OTHER INFORMATION: 2'-OH
<220> FEATURE:
<221> NAME/KEY: misc_feature
<222> LOCATION: (16)..(16)
<223> OTHER INFORMATION: 2'-F
<220> FEATURE:
<221> NAME/KEY: misc_feature
<222> LOCATION: (17)..(17)
<223> OTHER INFORMATION: 2'-OH
<220> FEATURE:
<221> NAME/KEY: misc_feature
<222> LOCATION: (18)..(18)
<223> OTHER INFORMATION: 2'-F
<220> FEATURE:
<221> NAME/KEY: misc_feature
<222> LOCATION: (19)..(19)
<223> OTHER INFORMATION: 2'-OH

<400> SEQUENCE: 73
uuugucucug guccuuacuu                                            20

<210> SEQ ID NO 74
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 2'-OH
<220> FEATURE:
<221> NAME/KEY: misc_feature
<222> LOCATION: (2)..(20)
<223> OTHER INFORMATION: phosphorthioate linkages
<220> FEATURE:
<221> NAME/KEY: misc_feature
<222> LOCATION: (2)..(2)
<223> OTHER INFORMATION: 2'-F
<220> FEATURE:
<221> NAME/KEY: misc_feature
<222> LOCATION: (3)..(3)
<223> OTHER INFORMATION: 2'-OH
<220> FEATURE:
<221> NAME/KEY: misc_feature
<222> LOCATION: (4)..(4)
<223> OTHER INFORMATION: 2'-F
<220> FEATURE:
<221> NAME/KEY: misc_feature
<222> LOCATION: (5)..(5)
<223> OTHER INFORMATION: 2'-OH
<220> FEATURE:
<221> NAME/KEY: misc_feature
<222> LOCATION: (6)..(6)
<223> OTHER INFORMATION: 2'-F
<220> FEATURE:
<221> NAME/KEY: misc_feature
<222> LOCATION: (7)..(7)
<223> OTHER INFORMATION: 2'-OH
<220> FEATURE:
<221> NAME/KEY: misc_feature
<222> LOCATION: (8)..(8)
<223> OTHER INFORMATION: 2'-F
<220> FEATURE:
<221> NAME/KEY: misc_feature
<222> LOCATION: (9)..(9)
<223> OTHER INFORMATION: 2'-OH
<220> FEATURE:
<221> NAME/KEY: misc_feature
<222> LOCATION: (10)..(10)
<223> OTHER INFORMATION: 2'-F
```

```
<220> FEATURE:
<221> NAME/KEY: misc_feature
<222> LOCATION: (11)..(11)
<223> OTHER INFORMATION: 2'-OH
<220> FEATURE:
<221> NAME/KEY: misc_feature
<222> LOCATION: (12)..(12)
<223> OTHER INFORMATION: 2'-F
<220> FEATURE:
<221> NAME/KEY: misc_feature
<222> LOCATION: (13)..(13)
<223> OTHER INFORMATION: 2'-OH
<220> FEATURE:
<221> NAME/KEY: misc_feature
<222> LOCATION: (14)..(14)
<223> OTHER INFORMATION: 2'-F
<220> FEATURE:
<221> NAME/KEY: misc_feature
<222> LOCATION: (15)..(15)
<223> OTHER INFORMATION: 2'-OH
<220> FEATURE:
<221> NAME/KEY: misc_feature
<222> LOCATION: (16)..(16)
<223> OTHER INFORMATION: 2'-F
<220> FEATURE:
<221> NAME/KEY: misc_feature
<222> LOCATION: (17)..(17)
<223> OTHER INFORMATION: 2'-OH
<220> FEATURE:
<221> NAME/KEY: misc_feature
<222> LOCATION: (19)..(19)
<223> OTHER INFORMATION: 2'-OH
<220> FEATURE:
<221> NAME/KEY: misc_feature
<222> LOCATION: (20)..(20)
<223> OTHER INFORMATION: 2'-F

<400> SEQUENCE: 74
uuugucucug guccuuacuu                                                    20

<210> SEQ ID NO 75
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phophodiester linkages
<220> FEATURE:
<221> NAME/KEY: misc_feature
<222> LOCATION: (1)..(1)
<223> OTHER INFORMATION: 2'-OH
<220> FEATURE:
<221> NAME/KEY: misc_feature
<222> LOCATION: (2)..(2)
<223> OTHER INFORMATION: 2'-F
<220> FEATURE:
<221> NAME/KEY: misc_feature
<222> LOCATION: (3)..(3)
<223> OTHER INFORMATION: 2'-OH
<220> FEATURE:
<221> NAME/KEY: misc_feature
<222> LOCATION: (4)..(4)
<223> OTHER INFORMATION: 2'-F
<220> FEATURE:
<221> NAME/KEY: misc_feature
<222> LOCATION: (5)..(5)
<223> OTHER INFORMATION: 2'-OH
<220> FEATURE:
<221> NAME/KEY: misc_feature
<222> LOCATION: (6)..(6)
<223> OTHER INFORMATION: 2'-F
<220> FEATURE:
<221> NAME/KEY: misc_feature
<222> LOCATION: (7)..(7)
```

```
<223> OTHER INFORMATION: 2'-OH
<220> FEATURE:
<221> NAME/KEY: misc_feature
<222> LOCATION: (8)..(8)
<223> OTHER INFORMATION: 2'-F
<220> FEATURE:
<221> NAME/KEY: misc_feature
<222> LOCATION: (9)..(9)
<223> OTHER INFORMATION: 2'-OH
<220> FEATURE:
<221> NAME/KEY: misc_feature
<222> LOCATION: (11)..(11)
<223> OTHER INFORMATION: 2'-OH
<220> FEATURE:
<221> NAME/KEY: misc_feature
<222> LOCATION: (12)..(12)
<223> OTHER INFORMATION: 2'-F
<220> FEATURE:
<221> NAME/KEY: misc_feature
<222> LOCATION: (13)..(13)
<223> OTHER INFORMATION: 2'-OH
<220> FEATURE:
<221> NAME/KEY: misc_feature
<222> LOCATION: (14)..(14)
<223> OTHER INFORMATION: 2'-F
<220> FEATURE:
<221> NAME/KEY: misc_feature
<222> LOCATION: (15)..(15)
<223> OTHER INFORMATION: 2'-OH
<220> FEATURE:
<221> NAME/KEY: misc_feature
<222> LOCATION: (16)..(16)
<223> OTHER INFORMATION: 2'-F
<220> FEATURE:
<221> NAME/KEY: misc_feature
<222> LOCATION: (17)..(17)
<223> OTHER INFORMATION: 2'-OH
<220> FEATURE:
<221> NAME/KEY: misc_feature
<222> LOCATION: (18)..(18)
<223> OTHER INFORMATION: 2'-F
<220> FEATURE:
<221> NAME/KEY: misc_feature
<222> LOCATION: (19)..(19)
<223> OTHER INFORMATION: 2'-OH
<220> FEATURE:
<221> NAME/KEY: misc_feature
<222> LOCATION: (20)..(20)
<223> OTHER INFORMATION: 2'-F

<400> SEQUENCE: 75
aaguaaggac cagagacaaa                                              20

<210> SEQ ID NO 76
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 2'-F
<220> FEATURE:
<221> NAME/KEY: misc_feature
<222> LOCATION: (1)..(20)
<223> OTHER INFORMATION: phosphodiester linkages
<220> FEATURE:
<221> NAME/KEY: misc_feature
<222> LOCATION: (2)..(2)
<223> OTHER INFORMATION: 2'-OH
<220> FEATURE:
<221> NAME/KEY: misc_feature
<222> LOCATION: (3)..(3)
<223> OTHER INFORMATION: 2'-F
<220> FEATURE:
<221> NAME/KEY: misc_feature
```

```
<222> LOCATION: (4)..(4)
<223> OTHER INFORMATION: 2'-OH
<220> FEATURE:
<221> NAME/KEY: misc_feature
<222> LOCATION: (5)..(5)
<223> OTHER INFORMATION: 2'-F
<220> FEATURE:
<221> NAME/KEY: misc_feature
<222> LOCATION: (6)..(6)
<223> OTHER INFORMATION: 2'-OH
<220> FEATURE:
<221> NAME/KEY: misc_feature
<222> LOCATION: (7)..(7)
<223> OTHER INFORMATION: 2'-F
<220> FEATURE:
<221> NAME/KEY: misc_feature
<222> LOCATION: (8)..(8)
<223> OTHER INFORMATION: 2'-OH
<220> FEATURE:
<221> NAME/KEY: misc_feature
<222> LOCATION: (9)..(9)
<223> OTHER INFORMATION: 2'-F
<220> FEATURE:
<221> NAME/KEY: misc_feature
<222> LOCATION: (10)..(10)
<223> OTHER INFORMATION: 2'-OH
<220> FEATURE:
<221> NAME/KEY: misc_feature
<222> LOCATION: (11)..(11)
<223> OTHER INFORMATION: 2'-F
<220> FEATURE:
<221> NAME/KEY: misc_feature
<222> LOCATION: (12)..(12)
<223> OTHER INFORMATION: 2'-OH
<220> FEATURE:
<221> NAME/KEY: misc_feature
<222> LOCATION: (13)..(13)
<223> OTHER INFORMATION: 2'-F
<220> FEATURE:
<221> NAME/KEY: misc_feature
<222> LOCATION: (14)..(14)
<223> OTHER INFORMATION: 2'-OH
<220> FEATURE:
<221> NAME/KEY: misc_feature
<222> LOCATION: (15)..(15)
<223> OTHER INFORMATION: 2'-F
<220> FEATURE:
<221> NAME/KEY: misc_feature
<222> LOCATION: (16)..(16)
<223> OTHER INFORMATION: 2'-OH
<220> FEATURE:
<221> NAME/KEY: misc_feature
<222> LOCATION: (17)..(17)
<223> OTHER INFORMATION: 2'-F
<220> FEATURE:
<221> NAME/KEY: misc_feature
<222> LOCATION: (18)..(18)
<223> OTHER INFORMATION: 2'-OH
<220> FEATURE:
<221> NAME/KEY: misc_feature
<222> LOCATION: (19)..(19)
<223> OTHER INFORMATION: 2'-F
<220> FEATURE:
<221> NAME/KEY: misc_feature
<222> LOCATION: (20)..(20)
<223> OTHER INFORMATION: 2'-OH

<400> SEQUENCE: 76
aaguaaggac cagagacaaa                                              20

<210> SEQ ID NO 77
<211> LENGTH: 20
<212> TYPE: RNA
<213> ORGANISM: Artificial
<220> FEATURE:
<223> OTHER INFORMATION: Synthetic Construct
<220> FEATURE:
```

```
<221> NAME/KEY: misc_feature
<222> LOCATION: (1)..(20)
<223> OTHER INFORMATION: phosphodiester linkages
<220> FEATURE:
<221> NAME/KEY: misc_feature
<222> LOCATION: (1)..(1)
<223> OTHER INFORMATION: 2'-F
<220> FEATURE:
<221> NAME/KEY: misc_feature
<222> LOCATION: (2)..(2)
<223> OTHER INFORMATION: 2'-OH
<220> FEATURE:
<221> NAME/KEY: misc_feature
<222> LOCATION: (3)..(3)
<223> OTHER INFORMATION: 2'-F
<220> FEATURE:
<221> NAME/KEY: misc_feature
<222> LOCATION: (4)..(4)
<223> OTHER INFORMATION: 2'-OH
<220> FEATURE:
<221> NAME/KEY: misc_feature
<222> LOCATION: (5)..(5)
<223> OTHER INFORMATION: 2'-F
<220> FEATURE:
<221> NAME/KEY: misc_feature
<222> LOCATION: (6)..(6)
<223> OTHER INFORMATION: 2'-OH
<220> FEATURE:
<221> NAME/KEY: misc_feature
<222> LOCATION: (7)..(7)
<223> OTHER INFORMATION: 2'-F
<220> FEATURE:
<221> NAME/KEY: misc_feature
<222> LOCATION: (8)..(8)
<223> OTHER INFORMATION: 2'-OH
<220> FEATURE:
<221> NAME/KEY: misc_feature
<222> LOCATION: (9)..(9)
<223> OTHER INFORMATION: 2'-F
<220> FEATURE:
<221> NAME/KEY: misc_feature
<222> LOCATION: (10)..(10)
<223> OTHER INFORMATION: 2'-OH
<220> FEATURE:
<221> NAME/KEY: misc_feature
<222> LOCATION: (11)..(11)
<223> OTHER INFORMATION: 2'-F
<220> FEATURE:
<221> NAME/KEY: misc_feature
<222> LOCATION: (12)..(12)
<223> OTHER INFORMATION: 2'-OH
<220> FEATURE:
<221> NAME/KEY: misc_feature
<222> LOCATION: (13)..(13)
<223> OTHER INFORMATION: 2'-F
<220> FEATURE:
<221> NAME/KEY: misc_feature
<222> LOCATION: (14)..(14)
<223> OTHER INFORMATION: 2'-OH
<220> FEATURE:
<221> NAME/KEY: misc_feature
<222> LOCATION: (15)..(15)
<223> OTHER INFORMATION: 2'-F
<220> FEATURE:
<221> NAME/KEY: misc_feature
<222> LOCATION: (16)..(16)
<223> OTHER INFORMATION: 2'-OH
<220> FEATURE:
<221> NAME/KEY: misc_feature
<222> LOCATION: (17)..(17)
<223> OTHER INFORMATION: 2'-F
<220> FEATURE:
<221> NAME/KEY: misc_feature
<222> LOCATION: (18)..(18)
<223> OTHER INFORMATION: 2'-OH
<220> FEATURE:
<221> NAME/KEY: misc_feature
<222> LOCATION: (19)..(19)
<223> OTHER INFORMATION: 2'-F
```

<220> FEATURE:
<221> NAME/KEY: misc_feature
<222> LOCATION: (20)..(20)
<223> OTHER INFORMATION: 2'-OH

<400> SEQUENCE: 77
uuugucucug guccuuacuu					20

<210> SEQ ID NO 78
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphorthioate linkages
<220> FEATURE:
<221> NAME/KEY: misc_feature
<222> LOCATION: (1)..(1)
<223> OTHER INFORMATION: 2'-F
<220> FEATURE:
<221> NAME/KEY: misc_feature
<222> LOCATION: (2)..(2)
<223> OTHER INFORMATION: 2'-OH
<220> FEATURE:
<221> NAME/KEY: misc_feature
<222> LOCATION: (3)..(3)
<223> OTHER INFORMATION: 2'-F
<220> FEATURE:
<221> NAME/KEY: misc_feature
<222> LOCATION: (4)..(4)
<223> OTHER INFORMATION: 2'-OH
<220> FEATURE:
<221> NAME/KEY: misc_feature
<222> LOCATION: (5)..(5)
<223> OTHER INFORMATION: 2'-F
<220> FEATURE:
<221> NAME/KEY: misc_feature
<222> LOCATION: (6)..(6)
<223> OTHER INFORMATION: 2'-OH
<220> FEATURE:
<221> NAME/KEY: misc_feature
<222> LOCATION: (7)..(7)
<223> OTHER INFORMATION: 2'-F
<220> FEATURE:
<221> NAME/KEY: misc_feature
<222> LOCATION: (8)..(8)
<223> OTHER INFORMATION: 2'-OH
<220> FEATURE:
<221> NAME/KEY: misc_feature
<222> LOCATION: (9)..(9)
<223> OTHER INFORMATION: 2'-F
<220> FEATURE:
<221> NAME/KEY: misc_feature
<222> LOCATION: (10)..(10)
<223> OTHER INFORMATION: 2'-OH
<220> FEATURE:
<221> NAME/KEY: misc_feature
<222> LOCATION: (11)..(11)
<223> OTHER INFORMATION: 2'-F
<220> FEATURE:
<221> NAME/KEY: misc_feature
<222> LOCATION: (12)..(12)
<223> OTHER INFORMATION: 2'-OH
<220> FEATURE:
<221> NAME/KEY: misc_feature
<222> LOCATION: (13)..(13)
<223> OTHER INFORMATION: 2'-F
<220> FEATURE:
<221> NAME/KEY: misc_feature
<222> LOCATION: (14)..(14)
<223> OTHER INFORMATION: 2'-OH
<220> FEATURE:
<221> NAME/KEY: misc_feature
<222> LOCATION: (15)..(15)

<223> OTHER INFORMATION: 2'-F
<220> FEATURE:
<221> NAME/KEY: misc_feature
<222> LOCATION: (16)..(16)
<223> OTHER INFORMATION: 2'-OH
<220> FEATURE:
<221> NAME/KEY: misc_feature
<222> LOCATION: (17)..(17)
<223> OTHER INFORMATION: 2'-F
<220> FEATURE:
<221> NAME/KEY: misc_feature
<222> LOCATION: (18)..(18)
<223> OTHER INFORMATION: 2'-OH
<220> FEATURE:
<221> NAME/KEY: misc_feature
<222> LOCATION: (19)..(19)
<223> OTHER INFORMATION: 2'-F
<220> FEATURE:
<221> NAME/KEY: misc_feature
<222> LOCATION: (20)..(20)
<223> OTHER INFORMATION: 2'-OH

<400> SEQUENCE: 78 uuugcucug guccuuacuu                                            20

<210> SEQ ID NO 79
<211> LENGTH: 20
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphodiester linkages
<220> FEATURE:
<221> NAME/KEY: misc_feature
<222> LOCATION: (1)..(1)
<223> OTHER INFORMATION: 2'-OH with deoxy sugar
<220> FEATURE:
<221> NAME/KEY: misc_feature
<222> LOCATION: (2)..(2)
<223> OTHER INFORMATION: 2'-F
<220> FEATURE:
<221> NAME/KEY: misc_feature
<222> LOCATION: (3)..(3)
<223> OTHER INFORMATION: 2'-OH with deoxy sugar
<220> FEATURE:
<221> NAME/KEY: misc_feature
<222> LOCATION: (4)..(4)
<223> OTHER INFORMATION: 2'-F
<220> FEATURE:
<221> NAME/KEY: misc_feature
<222> LOCATION: (5)..(5)
<223> OTHER INFORMATION: 2'-OH with deoxy sugar
<220> FEATURE:
<221> NAME/KEY: misc_feature
<222> LOCATION: (6)..(6)
<223> OTHER INFORMATION: 2'-F
<220> FEATURE:
<221> NAME/KEY: misc_feature
<222> LOCATION: (7)..(7)
<223> OTHER INFORMATION: 2'-OH with deoxy sugar
<220> FEATURE:
<221> NAME/KEY: misc_feature
<222> LOCATION: (8)..(8)
<223> OTHER INFORMATION: 2'-F
<220> FEATURE:
<221> NAME/KEY: misc_feature
<222> LOCATION: (9)..(9)
<223> OTHER INFORMATION: 2'-OH with deoxy sugar
<220> FEATURE:
<221> NAME/KEY: misc_feature
<222> LOCATION: (10)..(10)
<223> OTHER INFORMATION: 2'-F
<220> FEATURE:
<221> NAME/KEY: misc_feature

```
<222> LOCATION: (11)..(11)
<223> OTHER INFORMATION: 2'-OH with deoxy sugar
<220> FEATURE:
<221> NAME/KEY: misc_feature
<222> LOCATION: (12)..(12)
<223> OTHER INFORMATION: 2'-F
<220> FEATURE:
<221> NAME/KEY: misc_feature
<222> LOCATION: (13)..(13)
<223> OTHER INFORMATION: 2'-OH with deoxy sugar
<220> FEATURE:
<221> NAME/KEY: misc_feature
<222> LOCATION: (14)..(14)
<223> OTHER INFORMATION: 2'-F
<220> FEATURE:
<221> NAME/KEY: misc_feature
<222> LOCATION: (15)..(15)
<223> OTHER INFORMATION: 2'-OH with deoxy sugar
<220> FEATURE:
<221> NAME/KEY: misc_feature
<222> LOCATION: (16)..(16)
<223> OTHER INFORMATION: 2'-F
<220> FEATURE:
<221> NAME/KEY: misc_feature
<222> LOCATION: (17)..(17)
<223> OTHER INFORMATION: 2'-OH with deoxy sugar
<220> FEATURE:
<221> NAME/KEY: misc_feature
<222> LOCATION: (18)..(18)
<223> OTHER INFORMATION: 2'-F
<220> FEATURE:
<221> NAME/KEY: misc_feature
<222> LOCATION: (19)..(19)
<223> OTHER INFORMATION: 2'-OH with deoxy sugar
<220> FEATURE:
<221> NAME/KEY: misc_feature
<222> LOCATION: (20)..(20)
<223> OTHER INFORMATION: 2'-F

<400> SEQUENCE: 79
tutgtctctg gucctuactu                                                    20

<210> SEQ ID NO 80
<211> LENGTH: 20
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphorthioate linkages
<220> FEATURE:
<221> NAME/KEY: misc_feature
<222> LOCATION: (1)..(1)
<223> OTHER INFORMATION: 2'-F
<220> FEATURE:
<221> NAME/KEY: misc_feature
<222> LOCATION: (2)..(2)
<223> OTHER INFORMATION: 2'-OH with deoxy sugar
<220> FEATURE:
<221> NAME/KEY: misc_feature
<222> LOCATION: (3)..(3)
<223> OTHER INFORMATION: 2'-F
<220> FEATURE:
<221> NAME/KEY: misc_feature
<222> LOCATION: (4)..(4)
<223> OTHER INFORMATION: 2'-OH with deoxy sugar
<220> FEATURE:
<221> NAME/KEY: misc_feature
<222> LOCATION: (5)..(5)
<223> OTHER INFORMATION: 2'-F
<220> FEATURE:
<221> NAME/KEY: misc_feature
<222> LOCATION: (6)..(6)
<223> OTHER INFORMATION: 2'-OH with deoxy sugar
<220> FEATURE:
```

```
<221> NAME/KEY: misc_feature
<222> LOCATION: (7)..(7)
<223> OTHER INFORMATION: 2'-F
<220> FEATURE:
<221> NAME/KEY: misc_feature
<222> LOCATION: (8)..(8)
<223> OTHER INFORMATION: 2'-OH with deoxy sugar
<220> FEATURE:
<221> NAME/KEY: misc_feature
<222> LOCATION: (9)..(9)
<223> OTHER INFORMATION: 2'-F
<220> FEATURE:
<221> NAME/KEY: misc_feature
<222> LOCATION: (10)..(10)
<223> OTHER INFORMATION: 2'-OH with deoxy sugar
<220> FEATURE:
<221> NAME/KEY: misc_feature
<222> LOCATION: (11)..(11)
<223> OTHER INFORMATION: 2'-F
<220> FEATURE:
<221> NAME/KEY: misc_feature
<222> LOCATION: (12)..(12)
<223> OTHER INFORMATION: 2'-OH with deoxy sugar
<220> FEATURE:
<221> NAME/KEY: misc_feature
<222> LOCATION: (13)..(13)
<223> OTHER INFORMATION: 2'-F
<220> FEATURE:
<221> NAME/KEY: misc_feature
<222> LOCATION: (14)..(14)
<223> OTHER INFORMATION: 2'-OH with deoxy sugar
<220> FEATURE:
<221> NAME/KEY: misc_feature
<222> LOCATION: (15)..(15)
<223> OTHER INFORMATION: 2'-F
<220> FEATURE:
<221> NAME/KEY: misc_feature
<222> LOCATION: (16)..(16)
<223> OTHER INFORMATION: 2'-OH with deoxy sugar
<220> FEATURE:
<221> NAME/KEY: misc_feature
<222> LOCATION: (17)..(17)
<223> OTHER INFORMATION: 2'-F
<220> FEATURE:
<221> NAME/KEY: misc_feature
<222> LOCATION: (18)..(18)
<223> OTHER INFORMATION: 2'-OH with deoxy sugar
<220> FEATURE:
<221> NAME/KEY: misc_feature
<222> LOCATION: (19)..(19)
<223> OTHER INFORMATION: 2'-F
<220> FEATURE:
<221> NAME/KEY: misc_feature
<222> LOCATION: (20)..(20)
<223> OTHER INFORMATION: 2'-OH with deoxy sugar

<400> SEQUENCE: 80
utcautccug gtctctgtut                                                    20

<210> SEQ ID NO 81
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphodiester linkages
<220> FEATURE:
<221> NAME/KEY: misc_feature
<222> LOCATION: (1)..(1)
<223> OTHER INFORMATION: 2'-OH with deoxy sugar
<220> FEATURE:
<221> NAME/KEY: misc_feature
<222> LOCATION: (2)..(2)
<223> OTHER INFORMATION: 2'-F
```

```
<220> FEATURE:
<221> NAME/KEY: misc_feature
<222> LOCATION: (3)..(3)
<223> OTHER INFORMATION: 2'-OH with deoxy sugar
<220> FEATURE:
<221> NAME/KEY: misc_feature
<222> LOCATION: (4)..(4)
<223> OTHER INFORMATION: 2'-F
<220> FEATURE:
<221> NAME/KEY: misc_feature
<222> LOCATION: (5)..(5)
<223> OTHER INFORMATION: 2'-OH with deoxy sugar
<220> FEATURE:
<221> NAME/KEY: misc_feature
<222> LOCATION: (6)..(6)
<223> OTHER INFORMATION: 2'-F
<220> FEATURE:
<221> NAME/KEY: misc_feature
<222> LOCATION: (7)..(7)
<223> OTHER INFORMATION: 2'-OH with deoxy sugar
<220> FEATURE:
<221> NAME/KEY: misc_feature
<222> LOCATION: (8)..(8)
<223> OTHER INFORMATION: 2'-F
<220> FEATURE:
<221> NAME/KEY: misc_feature
<222> LOCATION: (9)..(9)
<223> OTHER INFORMATION: 2'-OH with deoxy sugar
<220> FEATURE:
<221> NAME/KEY: misc_feature
<222> LOCATION: (10)..(10)
<223> OTHER INFORMATION: 2'-F
<220> FEATURE:
<221> NAME/KEY: misc_feature
<222> LOCATION: (11)..(11)
<223> OTHER INFORMATION: 2'-OH with deoxy sugar
<220> FEATURE:
<221> NAME/KEY: misc_feature
<222> LOCATION: (12)..(12)
<223> OTHER INFORMATION: 2'-F
<220> FEATURE:
<221> NAME/KEY: misc_feature
<222> LOCATION: (13)..(13)
<223> OTHER INFORMATION: 2'-OH with deoxy sugar
<220> FEATURE:
<221> NAME/KEY: misc_feature
<222> LOCATION: (14)..(14)
<223> OTHER INFORMATION: 2'-F
<220> FEATURE:
<221> NAME/KEY: misc_feature
<222> LOCATION: (15)..(15)
<223> OTHER INFORMATION: 2'-OH with deoxy sugar
<220> FEATURE:
<221> NAME/KEY: misc_feature
<222> LOCATION: (16)..(16)
<223> OTHER INFORMATION: 2'-F
<220> FEATURE:
<221> NAME/KEY: misc_feature
<222> LOCATION: (17)..(17)
<223> OTHER INFORMATION: 2'-OH with deoxy sugar
<220> FEATURE:
<221> NAME/KEY: misc_feature
<222> LOCATION: (18)..(18)
<223> OTHER INFORMATION: 2'-F
<220> FEATURE:
<221> NAME/KEY: misc_feature
<222> LOCATION: (19)..(19)
<223> OTHER INFORMATION: 2'-OH with deoxy sugar
<220> FEATURE:
<221> NAME/KEY: misc_feature
<222> LOCATION: (20)..(20)
<223> OTHER INFORMATION: 2'-F

<400> SEQUENCE: 81
aaguaaggac cagagacaaa                                                20

<210> SEQ ID NO 82
```

```
<211> LENGTH: 20
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphodiester linkages
<220> FEATURE:
<221> NAME/KEY: misc_feature
<222> LOCATION: (1)..(1)
<223> OTHER INFORMATION: 2'-F
<220> FEATURE:
<221> NAME/KEY: misc_feature
<222> LOCATION: (2)..(2)
<223> OTHER INFORMATION: 2'-OH with deoxy sugar
<220> FEATURE:
<221> NAME/KEY: misc_feature
<222> LOCATION: (3)..(3)
<223> OTHER INFORMATION: 2'-F
<220> FEATURE:
<221> NAME/KEY: misc_feature
<222> LOCATION: (4)..(4)
<223> OTHER INFORMATION: 2'-OH with deoxy sugar
<220> FEATURE:
<221> NAME/KEY: misc_feature
<222> LOCATION: (5)..(5)
<223> OTHER INFORMATION: 2'-F
<220> FEATURE:
<221> NAME/KEY: misc_feature
<222> LOCATION: (6)..(6)
<223> OTHER INFORMATION: 2'-OH with deoxy sugar
<220> FEATURE:
<221> NAME/KEY: misc_feature
<222> LOCATION: (7)..(7)
<223> OTHER INFORMATION: 2'-F
<220> FEATURE:
<221> NAME/KEY: misc_feature
<222> LOCATION: (8)..(8)
<223> OTHER INFORMATION: 2'-OH with deoxy sugar
<220> FEATURE:
<221> NAME/KEY: misc_feature
<222> LOCATION: (9)..(9)
<223> OTHER INFORMATION: 2'-F
<220> FEATURE:
<221> NAME/KEY: misc_feature
<222> LOCATION: (10)..(10)
<223> OTHER INFORMATION: 2'-OH with deoxy sugar
<220> FEATURE:
<221> NAME/KEY: misc_feature
<222> LOCATION: (11)..(11)
<223> OTHER INFORMATION: 2'-F
<220> FEATURE:
<221> NAME/KEY: misc_feature
<222> LOCATION: (12)..(12)
<223> OTHER INFORMATION: 2'-OH with deoxy sugar
<220> FEATURE:
<221> NAME/KEY: misc_feature
<222> LOCATION: (13)..(13)
<223> OTHER INFORMATION: 2'-F
<220> FEATURE:
<221> NAME/KEY: misc_feature
<222> LOCATION: (14)..(14)
<223> OTHER INFORMATION: 2'-OH with deoxy sugar
<220> FEATURE:
<221> NAME/KEY: misc_feature
<222> LOCATION: (15)..(15)
<223> OTHER INFORMATION: 2'-F
<220> FEATURE:
<221> NAME/KEY: misc_feature
<222> LOCATION: (16)..(16)
<223> OTHER INFORMATION: 2'-OH with deoxy sugar
<220> FEATURE:
<221> NAME/KEY: misc_feature
<222> LOCATION: (17)..(17)
<223> OTHER INFORMATION: 2'-F
<220> FEATURE:
<221> NAME/KEY: misc_feature
```

```
<222> LOCATION: (18)..(18)
<223> OTHER INFORMATION: 2'-OH with deoxy sugar
<220> FEATURE:
<221> NAME/KEY: misc_feature
<222> LOCATION: (19)..(19)
<223> OTHER INFORMATION: 2'-F
<220> FEATURE:
<221> NAME/KEY: misc_feature
<222> LOCATION: (20)..(20)
<223> OTHER INFORMATION: 2'-OH with deoxy sugar

<400> SEQUENCE: 82
aagtaaggac cagagacaaa                                                    20

<210> SEQ ID NO 83
<211> LENGTH: 20
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphodiester linkages
<220> FEATURE:
<221> NAME/KEY: misc_feature
<222> LOCATION: (1)..(1)
<223> OTHER INFORMATION: 2'-OH with deoxy sugar
<220> FEATURE:
<221> NAME/KEY: misc_feature
<222> LOCATION: (2)..(2)
<223> OTHER INFORMATION: 2'-F
<220> FEATURE:
<221> NAME/KEY: misc_feature
<222> LOCATION: (3)..(3)
<223> OTHER INFORMATION: 2'-OH with deoxy sugar
<220> FEATURE:
<221> NAME/KEY: misc_feature
<222> LOCATION: (4)..(4)
<223> OTHER INFORMATION: 2'-F
<220> FEATURE:
<221> NAME/KEY: misc_feature
<222> LOCATION: (5)..(5)
<223> OTHER INFORMATION: 2'-OH with deoxy sugar
<220> FEATURE:
<221> NAME/KEY: misc_feature
<222> LOCATION: (6)..(6)
<223> OTHER INFORMATION: 2'-F
<220> FEATURE:
<221> NAME/KEY: misc_feature
<222> LOCATION: (7)..(7)
<223> OTHER INFORMATION: 2'-OH with deoxy sugar
<220> FEATURE:
<221> NAME/KEY: misc_feature
<222> LOCATION: (8)..(8)
<223> OTHER INFORMATION: 2'-F
<220> FEATURE:
<221> NAME/KEY: misc_feature
<222> LOCATION: (9)..(9)
<223> OTHER INFORMATION: 2'-OH with deoxy sugar
<220> FEATURE:
<221> NAME/KEY: misc_feature
<222> LOCATION: (10)..(10)
<223> OTHER INFORMATION: 2'-F
<220> FEATURE:
<221> NAME/KEY: misc_feature
<222> LOCATION: (11)..(11)
<223> OTHER INFORMATION: 2'-OH with deoxy sugar
<220> FEATURE:
<221> NAME/KEY: misc_feature
<222> LOCATION: (12)..(12)
<223> OTHER INFORMATION: 2'-F
<220> FEATURE:
<221> NAME/KEY: misc_feature
<222> LOCATION: (13)..(13)
<223> OTHER INFORMATION: 2'-OH with deoxy sugar
<220> FEATURE:
```

```
<221> NAME/KEY: misc_feature
<222> LOCATION: (14)..(14)
<223> OTHER INFORMATION: 2'-F
<220> FEATURE:
<221> NAME/KEY: misc_feature
<222> LOCATION: (15)..(15)
<223> OTHER INFORMATION: 2'-OH with deoxy sugar
<220> FEATURE:
<221> NAME/KEY: misc_feature
<222> LOCATION: (16)..(16)
<223> OTHER INFORMATION: 2'-F
<220> FEATURE:
<221> NAME/KEY: misc_feature
<222> LOCATION: (17)..(17)
<223> OTHER INFORMATION: 2'-OH with deoxy sugar
<220> FEATURE:
<221> NAME/KEY: misc_feature
<222> LOCATION: (18)..(18)
<223> OTHER INFORMATION: 2'-F
<220> FEATURE:
<221> NAME/KEY: misc_feature
<222> LOCATION: (19)..(19)
<223> OTHER INFORMATION: 2'-OH with deoxy sugar
<220> FEATURE:
<221> NAME/KEY: misc_feature
<222> LOCATION: (20)..(20)
<223> OTHER INFORMATION: 2'-F

<400> SEQUENCE: 83
utugucucug gtccutacut                                                         20

<210> SEQ ID NO 84
<211> LENGTH: 20
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphorthioate linkages
<220> FEATURE:
<221> NAME/KEY: misc_feature
<222> LOCATION: (1)..(1)
<223> OTHER INFORMATION: 2'-OH with deoxy sugar
<220> FEATURE:
<221> NAME/KEY: misc_feature
<222> LOCATION: (2)..(2)
<223> OTHER INFORMATION: 2'-F
<220> FEATURE:
<221> NAME/KEY: misc_feature
<222> LOCATION: (3)..(3)
<223> OTHER INFORMATION: 2'-OH with deoxy sugar
<220> FEATURE:
<221> NAME/KEY: misc_feature
<222> LOCATION: (4)..(4)
<223> OTHER INFORMATION: 2'-F
<220> FEATURE:
<221> NAME/KEY: misc_feature
<222> LOCATION: (5)..(5)
<223> OTHER INFORMATION: 2'-OH with deoxy sugar
<220> FEATURE:
<221> NAME/KEY: misc_feature
<222> LOCATION: (6)..(6)
<223> OTHER INFORMATION: 2'-F
<220> FEATURE:
<221> NAME/KEY: misc_feature
<222> LOCATION: (7)..(7)
<223> OTHER INFORMATION: 2'-OH with deoxy sugar
<220> FEATURE:
<221> NAME/KEY: misc_feature
<222> LOCATION: (8)..(8)
<223> OTHER INFORMATION: 2'-F
<220> FEATURE:
<221> NAME/KEY: misc_feature
<222> LOCATION: (9)..(9)
<223> OTHER INFORMATION: 2'-OH with deoxy sugar
```

```
<220> FEATURE:
<221> NAME/KEY: misc_feature
<222> LOCATION: (10)..(10)
<223> OTHER INFORMATION: 2'-F
<220> FEATURE:
<221> NAME/KEY: misc_feature
<222> LOCATION: (11)..(11)
<223> OTHER INFORMATION: 2'-OH with deoxy sugar
<220> FEATURE:
<221> NAME/KEY: misc_feature
<222> LOCATION: (12)..(12)
<223> OTHER INFORMATION: 2'-F
<220> FEATURE:
<221> NAME/KEY: misc_feature
<222> LOCATION: (13)..(13)
<223> OTHER INFORMATION: 2'-OH with deoxy sugar
<220> FEATURE:
<221> NAME/KEY: misc_feature
<222> LOCATION: (14)..(14)
<223> OTHER INFORMATION: 2'-F
<220> FEATURE:
<221> NAME/KEY: misc_feature
<222> LOCATION: (15)..(15)
<223> OTHER INFORMATION: 2'-OH with deoxy sugar
<220> FEATURE:
<221> NAME/KEY: misc_feature
<222> LOCATION: (16)..(16)
<223> OTHER INFORMATION: 2'-F
<220> FEATURE:
<221> NAME/KEY: misc_feature
<222> LOCATION: (17)..(17)
<223> OTHER INFORMATION: 2'-OH with deoxy sugar
<220> FEATURE:
<221> NAME/KEY: misc_feature
<222> LOCATION: (18)..(18)
<223> OTHER INFORMATION: 2'-F
<220> FEATURE:
<221> NAME/KEY: misc_feature
<222> LOCATION: (19)..(19)
<223> OTHER INFORMATION: 2'-OH with deoxy sugar
<220> FEATURE:
<221> NAME/KEY: misc_feature
<222> LOCATION: (20)..(20)
<223> OTHER INFORMATION: 2'-F

<400> SEQUENCE: 84
utugucucug gtccutacut                                                   20

```
<223> OTHER INFORMATION: 2'-OMe
<220> FEATURE:
<221> NAME/KEY: misc_feature
<222> LOCATION: (6)..(6)
<223> OTHER INFORMATION: 2'-F
<220> FEATURE:
<221> NAME/KEY: misc_feature
<222> LOCATION: (7)..(7)
<223> OTHER INFORMATION: 2'-OMe
<220> FEATURE:
<221> NAME/KEY: misc_feature
<222> LOCATION: (8)..(8)
<223> OTHER INFORMATION: 2'-F
<220> FEATURE:
<221> NAME/KEY: misc_feature
<222> LOCATION: (9)..(9)
<223> OTHER INFORMATION: 2'-OMe
<220> FEATURE:
<221> NAME/KEY: misc_feature
<222> LOCATION: (10)..(10)
<223> OTHER INFORMATION: 2'-F
<220> FEATURE:
<221> NAME/KEY: misc_feature
<222> LOCATION: (11)..(11)
<223> OTHER INFORMATION: 2'-OMe
<220> FEATURE:
<221> NAME/KEY: misc_feature
<222> LOCATION: (12)..(12)
<223> OTHER INFORMATION: 2'-F
<220> FEATURE:
<221> NAME/KEY: misc_feature
<222> LOCATION: (13)..(13)
<223> OTHER INFORMATION: 2'-OMe
<220> FEATURE:
<221> NAME/KEY: misc_feature
<222> LOCATION: (14)..(14)
<223> OTHER INFORMATION: 2'-F
<220> FEATURE:
<221> NAME/KEY: misc_feature
<222> LOCATION: (15)..(15)
<223> OTHER INFORMATION: 2'-OMe
<220> FEATURE:
<221> NAME/KEY: misc_feature
<222> LOCATION: (16)..(16)
<223> OTHER INFORMATION: 2'-F
<220> FEATURE:
<221> NAME/KEY: misc_feature
<222> LOCATION: (17)..(17)
<223> OTHER INFORMATION: 2'-OMe
<220> FEATURE:
<221> NAME/KEY: misc_feature
<222> LOCATION: (18)..(18)
<223> OTHER INFORMATION: 2'-F
<220> FEATURE:
<221> NAME/KEY: misc_feature
<222> LOCATION: (19)..(19)
<223> OTHER INFORMATION: 2'-OMe
<220> FEATURE:
<221> NAME/KEY: misc_feature
<222> LOCATION: (20)..(20)
<223> OTHER INFORMATION: 2'-F

<400> SEQUENCE: 85
uuugucucug guccuuacuu                                                    20

<210> SEQ ID NO 86
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphodiester linkages
<220> FEATURE:
<221> NAME/KEY: misc_feature
```

```
<222> LOCATION: (1)..(1)
<223> OTHER INFORMATION: 2'-OMe
<220> FEATURE:
<221> NAME/KEY: misc_feature
<222> LOCATION: (2)..(2)
<223> OTHER INFORMATION: 2'-F
<220> FEATURE:
<221> NAME/KEY: misc_feature
<222> LOCATION: (3)..(3)
<223> OTHER INFORMATION: 2'-OMe
<220> FEATURE:
<221> NAME/KEY: misc_feature
<222> LOCATION: (4)..(4)
<223> OTHER INFORMATION: 2'-F
<220> FEATURE:
<221> NAME/KEY: misc_feature
<222> LOCATION: (5)..(5)
<223> OTHER INFORMATION: 2'-OMe
<220> FEATURE:
<221> NAME/KEY: misc_feature
<222> LOCATION: (6)..(6)
<223> OTHER INFORMATION: 2'-F
<220> FEATURE:
<221> NAME/KEY: misc_feature
<222> LOCATION: (7)..(7)
<223> OTHER INFORMATION: 2'-OMe
<220> FEATURE:
<221> NAME/KEY: misc_feature
<222> LOCATION: (8)..(8)
<223> OTHER INFORMATION: 2'-F
<220> FEATURE:
<221> NAME/KEY: misc_feature
<222> LOCATION: (9)..(9)
<223> OTHER INFORMATION: 2'-OMe
<220> FEATURE:
<221> NAME/KEY: misc_feature
<222> LOCATION: (10)..(10)
<223> OTHER INFORMATION: 2'-F
<220> FEATURE:
<221> NAME/KEY: misc_feature
<222> LOCATION: (11)..(11)
<223> OTHER INFORMATION: 2'-OMe
<220> FEATURE:
<221> NAME/KEY: misc_feature
<222> LOCATION: (12)..(12)
<223> OTHER INFORMATION: 2'-F
<220> FEATURE:
<221> NAME/KEY: misc_feature
<222> LOCATION: (13)..(13)
<223> OTHER INFORMATION: 2'-OMe
<220> FEATURE:
<221> NAME/KEY: misc_feature
<222> LOCATION: (14)..(14)
<223> OTHER INFORMATION: 2'-F
<220> FEATURE:
<221> NAME/KEY: misc_feature
<222> LOCATION: (15)..(15)
<223> OTHER INFORMATION: 2'-OMe
<220> FEATURE:
<221> NAME/KEY: misc_feature
<222> LOCATION: (16)..(16)
<223> OTHER INFORMATION: 2'-F
<220> FEATURE:
<221> NAME/KEY: misc_feature
<222> LOCATION: (17)..(17)
<223> OTHER INFORMATION: 2'-OMe
<220> FEATURE:
<221> NAME/KEY: misc_feature
<222> LOCATION: (18)..(18)
<223> OTHER INFORMATION: 2'-F
<220> FEATURE:
<221> NAME/KEY: misc_feature
<222> LOCATION: (19)..(19)
<223> OTHER INFORMATION: 2'-OMe
<220> FEATURE:
<221> NAME/KEY: misc_feature
<222> LOCATION: (20)..(20)
<223> OTHER INFORMATION: 2'-F
```

<400> SEQUENCE: 86
uuugucucug guccuuacuu						20

<210> SEQ ID NO 87
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphodiester linkages
<220> FEATURE:
<221> NAME/KEY: misc_feature
<222> LOCATION: (1)..(1)
<223> OTHER INFORMATION: 2'-OMe
<220> FEATURE:
<221> NAME/KEY: misc_feature
<222> LOCATION: (2)..(2)
<223> OTHER INFORMATION: 2'-F
<220> FEATURE:
<221> NAME/KEY: misc_feature
<222> LOCATION: (3)..(3)
<223> OTHER INFORMATION: 2'-OMe
<220> FEATURE:
<221> NAME/KEY: misc_feature
<222> LOCATION: (4)..(4)
<223> OTHER INFORMATION: 2'-F
<220> FEATURE:
<221> NAME/KEY: misc_feature
<222> LOCATION: (5)..(5)
<223> OTHER INFORMATION: 2'-OMe
<220> FEATURE:
<221> NAME/KEY: misc_feature
<222> LOCATION: (6)..(6)
<223> OTHER INFORMATION: 2'-F
<220> FEATURE:
<221> NAME/KEY: misc_feature
<222> LOCATION: (7)..(7)
<223> OTHER INFORMATION: 2'-OMe
<220> FEATURE:
<221> NAME/KEY: misc_feature
<222> LOCATION: (8)..(8)
<223> OTHER INFORMATION: 2'-F
<220> FEATURE:
<221> NAME/KEY: misc_feature
<222> LOCATION: (9)..(9)
<223> OTHER INFORMATION: 2'-OMe
<220> FEATURE:
<221> NAME/KEY: misc_feature
<222> LOCATION: (10)..(10)
<223> OTHER INFORMATION: 2'-F
<220> FEATURE:
<221> NAME/KEY: misc_feature
<222> LOCATION: (11)..(11)
<223> OTHER INFORMATION: 2'-OMe
<220> FEATURE:
<221> NAME/KEY: misc_feature
<222> LOCATION: (12)..(12)
<223> OTHER INFORMATION: 2'-F
<220> FEATURE:
<221> NAME/KEY: misc_feature
<222> LOCATION: (13)..(13)
<223> OTHER INFORMATION: 2'-OMe
<220> FEATURE:
<221> NAME/KEY: misc_feature
<222> LOCATION: (14)..(14)
<223> OTHER INFORMATION: 2'-F
<220> FEATURE:
<221> NAME/KEY: misc_feature
<222> LOCATION: (15)..(15)
<223> OTHER INFORMATION: 2'-OMe
<220> FEATURE:
<221> NAME/KEY: misc_feature
<222> LOCATION: (16)..(16)
<223> OTHER INFORMATION: 2'-F -continued

```
<220> FEATURE:
<221> NAME/KEY: misc_feature
<222> LOCATION: (17)..(17)
<223> OTHER INFORMATION: 2'-OMe
<220> FEATURE:
<221> NAME/KEY: misc_feature
<222> LOCATION: (18)..(18)
<223> OTHER INFORMATION: 2'-F
<220> FEATURE:
<221> NAME/KEY: misc_feature
<222> LOCATION: (19)..(19)
<223> OTHER INFORMATION: 2'-OMe
<220> FEATURE:
<221> NAME/KEY: misc_feature
<222> LOCATION: (20)..(20)
<223> OTHER INFORMATION: 2'-F

<400> SEQUENCE: 87
uuugucucug guccuuacuu                                               20

<210> SEQ ID NO 88
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphodiester linkages
<220> FEATURE:
<221> NAME/KEY: misc_feature
<222> LOCATION: (1)..(1)
<223> OTHER INFORMATION: 2'-F
<220> FEATURE:
<221> NAME/KEY: misc_feature
<222> LOCATION: (2)..(2)
<223> OTHER INFORMATION: 2'-OMe
<220> FEATURE:
<221> NAME/KEY: misc_feature
<222> LOCATION: (3)..(3)
<223> OTHER INFORMATION: 2'-F
<220> FEATURE:
<221> NAME/KEY: misc_feature
<222> LOCATION: (4)..(4)
<223> OTHER INFORMATION: 2'-OMe
<220> FEATURE:
<221> NAME/KEY: misc_feature
<222> LOCATION: (5)..(5)
<223> OTHER INFORMATION: 2'-F
<220> FEATURE:
<221> NAME/KEY: misc_feature
<222> LOCATION: (6)..(6)
<223> OTHER INFORMATION: 2'-OMe
<220> FEATURE:
<221> NAME/KEY: misc_feature
<222> LOCATION: (7)..(7)
<223> OTHER INFORMATION: 2'-F
<220> FEATURE:
<221> NAME/KEY: misc_feature
<222> LOCATION: (8)..(8)
<223> OTHER INFORMATION: 2'-OMe
<220> FEATURE:
<221> NAME/KEY: misc_feature
<222> LOCATION: (9)..(9)
<223> OTHER INFORMATION: 2'-F
<220> FEATURE:
<221> NAME/KEY: misc_feature
<222> LOCATION: (10)..(10)
<223> OTHER INFORMATION: 2'-OMe
<220> FEATURE:
<221> NAME/KEY: misc_feature
<222> LOCATION: (11)..(11)
<223> OTHER INFORMATION: 2'-F
<220> FEATURE:
<221> NAME/KEY: misc_feature
<222> LOCATION: (12)..(12)
```

```
<223> OTHER INFORMATION: 2'-OMe
<220> FEATURE:
<221> NAME/KEY: misc_feature
<222> LOCATION: (13)..(13)
<223> OTHER INFORMATION: 2'-F
<220> FEATURE:
<221> NAME/KEY: misc_feature
<222> LOCATION: (14)..(14)
<223> OTHER INFORMATION: 2'-OMe
<220> FEATURE:
<221> NAME/KEY: misc_feature
<222> LOCATION: (15)..(15)
<223> OTHER INFORMATION: 2'-F
<220> FEATURE:
<221> NAME/KEY: misc_feature
<222> LOCATION: (16)..(16)
<223> OTHER INFORMATION: 2'-OMe
<220> FEATURE:
<221> NAME/KEY: misc_feature
<222> LOCATION: (17)..(17)
<223> OTHER INFORMATION: 2'-F
<220> FEATURE:
<221> NAME/KEY: misc_feature
<222> LOCATION: (18)..(18)
<223> OTHER INFORMATION: 2'-OMe
<220> FEATURE:
<221> NAME/KEY: misc_feature
<222> LOCATION: (19)..(19)
<223> OTHER INFORMATION: 2'-F
<220> FEATURE:
<221> NAME/KEY: misc_feature
<222> LOCATION: (20)..(20)
<223> OTHER INFORMATION: 2'-OMe

<400> SEQUENCE: 88
uuugucucug guccuuacuu                                               20

<210> SEQ ID NO 89
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphodiester linkages
<220> FEATURE:
<221> NAME/KEY: misc_feature
<222> LOCATION: (1)..(1)
<223> OTHER INFORMATION: 2'-F
<220> FEATURE:
<221> NAME/KEY: misc_feature
<222> LOCATION: (2)..(2)
<223> OTHER INFORMATION: 2'-OMe
<220> FEATURE:
<221> NAME/KEY: misc_feature
<222> LOCATION: (3)..(3)
<223> OTHER INFORMATION: 2'-F
<220> FEATURE:
<221> NAME/KEY: misc_feature
<222> LOCATION: (4)..(4)
<223> OTHER INFORMATION: 2'-OMe
<220> FEATURE:
<221> NAME/KEY: misc_feature
<222> LOCATION: (5)..(5)
<223> OTHER INFORMATION: 2'-F
<220> FEATURE:
<221> NAME/KEY: misc_feature
<222> LOCATION: (6)..(6)
<223> OTHER INFORMATION: 2'-OMe
<220> FEATURE:
<221> NAME/KEY: misc_feature
<222> LOCATION: (7)..(7)
<223> OTHER INFORMATION: 2'-F
<220> FEATURE:
<221> NAME/KEY: misc_feature
```

```
<222> LOCATION: (8)..(8)
<223> OTHER INFORMATION: 2'-OMe
<220> FEATURE:
<221> NAME/KEY: misc_feature
<222> LOCATION: (9)..(9)
<223> OTHER INFORMATION: 2'-F
<220> FEATURE:
<221> NAME/KEY: misc_feature
<222> LOCATION: (10)..(10)
<223> OTHER INFORMATION: 2'-OMe
<220> FEATURE:
<221> NAME/KEY: misc_feature
<222> LOCATION: (11)..(11)
<223> OTHER INFORMATION: 2'-F
<220> FEATURE:
<221> NAME/KEY: misc_feature
<222> LOCATION: (12)..(12)
<223> OTHER INFORMATION: 2'-OMe
<220> FEATURE:
<221> NAME/KEY: misc_feature
<222> LOCATION: (13)..(13)
<223> OTHER INFORMATION: 2'-F
<220> FEATURE:
<221> NAME/KEY: misc_feature
<222> LOCATION: (14)..(14)
<223> OTHER INFORMATION: 2'-OMe
<220> FEATURE:
<221> NAME/KEY: misc_feature
<222> LOCATION: (15)..(15)
<223> OTHER INFORMATION: 2'-F
<220> FEATURE:
<221> NAME/KEY: misc_feature
<222> LOCATION: (16)..(16)
<223> OTHER INFORMATION: 2'-OMe
<220> FEATURE:
<221> NAME/KEY: misc_feature
<222> LOCATION: (17)..(17)
<223> OTHER INFORMATION: 2'-F
<220> FEATURE:
<221> NAME/KEY: misc_feature
<222> LOCATION: (18)..(18)
<223> OTHER INFORMATION: 2'-OMe
<220> FEATURE:
<221> NAME/KEY: misc_feature
<222> LOCATION: (19)..(19)
<223> OTHER INFORMATION: 2'-F
<220> FEATURE:
<221> NAME/KEY: misc_feature
<222> LOCATION: (20)..(20)
<223> OTHER INFORMATION: 2'-OMe

<400> SEQUENCE: 89
aaguaaggac cagagacaaa                                                    20

<210> SEQ ID NO 90
<211> LENGTH: 19
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(19)
<223> OTHER INFORMATION: phosphodiester linkages
<220> FEATURE:
<221> NAME/KEY: misc_feature
<222> LOCATION: (1)..(1)
<223> OTHER INFORMATION: 2'-OMe
<220> FEATURE:
<221> NAME/KEY: misc_feature
<222> LOCATION: (2)..(2)
<223> OTHER INFORMATION: 2'-F
<220> FEATURE:
<221> NAME/KEY: misc_feature
<222> LOCATION: (3)..(3)
<223> OTHER INFORMATION: 2'-OMe
<220> FEATURE:
```

```
<221> NAME/KEY: misc_feature
<222> LOCATION: (4)..(4)
<223> OTHER INFORMATION: 2'-F
<220> FEATURE:
<221> NAME/KEY: misc_feature
<222> LOCATION: (5)..(5)
<223> OTHER INFORMATION: 2'-OMe
<220> FEATURE:
<221> NAME/KEY: misc_feature
<222> LOCATION: (6)..(6)
<223> OTHER INFORMATION: 2'-F
<220> FEATURE:
<221> NAME/KEY: misc_feature
<222> LOCATION: (7)..(7)
<223> OTHER INFORMATION: 2'-OMe
<220> FEATURE:
<221> NAME/KEY: misc_feature
<222> LOCATION: (8)..(8)
<223> OTHER INFORMATION: 2'-F
<220> FEATURE:
<221> NAME/KEY: misc_feature
<222> LOCATION: (9)..(9)
<223> OTHER INFORMATION: 2'-OMe
<220> FEATURE:
<221> NAME/KEY: misc_feature
<222> LOCATION: (10)..(10)
<223> OTHER INFORMATION: 2'-F
<220> FEATURE:
<221> NAME/KEY: misc_feature
<222> LOCATION: (11)..(11)
<223> OTHER INFORMATION: 2'-OMe
<220> FEATURE:
<221> NAME/KEY: misc_feature
<222> LOCATION: (12)..(12)
<223> OTHER INFORMATION: 2'-F
<220> FEATURE:
<221> NAME/KEY: misc_feature
<222> LOCATION: (13)..(13)
<223> OTHER INFORMATION: 2'-OMe
<220> FEATURE:
<221> NAME/KEY: misc_feature
<222> LOCATION: (14)..(14)
<223> OTHER INFORMATION: 2'-F
<220> FEATURE:
<221> NAME/KEY: misc_feature
<222> LOCATION: (15)..(15)
<223> OTHER INFORMATION: 2'-OMe
<220> FEATURE:
<221> NAME/KEY: misc_feature
<222> LOCATION: (16)..(16)
<223> OTHER INFORMATION: 2'-F
<220> FEATURE:
<221> NAME/KEY: misc_feature
<222> LOCATION: (17)..(17)
<223> OTHER INFORMATION: 2'-OMe
<220> FEATURE:
<221> NAME/KEY: misc_feature
<222> LOCATION: (18)..(18)
<223> OTHER INFORMATION: 2'-F
<220> FEATURE:
<221> NAME/KEY: misc_feature
<222> LOCATION: (19)..(19)
<223> OTHER INFORMATION: 2'-OMe

<400> SEQUENCE: 90
auguagaaug uauuuaccc                                                19

<210> SEQ ID NO 91
<211> LENGTH: 19
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(19)
<223> OTHER INFORMATION: phosphodiester linkages
```

-continued

```
<220> FEATURE:
<221> NAME/KEY: misc_feature
<222> LOCATION: (1)..(1)
<223> OTHER INFORMATION: 2'-F
<220> FEATURE:
<221> NAME/KEY: misc_feature
<222> LOCATION: (2)..(2)
<223> OTHER INFORMATION: 2'-OMe
<220> FEATURE:
<221> NAME/KEY: misc_feature
<222> LOCATION: (3)..(3)
<223> OTHER INFORMATION: 2'-F
<220> FEATURE:
<221> NAME/KEY: misc_feature
<222> LOCATION: (4)..(4)
<223> OTHER INFORMATION: 2'-OMe
<220> FEATURE:
<221> NAME/KEY: misc_feature
<222> LOCATION: (5)..(5)
<223> OTHER INFORMATION: 2'-F
<220> FEATURE:
<221> NAME/KEY: misc_feature
<222> LOCATION: (6)..(6)
<223> OTHER INFORMATION: 2'-OMe
<220> FEATURE:
<221> NAME/KEY: misc_feature
<222> LOCATION: (7)..(7)
<223> OTHER INFORMATION: 2'-F
<220> FEATURE:
<221> NAME/KEY: misc_feature
<222> LOCATION: (8)..(8)
<223> OTHER INFORMATION: 2'-OMe
<220> FEATURE:
<221> NAME/KEY: misc_feature
<222> LOCATION: (9)..(9)
<223> OTHER INFORMATION: 2'-F
<220> FEATURE:
<221> NAME/KEY: misc_feature
<222> LOCATION: (10)..(10)
<223> OTHER INFORMATION: 2'-OMe
<220> FEATURE:
<221> NAME/KEY: misc_feature
<222> LOCATION: (11)..(11)
<223> OTHER INFORMATION: 2'-F
<220> FEATURE:
<221> NAME/KEY: misc_feature
<222> LOCATION: (12)..(12)
<223> OTHER INFORMATION: 2'-OMe
<220> FEATURE:
<221> NAME/KEY: misc_feature
<222> LOCATION: (13)..(13)
<223> OTHER INFORMATION: 2'-F
<220> FEATURE:
<221> NAME/KEY: misc_feature
<222> LOCATION: (14)..(14)
<223> OTHER INFORMATION: 2'-OMe
<220> FEATURE:
<221> NAME/KEY: misc_feature
<222> LOCATION: (15)..(15)
<223> OTHER INFORMATION: 2'-F
<220> FEATURE:
<221> NAME/KEY: misc_feature
<222> LOCATION: (16)..(16)
<223> OTHER INFORMATION: 2'-OMe
<220> FEATURE:
<221> NAME/KEY: misc_feature
<222> LOCATION: (17)..(17)
<223> OTHER INFORMATION: 2'-F
<220> FEATURE:
<221> NAME/KEY: misc_feature
<222> LOCATION: (18)..(18)
<223> OTHER INFORMATION: 2'-OMe
<220> FEATURE:
<221> NAME/KEY: misc_feature
<222> LOCATION: (19)..(19)
<223> OTHER INFORMATION: 2'-F

<400> SEQUENCE: 91
```
ggguaaauac auucuacau                                                19

<210> SEQ ID NO 92
<211> LENGTH: 19
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(17)
<223> OTHER INFORMATION: phosphodiester linkages
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (19)..(19)
<223> OTHER INFORMATION: 2'-O-methyl

<400> SEQUENCE: 92
uuugaaaaug uugaucucc                                                19

<210> SEQ ID NO 93
<211> LENGTH: 19
<212> TYPE: RNA
<213> ORGANISM: Artificial
<220> FEATURE:
<223> OTHER INFORMATION: Synthetic Construct

<400> SEQUENCE: 93
aaacuuuuac aacuagagg                                                19

<210> SEQ ID NO 94
<211> LENGTH: 19
<212> TYPE: RNA
<213> ORGANISM: Artificial
<220> FEATURE:
<223> OTHER INFORMATION: Synthetic Construct
<220> FEATURE:
<221> NAME/KEY: misc_feature

```
<222> LOCATION: (1)..(17)
<223> OTHER INFORMATION: phosphodiester linkages
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (19)..(19)
<223> OTHER INFORMATION: 2'-O-methyl

<400> SEQUENCE: 94
uugucucugg uccuuacuu                                                 19

<210> SEQ ID NO 95
<211> LENGTH: 19
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(17)
<223> OTHER INFORMATION: phosphodiester linkages
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (9)..(9)
<223> OTHER INFORMATION: 2'-O-methyl
<220> FEATURE:
```

```
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (19)..(19)
<223> OTHER INFORMATION: 2'-O-methyl

<400> SEQUENCE: 95
ucuuaucacc uuuagcucu                                              19

<210> SEQ ID NO 96
<211> LENGTH: 19
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(17)
<223> OTHER INFORMATION: phosphodiester linkages
<220> FEATURE:
<221> NAME/KEY: misc_feature
<222> LOCATION: (2)..(2)
<223> OTHER INFORMATION: 2'-O-methyl
<220> FEATURE:
<221> NAME/KEY: misc_feature
<222> LOCATION: (4)..(4)
<223> OTHER INFORMATION: 2'-O-methyl
<220> FEATURE:
<221> NAME/KEY: misc_feature
<222> LOCATION: (6)..(6)
<223> OTHER INFORMATION: 2'-O-methyl
<220> FEATURE:
<221> NAME/KEY: misc_feature
<222> LOCATION: (8)..(8)
<223> OTHER INFORMATION: 2'-O-methyl
<220> FEATURE:
<221> NAME/KEY: misc_feature
<222> LOCATION: (10)..(10)
<223> OTHER INFORMATION: 2'-O-methyl
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (14)..(14)
<223> OTHER INFORMATION: 2'-O-methyl
<220> FEATURE:
<221> NAME/KEY: misc_feature
<222> LOCATION: (16)..(16)
<223> OTHER INFORMATION: 2'-O-methyl
<220> FEATURE:
<221> NAME/KEY: misc_feature
<222> LOCATION: (18)..(18)
<223> OTHER INFORMATION: 2'-O-methyl

<400> SEQUENCE: 96
agaauagugg aaaucgaga                                              19

<210> SEQ ID NO 97
<211> LENGTH: 19
```

```
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (2)..(18)
<223> OTHER INFORMATION: phosphodiester linkages
<220> FEATURE:
<221> NAME/KEY: misc_feature
<222> LOCATION: (2)..(2)
<223> OTHER INFORMATION: 2'-O-methyl
<220> FEATURE:
<221> NAME/KEY: misc_feature
<222> LOCATION: (4)..(4)
<223> OTHER INFORMATION: 2'-O-methyl
<220> FEATURE:
<221> NAME/KEY: misc_feature
<222> LOCATION: (6)..(6)
<223> OTHER INFORMATION: 2'-O-methyl
<220> FEATURE:
<221> NAME/KEY: misc_feature
<222> LOCATION: (8)..(8)
<223> OTHER INFORMATION: 2'-O-methyl
<220> FEATURE:
<221> NAME/KEY: misc_feature
<222> LOCATION: (10)..(10)
<223> OTHER INFORMATION: 2'-O-methyl
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (14)..(14)
<223> OTHER INFORMATION: 2'-O-methyl
<220> FEATURE:
<221> NAME/KEY: misc_feature
<222> LOCATION: (16)..(16)
<223> OTHER INFORMATION: 2'-O-methyl
<220> FEATURE:
<221> NAME/KEY: misc_feature
<222> LOCATION: (18)..(18)
<223> OTHER INFORMATION: 2'-O-methyl

<400> SEQUENCE: 97
aaacuuuuac aacuagagg                                              19

<210> SEQ ID NO 98
<211> LENGTH: 19
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(19)
<223> OTHER INFORMATION: 2'-O-methyl
<220> FEATURE:
<221> NAME/KEY: misc_feature
<222> LOCATION: (2)..(19)
<223> OTHER INFORMATION: phosphodiester linkages

<400> SEQUENCE: 98
aaacuuuuac aacuagagg                                              19

<210> SEQ ID NO 99
<211> LENGTH: 19
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (2)..(18)
```

<223> OTHER INFORMATION: 2'-O-methyl and phosphodiester linkage

<400> SEQUENCE: 99
aaacuuuuac aacuagagg                                                19

<210> SEQ ID NO 100
<211> LENGTH: 19
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(18)
<223> OTHER INFORMATION: phosphodiester linkage
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (2)..(2)
<223> OTHER INFORMATION: 2'-deoxy-2-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature

```
<222> LOCATION: (16)..(16)
<223> OTHER INFORMATION: 2'-deoxy-2-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2-fluoro
<220> FEATURE:
<221> NAME/KEY: misc_feature
<222> LOCATION: (19)..(19)
<223> OTHER INFORMATION: 2'-O-methyl

<400> SEQUENCE: 100
uugucucugg uccuuacuu                                                  19

<210> SEQ ID NO 101
<211> LENGTH: 15
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(15)
<223> OTHER INFORMATION: phosphodiester linkage
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
```

```
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl

<400> SEQUENCE: 101
ugucauauuc cugga                                                          15

<210> SEQ ID NO 102
<211> LENGTH: 19
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 2'-deoxy-2'-fluoro
<220> FEATURE:
<221> NAME/KEY: misc_feature
<222> LOCATION: (2)..(19)
<223> OTHER INFORMATION: phosphodiester linkage
<220> FEATURE:
<221> NAME/KEY: misc_feature
<222> LOCATION: (2)..(2)
<223> OTHER INFORMATION: 2'-O-methyl
<220> FEATURE:
<221> NAME/KEY: misc_feature
<222> LOCATION: (3)..(3)
<223> OTHER INFORMATION: 2'-deoxy-2'-fluoro
<220> FEATURE:
<221> NAME/KEY: misc_feature
<222> LOCATION: (4)..(4)
<223> OTHER INFORMATION: 2'-O-methyl
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-O-methyl
<220> FEATURE:
<221> NAME/KEY: misc_feature
<222> LOCATION: (7)..(7)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-O-methyl
<220> FEATURE:
<221> NAME/KEY: misc_feature
<222> LOCATION: (9)..(9)
<223> OTHER INFORMATION: 2'-deoxy-2'-fluoro
<220> FEATURE:
<221> NAME/KEY: misc_feature
<222> LOCATION: (10)..(10)
<223> OTHER INFORMATION: 2'-O-methyl
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (13)..(13)
<223> OTHER INFORMATION: 2'-deoxy-2'-fluoro
```

```
<220> FEATURE:
<221> NAME/KEY: misc_feature
<222> LOCATION: (14)..(14)
<223> OTHER INFORMATION: 2'-O-methyl
<220> FEATURE:
<221> NAME/KEY: misc_feature
<222> LOCATION: (15)..(15)
<223> OTHER INFORMATION: 2'-deoxy-2'-fluoro
<220> FEATURE:
<221> NAME/KEY: misc_feature
<222> LOCATION: (16)..(16)
<223> OTHER INFORMATION: 2'-O-methyl
<220> FEATURE:
<221> NAME/KEY: misc_feature
<222> LOCATION: (17)..(17)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-O-methyl
<220> FEATURE:
<221> NAME/KEY: misc_feature
<222> LOCATION: (19)..(19)
<223> OTHER INFORMATION: 2'-deoxy-2'-fluoro

<400> SEQUENCE: 102
acaguauaag gaccuagga                                                       19

<210> SEQ ID NO 103
<211> LENGTH: 19
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(18)
<223> OTHER INFORMATION: phosphodiester linkages
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
```

```
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(19)
<223> OTHER INFORMATION: 2'-O-methyl

<400> SEQUENCE: 103
uccuggaucc uucaccaau                                                   19

<210> SEQ ID NO 104
<211> LENGTH: 19
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 2'-deoxy-2'-fluoro
<220> FEATURE:
<221> NAME/KEY: misc_feature
<222> LOCATION: (2)..(19)
<223> OTHER INFORMATION: phosphodiester linkage
<220> FEATURE:
<221> NAME/KEY: misc_feature
<222> LOCATION: (2)..(2)
<223> OTHER INFORMATION: 2'-O-methyl
<220> FEATURE:
<221> NAME/KEY: misc_feature
<222> LOCATION: (3)..(3)
<223> OTHER INFORMATION: 2'-deoxy-2'-fluoro
<220> FEATURE:
<221> NAME/KEY: misc_feature
<222> LOCATION: (4)..(4)
<223> OTHER INFORMATION: 2'-O-methyl
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-O-methyl
<220> FEATURE:
<221> NAME/KEY: misc_feature
```

```
<222> LOCATION: (7)..(7)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-O-methyl
<220> FEATURE:
<221> NAME/KEY: misc_feature
<222> LOCATION: (9)..(9)
<223> OTHER INFORMATION: 2'-deoxy-2'-fluoro
<220> FEATURE:
<221> NAME/KEY: misc_feature
<222> LOCATION: (10)..(10)
<223> OTHER INFORMATION: 2'-O-methyl
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (13)..(13)
<223> OTHER INFORMATION: 2'-deoxy-2'-fluoro
<220> FEATURE:
<221> NAME/KEY: misc_feature
<222> LOCATION: (14)..(14)
<223> OTHER INFORMATION: 2'-O-methyl
<220> FEATURE:
<221> NAME/KEY: misc_feature
<222> LOCATION: (15)..(15)
<223> OTHER INFORMATION: 2'-deoxy-2'-fluoro
<220> FEATURE:
<221> NAME/KEY: misc_feature
<222> LOCATION: (16)..(16)
<223> OTHER INFORMATION: 2'-O-methyl
<220> FEATURE:
<221> NAME/KEY: misc_feature
<222> LOCATION: (17)..(17)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-O-methyl
<220> FEATURE:
<221> NAME/KEY: misc_feature
<222> LOCATION: (19)..(19)
<223> OTHER INFORMATION: 2'-deoxy-2'-fluoro

<400> SEQUENCE: 104
aggaccuagg aagugguua                                              19

<210> SEQ ID NO 105
<211> LENGTH: 19
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(18)
<223> OTHER INFORMATION: phosphodiester linkage
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
```

<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(19)
<223> OTHER INFORMATION: 2'-O-methyl

<400> SEQUENCE: 105
ucuuaucacc uuuagcucu                                                19

<210> SEQ ID NO 106
<211> LENGTH: 19
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 2'-deoxy-2'-fluoro

```
<220> FEATURE:
<221> NAME/KEY: misc_feature
<222> LOCATION: (2)..(19)
<223> OTHER INFORMATION: phosphodiester linkage
<220> FEATURE:
<221> NAME/KEY: misc_feature
<222> LOCATION: (2)..(2)
<223> OTHER INFORMATION: 2'-O-methyl
<220> FEATURE:
<221> NAME/KEY: misc_feature
<222> LOCATION: (3)..(3)
<223> OTHER INFORMATION: 2'-deoxy-2'-fluoro
<220> FEATURE:
<221> NAME/KEY: misc_feature
<222> LOCATION: (4)..(4)
<223> OTHER INFORMATION: 2'-O-methyl
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-O-methyl
<220> FEATURE:
<221> NAME/KEY: misc_feature
<222> LOCATION: (7)..(7)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-O-methyl
<220> FEATURE:
<221> NAME/KEY: misc_feature
<222> LOCATION: (9)..(9)
<223> OTHER INFORMATION: 2'-deoxy-2'-fluoro
<220> FEATURE:
<221> NAME/KEY: misc_feature
<222> LOCATION: (10)..(10)
<223> OTHER INFORMATION: 2'-O-methyl
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (13)..(13)
<223> OTHER INFORMATION: 2'-deoxy-2'-fluoro
<220> FEATURE:
<221> NAME/KEY: misc_feature
<222> LOCATION: (14)..(14)
<223> OTHER INFORMATION: 2'-O-methyl
<220> FEATURE:
<221> NAME/KEY: misc_feature
<222> LOCATION: (15)..(15)
<223> OTHER INFORMATION: 2'-deoxy-2'-fluoro
<220> FEATURE:
<221> NAME/KEY: misc_feature
<222> LOCATION: (16)..(16)
<223> OTHER INFORMATION: 2'-O-methyl
<220> FEATURE:
<221> NAME/KEY: misc_feature
<222> LOCATION: (17)..(17)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-O-methyl
<220> FEATURE:
<221> NAME/KEY: misc_feature
<222> LOCATION: (19)..(19)
<223> OTHER INFORMATION: 2'-deoxy-2'-fluoro

<400> SEQUENCE: 106
```
agaauagugg aaaucgaga                                           19

<210> SEQ ID NO 107
<211> LENGTH: 19
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(18)
<223> OTHER INFORMATION: phosphodiester linkage
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature

```
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(19)
<223> OTHER INFORMATION: 2'-O-methyl

<400> SEQUENCE: 107
auacucagaa ggugucuuc                                                      19

<210> SEQ ID NO 108
<211> LENGTH: 19
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 2'-deoxy-2'-fluoro
<220> FEATURE:
<221> NAME/KEY: misc_feature
<222> LOCATION: (2)..(19)
<223> OTHER INFORMATION: phosphodiester linkage
<220> FEATURE:
<221> NAME/KEY: misc_feature
<222> LOCATION: (2)..(2)
<223> OTHER INFORMATION: 2'-O-methyl
<220> FEATURE:
<221> NAME/KEY: misc_feature
<222> LOCATION: (3)..(3)
<223> OTHER INFORMATION: 2'-deoxy-2'-fluoro
<220> FEATURE:
<221> NAME/KEY: misc_feature
<222> LOCATION: (4)..(4)
<223> OTHER INFORMATION: 2'-O-methyl
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-O-methyl
<220> FEATURE:
<221> NAME/KEY: misc_feature
<222> LOCATION: (7)..(7)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-O-methyl
<220> FEATURE:
<221> NAME/KEY: misc_feature
<222> LOCATION: (9)..(9)
<223> OTHER INFORMATION: 2'-deoxy-2'-fluoro
<220> FEATURE:
<221> NAME/KEY: misc_feature
<222> LOCATION: (10)..(10)
<223> OTHER INFORMATION: 2'-O-methyl
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (13)..(13)
<223> OTHER INFORMATION: 2'-deoxy-2'-fluoro
<220> FEATURE:
```

```
<221> NAME/KEY: misc_feature
<222> LOCATION: (14)..(14)
<223> OTHER INFORMATION: 2'-O-methyl
<220> FEATURE:
<221> NAME/KEY: misc_feature
<222> LOCATION: (15)..(15)
<223> OTHER INFORMATION: 2'-deoxy-2'-fluoro
<220> FEATURE:
<221> NAME/KEY: misc_feature
<222> LOCATION: (16)..(16)
<223> OTHER INFORMATION: 2'-O-methyl
<220> FEATURE:
<221> NAME/KEY: misc_feature
<222> LOCATION: (17)..(17)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-O-methyl
<220> FEATURE:
<221> NAME/KEY: misc_feature
<222> LOCATION: (19)..(19)
<223> OTHER INFORMATION: 2'-deoxy-2'-fluoro

<400> SEQUENCE: 108
uaugagucuu ccacagaag                                                    19

<210> SEQ ID NO 109
<211> LENGTH: 19
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(18)
<223> OTHER INFORMATION: phosphodiester linkage
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
```

```
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(19)
<223> OTHER INFORMATION: 2'-O-methyl

<400> SEQUENCE: 109
uuugaaaaug uugaucucc                                                    19

<210> SEQ ID NO 110
<211> LENGTH: 19
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 2'-deoxy-2'-fluoro
<220> FEATURE:
<221> NAME/KEY: misc_feature
<222> LOCATION: (2)..(19)
<223> OTHER INFORMATION: phosphodiester linkage
<220> FEATURE:
<221> NAME/KEY: misc_feature
<222> LOCATION: (2)..(2)
<223> OTHER INFORMATION: 2'-O-methyl
<220> FEATURE:
<221> NAME/KEY: misc_feature
<222> LOCATION: (3)..(3)
<223> OTHER INFORMATION: 2'-deoxy-2'-fluoro
<220> FEATURE:
<221> NAME/KEY: misc_feature
<222> LOCATION: (4)..(4)
<223> OTHER INFORMATION: 2'-O-methyl
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-O-methyl
<220> FEATURE:
<221> NAME/KEY: misc_feature
<222> LOCATION: (7)..(7)
```

```
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-O-methyl
<220> FEATURE:
<221> NAME/KEY: misc_feature
<222> LOCATION: (9)..(9)
<223> OTHER INFORMATION: 2'-deoxy-2'-fluoro
<220> FEATURE:
<221> NAME/KEY: misc_feature
<222> LOCATION: (10)..(10)
<223> OTHER INFORMATION: 2'-O-methyl
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (13)..(13)
<223> OTHER INFORMATION: 2'-deoxy-2'-fluoro
<220> FEATURE:
<221> NAME/KEY: misc_feature
<222> LOCATION: (14)..(14)
<223> OTHER INFORMATION: 2'-O-methyl
<220> FEATURE:
<221> NAME/KEY: misc_feature
<222> LOCATION: (15)..(15)
<223> OTHER INFORMATION: 2'-deoxy-2'-fluoro
<220> FEATURE:
<221> NAME/KEY: misc_feature
<222> LOCATION: (16)..(16)
<223> OTHER INFORMATION: 2'-O-methyl
<220> FEATURE:
<221> NAME/KEY: misc_feature
<222> LOCATION: (17)..(17)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-O-methyl
<220> FEATURE:
<221> NAME/KEY: misc_feature
<222> LOCATION: (19)..(19)
<223> OTHER INFORMATION: 2'-deoxy-2'-fluoro

<400> SEQUENCE: 110
aaacuuuuac aacuagagg                                                19

<210> SEQ ID NO 111
<211> LENGTH: 19
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (2)..(18)
<223> OTHER INFORMATION: phosphodiester linkage
<220> FEATURE:
<221> NAME/KEY: misc_feature
<222> LOCATION: (2)..(2)
<223> OTHER INFORMATION: 2'-O-methoxyethyl (MOE)
<220> FEATURE:
<221> NAME/KEY: misc_feature
<222> LOCATION: (4)..(4)
<223> OTHER INFORMATION: 2'-O-methoxyethyl (MOE)
<220> FEATURE:
<221> NAME/KEY: misc_feature
<222> LOCATION: (6)..(6)
<223> OTHER INFORMATION: 2'-O-methoxyethyl (MOE)
<220> FEATURE:
<221> NAME/KEY: misc_feature
```

-continued

```
<222> LOCATION: (8)..(8)
<223> OTHER INFORMATION: 2'-O-methoxyethyl (MOE)
<220> FEATURE:
<221> NAME/KEY: misc_feature
<222> LOCATION: (10)..(10)
<223> OTHER INFORMATION: 2'-O-methoxyethyl (MOE)
<220> FEATURE:
<221> NAME/KEY: misc_feature
<222> LOCATION: (12)..(12)
<223> OTHER INFORMATION: 2'-O-methoxyethyl (MOE)
<220> FEATURE:
<221> NAME/KEY: misc_feature
<222> LOCATION: (14)..(14)
<223> OTHER INFORMATION: 2'-O-methoxyethyl (MOE)
<220> FEATURE:
<221> NAME/KEY: misc_feature
<222> LOCATION: (16)..(16)
<223> OTHER INFORMATION: 2'-O-methoxyethyl (MOE)
<220> FEATURE:
<221> NAME/KEY: misc_feature
<222> LOCATION: (18)..(18)
<223> OTHER INFORMATION: 2'-O-methoxyethyl (MOE)

<400> SEQUENCE: 111
aaacuuuuac aacuagagg                                                19

<210> SEQ ID NO 112
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: ribo with phosphorothioate linkage

<400> SEQUENCE: 112
uuugaaaaug uugaucuccu                                               20

<210> SEQ ID NO 113
<211> LENGTH: 19
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(19)
<223> OTHER INFORMATION: ribo with phosphorothioate linkage

<400> SEQUENCE: 113
aaacuuuuac aacuagagg                                                19

<210> SEQ ID NO 114
<211> LENGTH: 19
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 2'-O-methyl with phosphodiester linkage
<220> FEATURE:
<221> NAME/KEY: misc_feature
<222> LOCATION: (3)..(3)
<223> OTHER INFORMATION: 2'-O-methyl with phosphodiester linkage
<220> FEATURE:
<221> NAME/KEY: misc_feature
<222> LOCATION: (5)..(5)
<223> OTHER INFORMATION: 2'-O-methyl with phosphodiester linkage
<220> FEATURE:
```

```
<221> NAME/KEY: misc_feature
<222> LOCATION: (15)..(15)
<223> OTHER INFORMATION: 2'-O-methyl with phosphodiester linkage
<220> FEATURE:
<221> NAME/KEY: misc_feature
<222> LOCATION: (17)..(17)
<223> OTHER INFORMATION: 2'-O-methyl with phosphodiester linkage
<220> FEATURE:
<221> NAME/KEY: misc_feature
<222> LOCATION: (19)..(19)
<223> OTHER INFORMATION: 2'-O-methyl

<400> SEQUENCE: 114
uugucucugg uccuuacuu                                                   19

<210> SEQ ID NO 115
<211> LENGTH: 19
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 2'-O-methyl with phosphodiester linkage
<220> FEATURE:
<221> NAME/KEY: misc_feature
<222> LOCATION: (3)..(3)
<223> OTHER INFORMATION: 2'-O-methyl with phosphodiester linkage
<220> FEATURE:
<221> NAME/KEY: misc_feature
<222> LOCATION: (5)..(5)
<223> OTHER INFORMATION: 2'-O-methyl with phosphodiester linkage
<220> FEATURE:
<221> NAME/KEY: misc_feature
<222> LOCATION: (15)..(15)
<223> OTHER INFORMATION: 2'-O-methyl with phosphodiester linkage
<220> FEATURE:
<221> NAME/KEY: misc_feature
<222> LOCATION: (17)..(17)
<223> OTHER INFORMATION: 2'-O-methyl with phosphodiester linkage
<220> FEATURE:
<221> NAME/KEY: misc_feature
<222> LOCATION: (19)..(19)
<223> OTHER INFORMATION: 2'-O-methyl

<400> SEQUENCE: 115
ugcuagccuc uggauuuga                                                   19

<210> SEQ ID NO 116
<211> LENGTH: 19
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (2)..(2)
<223> OTHER INFORMATION: 2'-O-methyl with phosphodiester linkage
<220> FEATURE:
<221> NAME/KEY: misc_feature
<222> LOCATION: (4)..(4)
<223> OTHER INFORMATION: 2'-O-methyl with phosphodiester linkage
<220> FEATURE:
<221> NAME/KEY: misc_feature
<222> LOCATION: (6)..(6)
<223> OTHER INFORMATION: 2'-O-methyl with phosphodiester linkage
<220> FEATURE:
<221> NAME/KEY: misc_feature
<222> LOCATION: (8)..(8)
<223> OTHER INFORMATION: 2'-O-methyl with phosphodiester linkage
<220> FEATURE:
<221> NAME/KEY: misc_feature
<222> LOCATION: (10)..(10)
<223> OTHER INFORMATION: 2'-O-methyl with phosphodiester linkage
```

```
<220> FEATURE:
<221> NAME/KEY: misc_feature
<222> LOCATION: (12)..(12)
<223> OTHER INFORMATION: 2'-O-methyl with phosphodiester linkage
<220> FEATURE:
<221> NAME/KEY: misc_feature
<222> LOCATION: (14)..(14)
<223> OTHER INFORMATION: 2'-O-methyl with phosphodiester linkage
<220> FEATURE:
<221> NAME/KEY: misc_feature
<222> LOCATION: (16)..(16)
<223> OTHER INFORMATION: 2'-O-methyl with phosphodiester linkage
<220> FEATURE:
<221> NAME/KEY: misc_feature
<222> LOCATION: (18)..(18)
<223> OTHER INFORMATION: 2'-O-methyl with phosphodiester linkage

<400> SEQUENCE: 116
acgaucggag accuaaacu                                                      19

<210> SEQ ID NO 117
<211> LENGTH: 19
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (2)..(2)
<223> OTHER INFORMATION: 2'-O-methyl with phosphodiester linkage
<220> FEATURE:
<221> NAME/KEY: misc_feature
<222> LOCATION: (4)..(4)
<223> OTHER INFORMATION: 2'-O-methyl with phosphodiester linkage
<220> FEATURE:
<221> NAME/KEY: misc_feature
<222> LOCATION: (16)..(16)
<223> OTHER INFORMATION: 2'-O-methyl with phosphodiester linkage
<220> FEATURE:
<221> NAME/KEY: misc_feature
<222> LOCATION: (18)..(18)
<223> OTHER INFORMATION: 2'-O-methyl with phosphodiester linkage

<400> SEQUENCE: 117
aacagagacc aggaaugaa                                                      19

<210> SEQ ID NO 118
<211> LENGTH: 19
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (2)..(2)
<223> OTHER INFORMATION: 2'-O-methyl with phosphodiester linkage
<220> FEATURE:
<221> NAME/KEY: misc_feature
<222> LOCATION: (4)..(4)
<223> OTHER INFORMATION: 2'-O-methyl with phosphodiester linkage
<220> FEATURE:
<221> NAME/KEY: misc_feature
<222> LOCATION: (16)..(16)
<223> OTHER INFORMATION: 2'-O-methyl with phosphodiester linkage
<220> FEATURE:
<221> NAME/KEY: misc_feature
<222> LOCATION: (18)..(18)
<223> OTHER INFORMATION: 2'-O-methyl with phosphodiester linkage

<400> SEQUENCE: 118
acgaucggag accuaaacu                                                      19

<210> SEQ ID NO 119
```

```
<211> LENGTH: 20
<212> TYPE: DNA
<213> ORGANISM: Artificial
<220> FEATURE:
<223> OTHER INFORMATION: Synthetic Construct

<400> SEQUENCE: 119
ctgctagcct ctggatttga                                              20

<210> SEQ ID NO 120
<211> LENGTH: 19
<212> TYPE: RNA
<213> ORGANISM: Artificial
<220> FEATURE:
<223> OTHER INFORMATION: Synthetic Construct

<400> SEQUENCE: 120
uugucucugg uccuuacuu                                               19

<210> SEQ ID NO 121
<211> LENGTH: 19
<212> TYPE: RNA
<213> ORGANISM: Artificial
<220> FEATURE:
<223> OTHER INFORMATION: Synthetic Construct

<400> SEQUENCE: 121
aaguaaggac cagagacaa                                               19

<210> SEQ ID NO 122
<211> LENGTH: 19
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (2)..(2)
<223> OTHER INFORMATION: 2'-F
<220> FEATURE:
<221> NAME/KEY: misc_feature
<222> LOCATION: (4)..(4)
<223> OTHER INFORMATION: 2'-F
<220> FEATURE:
<221> NAME/KEY: misc_feature
<222> LOCATION: (6)..(6)
<223> OTHER INFORMATION: 2'-F
<220> FEATURE:
<221> NAME/KEY: misc_feature
<222> LOCATION: (8)..(8)
<223> OTHER INFORMATION: 2'-F
<220> FEATURE:
<221> NAME/KEY: misc_feature
<222> LOCATION: (10)..(10)
<223> OTHER INFORMATION: 2'-F
<220> FEATURE:
<221> NAME/KEY: misc_feature
<222> LOCATION: (12)..(12)
<223> OTHER INFORMATION: 2'-F
<220> FEATURE:
<221> NAME/KEY: misc_feature
<222> LOCATION: (14)..(14)
<223> OTHER INFORMATION: 2'-F
<220> FEATURE:
<221> NAME/KEY: misc_feature
<222> LOCATION: (16)..(16)
<223> OTHER INFORMATION: 2'-F
<220> FEATURE:
<221> NAME/KEY: misc_feature
<222> LOCATION: (18)..(18)
<223> OTHER INFORMATION: 2'-F

<400> SEQUENCE: 122
```
uugucucugg uccuuacuu                                              19

<210> SEQ ID NO 123
<211> LENGTH: 19
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(3)
<223> OTHER INFORMATION: 2'-F
<220> FEATURE:
<221> NAME/KEY: misc_feature
<222> LOCATION: (3)..(3)
<223> OTHER INFORMATION: 2'-F
<220> FEATURE:
<221> NAME/KEY: misc_feature
<222> LOCATION: (5)..(5)
<223> OTHER INFORMATION: 2'-F
<220> FEATURE:
<221> NAME/KEY: misc_feature
<222> LOCATION: (7)..(7)
<223> OTHER INFORMATION: 2'-F
<220> FEATURE:
<221> NAME/KEY: misc_feature
<222> LOCATION: (9)..(9)
<223> OTHER INFORMATION: 2'-F
<220> FEATURE:
<221> NAME/KEY: misc_feature
<222> LOCATION: (11)..(11)
<223> OTHER INFORMATION: 2'-F
<220> FEATURE:
<221> NAME/KEY: misc_feature
<222> LOCATION: (13)..(13)
<223> OTHER INFORMATION: 2'-F
<220> FEATURE:
<221> NAME/KEY: misc_feature
<222> LOCATION: (15)..(15)
<223> OTHER INFORMATION: 2'-F
<220> FEATURE:
<221> NAME/KEY: misc_feature
<222> LOCATION: (17)..(17)
<223> OTHER INFORMATION: 2'-F
<220> FEATURE:
<221> NAME/KEY: misc_feature
<222> LOCATION: (19)..(19)
<223> OTHER INFORMATION: 2'-F

<400> SEQUENCE: 123
aaguaaggac cagagacaa                                              19

<210> SEQ ID NO 124
<211> LENGTH: 20
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphodiester linkage

<400> SEQUENCE: 124
aagtaaggac cagagacaaa                                             20

<210> SEQ ID NO 125
<211> LENGTH: 20
<212> TYPE: DNA
<213> ORGANISM: Artificial
<220> FEATURE:
<223> OTHER INFORMATION: Synthetic Construct
<220> FEATURE:

```
<221> NAME/KEY: misc_feature
<222> LOCATION: (1)..(20)
<223> OTHER INFORMATION: phosphodiester linkage
<220> FEATURE:
<221> NAME/KEY: misc_feature
<222> LOCATION: (1)..(1)
<223> OTHER INFORMATION: 2'-OMe
<220> FEATURE:
<221> NAME/KEY: misc_feature
<222> LOCATION: (3)..(3)
<223> OTHER INFORMATION: 2'-OMe
<220> FEATURE:
<221> NAME/KEY: misc_feature
<222> LOCATION: (5)..(5)
<223> OTHER INFORMATION: 2'-OMe
<220> FEATURE:
<221> NAME/KEY: misc_feature
<222> LOCATION: (7)..(7)
<223> OTHER INFORMATION: 2'-OMe
<220> FEATURE:
<221> NAME/KEY: misc_feature
<222> LOCATION: (9)..(9)
<223> OTHER INFORMATION: 2'-OMe
<220> FEATURE:
<221> NAME/KEY: misc_feature
<222> LOCATION: (11)..(11)
<223> OTHER INFORMATION: 2'-OMe
<220> FEATURE:
<221> NAME/KEY: misc_feature
<222> LOCATION: (13)..(13)
<223> OTHER INFORMATION: 2'-OMe
<220> FEATURE:
<221> NAME/KEY: misc_feature
<222> LOCATION: (15)..(15)
<223> OTHER INFORMATION: 2'-OMe
<220> FEATURE:
<221> NAME/KEY: misc_feature
<222> LOCATION: (17)..(17)
<223> OTHER INFORMATION: 2'-OMe
<220> FEATURE:
<221> NAME/KEY: misc_feature
<222> LOCATION: (19)..(19)
<223> OTHER INFORMATION: 2'-OMe

<400> SEQUENCE: 125
aagtaaggac cagagacaaa                                                   20

<210> SEQ ID NO 126
<211> LENGTH: 20
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphorothioate linkage
<220> FEATURE:
<221> NAME/KEY: misc_feature
<222> LOCATION: (1)..(1)
<223> OTHER INFORMATION: 2'-F
<220> FEATURE:
<221> NAME/KEY: misc_feature
<222> LOCATION: (2)..(2)
<223> OTHER INFORMATION: 2'-H
<220> FEATURE:
<221> NAME/KEY: misc_feature
<222> LOCATION: (3)..(3)
<223> OTHER INFORMATION: 2'-F
<220> FEATURE:
<221> NAME/KEY: misc_feature
<222> LOCATION: (4)..(4)
<223> OTHER INFORMATION: 2'-H
<220> FEATURE:
<221> NAME/KEY: misc_feature
<222> LOCATION: (5)..(5)
<223> OTHER INFORMATION: 2'-F
```

```
<220> FEATURE:
<221> NAME/KEY: misc_feature
<222> LOCATION: (6)..(6)
<223> OTHER INFORMATION: 2'-H
<220> FEATURE:
<221> NAME/KEY: misc_feature
<222> LOCATION: (7)..(7)
<223> OTHER INFORMATION: 2'-F
<220> FEATURE:
<221> NAME/KEY: misc_feature
<222> LOCATION: (8)..(8)
<223> OTHER INFORMATION: 2'-H
<220> FEATURE:
<221> NAME/KEY: misc_feature
<222> LOCATION: (9)..(9)
<223> OTHER INFORMATION: 2'-F
<220> FEATURE:
<221> NAME/KEY: misc_feature
<222> LOCATION: (10)..(10)
<223> OTHER INFORMATION: 5-methyl cytidines; 2'-H
<220> FEATURE:
<221> NAME/KEY: misc_feature
<222> LOCATION: (11)..(11)
<223> OTHER INFORMATION: 2'-F
<220> FEATURE:
<221> NAME/KEY: misc_feature
<222> LOCATION: (12)..(12)
<223> OTHER INFORMATION: 2'-H
<220> FEATURE:
<221> NAME/KEY: misc_feature
<222> LOCATION: (13)..(13)
<223> OTHER INFORMATION: 2'-F
<220> FEATURE:
<221> NAME/KEY: misc_feature
<222> LOCATION: (14)..(14)
<223> OTHER INFORMATION: 2'-H
<220> FEATURE:
<221> NAME/KEY: misc_feature
<222> LOCATION: (15)..(15)
<223> OTHER INFORMATION: 2'-F
<220> FEATURE:
<221> NAME/KEY: misc_feature
<222> LOCATION: (16)..(16)
<223> OTHER INFORMATION: 2'-H
<220> FEATURE:
<221> NAME/KEY: misc_feature
<222> LOCATION: (17)..(17)
<223> OTHER INFORMATION: 2'-F
<220> FEATURE:
<221> NAME/KEY: misc_feature
<222> LOCATION: (18)..(18)
<223> OTHER INFORMATION: 2'-H
<220> FEATURE:
<221> NAME/KEY: misc_feature
<222> LOCATION: (19)..(19)
<223> OTHER INFORMATION: 2'-F
<220> FEATURE:
<221> NAME/KEY: misc_feature
<222> LOCATION: (20)..(20)
<223> OTHER INFORMATION: 2'-H

<400> SEQUENCE: 126
aagtaaggac cagagacaaa                                               20

<210> SEQ ID NO 127
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphodiester linkages
<220> FEATURE:
<221> NAME/KEY: misc_feature
<222> LOCATION: (1)..(1)
```

```
<223> OTHER INFORMATION: 2'-H
<220> FEATURE:
<221> NAME/KEY: misc_feature
<222> LOCATION: (2)..(2)
<223> OTHER INFORMATION: 2'-F
<220> FEATURE:
<221> NAME/KEY: misc_feature
<222> LOCATION: (3)..(3)
<223> OTHER INFORMATION: 2'-H
<220> FEATURE:
<221> NAME/KEY: misc_feature
<222> LOCATION: (4)..(4)
<223> OTHER INFORMATION: 2'-F
<220> FEATURE:
<221> NAME/KEY: misc_feature
<222> LOCATION: (5)..(5)
<223> OTHER INFORMATION: 2'-H
<220> FEATURE:
<221> NAME/KEY: misc_feature
<222> LOCATION: (6)..(6)
<223> OTHER INFORMATION: 2'-F
<220> FEATURE:
<221> NAME/KEY: misc_feature
<222> LOCATION: (7)..(7)
<223> OTHER INFORMATION: 2'-H
<220> FEATURE:
<221> NAME/KEY: misc_feature
<222> LOCATION: (8)..(8)
<223> OTHER INFORMATION: 2'-F
<220> FEATURE:
<221> NAME/KEY: misc_feature
<222> LOCATION: (9)..(9)
<223> OTHER INFORMATION: 2'-H
<220> FEATURE:
<221> NAME/KEY: misc_feature
<222> LOCATION: (10)..(10)
<223> OTHER INFORMATION: 5-methyl cytidine; 2'-F
<220> FEATURE:
<221> NAME/KEY: misc_feature
<222> LOCATION: (11)..(11)
<223> OTHER INFORMATION: 2'-H
<220> FEATURE:
<221> NAME/KEY: misc_feature
<222> LOCATION: (12)..(12)
<223> OTHER INFORMATION: 2'-F
<220> FEATURE:
<221> NAME/KEY: misc_feature
<222> LOCATION: (13)..(13)
<223> OTHER INFORMATION: 2'-H
<220> FEATURE:
<221> NAME/KEY: misc_feature
<222> LOCATION: (14)..(14)
<223> OTHER INFORMATION: 2'-F
<220> FEATURE:
<221> NAME/KEY: misc_feature
<222> LOCATION: (15)..(15)
<223> OTHER INFORMATION: 2'-H
<220> FEATURE:
<221> NAME/KEY: misc_feature
<222> LOCATION: (16)..(16)
<223> OTHER INFORMATION: 2'-F
<220> FEATURE:
<221> NAME/KEY: misc_feature
<222> LOCATION: (17)..(17)
<223> OTHER INFORMATION: 5-methyl cytidine; 2'-H
<220> FEATURE:
<221> NAME/KEY: misc_feature
<222> LOCATION: (18)..(18)
<223> OTHER INFORMATION: 2'-F
<220> FEATURE:
<221> NAME/KEY: misc_feature
<222> LOCATION: (19)..(19)
<223> OTHER INFORMATION: 2'-H
<220> FEATURE:
<221> NAME/KEY: misc_feature
<222> LOCATION: (20)..(20)
<223> OTHER INFORMATION: 2'-F

<400> SEQUENCE: 127
```
aaguaaggac cagagacaaa          20

<210> SEQ ID NO 128
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphodiester linkage
<220> FEATURE:
<221> NAME/KEY: misc_feature
<222> LOCATION: (1)..(1)
<223> OTHER INFORMATION: 2'-F
<220> FEATURE:
<221> NAME/KEY: misc_feature
<222> LOCATION: (2)..(2)
<223> OTHER INFORMATION: 2'-OMe
<220> FEATURE:
<221> NAME/KEY: misc_feature
<222> LOCATION: (3)..(3)
<223> OTHER INFORMATION: 2'-F
<220> FEATURE:
<221> NAME/KEY: misc_feature
<222> LOCATION: (4)..(4)
<223> OTHER INFORMATION: 2'-OMe
<220> FEATURE:
<221> NAME/KEY: misc_feature
<222> LOCATION: (5)..(5)
<223> OTHER INFORMATION: 2'-F
<220> FEATURE:
<221> NAME/KEY: misc_feature
<222> LOCATION: (6)..(6)
<223> OTHER INFORMATION: 2'-OMe
<220> FEATURE:
<221> NAME/KEY: misc_feature
<222> LOCATION: (7)..(7)
<223> OTHER INFORMATION: 2'-F
<220> FEATURE:
<221> NAME/KEY: misc_feature
<222> LOCATION: (8)..(8)
<223> OTHER INFORMATION: 2'-OMe
<220> FEATURE:
<221> NAME/KEY: misc_feature
<222> LOCATION: (9)..(9)
<223> OTHER INFORMATION: 2'-F
<220> FEATURE:
<221> NAME/KEY: misc_feature
<222> LOCATION: (10)..(10)
<223> OTHER INFORMATION: 2'-OMe
<220> FEATURE:
<221> NAME/KEY: misc_feature
<222> LOCATION: (11)..(11)
<223> OTHER INFORMATION: 2'-F
<220> FEATURE:
<221> NAME/KEY: misc_feature
<222> LOCATION: (12)..(12)
<223> OTHER INFORMATION: 2'-OMe
<220> FEATURE:
<221> NAME/KEY: misc_feature
<222> LOCATION: (13)..(13)
<223> OTHER INFORMATION: 2'-F
<220> FEATURE:
<221> NAME/KEY: misc_feature
<222> LOCATION: (14)..(14)
<223> OTHER INFORMATION: 2'-OMe
<220> FEATURE:
<221> NAME/KEY: misc_feature
<222> LOCATION: (15)..(15)
<223> OTHER INFORMATION: 2'-F
<220> FEATURE:
<221> NAME/KEY: misc_feature
<222> LOCATION: (16)..(16)
<223> OTHER INFORMATION: 2'-OMe
<220> FEATURE:

```
<221> NAME/KEY: misc_feature
<222> LOCATION: (17)..(17)
<223> OTHER INFORMATION: 2'-F
<220> FEATURE:
<221> NAME/KEY: misc_feature
<222> LOCATION: (18)..(18)
<223> OTHER INFORMATION: 2'-OMe
<220> FEATURE:
<221> NAME/KEY: misc_feature
<222> LOCATION: (19)..(19)
<223> OTHER INFORMATION: 2'-F
<220> FEATURE:
<221> NAME/KEY: misc_feature
<222> LOCATION: (20)..(20)
<223> OTHER INFORMATION: 2'-OMe

<400> SEQUENCE: 128
uuugucucug guccuuacuu                                               20

<210> SEQ ID NO 129
<211> LENGTH: 20
<212> TYPE: RNA
<213> ORGANISM: Artificial
<220> FEATURE:
<223> OTHER INFORMATION: Synthetic Construct

<400> SEQUENCE: 129
uuugucucug guccuuacuu                                               20

<210> SEQ ID NO 130
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphodiester linkage
<220> FEATURE:
<221> NAME/KEY: misc_feature
<222> LOCATION: (1)..(1)
<223> OTHER INFORMATION: 2'-F
<220> FEATURE:
<221> NAME/KEY: misc_feature
<222> LOCATION: (2)..(2)
<223> OTHER INFORMATION: 2'-OMe
<220> FEATURE:
<221> NAME/KEY: misc_feature
<222> LOCATION: (3)..(3)
<223> OTHER INFORMATION: 2'-F
<220> FEATURE:
<221> NAME/KEY: misc_feature
<222> LOCATION: (4)..(4)
<223> OTHER INFORMATION: 2'-OMe
<220> FEATURE:
<221> NAME/KEY: misc_feature
<222> LOCATION: (5)..(5)
<223> OTHER INFORMATION: 2'-F
<220> FEATURE:
<221> NAME/KEY: misc_feature
<222> LOCATION: (6)..(6)
<223> OTHER INFORMATION: 2'-OMe
<220> FEATURE:
<221> NAME/KEY: misc_feature
<222> LOCATION: (7)..(7)
<223> OTHER INFORMATION: 2'-F
<220> FEATURE:
<221> NAME/KEY: misc_feature
<222> LOCATION: (8)..(8)
<223> OTHER INFORMATION: 2'-OMe
<220> FEATURE:
<221> NAME/KEY: misc_feature
<222> LOCATION: (9)..(9)
<223> OTHER INFORMATION: 2'-F
```

```
<220> FEATURE:
<221> NAME/KEY: misc_feature
<222> LOCATION: (10)..(10)
<223> OTHER INFORMATION: 2'-OMe
<220> FEATURE:
<221> NAME/KEY: misc_feature
<222> LOCATION: (11)..(11)
<223> OTHER INFORMATION: 2'-F
<220> FEATURE:
<221> NAME/KEY: misc_feature
<222> LOCATION: (12)..(12)
<223> OTHER INFORMATION: 2'-OMe
<220> FEATURE:
<221> NAME/KEY: misc_feature
<222> LOCATION: (13)..(13)
<223> OTHER INFORMATION: 2'-F
<220> FEATURE:
<221> NAME/KEY: misc_feature
<222> LOCATION: (14)..(14)
<223> OTHER INFORMATION: 2'-OMe
<220> FEATURE:
<221> NAME/KEY: misc_feature
<222> LOCATION: (15)..(15)
<223> OTHER INFORMATION: 2'-F
<220> FEATURE:
<221> NAME/KEY: misc_feature
<222> LOCATION: (16)..(16)
<223> OTHER INFORMATION: 2'-OMe
<220> FEATURE:
<221> NAME/KEY: misc_feature
<222> LOCATION: (17)..(17)
<223> OTHER INFORMATION: 2'-F
<220> FEATURE:
<221> NAME/KEY: misc_feature
<222> LOCATION: (18)..(18)
<223> OTHER INFORMATION: 2'-OMe
<220> FEATURE:
<221> NAME/KEY: misc_feature
<222> LOCATION: (19)..(19)
<223> OTHER INFORMATION: 2'-F
<220> FEATURE:
<221> NAME/KEY: misc_feature
<222> LOCATION: (20)..(20)
<223> OTHER INFORMATION: 2'-OMe

<400> SEQUENCE: 130
aaguaaggac cagagacaaa                                                   20

<210> SEQ ID NO 131
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphodiester linkage
<220> FEATURE:
<221> NAME/KEY: misc_feature
<222> LOCATION: (1)..(1)
<223> OTHER INFORMATION: 2'-OMe
<220> FEATURE:
<221> NAME/KEY: misc_feature
<222> LOCATION: (2)..(2)
<223> OTHER INFORMATION: 2'-F
<220> FEATURE:
<221> NAME/KEY: misc_feature
<222> LOCATION: (3)..(3)
<223> OTHER INFORMATION: 2'-OMe
<220> FEATURE:
<221> NAME/KEY: misc_feature
<222> LOCATION: (4)..(4)
<223> OTHER INFORMATION: 2'-F
<220> FEATURE:
<221> NAME/KEY: misc_feature
<222> LOCATION: (5)..(5)
```

```
<223> OTHER INFORMATION: 2'-OMe
<220> FEATURE:
<221> NAME/KEY: misc_feature
<222> LOCATION: (6)..(6)
<223> OTHER INFORMATION: 2'-F
<220> FEATURE:
<221> NAME/KEY: misc_feature
<222> LOCATION: (7)..(7)
<223> OTHER INFORMATION: 2'-OMe
<220> FEATURE:
<221> NAME/KEY: misc_feature
<222> LOCATION: (8)..(8)
<223> OTHER INFORMATION: 2'-F
<220> FEATURE:
<221> NAME/KEY: misc_feature
<222> LOCATION: (9)..(9)
<223> OTHER INFORMATION: 2'-OMe
<220> FEATURE:
<221> NAME/KEY: misc_feature
<222> LOCATION: (10)..(10)
<223> OTHER INFORMATION: 2'-F
<220> FEATURE:
<221> NAME/KEY: misc_feature
<222> LOCATION: (11)..(11)
<223> OTHER INFORMATION: 2'-OMe
<220> FEATURE:
<221> NAME/KEY: misc_feature
<222> LOCATION: (12)..(12)
<223> OTHER INFORMATION: 2'-F
<220> FEATURE:
<221> NAME/KEY: misc_feature
<222> LOCATION: (13)..(13)
<223> OTHER INFORMATION: 2'-OMe
<220> FEATURE:
<221> NAME/KEY: misc_feature
<222> LOCATION: (14)..(14)
<223> OTHER INFORMATION: 2'-F
<220> FEATURE:
<221> NAME/KEY: misc_feature
<222> LOCATION: (15)..(15)
<223> OTHER INFORMATION: 2'-OMe
<220> FEATURE:
<221> NAME/KEY: misc_feature
<222> LOCATION: (16)..(16)
<223> OTHER INFORMATION: 2'-F
<220> FEATURE:
<221> NAME/KEY: misc_feature
<222> LOCATION: (17)..(17)
<223> OTHER INFORMATION: 2'-OMe
<220> FEATURE:
<221> NAME/KEY: misc_feature
<222> LOCATION: (18)..(18)
<223> OTHER INFORMATION: 2'-F
<220> FEATURE:
<221> NAME/KEY: misc_feature
<222> LOCATION: (19)..(19)
<223> OTHER INFORMATION: 2'-OMe
<220> FEATURE:
<221> NAME/KEY: misc_feature
<222> LOCATION: (20)..(20)
<223> OTHER INFORMATION: 2'-F

<400> SEQUENCE: 131
aaguaaggac cagagacaaa                                                 20

<210> SEQ ID NO 132
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphodiester linkage
<220> FEATURE:
<221> NAME/KEY: misc_feature
```

```
<222> LOCATION: (1)..(1)
<223> OTHER INFORMATION: 2'OMe
<220> FEATURE:
<221> NAME/KEY: misc_feature
<222> LOCATION: (2)..(2)
<223> OTHER INFORMATION: 2'-F
<220> FEATURE:
<221> NAME/KEY: misc_feature
<222> LOCATION: (3)..(3)
<223> OTHER INFORMATION: 2'OMe
<220> FEATURE:
<221> NAME/KEY: misc_feature
<222> LOCATION: (4)..(4)
<223> OTHER INFORMATION: 2'-F
<220> FEATURE:
<221> NAME/KEY: misc_feature
<222> LOCATION: (5)..(5)
<223> OTHER INFORMATION: 2'OMe
<220> FEATURE:
<221> NAME/KEY: misc_feature
<222> LOCATION: (6)..(6)
<223> OTHER INFORMATION: 2'-F
<220> FEATURE:
<221> NAME/KEY: misc_feature
<222> LOCATION: (7)..(7)
<223> OTHER INFORMATION: 2'OMe
<220> FEATURE:
<221> NAME/KEY: misc_feature
<222> LOCATION: (8)..(8)
<223> OTHER INFORMATION: 2'-F
<220> FEATURE:
<221> NAME/KEY: misc_feature
<222> LOCATION: (9)..(9)
<223> OTHER INFORMATION: 2'OMe
<220> FEATURE:
<221> NAME/KEY: misc_feature
<222> LOCATION: (10)..(10)
<223> OTHER INFORMATION: 2'-F
<220> FEATURE:
<221> NAME/KEY: misc_feature
<222> LOCATION: (11)..(11)
<223> OTHER INFORMATION: 2'OMe
<220> FEATURE:
<221> NAME/KEY: misc_feature
<222> LOCATION: (12)..(12)
<223> OTHER INFORMATION: 2'-F
<220> FEATURE:
<221> NAME/KEY: misc_feature
<222> LOCATION: (13)..(13)
<223> OTHER INFORMATION: 2'OMe
<220> FEATURE:
<221> NAME/KEY: misc_feature
<222> LOCATION: (14)..(14)
<223> OTHER INFORMATION: 2'-F
<220> FEATURE:
<221> NAME/KEY: misc_feature
<222> LOCATION: (15)..(15)
<223> OTHER INFORMATION: 2'OMe
<220> FEATURE:
<221> NAME/KEY: misc_feature
<222> LOCATION: (16)..(16)
<223> OTHER INFORMATION: 2'-F
<220> FEATURE:
<221> NAME/KEY: misc_feature
<222> LOCATION: (17)..(17)
<223> OTHER INFORMATION: 2'OMe
<220> FEATURE:
<221> NAME/KEY: misc_feature
<222> LOCATION: (18)..(18)
<223> OTHER INFORMATION: 2'-F
<220> FEATURE:
<221> NAME/KEY: misc_feature
<222> LOCATION: (19)..(19)
<223> OTHER INFORMATION: 2'OMe
<220> FEATURE:
<221> NAME/KEY: misc_feature
<222> LOCATION: (20)..(20)
<223> OTHER INFORMATION: 2'-F
```

-continued

<400> SEQUENCE: 132
aaguaaggac cagagacaaa                                              20

<210> SEQ ID NO 133
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphodiester linkage
<220> FEATURE:
<221> NAME/KEY: misc_feature
<222> LOCATION: (1)..(1)
<223> OTHER INFORMATION: 2'-F
<220> FEATURE:
<221> NAME/KEY: misc_feature
<222> LOCATION: (2)..(2)
<223> OTHER INFORMATION: 2'-OMe
<220> FEATURE:
<221> NAME/KEY: misc_feature
<222> LOCATION: (3)..(3)
<223> OTHER INFORMATION: 2'-F
<220> FEATURE:
<221> NAME/KEY: misc_feature
<222> LOCATION: (4)..(4)
<223> OTHER INFORMATION: 2'-OMe
<220> FEATURE:
<221> NAME/KEY: misc_feature
<222> LOCATION: (5)..(5)
<223> OTHER INFORMATION: 2'-F
<220> FEATURE:
<221> NAME/KEY: misc_feature
<222> LOCATION: (6)..(6)
<223> OTHER INFORMATION: 2'-OMe
<220> FEATURE:
<221> NAME/KEY: misc_feature
<222> LOCATION: (7)..(7)
<223> OTHER INFORMATION: 2'-F
<220> FEATURE:
<221> NAME/KEY: misc_feature
<222> LOCATION: (8)..(8)
<223> OTHER INFORMATION: 2'-OMe
<220> FEATURE:
<221> NAME/KEY: misc_feature
<222> LOCATION: (9)..(9)
<223> OTHER INFORMATION: 2'-F
<220> FEATURE:
<221> NAME/KEY: misc_feature
<222> LOCATION: (10)..(10)
<223> OTHER INFORMATION: 2'-OMe
<220> FEATURE:
<221> NAME/KEY: misc_feature
<222> LOCATION: (11)..(11)
<223> OTHER INFORMATION: 2'-F
<220> FEATURE:
<221> NAME/KEY: misc_feature
<222> LOCATION: (12)..(12)
<223> OTHER INFORMATION: 2'-OMe
<220> FEATURE:
<221> NAME/KEY: misc_feature
<222> LOCATION: (13)..(13)
<223> OTHER INFORMATION: 2'-F
<220> FEATURE:
<221> NAME/KEY: misc_feature
<222> LOCATION: (14)..(14)
<223> OTHER INFORMATION: 2'-OMe
<220> FEATURE:
<221> NAME/KEY: misc_feature
<222> LOCATION: (15)..(15)
<223> OTHER INFORMATION: 2'-F
<220> FEATURE:
<221> NAME/KEY: misc_feature
<222> LOCATION: (16)..(16)
<223> OTHER INFORMATION: 2'-OMe

```
<220> FEATURE:
<221> NAME/KEY: misc_feature
<222> LOCATION: (17)..(17)
<223> OTHER INFORMATION: 2'-F
<220> FEATURE:
<221> NAME/KEY: misc_feature
<222> LOCATION: (18)..(18)
<223> OTHER INFORMATION: 2'-OMe
<220> FEATURE:
<221> NAME/KEY: misc_feature
<222> LOCATION: (19)..(19)
<223> OTHER INFORMATION: 2'-F
<220> FEATURE:
<221> NAME/KEY: misc_feature
<222> LOCATION: (20)..(20)
<223> OTHER INFORMATION: 2'-OMe

<400> SEQUENCE: 133
aaguaaggac cagagacaaa                                                     20

<210> SEQ ID NO 134
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphodiester linkage
<220> FEATURE:
<221> NAME/KEY: misc_feature
<222> LOCATION: (1)..(1)
<223> OTHER INFORMATION: 2'-F
<220> FEATURE:
<221> NAME/KEY: misc_feature
<222> LOCATION: (2)..(2)
<223> OTHER INFORMATION: 2'-OMe
<220> FEATURE:
<221> NAME/KEY: misc_feature
<222> LOCATION: (3)..(3)
<223> OTHER INFORMATION: 2'-F
<220> FEATURE:
<221> NAME/KEY: misc_feature
<222> LOCATION: (4)..(4)
<223> OTHER INFORMATION: 2'-OMe
<220> FEATURE:
<221> NAME/KEY: misc_feature
<222> LOCATION: (5)..(5)
<223> OTHER INFORMATION: 2'-F
<220> FEATURE:
<221> NAME/KEY: misc_feature
<222> LOCATION: (6)..(6)
<223> OTHER INFORMATION: 2'-OMe
<220> FEATURE:
<221> NAME/KEY: misc_feature
<222> LOCATION: (7)..(7)
<223> OTHER INFORMATION: 2'-F
<220> FEATURE:
<221> NAME/KEY: misc_feature
<222> LOCATION: (8)..(8)
<223> OTHER INFORMATION: 2'-OMe
<220> FEATURE:
<221> NAME/KEY: misc_feature
<222> LOCATION: (9)..(9)
<223> OTHER INFORMATION: 2'-F
<220> FEATURE:
<221> NAME/KEY: misc_feature
<222> LOCATION: (10)..(10)
<223> OTHER INFORMATION: 2'-OMe
<220> FEATURE:
<221> NAME/KEY: misc_feature
<222> LOCATION: (11)..(11)
<223> OTHER INFORMATION: 2'-F
<220> FEATURE:
<221> NAME/KEY: misc_feature
<222> LOCATION: (12)..(12)
```

```
<223> OTHER INFORMATION: 2'-OMe
<220> FEATURE:
<221> NAME/KEY: misc_feature
<222> LOCATION: (13)..(13)
<223> OTHER INFORMATION: 2'-F
<220> FEATURE:
<221> NAME/KEY: misc_feature
<222> LOCATION: (14)..(14)
<223> OTHER INFORMATION: 2'-OMe
<220> FEATURE:
<221> NAME/KEY: misc_feature
<222> LOCATION: (15)..(15)
<223> OTHER INFORMATION: 2'-F
<220> FEATURE:
<221> NAME/KEY: misc_feature
<222> LOCATION: (16)..(16)
<223> OTHER INFORMATION: 2'-OMe
<220> FEATURE:
<221> NAME/KEY: misc_feature
<222> LOCATION: (17)..(17)
<223> OTHER INFORMATION: 2'-F
<220> FEATURE:
<221> NAME/KEY: misc_feature
<222> LOCATION: (18)..(18)
<223> OTHER INFORMATION: 2'-OMe
<220> FEATURE:
<221> NAME/KEY: misc_feature
<222> LOCATION: (19)..(19)
<223> OTHER INFORMATION: 2'-F
<220> FEATURE:
<221> NAME/KEY: misc_feature
<222> LOCATION: (20)..(20)
<223> OTHER INFORMATION: 2'-OMe

<400> SEQUENCE: 134
uuugucucug guccuuacuu                                              20

<210> SEQ ID NO 135
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphorthioate linkage
<220> FEATURE:
<221> NAME/KEY: misc_feature
<222> LOCATION: (1)..(1)
<223> OTHER INFORMATION: 2'-F
<220> FEATURE:
<221> NAME/KEY: misc_feature
<222> LOCATION: (3)..(3)
<223> OTHER INFORMATION: 2'-F
<220> FEATURE:
<221> NAME/KEY: misc_feature
<222> LOCATION: (5)..(5)
<223> OTHER INFORMATION: 2'-F
<220> FEATURE:
<221> NAME/KEY: misc_feature
<222> LOCATION: (7)..(7)
<223> OTHER INFORMATION: 2'-F
<220> FEATURE:
<221> NAME/KEY: misc_feature
<222> LOCATION: (9)..(9)
<223> OTHER INFORMATION: 2'-F
<220> FEATURE:
<221> NAME/KEY: misc_feature
<222> LOCATION: (11)..(11)
<223> OTHER INFORMATION: 2'-F
<220> FEATURE:
<221> NAME/KEY: misc_feature
<222> LOCATION: (13)..(13)
<223> OTHER INFORMATION: 2'-F
<220> FEATURE:
<221> NAME/KEY: misc_feature
```

-continued

```
<222> LOCATION: (15)..(15)
<223> OTHER INFORMATION: 2'-F
<220> FEATURE:
<221> NAME/KEY: misc_feature
<222> LOCATION: (17)..(17)
<223> OTHER INFORMATION: 2'-F
<220> FEATURE:
<221> NAME/KEY: misc_feature
<222> LOCATION: (19)..(19)
<223> OTHER INFORMATION: 2'-F

<400> SEQUENCE: 135
uuugucucug guccuuacuu                                                      20

<210> SEQ ID NO 136
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphorothioate linkage
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (2)..(2)
<223> OTHER INFORMATION: ribo
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: ribo
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: ribo
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: ribo
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: ribo
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: ribo
<220> FEATURE:
<221> NAME/KEY: misc_feature
<222> LOCATION: (13)..(13)
<223> OTHER INFORMATION: 2'-O-methyl
<220> FEATURE:
```

```
<221> NAME/KEY: misc_feature
<222> LOCATION: (14)..(14)
<223> OTHER INFORMATION: ribo
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: ribo
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: ribo
<220> FEATURE:
<221> NAME/KEY: misc_feature
<222> LOCATION: (19)..(19)
<223> OTHER INFORMATION: 2'-O-methyl

<400> SEQUENCE: 136
uuugucucug guccuuacuu                                                    20

<210> SEQ ID NO 137
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (2)..(2)
<223> OTHER INFORMATION: 2'-deoxy-2'-fluoro with phosphodiester linkage
<220> FEATURE:
<221> NAME/KEY: misc_feature
<222> LOCATION: (4)..(4)
<223> OTHER INFORMATION: 2'-deoxy-2'-fluoro with phosphodiester linkage
<220> FEATURE:
<221> NAME/KEY: misc_feature
<222> LOCATION: (6)..(6)
<223> OTHER INFORMATION: 2'-deoxy-2'-fluoro with phosphodiester linkage
<220> FEATURE:
<221> NAME/KEY: misc_feature
<222> LOCATION: (8)..(8)
<223> OTHER INFORMATION: 2'-deoxy-2'-fluoro with phosphodiester linkage
<220> FEATURE:
<221> NAME/KEY: misc_feature
<222> LOCATION: (10)..(10)
<223> OTHER INFORMATION: 2'-deoxy-2'-fluoro with phosphodiester linkage
<220> FEATURE:
<221> NAME/KEY: misc_feature
<222> LOCATION: (12)..(12)
<223> OTHER INFORMATION: 2'-deoxy-2'-fluoro with phosphodiester linkage
<220> FEATURE:
<221> NAME/KEY: misc_feature
<222> LOCATION: (14)..(14)
<223> OTHER INFORMATION: 2'-deoxy-2'-fluoro with phosphodiester linkage
<220> FEATURE:
<221> NAME/KEY: misc_feature
<222> LOCATION: (16)..(16)
<223> OTHER INFORMATION: 2'-deoxy-2'-fluoro with phosphodiester linkage
<220> FEATURE:
<221> NAME/KEY: misc_feature
<222> LOCATION: (18)..(18)
<223> OTHER INFORMATION: 2'-deoxy-2'-fluoro with phosphodiester linkage
<220> FEATURE:
<221> NAME/KEY: misc_feature
<222> LOCATION: (20)..(20)
<223> OTHER INFORMATION: 2'-deoxy-2'-fluoro

<400> SEQUENCE: 137
uuugucucug guccuuacuu                                                    20
```

```
<210> SEQ ID NO 138
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (2)..(2)
<223> OTHER INFORMATION: 2'-deoxy-2'-fluoro with phosphodiester linkage
<220> FEATURE:
<221> NAME/KEY: misc_feature
<222> LOCATION: (4)..(4)
<223> OTHER INFORMATION: 2'-deoxy-2'-fluoro with phosphodiester linkage
<220> FEATURE:
<221> NAME/KEY: misc_feature
<222> LOCATION: (6)..(6)
<223> OTHER INFORMATION: 2'-deoxy-2'-fluoro with phosphodiester linkage
<220> FEATURE:
<221> NAME/KEY: misc_feature
<222> LOCATION: (8)..(8)
<223> OTHER INFORMATION: 2'-deoxy-2'-fluoro with phosphodiester linkage
<220> FEATURE:
<221> NAME/KEY: misc_feature
<222> LOCATION: (10)..(10)
<223> OTHER INFORMATION: 2'-deoxy-2'-fluoro with phosphodiester linkage
<220> FEATURE:
<221> NAME/KEY: misc_feature
<222> LOCATION: (12)..(12)
<223> OTHER INFORMATION: 2'-deoxy-2'-fluoro with phosphodiester linkage
<220> FEATURE:
<221> NAME/KEY: misc_feature
<222> LOCATION: (14)..(14)
<223> OTHER INFORMATION: 2'-deoxy-2'-fluoro with phosphodiester linkage
<220> FEATURE:
<221> NAME/KEY: misc_feature
<222> LOCATION: (16)..(16)
<223> OTHER INFORMATION: 2'-deoxy-2'-fluoro with phosphodiester linkage
<220> FEATURE:
<221> NAME/KEY: misc_feature
<222> LOCATION: (18)..(18)
<223> OTHER INFORMATION: 2'-deoxy-2'-fluoro with phosphodiester linkage
<220> FEATURE:
<221> NAME/KEY: misc_feature
<222> LOCATION: (20)..(20)
<223> OTHER INFORMATION: 2'-deoxy-2'-fluoro

<400> SEQUENCE: 138
uuugucucug guccuuacuu                                                 20

<210> SEQ ID NO 139
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (2)..(2)
<223> OTHER INFORMATION: 2'-deoxy-2'-fluoro with phosphodiester linkage
<220> FEATURE:
<221> NAME/KEY: misc_feature
<222> LOCATION: (4)..(4)
<223> OTHER INFORMATION: 2'-deoxy-2'-fluoro with phosphodiester linkage
<220> FEATURE:
<221> NAME/KEY: misc_feature
<222> LOCATION: (6)..(6)
<223> OTHER INFORMATION: 2'-deoxy-2'-fluoro with phosphodiester linkage
<220> FEATURE:
<221> NAME/KEY: misc_feature
<222> LOCATION: (8)..(8)
<223> OTHER INFORMATION: 2'-deoxy-2'-fluoro with phosphodiester linkage
<220> FEATURE:
<221> NAME/KEY: misc_feature
<222> LOCATION: (10)..(10)
```

```
<223> OTHER INFORMATION: 2'-deoxy-2'-fluoro with phosphodiester linkage
<220> FEATURE:
<221> NAME/KEY: misc_feature
<222> LOCATION: (12)..(12)
<223> OTHER INFORMATION: 2'-deoxy-2'-fluoro with phosphodiester linkage
<220> FEATURE:
<221> NAME/KEY: misc_feature
<222> LOCATION: (14)..(14)
<223> OTHER INFORMATION: 2'-deoxy-2'-fluoro with phosphodiester linkage
<220> FEATURE:
<221> NAME/KEY: misc_feature
<222> LOCATION: (16)..(16)
<223> OTHER INFORMATION: 2'-deoxy-2'-fluoro with phosphodiester linkage
<220> FEATURE:
<221> NAME/KEY: misc_feature
<222> LOCATION: (18)..(18)
<223> OTHER INFORMATION: 2'-deoxy-2'-fluoro with phosphodiester linkage
<220> FEATURE:
<221> NAME/KEY: misc_feature
<222> LOCATION: (20)..(20)
<223> OTHER INFORMATION: 2'-deoxy-2'-fluoro with phosphodiester linkage

<400> SEQUENCE: 139
aaacagagac caggaaugaa                                               20

<210> SEQ ID NO 140
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-deoxy-2'-fluoro with phosphodiester linkage
<220> FEATURE:
<221> NAME/KEY: misc_feature
<222> LOCATION: (5)..(5)
<223> OTHER INFORMATION: 2'-deoxy-2'-fluoro with phosphodiester linkage
<220> FEATURE:
<221> NAME/KEY: misc_feature
<222> LOCATION: (7)..(7)
<223> OTHER INFORMATION: 2'-deoxy-2'-fluoro with phosphodiester linkage
<220> FEATURE:
<221> NAME/KEY: misc_feature
<222> LOCATION: (9)..(9)
<223> OTHER INFORMATION: 2'-deoxy-2'-fluoro with phosphodiester linkage
<220> FEATURE:
<221> NAME/KEY: misc_feature
<222> LOCATION: (11)..(11)
<223> OTHER INFORMATION: 2'-deoxy-2'-fluoro with phosphodiester linkage
<220> FEATURE:
<221> NAME/KEY: misc_feature
<222> LOCATION: (13)..(13)
<223> OTHER INFORMATION: 2'-deoxy-2'-fluoro with phosphodiester linkage
<220> FEATURE:
<221> NAME/KEY: misc_feature
<222> LOCATION: (15)..(15)
<223> OTHER INFORMATION: 2'-deoxy-2'-fluoro with phosphodiester linkage
<220> FEATURE:
<221> NAME/KEY: misc_feature
<222> LOCATION: (17)..(17)
<223> OTHER INFORMATION: 2'-deoxy-2'-fluoro with phosphodiester linkage
<220> FEATURE:
<221> NAME/KEY: misc_feature
<222> LOCATION: (19)..(19)
<223> OTHER INFORMATION: 2'-deoxy-2'-fluoro with phosphodiester linkage

<400> SEQUENCE: 140
aaacagagac caggaaugaa                                               20
```

```
<210> SEQ ID NO 141
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphodiester linkage
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
```

<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(19)
<223> OTHER INFORMATION: 2'-O-methyl
<220> FEATURE:
<221> NAME/KEY: misc_feature
<222> LOCATION: (20)..(20)
<223> OTHER INFORMATION: 2'-deoxy-2'-fluoro

<400> SEQUENCE: 141
uuugucucug guccuuacuu                                             20

<210> SEQ ID NO 142
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphodiester linkage
<220> FEATURE:
<221> NAME/KEY: misc_feature
<222> LOCATION: (1)..(1)
<223> OTHER INFORMATION: 2'-deoxy-2'-fluoro
<220> FEATURE:
<221> NAME/KEY: misc_feature
<222> LOCATION: (2)..(2)
<223> OTHER INFORMATION: 2'-O-methyl
<220> FEATURE:
<221> NAME/KEY: misc_feature
<222> LOCATION: (3)..(3)
<223> OTHER INFORMATION: 2'-deoxy-2'-fluoro
<220> FEATURE:
<221> NAME/KEY: misc_feature
<222> LOCATION: (4)..(4)
<223> OTHER INFORMATION: 2'-O-methyl
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-O-methyl
<220> FEATURE:
<221> NAME/KEY: misc_feature
<222> LOCATION: (7)..(7)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-O-methyl
<220> FEATURE:
<221> NAME/KEY: misc_feature
<222> LOCATION: (9)..(9)
<223> OTHER INFORMATION: 2'-deoxy-2'-fluoro
<220> FEATURE:
<221> NAME/KEY: misc_feature
<222> LOCATION: (10)..(10)
<223> OTHER INFORMATION: 2'-O-methyl
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (13)..(13)
<223> OTHER INFORMATION: 2'-deoxy-2'-fluoro

```
<220> FEATURE:
<221> NAME/KEY: misc_feature
<222> LOCATION: (14)..(14)
<223> OTHER INFORMATION: 2'-O-methyl
<220> FEATURE:
<221> NAME/KEY: misc_feature
<222> LOCATION: (15)..(15)
<223> OTHER INFORMATION: 2'-deoxy-2'-fluoro
<220> FEATURE:
<221> NAME/KEY: misc_feature
<222> LOCATION: (16)..(16)
<223> OTHER INFORMATION: 2'-O-methyl
<220> FEATURE:
<221> NAME/KEY: misc_feature
<222> LOCATION: (17)..(17)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-O-methyl
<220> FEATURE:
<221> NAME/KEY: misc_feature
<222> LOCATION: (19)..(19)
<223> OTHER INFORMATION: 2'-deoxy-2'-fluoro
<220> FEATURE:
<221> NAME/KEY: misc_feature
<222> LOCATION: (20)..(20)
<223> OTHER INFORMATION: 2'-O-methyl

<400> SEQUENCE: 142
uuugucucug guccuuacuu                                                20

<210> SEQ ID NO 143
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphodiester linkage
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
```

```
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(19)
<223> OTHER INFORMATION: 2'-O-methyl
<220> FEATURE:
<221> NAME/KEY: misc_feature
<222> LOCATION: (20)..(20)
<223> OTHER INFORMATION: 2'-deoxy-2'-fluoro

<400> SEQUENCE: 143
aaguaaggac cagagacaaa                                                     20

<210> SEQ ID NO 144
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphodiester linkage
<220> FEATURE:
<221> NAME/KEY: misc_feature
<222> LOCATION: (1)..(1)
<223> OTHER INFORMATION: 2'-deoxy-2'-fluoro
<220> FEATURE:
<221> NAME/KEY: misc_feature
<222> LOCATION: (2)..(2)
<223> OTHER INFORMATION: 2'-O-methyl
<220> FEATURE:
<221> NAME/KEY: misc_feature
<222> LOCATION: (3)..(3)
<223> OTHER INFORMATION: 2'-deoxy-2'-fluoro
<220> FEATURE:
<221> NAME/KEY: misc_feature
<222> LOCATION: (4)..(4)
<223> OTHER INFORMATION: 2'-O-methyl
<220> FEATURE:
<221> NAME/KEY: misc_feature
```

```
<222> LOCATION: (5)..(5)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-O-methyl
<220> FEATURE:
<221> NAME/KEY: misc_feature
<222> LOCATION: (7)..(7)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-O-methyl
<220> FEATURE:
<221> NAME/KEY: misc_feature
<222> LOCATION: (9)..(9)
<223> OTHER INFORMATION: 2'-deoxy-2'-fluoro
<220> FEATURE:
<221> NAME/KEY: misc_feature
<222> LOCATION: (10)..(10)
<223> OTHER INFORMATION: 2'-O-methyl
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (13)..(13)
<223> OTHER INFORMATION: 2'-deoxy-2'-fluoro
<220> FEATURE:
<221> NAME/KEY: misc_feature
<222> LOCATION: (14)..(14)
<223> OTHER INFORMATION: 2'-O-methyl
<220> FEATURE:
<221> NAME/KEY: misc_feature
<222> LOCATION: (15)..(15)
<223> OTHER INFORMATION: 2'-deoxy-2'-fluoro
<220> FEATURE:
<221> NAME/KEY: misc_feature
<222> LOCATION: (16)..(16)
<223> OTHER INFORMATION: 2'-O-methyl
<220> FEATURE:
<221> NAME/KEY: misc_feature
<222> LOCATION: (17)..(17)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-O-methyl
<220> FEATURE:
<221> NAME/KEY: misc_feature
<222> LOCATION: (19)..(19)
<223> OTHER INFORMATION: 2'-deoxy-2'-fluoro
<220> FEATURE:
<221> NAME/KEY: misc_feature
<222> LOCATION: (20)..(20)
<223> OTHER INFORMATION: 2'-O-methyl

<400> SEQUENCE: 144
uuugucucug guccuuacuu                                                 20

<210> SEQ ID NO 145
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphodiester linkage
<220> FEATURE:
```

-continued

```
<221> NAME/KEY: misc_feature
<222> LOCATION: (1)..(1)
<223> OTHER INFORMATION: 2'-deoxy-2'-fluoro
<220> FEATURE:
<221> NAME/KEY: misc_feature
<222> LOCATION: (2)..(2)
<223> OTHER INFORMATION: 2'-O-methyl
<220> FEATURE:
<221> NAME/KEY: misc_feature
<222> LOCATION: (3)..(3)
<223> OTHER INFORMATION: 2'-deoxy-2'-fluoro
<220> FEATURE:
<221> NAME/KEY: misc_feature
<222> LOCATION: (4)..(4)
<223> OTHER INFORMATION: 2'-O-methyl
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-O-methyl
<220> FEATURE:
<221> NAME/KEY: misc_feature
<222> LOCATION: (7)..(7)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-O-methyl
<220> FEATURE:
<221> NAME/KEY: misc_feature
<222> LOCATION: (9)..(9)
<223> OTHER INFORMATION: 2'-deoxy-2'-fluoro
<220> FEATURE:
<221> NAME/KEY: misc_feature
<222> LOCATION: (10)..(10)
<223> OTHER INFORMATION: 2'-O-methyl
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (13)..(13)
<223> OTHER INFORMATION: 2'-deoxy-2'-fluoro
<220> FEATURE:
<221> NAME/KEY: misc_feature
<222> LOCATION: (14)..(14)
<223> OTHER INFORMATION: 2'-O-methyl
<220> FEATURE:
<221> NAME/KEY: misc_feature
<222> LOCATION: (15)..(15)
<223> OTHER INFORMATION: 2'-deoxy-2'-fluoro
<220> FEATURE:
<221> NAME/KEY: misc_feature
<222> LOCATION: (16)..(16)
<223> OTHER INFORMATION: 2'-O-methyl
<220> FEATURE:
<221> NAME/KEY: misc_feature
<222> LOCATION: (17)..(17)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-O-methyl
<220> FEATURE:
<221> NAME/KEY: misc_feature
<222> LOCATION: (19)..(19)
<223> OTHER INFORMATION: 2'-deoxy-2'-fluoro
<220> FEATURE:
<221> NAME/KEY: misc_feature
<222> LOCATION: (20)..(20)
<223> OTHER INFORMATION: 2'-O-methyl
```

<400> SEQUENCE: 145
aaguaaggac cagagacaaa                                                     20

<210> SEQ ID NO 146
<211> LENGTH: 19
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphodiester linkage
<220> FEATURE:
<221> NAME/KEY: misc_feature
<222> LOCATION: (1)..(1)
<223> OTHER INFORMATION: 2'-deoxy-2'-fluoro
<220> FEATURE:
<221> NAME/KEY: misc_feature
<222> LOCATION: (2)..(2)
<223> OTHER INFORMATION: 2'-O-methyl
<220> FEATURE:
<221> NAME/KEY: misc_feature
<222> LOCATION: (3)..(3)
<223> OTHER INFORMATION: 2'-deoxy-2'-fluoro
<220> FEATURE:
<221> NAME/KEY: misc_feature
<222> LOCATION: (4)..(4)
<223> OTHER INFORMATION: 2'-O-methyl
<220> FEATURE:
<221> NAME/KEY: misc_feature
<222> LOCATION: (5)..(5)
<223> OTHER INFORMATION: 2'-deoxy-2'-fluoro
<220> FEATURE:
<221> NAME/KEY: misc_feature
<222> LOCATION: (6)..(6)
<223> OTHER INFORMATION: 2'-O-methyl
<220> FEATURE:
<221> NAME/KEY: misc_feature
<222> LOCATION: (7)..(7)
<223> OTHER INFORMATION: 2'-deoxy-2'-fluoro
<220> FEATURE:
<221> NAME/KEY: misc_feature
<222> LOCATION: (8)..(8)
<223> OTHER INFORMATION: 2'-O-methyl
<220> FEATURE:
<221> NAME/KEY: misc_feature
<222> LOCATION: (9)..(9)
<223> OTHER INFORMATION: 2'-deoxy-2'-fluoro
<220> FEATURE:
<221> NAME/KEY: misc_feature
<222> LOCATION: (10)..(10)
<223> OTHER INFORMATION: 2'-O-methyl
<220> FEATURE:
<221> NAME/KEY: misc_feature
<222> LOCATION: (11)..(11)
<223> OTHER INFORMATION: 2'-deoxy-2'-fluoro
<220> FEATURE:
<221> NAME/KEY: misc_feature
<222> LOCATION: (12)..(12)
<223> OTHER INFORMATION: 2'-O-methyl
<220> FEATURE:
<221> NAME/KEY: misc_feature
<222> LOCATION: (13)..(13)
<223> OTHER INFORMATION: 2'-deoxy-2'-fluoro
<220> FEATURE:
<221> NAME/KEY: misc_feature
<222> LOCATION: (14)..(14)
<223> OTHER INFORMATION: 2'-O-methyl
<220> FEATURE:
<221> NAME/KEY: misc_feature
<222> LOCATION: (15)..(15)
<223> OTHER INFORMATION: 2'-deoxy-2'-fluoro
<220> FEATURE:
<221> NAME/KEY: misc_feature
<222> LOCATION: (16)..(16)

```
<223> OTHER INFORMATION: 2'-O-methyl
<220> FEATURE:
<221> NAME/KEY: misc_feature
<222> LOCATION: (17)..(17)
<223> OTHER INFORMATION: 2'-deoxy-2'-fluoro
<220> FEATURE:
<221> NAME/KEY: misc_feature
<222> LOCATION: (18)..(18)
<223> OTHER INFORMATION: 2'-O-methyl
<220> FEATURE:
<221> NAME/KEY: misc_feature
<222> LOCATION: (19)..(19)
<223> OTHER INFORMATION: 2'-deoxy-2'-fluoro
<220> FEATURE:
<221> NAME/KEY: misc_feature
<222> LOCATION: (20)..(20)
<223> OTHER INFORMATION: 2'-O-methyl

<400> SEQUENCE: 146
aaguaaggac cagagacaa                                                19

<210> SEQ ID NO 147
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: phosphorothioate linkage
<220> FEATURE:
<221> NAME/KEY: misc_feature
<222> LOCATION: (1)..(1)
<223> OTHER INFORMATION: 2'-O-methyl
<220> FEATURE:
<221> NAME/KEY: misc_feature
<222> LOCATION: (2)..(2)
<223> OTHER INFORMATION: 2'-deoxy-2'-fluoro
<220> FEATURE:
<221> NAME/KEY: misc_feature
<222> LOCATION: (3)..(3)
<223> OTHER INFORMATION: 2'-O-methyl
<220> FEATURE:
<221> NAME/KEY: misc_feature
<222> LOCATION: (4)..(4)
<223> OTHER INFORMATION: 2'-deoxy-2'-fluoro
<220> FEATURE:
<221> NAME/KEY: misc_feature
<222> LOCATION: (5)..(5)
<223> OTHER INFORMATION: 2'-O-methyl
<220> FEATURE:
<221> NAME/KEY: misc_feature
<222> LOCATION: (6)..(6)
<223> OTHER INFORMATION: 2'-deoxy-2'-fluoro
<220> FEATURE:
<221> NAME/KEY: misc_feature
<222> LOCATION: (7)..(7)
<223> OTHER INFORMATION: 2'-O-methyl
<220> FEATURE:
<221> NAME/KEY: misc_feature
<222> LOCATION: (8)..(8)
<223> OTHER INFORMATION: 2'-deoxy-2'-fluoro
<220> FEATURE:
<221> NAME/KEY: misc_feature
<222> LOCATION: (9)..(9)
<223> OTHER INFORMATION: 2'-O-methyl
<220> FEATURE:
<221> NAME/KEY: misc_feature
<222> LOCATION: (10)..(10)
<223> OTHER INFORMATION: 2'-deoxy-2'-fluoro
<220> FEATURE:
<221> NAME/KEY: misc_feature
<222> LOCATION: (11)..(11)
<223> OTHER INFORMATION: 2'-O-methyl
<220> FEATURE:
<221> NAME/KEY: misc_feature
```

<222> LOCATION: (12)..(12)
<223> OTHER INFORMATION: 2'-deoxy-2'-fluoro
<220> FEATURE:
<221> NAME/KEY: misc_feature
<222> LOCATION: (13)..(13)
<223> OTHER INFORMATION: 2'-O-methyl
<220> FEATURE:
<221> NAME/KEY: misc_feature
<222> LOCATION: (14)..(14)
<223> OTHER INFORMATION: 2'-deoxy-2'-fluoro
<220> FEATURE:
<221> NAME/KEY: misc_feature
<222> LOCATION: (15)..(15)
<223> OTHER INFORMATION: 2'-O-methyl
<220> FEATURE:
<221> NAME/KEY: misc_feature
<222> LOCATION: (16)..(16)
<223> OTHER INFORMATION: 2'-deoxy-2'-fluoro
<220> FEATURE:
<221> NAME/KEY: misc_feature
<222> LOCATION: (17)..(17)
<223> OTHER INFORMATION: 2'-O-methyl
<220> FEATURE:
<221> NAME/KEY: misc_feature
<222> LOCATION: (18)..(18)
<223> OTHER INFORMATION: 2'-deoxy-2'-fluoro
<220> FEATURE:
<221> NAME/KEY: misc_feature
<222> LOCATION: (19)..(19)
<223> OTHER INFORMATION: 2'-O-methyl
<220> FEATURE:
<221> NAME/KEY: misc_feature
<222> LOCATION: (20)..(20)
<223> OTHER INFORMATION: 2'-deoxy-2'-fluoro

<400> SEQUENCE: 147
uuugucucug guccuuacuu                                           20

<210> SEQ ID NO 148
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(1)
<223> OTHER INFORMATION: 2'-deoxy-2'-fluoro with phosphodiester linkage
<220> FEATURE:
<221> NAME/KEY: misc_feature
<222> LOCATION: (3)..(3)
<223> OTHER INFORMATION: 2'-deoxy-2'-fluoro with phosphodiester linkage
<220> FEATURE:
<221> NAME/KEY: misc_feature
<222> LOCATION: (5)..(5)
<223> OTHER INFORMATION: 2'-deoxy-2'-fluoro with phosphodiester linkage
<220> FEATURE:
<221> NAME/KEY: misc_feature
<222> LOCATION: (7)..(7)
<223> OTHER INFORMATION: 2'-deoxy-2'-fluoro with phosphodiester linkage
<220> FEATURE:
<221> NAME/KEY: misc_feature
<222> LOCATION: (9)..(9)
<223> OTHER INFORMATION: 2'-deoxy-2'-fluoro with phosphodiester linkage
<220> FEATURE:
<221> NAME/KEY: misc_feature
<222> LOCATION: (11)..(11)
<223> OTHER INFORMATION: 2'-deoxy-2'-fluoro with phosphodiester linkage
<220> FEATURE:
<221> NAME/KEY: misc_feature
<222> LOCATION: (13)..(13)
<223> OTHER INFORMATION: 2'-deoxy-2'-fluoro with phosphodiester linkage
<220> FEATURE:
<221> NAME/KEY: misc_feature
<222> LOCATION: (15)..(15)
<223> OTHER INFORMATION: 2'-deoxy-2'-fluoro with phosphodiester linkage
<220> FEATURE:

```
<221> NAME/KEY: misc_feature
<222> LOCATION: (17)..(17)
<223> OTHER INFORMATION: 2'-deoxy-2'-fluoro with phosphodiester linkage
<220> FEATURE:
<221> NAME/KEY: misc_feature
<222> LOCATION: (19)..(19)
<223> OTHER INFORMATION: 2'-deoxy-2'-fluoro with phosphodiester linkage

<400> SEQUENCE: 148
uuugucucug guccuuacuu                                                20

<210> SEQ ID NO 149
<211> LENGTH: 20
<212> TYPE: RNA
<213> ORGANISM: Artificial
<220> FEATURE:
<223> OTHER INFORMATION: Synthetic Construct
<220> FEATURE:
<221> NAME/KEY: misc_feature
<222> LOCATION: (1)..(20)
<223> OTHER INFORMATION: ribo with phosphorothioate linkage

<400> SEQUENCE: 149
uuugaaaaug uugaucuccu                                                20

<210> SEQ ID NO 150
<211> LENGTH: 20
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(3)
<223> OTHER INFORMATION: 2'-O-methoxyethyl
<220> FEATURE:
<221> NAME/KEY: misc_feature
<222> LOCATION: (13)..(20)
<223> OTHER INFORMATION: 2'-O-methoxyethyl

<400> SEQUENCE: 150
tccgtcatcg ctcctcaggg                                                20

<210> SEQ ID NO 151
<211> LENGTH: 20
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(5)
<223> OTHER INFORMATION: 2'-O-methoxyethyl
<220> FEATURE:
<221> NAME/KEY: misc_feature
<222> LOCATION: (16)..(20)
<223> OTHER INFORMATION: 2'-O-methoxyethyl

<400> SEQUENCE: 151
gtgcgcgcga gcccgaaatc                                                20

<210> SEQ ID NO 152
<211> LENGTH: 20
<212> TYPE: DNA
<213> ORGANISM: Artificial
<220> FEATURE:
<223> OTHER INFORMATION: Oligonucleotide
<220> FEATURE:
<221> NAME/KEY: misc_feature
<222> LOCATION: (1)..(5)
<223> OTHER INFORMATION: 2'-O-methoxyethyl
```

```
<220> FEATURE:
<221> NAME/KEY: misc_feature
<222> LOCATION: (16)..(20)
<223> OTHER INFORMATION: 2'-O-methoxyethyl

<400> SEQUENCE: 152
atgcattctg cccccaagga                                                    20

<210> SEQ ID NO 153
<211> LENGTH: 14796
<212> TYPE: DNA
<213> ORGANISM: Homo sapiens
<300> PUBLICATION INFORMATION:
<308> DATABASE ACCESSION NUMBER: U75285
<309> DATABASE ENTRY DATE: 2004-09-02
<313> RELEVANT RESIDUES IN SEQ ID NO: (1)..(14796)

<400> SEQUENCE: 153
tctagacatg cggatatatt caagctgggc acagcacagc agccccaccc caggcagctt         60
gaaatcagag ctggggtcca aagggaccac accccgaggg actgtgtggg ggtcggggca        120
cacaggccac tgcttccccc cgtctttctc agccattcct gaagtcagcc tcactctgct        180
tctcagggat ttcaaatgtg cagagactct ggcacttttg tagaagcccc ttctggtcct        240
aacttacacc tggatgctgt ggggctgcag ctgctgctcg ggctcgggag gatgctgggg        300
gcccggtgcc catgagcttt tgaagctcct ggaactcggt tttgagggtg ttcaggtcca        360
ggtggacacc tgggctgtcc ttgtccatgc atttgatgac attgtgtgca gaagtgaaaa        420
ggagttaggc cgggcatgct ggcttatgcc tgtaatccca gcactttggg aggctgaggc        480
gggtggatca cgaggtcagg agttcaatac cagcctggcc aagatggtga accccgtctc       540
ctactaaaaa tacaaaaaaa ttagccgggc atggtggcgg gcgcatgtaa tcccagctac       600
tgggggggct gaggcagaga attgctggaa cccaggagat ggaggttgca gtgagccaag       660
attgtgccac tgcactgcac tccagcctgg cgacagagca agactctgtc tcaaaaaaaa       720
aaaaaaaaag tgaaaaggag ttgttccttt cctccctcct gagggcaggc aactgctgcg       780
gttgccagtg gaggtggtgc gtccttggtc tgtgcctggg ggccacccca gcagaggcca       840
tggtggtgcc agggcccggt tagcgagcca atcagcagga cccaggggcg acctgccaaa       900
gtcaactgga tttgataact gcagcgaagt taagtttcct gattttgatg attgtgttgt       960
ggttgtgtaa gagaatgaag tatttcgggg tagtatggta atgccttcaa cttacaaacg      1020
gttcaggtaa accacccata tacatacata tacatgcatg tgatatatac atacagggg       1080 atgtgtgtgt gttcacatat atgaggggag agagactagg ggagagaaag taggttgggg      1140
agagggagag agaaaggaaa acaggagaca gagagagagc ggggagtaga gagagggaag      1200
gggtaagaga gggagaggag gagagaaagg gaggaagaag cagagagtga atgttaaagg      1260
aaacaggcaa aacataaaca gaaaatctgg gtgaagggta tatgagtatt ctttgtacta      1320
ttcttgcaat tatctttttat ttaaattgac atcgggccgg gcgcagtggc tcacatctgt      1380
aatcccagca ctttgggagg ccgaggcagg cagatcactt gaggtcagga gtttgagacc      1440
agcctggcaa acatggtgaa acccatctc tactaaaaat acaaaaatta gcctggtgtg      1500
gtggtgcatg cctttaatct cagctactcg ggaggctgag gcaggagaat cgcttgaacc      1560
cgtggcgggg aggaggttgc agtgagctga gatcatgcca ctgcactcca gcctgggcga      1620
tagagcgaga ctcagtttca aataaataaa taaacatcaa aataaaaagt tactgtatta      1680
aagaatgggg gcggggtggg aggggtgggg agaggttgca aaaataaata aataaataaa      1740
```

```
taaacccccaa aatgaaaaag acagtggagg caccaggcct gcgtgggggct ggagggctaa    1800
taaggccagg cctcttatct ctggccatag aaccagagaa gtgagtggat gtgatgccca    1860
gctccagaag tgactccaga acaccctgtt ccaaagcaga ggacacactg attttttttt    1920
taataggctg caggacttac tgttggtggg acgccctgct ttgcgaaggg aaaggaggag    1980
tttgccctga gcacaggccc ccaccctcca ctgggctttc cccagctccc ttgtcttctt    2040
atcacggtag tggcccagtc cctggcccct gactccagaa ggtggccctc ctggaaaccc    2100
aggtcgtgca gtcaacgatg tactcgccgg acagcgatg tctgctgcac tccatccctc    2160
ccctgttcat ttgtccttca tgcccgtctg gagtagatgc ttttttgcaga ggtggcaccc    2220
tgtaaagctc tcctgtctga ctttttttt tttttttagac tgagtttttgc tcttgttgcc    2280
taggctggag tgcaatggca caatctcagc tcactgcacc ctctgcctcc cgggttcaag    2340
cgattctcct gcctcagcct cccgagtagt tgggattaca ggcatgcacc accacgccca    2400
gctaattttt gtatttttag tagagacaag gtttcaccgt gatggccagg ctggtcttga    2460
actccaggac tcaagtgatg ctcctgccta ggcctctcaa agtgttggga ttacaggcgt    2520
gagccactgc accccggcctg cacgcgttct ttgaaagcag tcgaggggggc gctaggtgtg    2580
ggcagggacg agctggcgcg gcgtcgctgg gtgcaccgcg accacgggca gagccacgcg    2640
gcgggaggac tacaactccc ggcacacccc gcgccgcccc gcctctactc ccagaaggcc    2700
gcggggggtg gaccgcctaa gagggcgtgc gctcccgaca tgccccgcgg cgcgccatta    2760
accgccagat ttgaatcgcg ggacccgttg gcagaggtgg cggcggcggc atgggtgccc    2820
cgacgttgcc ccctgcctgg cagcccttttc tcaaggacca ccgcatctct acattcaaga    2880
actggccctt cttggagggc tgcgcctgca ccccggagcg ggtgagactg cccggcctcc    2940
tggggtcccc cacgcccgcc ttgccctgtc cctagcgagg ccactgtgac tgggcctcgg    3000
gggtacaagc cgccctcccc tccccgtcct gtccccagcg aggccactgt ggctgggccc    3060
cttgggtcca ggccggcctc ccctcccctgc tttgtcccca tcgaggcctt tgtggctggg    3120
cctcggggtt ccgggctgcc acgtccactc acgagctgtg ctgtcccttg cagatggccg    3180
aggctggctt catccactgc cccactgaga acgagccaga cttggcccag tgtttcttct    3240
gcttcaagga gctggaaggc tgggagccag atgacgaccc catgtaagtc ttctctggcc    3300
agcctcgatg ggctttgttt tgaactgagt tgtcaaaaga tttgagttgc aaagacactt    3360
agtatgggag ggttgctttc caccctcatt gcttcttaaa cagctgttgt gaacggatac    3420
ctctctatat gctggtgcct tggtgatgct tacaacctaa ttaaatctca tttgaccaaa    3480
atgccttggg gtggacgtaa gatgcctgat gcctttcatg ttcaacagaa tacatcagca    3540
gaccctgttg ttgtgaactc ccaggaatgt ccaagtgctt tttttgagat ttttttaaaaa    3600
acagtttaat tgaaatataa cctacacagc acaaaaatta ccctttgaaa gtgtgcactt    3660
cacactttcg gaggctgagg cgggcggatc acctgaggtc aggagttcaa gacctgcctg    3720
gccaacttgg cgaaaccccg tctctactaa aaatacaaaa attagccggg catggtagcg    3780
cacgcccgta atcccagcta ctcgggaggc taaggcagga gaatcgcttg aacctgggag    3840
gcggaggttg cagtgagccg agattgtgcc aatgcactcc agcctcggcg acagagcgag    3900
actccgtcat aaaaataaaa aattgaaaaa aaaaaagaa agaaagcata tacttcagtg    3960
ttgttctgga ttttttttctt caagatgcct agttaatgac aatgaaattc tgtactcgga    4020
tggtatctgt ctttccacac tgtaatgcca tattcttttc tcaccttttt ttctgtcgga    4080
ttcagttgct tccacagctt taattttttt ccctggaga atcaccccag ttgttttctct    4140
```

```
ttttggccag aagagagtag ctgttttttt tcttagtatg tttgctatgg tggttatact    4200
gcatccccgt aatcactggg aaaagatcag tggtattctt cttgaaaatg aataagtgtt    4260
atgatatttt cagattagag ttacaactgg ctgtcttttt ggactttgtg tggccatgtt    4320
ttcattgtaa tgcagttctg gtaacggtga tagtcagtta tacagggaga ctcccctagc    4380
agaaaatgag agtgtgagct aggggggtccc ttggggaacc cggggcaata atgcccttct    4440
ctgcccttaa tccttacagt gggccgggca cggtggctta cgcctgtaat accagcactt    4500
tgggaggccg aggcgggcgg atcacgaggt caggagatcg agaccatctt ggctaatacg    4560
gtgaaacccc gtctccacta aaatacaaaa aattagccg ggcgtggtgg tgggcgcctg    4620
tagtcccagc tactcgggag gctgaggcag gagaatggcg tgaacccagg aggcggagct    4680
tgcagtgagc cgagattgca ccactgcact ccagcctggg cgacaaatg agactccgtc    4740 tcaaaaaaaa aaaaaaaga aaaaaatctt tacagtggat tacataacaa ttccagtgaa    4800
atgaaattac ttcaaacagt tccttgagaa tgttggaggg atttgacatg taattccttt    4860
ggacatatac catgtaacac ttttccaact aattgctaag gaagtccaga taaaatagat    4920
acattagcca cacagatgtg gggggagatg tccacaggga gagagaaggt gctaagaggt    4980
gccatatggg aatgtggctt gggcaaagca ctgatgccat caacttcaga cttgacgtct    5040
tactcctgag gcagagcagg gtgtgcctgt ggagggcgtg gggaggtggc ccgtggggag    5100
tggactgccg ctttaatccc ttcagctgcc tttccgctgt tgttttgatt tttctagaga    5160
ggaacataaa aagcattcgt ccggttgcgc tttcctttct gtcaagaagc agtttgaaga    5220
attacccctt ggtgaatttt tgaaactgga cagagaaaga gccaagaaca aaattgtatg    5280
tattgggaat aagaactgct caaaccctgt tcaatgtctt tagcactaaa ctacctagtc    5340
cctcaaaggg actctgtgtt ttcctcagga agcattttt tttttttttct gagatagagt    5400 ttcactcttg ttgcccaggc tggagtgcaa tggtgcaatc ttggctcact gcaacctctg    5460
cctctcgggt tcaagtgatt ctcctgcctc agcctcccaa gtaactggga ttacagggaa    5520
gtgccaccac acccagctaa ttttttgtatt tttagtagag atggggtttc accacattgc    5580
ccaggctggt cttgaactcc tgacctcgtg attcgcccac cttggcctcc caaagtgctg    5640
ggattacagg cgtgaaccac cacgcctggc ttttttttttt ttgttctgag acacagtttc    5700
actctgttac ccaggctgga gtagggtggc ctgatctcgg atcactgcaa cctccgcctc    5760
ctgggctcaa gtgatttgcc tgcttcagcc tcccaagtag ccgagattac aggcatgtgc    5820
caccacaccc aggtaatttt tgtatttttg gtagagacga ggtttcacca tgttggccag    5880
gctggttttg aactcctgac ctcaggtgat ccacccgcct cagcctccca aagtgctgag    5940
attataggtg tgagccacca cacctggcct caggaagtat ttttattttt aaatttattt    6000
atttatttga gatggagtct tgctctgtcg cccaggctag agtgcagcga cgggatctcg    6060
gctcactgca agctccgccc ccaggttca agccattctc ctgcctcagc ctcccgagta    6120
gctgggacta caggcgcccg ccaccacacc cggctaattt ttttgtattt ttagtagaga    6180
cgggttttca ccgtgttagc caggagggtc ttgatctcct gacctcgtga tctgcctgcc    6240
tcggcctccc aaagtgctgg gattacaggt gtgagccacc acaccggct attttttattt    6300 ttttgagaca gggactcact ctgtcacctg gctgcagtg cagtggtaca ccatagctca    6360
ctgcagcctc gaactcctga gctcaagtga tcctcccacc tcatcctcac aagtaattgg    6420
gactacaggt gcacccccacc atgcccacct aatttatttta tttatttatt tatttatttt    6480
```

```
catagagatg agggttccct gtgttgtcca ggctggtctt gaactcctga gctcacggga    6540
tccttttgcc tgggcctccc aaagtgctga gattacaggc atgagccacc gtgcccagct    6600
aggaatcatt tttaaagccc ctaggatgtc tgtgtgattt aaagctcct ggagtgtggc    6660 cggtataagt atataccggt ataagtaaat cccacatttt gtgtcagtat ttactagaaa    6720
cttagtcatt tatctgaagt tgaaatgtaa ctgggcttta tttatttatt tatttattta    6780 tttatttta attttttttt ttgagacgag tctcactttg tcacccaggc tggagtgcag    6840
tggcacgatc tcggctcact gcaacctctg cctcccgggg tcaagcgatt ctcctgcctt    6900
agcctcccga gtagctggga ctacaggcac gcaccaccat gcctggctaa ttttgtatt     6960 tttagtagac ggggttttcac catgctggcc aagctggtct caaactcctg accttgtgat    7020
ctgcccgctt tagcctccca gagtgctggg attacaggca tgagccacca tgcgtggtct    7080
ttttaaaatt ttttgatttt tttttttttt gagacagagc cttgctctgt cgcccaggct    7140
ggagtgcagt ggcacgatct cagctcacta caagctccgc ctcccgggtt cacgccattc    7200
ttctgcctca gcctcctgag tagctgggac tacaggtgcc caccaccacg cctggctaat    7260 ttttttggt attttattta gagacaaggt ttcatcatgt tggccaggct ggtctcaaac    7320
tcctgacctc aagtgatctg cctgcctcgg cctcccaaag cgctgagatt acaggtgtga    7380
tctactgcgc caggcctggg cgtcatatat tcttattgc taagtctggc agccccacac    7440
agaataagta ctgggggatt ccatatcctt gtagcaaagc cctgggtgga gagtcaggag    7500
atgttgtagt tctgtctctg ccacttgcag actttgagtt taagccagtc gtgctcatgc    7560
tttccttgct aaatagaggt tagaccccct atcccatggt ttctcaggtt gcttttcagc    7620
ttgaaaattg tattcctttg tagagatcag cgtaaaataa ttctgtcctt atatgtggct    7680
ttattttaat ttgagacaga gtgtcactca gtcgcccagg ctggagtgtg tggtgcgat    7740 cttggctcac tgcgacctcc acctcccagg ttcaagcgat tctcgtgcct caggctccca    7800
agtagctgag attataggtg tgtgccacca ggcccagcta acttttgtat ttttagtaga    7860
gacagggttt tgccatgttg gctaagctgg tctcgaactc ctggcctcaa gtgatctgcc    7920
cgccttggca tccaaagtg ctgggattac aggtgtgaac caccacacct ggcctcaata    7980
tagtggcttt taagtgctaa ggactgagat tgtgttttgt caggaagagg ccagttgtgg    8040
gtgaagcatg ctgtgagaga gcttgtcacc tggttgaggt tgtgggagct gcagcgtggg    8100
aactggaaag tgggctgggg atcatctttt tccaggtcag gggtcagcca gcttttctgc    8160
agcgtgccat agaccatctc ttagccctcg tgggtcagag tctctgttgc atattgtctt    8220
ttgttgtttt tcacaacctt ttagaaacat aaaaagcatt cttagcccgt gggctggaca    8280
aaaaaaggcc atgacgggct gtatggattt ggcccagcag gcccttgctt gccaagccct    8340
gttttagaca aggagcagct tgtgtgcctg gaaccatcat gggcacaggg gaggagcaga    8400
gtggatgtgg aggtgtgagc tggaaaccag gtcccagagc gctgagaaag acagagggtt    8460
tttgcccttg caagtagagc aactgaaatc tgacaccatc cagttccaga aagccctgaa    8520
gtgctggtgg acgctgcggg gtgctccgct ctagggttac agggatgaag atgcagtctg    8580 gtaggggag tccactcacc tgttggaaga tgtgattaag aaaagtagac tttcaggggcc    8640 gggcatggtg gctcacgcct gtaatcccag cactttggga ggccgaggcg ggtggatcac    8700
gaggtcagga gatcgagacc atcctggcta acatggtgaa accccgtctt tactaaaaat    8760
acaaaaaatt agctgggcgt ggtggcgggc gcctgtagtc ccagctactc gggaggctga    8820
ggcaggagaa tggcgtgaac ctgggaggtg gagcttgctg tgagccgaga tcgcgccact    8880
```

```
gcactccagc ctgggcgaca gagcgagact ccgtctcaaa aaaaaaaaaa aaagtaggct  8940
ttcatgatgt gtgagctgaa ggcgcagtag gcagaagtag aggcctcagt ccctgcagga  9000
gaccccctcgg tctctatctc ctgatagtca gacccagcca cactggaaag aggggagaca  9060
ttacagcctg cgagaaaagt agggagattt aaaaactgct tggcttttat tttgaactgt  9120
tttttttgtt tgtttgtttt ccccaattca gaatacagaa tacttttatg gatttgtttt  9180
tattacttta attttgaaac aatataatct ttttttttgtt gttttttttga cagggtct  9240
tactctgtca cccaggctga gtgcagtggt gtgatcttgg ctcacctcag cctcgacccc  9300
ctgggctcaa atgattctcc cacctcagct tcccaagtag ctgggaccac aggtgcgtgt  9360
gttgcgctat acaaatcctg aagacaagga tgctgttgct ggtgatgctg gggattccca  9420
agatcccaga tttgatggca ggatgcccct gtctgctgcc ttgccagggt gccaggaggg  9480
cgctgctgtg gaagctgagg cccggccatc cagggcgatg cattgggcgc tgattcttgt  9540
tcctgctgct gcctcggtgc ttagcttttg aaacaatgaa ataaattaga accagtgtga  9600
aaatcgatca gggaataaat ttaatgtgga aataaactga acaacttagt tcttcataag  9660
agtttacttg gtaaatactt gtgatgagga caaaacgaag cactagaagg agaggcgagt  9720
tgtagacctg ggtggcagga gtgttttgtt tgttttcttt ggcagggtct tgctctgttg  9780
ctcaggctgg agtacagtgg cacaatcaca gctcactata gcctcgacct cctggactca  9840
agcaatcctc ctgcctcagc ctcccagtag ctgggactac aggcgcatgc caccatgcct  9900
ggctaatttt aaattttttt ttttctcttt tttgagatgg aatctcactc tgtcgcccag  9960
gctggagtgc agtggcgtga tctcggctga cggcaagctc cgcctcccag gttcactcca 10020
ttcgcctgcc tcagcctccc aagtagctgg gactacaggc gctgggatta caaacccaaa 10080
cccaaagtgc tgggattaca ggcgtgagcc actgcacccg gcctgttttg tctttcaata 10140
gcaagagttg tgtttgcttc gcccctacct ttagtggaaa aatgtataaa atggagatat 10200
tgacctccac attggggtgg ttaaattata gcatgtatgc aaaggagctt cgctaattta 10260
aggcttttttt gaaagagaag aaactgaata atccatgtgt gtatatatat tttaaaagcc 10320
atggtcatct ttccatatca gtaaagctga ggctccctgg gactgcagag ttgtccatca 10380
cagtccatta taagtgcgct gctgggccag gtgcagtggc ttgtgcctga atcccagcac 10440
tttgggaggc caaggcagga ggattcattg agcccaggag ttttgaggcg agcctgggca 10500
atgtggccag acctcatctc ttcaaaaaat acacaaaaaa ttagccaggc atggtggcac 10560
gtgcctgtag tctcagctac tcaggaggct gaggtgggag gatcactttg agccttgcag 10620
gtcaaagctg cagtaagcca tgatcttgcc actgcattcc agcctggatg acagagcgag 10680
accctgtctc taaaaaaaaa aaaaccaaa cggtgcactg ttttcttttt tcttatcaat 10740
ttattatttt taaattaaat tttcttttaa taatttataa attataaatt tatattaaaa 10800
aatgacaaat ttttattact tatacatgag gtaaaactta ggatatataa agtacatatt 10860
gaaaagtaat ttttttggctg gcacagtggc tcacacctgt aatcccagca ctttgggagg 10920
ccgtggcggg cagatcacat gagatcatga gttcgagacc aacctgacca acatggagag 10980
accccatctc tactaaaaat acaaaattag ccggggtggt ggcgcatgcc tgtaatccca 11040
gctactcggg aggctgaggc aggagaatct cttgaacccg ggaggcagag gttgcggtga 11100
gccaagatcg tgcctttgca caccagccta ggcaacaaga gcgaaagtcc gtctcaaaaa 11160
aaaagtaatt tttttttaagt taacctctgt cagcaaacaa atttaaccca ataaaggtct 11220
```

```
ttgttttta  atgtagtaga  ggagttaggg  tttataaaaa  atatggtagg  gaagggggtc   11280
cctggatttg  ctaatgtgat  tgtcatttgc  cccttaggag  agagctctgt  tagcagaatg   11340
aaaaaattgg  aagccagatt  cagggaggga  ctggaagcaa  agaatttct   gttcgaggaa   11400
gagcctgatg  tttgccaggg  tctgtttaac  tggacatgaa  gaggaaggct  ctggactttc   11460
ctccaggagt  ttcaggagaa  aggtagggca  gtggttaaga  gcagagctct  gcctagacta   11520
gctggggtgc  ctagactagc  tggggtgccc  agactagctg  gggtgcctag  actagctggg   11580
tactttgagt  ggctccttca  gcctggacct  cggtttcctc  acctgtatag  tagagatatg   11640
ggagcaccca  gcgcaggatc  actgtgaaca  taaatcagtt  aatggaggaa  gcaggtagag   11700
tggtgctggg  tgcataccaa  gcactccgtc  agtgtttcct  gttattcgat  gattaggagg   11760
cagcttaaac  tagagggagt  tgagctgaat  caggatgttt  gtcccaggta  gctgggaatc   11820
tgcctagccc  agtgcccagt  ttatttaggt  gctctctcag  tgttccctga  ttgttttttc   11880
ctttgtcatc  ttatctacag  gatgtgactg  ggaagctctg  gtttcagtgt  catgtgtcta   11940
ttctttattt  ccaggcaaag  gaaaccaaca  ataagaagaa  agaatttgag  gaaactgcga   12000
agaaagtgcg  ccgtgccatc  gagcagctgg  ctgccatgga  ttgaggcctc  tggccggagc   12060
tgcctggtcc  cagagtggct  gcaccacttc  cagggtttat  tccctggtgc  caccagcctt   12120
cctgtgggcc  ccttagcaat  gtcttaggaa  aggagatcaa  cattttcaaa  ttagatgttt   12180
caactgtgct  cctgttttgt  cttgaaagtg  gcaccagagg  tgcttctgcc  tgtgcagcgg   12240
gtgctgctgg  taacagtggc  tgcttctctc  tctctctctc  tttttgggg   gctcatttt    12300
gctgttttga  ttcccgggct  taccaggtga  gaagtgaggg  aggaagaagg  cagtgtccct   12360
tttgctagag  ctgacagctt  tgttcgcgtg  ggcagagcct  tccacagtga  atgtgtctgg   12420
acctcatgtt  gttgaggctg  tcacagtcct  gagtgtggac  ttggcaggtg  cctgttgaat   12480
ctgagctgca  ggttccttat  ctgtcacacc  tgtgcctcct  cagaggacag  ttttttttgtt  12540
gttgtgtttt  tttgttttt   tttttggta   gatgcatgac  ttgtgtgtga  tgagagaatg   12600
gagacagagt  ccctggctcc  tctactgttt  aacaacatgg  ctttcttatt  tgtttgaat    12660
tgttaattca  cagaatagca  caaactacaa  ttaaaactaa  gcacaaagcc  attctaagtc   12720
attgggaaaa  cggggtgaac  ttcaggtgga  tgaggagaca  gaatagagtg  ataggaagcg   12780
tctggcagat  actccttttg  ccactgctgt  gtgattagac  aggcccagtg  agccgcgggg   12840
cacatgctgg  ccgctcctcc  ctcagaaaaa  ggcagtggcc  taaatccttt  ttaaatgact   12900
tggctcgatg  ctgtggggga  ctggctgggc  tgctgcaggc  cgtgtgtctg  tcagcccaac   12960
cttcacatct  gtcacgttct  ccacacgggg  gagagacgca  gtccgcccag  gtccccgctt   13020
tctttggagg  cagcagctcc  cgcagggctg  aagtctggcg  taagatgatg  gatttgattc   13080
gccctcctcc  ctgtcataga  gctgcagggt  ggattgttac  agcttcgctg  gaaacctctg   13140
gaggtcatct  cggctgttcc  tgagaaataa  aaagcctgtc  atttcaaaca  ctgctgtgga   13200
ccctactggg  tttttaaaat  attgtcagtt  tttcatcgtc  gtcccctagcc tgccaacagc   13260
catctgccca  gacagccgca  gtgaggatga  gcgtcctggc  agagacgcag  ttgtctctgg   13320
gcgcttgcca  gagccacgaa  ccccagacct  gtttgtatca  tccgggctcc  ttccgggcag   13380
aaacaactga  aaatgcactt  cagacccact  tatttatgcc  acatctgagt  cggcctgaga   13440
tagacttttc  cctctaaact  gggagaatat  cacagtggtt  tttgttagca  gaaaatgcac   13500
tccagcctct  gtactcatct  aagctgctta  ttttttgatat  ttgtgtcagt  ctgtaaatgt   13560
atacttcact  ttaataactg  ttgcttagta  attggctttg  tagagaagct  ggaaaaaat    13620
```

```
ggttttgtct tcaactcctt tgcatgccag gcggtgatgt ggatctcggc ttctgtgagc    13680
ctgtgctgtg ggcagggctg agctggagcc gccctctca gcccgcctgc cacggccttt    13740
ccttaaaggc catccttaaa accagaccct catggctgcc agcacctgaa agcttcctcg    13800
acatctgtta ataaagccgt aggcccttgt ctaagcgcaa ccgcctagac tttctttcag    13860
atacatgtcc acatgtccat ttttcaggtt ctctaagttg gagtggagtc tgggaagggt    13920
tgtgaatgag gcttctgggc tatgggtgag gttccaatgg caggttagag cccctcgggc    13980
caactgccat cctggaaagt agagacagca gtgcccgctg cccagaagag accagcaagc    14040
caaactggag cccccattgc aggctgtcgc catgtggaaa gagtaactca caattgccaa    14100
taaagtctca tgtggtttta tctactttt ttttcttttt cttttttttt gagacaaggc    14160
cttgccctcc caggctggag tgcagtggaa tgaccacagc tcaccgcaac ctcaaattct    14220
tgcgttcaag tgaacctccc actttagcct cccaagtagc tgggactaca ggcgcacgcc    14280
atcacacccg gctaattgaa aattttttt tttgtttag atggaatctc actttgttgc    14340
ccaggctggt ctcaaactcc tgggctcaag tgatcatcct gcttcagcgt ccgacttgtt    14400
ggtattatag gcgtgagcca ctgggcctga cctagctacc attttttaat gcagaaatga    14460
agacttgtag aaatgaaata acttgtccag gatagtcgaa taagtaactt ttagagctgg    14520
gatttgaacc caggcaatct ggctccagag ctgggccctc actgctgaag gacactgtca    14580
gcttgggagg gtggctatgg tcggctgtct gattctaggg agtgagggct gtctttaaag    14640
caccccattc cattttcaga cagctttgtc agaaaggctg tcatatggag ctgacacctg    14700
cctccccaag gcttccatag atcctctctg tacattgtaa ccttttattt tgaaatgaaa    14760
attcacagga agttgtaagg ctagtacagg ggatcc                             14796

<210> SEQ ID NO 154
<211> LENGTH: 21
<212> TYPE: DNA
<213> ORGANISM: Artificial
<220> FEATURE:
<223> OTHER INFORMATION: Forward Primer

<400> SEQUENCE: 154
aaggaccacc gcatctctac a                                             21

<210> SEQ ID NO 155
<211> LENGTH: 20
<212> TYPE: DNA
<213> ORGANISM: Artificial
<220> FEATURE:
<223> OTHER INFORMATION: Reverse primer

<400> SEQUENCE: 155
gaagatggtg atgggatttc                                               20

<210> SEQ ID NO 156
<211> LENGTH: 20
<212> TYPE: DNA
<213> ORGANISM: Artificial
<220> FEATURE:
<223> OTHER INFORMATION: PCR probe

<400> SEQUENCE: 156
caagcttccc gttctcagcc                                               20

<210> SEQ ID NO 157
```

```
<211> LENGTH: 21
<212> TYPE: DNA
<213> ORGANISM: Artificial
<220> FEATURE:
<223> OTHER INFORMATION: Forward primer

<400> SEQUENCE: 157
aaggaccacc gcatctctac a                                               21
```

COMPOSITIONS COMPRISING ALTERNATING 2'-MODIFIED NUCLEOSIDES FOR USE IN GENE MODULATION

CROSS REFERENCE TO RELATED APPLICATIONS

The present application is a continuation of U.S. application Ser. No. 15/623,193 filed Jun. 14, 2007, which is a continuation of U.S. application Ser. No. 14/834,224 filed Aug. 24, 2015, which is a continuation of U.S. application Ser. No. 10/860,265 filed Jun. 3, 2004, issued as U.S. Pat. No. 9,150,605 on Oct. 6, 2015, which is a continuation in part of U.S. application Ser. No. 10/701,007, filed Nov. 4, 2003, issued as U.S. Pat. No. 8,604,183 on Dec. 10, 2013, and also claims benefit to U.S. Provisional Application Ser. No. 60/423,760 filed Nov. 5, 2002 and Ser. No. 60/555,521, filed Mar. 22, 2004. Each of these applications is incorporated herein in its entirety.

SEQUENCE LISTING

The present application is being filed along with a Sequence Listing in electronic format. The Sequence Listing is provided as a file entitled ISIS5482USC3SEQ.ST25.txt, created Feb. 2, 2019, which is 196 Kb in size. The information in the electronic format of the sequence listing is incorporated herein by reference in its entirety.

FIELD OF THE INVENTION

The present invention provides modified oligomeric compounds and compositions comprising such modified oligomeric compounds that modulate gene expression. In a preferred embodiment such modulation is via the RNA interference pathway. The modified oligomeric compounds of the invention include one or more alternating motifs that can enhance various physical properties and attributes compared to wild type nucleic acids. The modified oligomeric compounds are used alone or in compositions to modulate the targeted nucleic acids. The compositions are useful for targeting selected nucleic acid molecules and modulating the expression of one or more genes. In preferred embodiments the compositions of the present invention hybridize to a portion of a target RNA resulting in loss of normal function of the target RNA.

BACKGROUND OF THE INVENTION

In many species, introduction of double-stranded RNA (dsRNA) induces potent and specific gene silencing. This phenomenon occurs in both plants and animals and has roles in viral defense and transposon silencing mechanisms. This phenomenon was originally described more than a decade ago by researchers working with the petunia flower. While trying to deepen the purple color of these flowers, Jorgensen et al. introduced a pigment-producing gene under the control of a powerful promoter. Instead of the expected deep purple color, many of the flowers appeared variegated or even white. Jorgensen named the observed phenomenon "cosuppression", since the expression of both the introduced gene and the homologous endogenous gene was suppressed (Napoli et al., *Plant Cell*, 1990, 2, 279-289; Jorgensen et al., *Plant Mol. Biol.*, 1996, 31, 957-973).

Cosuppression has since been found to occur in many species of plants, fungi, and has been particularly well characterized in *Neurospora crassa*, where it is known as "quelling" (Cogoni and Macino, *Genes Dev.* 2000, 10, 638-643; Guru, Nature, 2000, 404, 804-808).

The first evidence that dsRNA could lead to gene silencing in animals came from work in the nematode, *Caenorhabditis elegans*. In 1995, researchers Guo and Kemphues were attempting to use antisense RNA to shut down expression of the par-1 gene in order to assess its function. As expected, injection of the antisense RNA disrupted expression of par-1, but quizzically, injection of the sense-strand control also disrupted expression (Guo and Kempheus, *Cell*, 1995, 81, 611-620). This result was a puzzle until Fire et al. injected dsRNA (a mixture of both sense and antisense strands) into *C. elegans*. This injection resulted in much more efficient silencing than injection of either the sense or the antisense strands alone. Injection of just a few molecules of dsRNA per cell was sufficient to completely silence the homologous gene's expression. Furthermore, injection of dsRNA into the gut of the worm caused gene silencing not only throughout the worm, but also in first generation offspring (Fire et al., Nature, 1998, 391, 806-811).

The potency of this phenomenon led Timmons and Fire to explore the limits of the dsRNA effects by feeding nematodes bacteria that had been engineered to express dsRNA homologous to the *C. elegans* unc-22 gene. Surprisingly, these worms developed an unc-22 null-like phenotype (Timmons and Fire, Nature 1998, 395, 854; Timmons et al., *Gene*, 2001, 263, 103-112). Further work showed that soaking worms in dsRNA was also able to induce silencing (Tabara et al., *Science*, 1998, 282, 430-431). PCT publication WO 01/48183 discloses methods of inhibiting expression of a target gene in a nematode worm involving feeding to the worm a food organism which is capable of producing a double-stranded RNA structure having a nucleotide sequence substantially identical to a portion of the target gene following ingestion of the food organism by the nematode, or by introducing a DNA capable of producing the double-stranded RNA structure (Bogaert et al., 2001).

The posttranscriptional gene silencing defined in *Caenorhabditis elegans* resulting from exposure to double-stranded RNA (dsRNA) has since been designated as RNA interference (RNAi). This term has come to generalize all forms of gene silencing involving dsRNA leading to the sequence-specific reduction of endogenous targeted mRNA levels; unlike co-suppression, in which transgenic DNA leads to silencing of both the transgene and the endogenous gene.

Introduction of exogenous double-stranded RNA (dsRNA) into *Caenorhabditis elegans* has been shown to specifically and potently disrupt the activity of genes containing homologous sequences. Montgomery et al. suggests that the primary interference effects of dsRNA are post-transcriptional; this conclusion being derived from examination of the primary DNA sequence after dsRNA-mediated interference a finding of no evidence of alterations followed by studies involving alteration of an upstream operon having no effect on the activity of its downstream gene. These results argue against an effect on initiation or elongation of transcription. Finally they observed by in situ hybridization, that dsRNA-mediated interference produced a substantial, although not complete, reduction in accumulation of nascent transcripts in the nucleus, while cytoplasmic accumulation of transcripts was virtually eliminated. These results indicate that the endogenous mRNA is the primary target for interference and suggest a mechanism that degrades the targeted mRNA before translation can occur. It was also found that this mechanism is not dependent on the SMG system, an mRNA surveillance system in *C. elegans* responsible for targeting and destroying aberrant messages. The authors further suggest a model of how dsRNA might function as a catalytic mechanism to target homologous mRNAs for degradation. (Montgomery et al., *Proc. Natl. Acad. Sci. USA,* 1998, 95, 15502-15507).

Recently, the development of a cell-free system from syncytial blastoderm *Drosophila* embryos that recapitulates many of the features of RNAi has been reported. The interference observed in this reaction is sequence specific, is promoted by dsRNA but not single-stranded RNA, functions by specific mRNA degradation, and requires a minimum length of dsRNA. Furthermore, preincubation of dsRNA potentiates its activity demonstrating that RNAi can be mediated by sequence-specific processes in soluble reactions (Tuschl et al., *Genes Dev.,* 1999, 13, 3191-3197).

In subsequent experiments, Tuschl et al, using the *Drosophila* in vitro system, demonstrated that 21- and 22-nt RNA fragments are the sequence-specific mediators of RNAi. These fragments, which they termed short interfering RNAs (siRNAs) were shown to be generated by an RNase III-like processing reaction from long dsRNA. They also showed that chemically synthesized siRNA duplexes with overhanging 3' ends mediate efficient target RNA cleavage in the *Drosophila* lysate, and that the cleavage site is located near the center of the region spanned by the guiding siRNA. In addition, they suggest that the direction of dsRNA processing determines whether sense or antisense target RNA can be cleaved by the siRNA-protein complex (Elbashir et al., *Genes Dev.,* 2001, 15, 188-200). Further characterization of the suppression of expression of endogenous and heterologous genes caused by the 21-23 nucleotide siRNAs have been investigated in several mammalian cell lines, including human embryonic kidney (293) and HeLa cells (Elbashir et al., *Nature,* 2001, 411, 494-498).

Most recently, Tijsterman et al. have shown that, in fact, single-stranded RNA oligomers of antisense polarity can be potent inducers of gene silencing. As is the case for co-suppression, they showed that antisense RNAs act independently of the RNAi genes rde-1 and rde-4 but require the mutator/RNAi gene mut-7 and a putative DEAD box RNA helicase, mut-14. According to the authors, their data favor the hypothesis that gene silencing is accomplished by RNA primer extension using the mRNA as template, leading to dsRNA that is subsequently degraded suggesting that single-stranded RNA oligomers are ultimately responsible for the RNAi phenomenon (Tijsterman et al., *Science,* 2002, 295, 694-697).

Several recent publications have described the structural requirements for the dsRNA trigger required for RNAi activity. Recent reports have indicated that ideal dsRNA sequences are 21nt in length containing 2 nt 3'-end overhangs (Elbashir et al, EMBO (2001), 20, 6877-6887, Sabine Brantl, *Biochimica et Biophysica Acta,* 2002, 1575, 15-25.) In this system, substitution of the 4 nucleosides from the 3'-end with 2'-deoxynucleosides has been demonstrated to not affect activity. On the other hand, substitution with 2'-deoxynucleosides or 2'-OMe-nucleosides throughout the sequence (sense or antisense) was shown to be deleterious to RNAi activity.

Investigation of the structural requirements for RNA silencing in *C. elegans* has demonstrated modification of the internucleotide linkage (phosphorothioate) to not interfere with activity (Parrish et al., *Molecular Cell,* 2000, 6, 1077-1087.) It was also shown by Parrish et al., that chemical modification like 2'-amino or 5'-iodouridine are well tolerated in the sense strand but not the antisense strand of the dsRNA suggesting differing roles for the 2 strands in RNAi. Base modification such as guanine to inosine (where one hydrogen bond is lost) has been demonstrated to decrease RNAi activity independently of the position of the modification (sense or antisense). Same "position independent" loss of activity has been observed following the introduction of mismatches in the dsRNA trigger. Some types of modifications, for example introduction of sterically demanding bases such as 5-iodoU, have been shown to be deleterious to RNAi activity when positioned in the antisense strand, whereas modifications positioned in the sense strand were shown to be less detrimental to RNAi activity. As was the case for the 21 nt dsRNA sequences, RNA-DNA heteroduplexes did not serve as triggers for RNAi. However, dsRNA containing 2'-F-2'-deoxynucleosides appeared to be efficient in triggering RNAi response independent of the position (sense or antisense) of the 2'-F-2'-deoxynucleosides.

In one experiment the reduction of gene expression was studied using electroporated dsRNA and a 25mer morpholino in post implantation mouse embryos (Mellitzer et al., *Mechanisms of Development,* 2002, 118, 57-63). The morpholino oligomer did show activity but was not as effective as the dsRNA.

A number of PCT applications have recently been published that relate to the RNAi phenomenon. These include: PCT publication WO 00/44895; PCT publication WO 00/49035; PCT publication WO 00/63364; PCT publication WO 01/36641; PCT publication WO 01/36646; PCT publication WO 99/32619; PCT publication WO 00/44914; PCT publication WO 01/29058; and PCT publication WO 01/75164.

U.S. Pat. Nos. 5,898,031 and 6,107,094, each of which is commonly owned with this application and each of which is herein incorporated by reference, describe certain oligonucleotide having RNA like properties. When hybridized with RNA, these olibonucleotides serve as substrates for a dsRNase enzyme with resultant cleavage of the RNA by the enzyme.

In another recently published paper (Martinez et al., *Cell,* 2002, 110, 563-574) it was shown that double stranded as well as single stranded siRNA resides in the RNA-induced silencing complex (RISC) together with eIF2C1 and eIF2C2 (human GERp950 Argonaute proteins. The activity of 5'-phosphorylated single stranded siRNA was comparable to the double stranded siRNA in the system studied. In a related study, the inclusion of a 5'-phosphate moiety was shown to enhance activity of siRNA's in vivo in *Drosophilia* embryos (Boutla, et al., *Curr. Biol.,* 2001, 11, 1776-1780). In another study, it was reported that the 5'-phosphate was required for siRNA function in human HeLa cells (Schwarz et al., *Molecular Cell,* 2002, 10, 537-548).

One group of researchers looked at single strand asRNA and double strand siRNA having 2'-O-methyl groups at select positions (Amarzguioui et al., *Nucleic Acids Research,* 2003, 31(2), 589-595). They compared single strand asRNA wild type with 2'-O—$CH_3$ containing asRNA and showed that the 2'-O-methyl asRNA's showed good activity dependent on the positioning of the modifications but less than wild type. When they put 2'-O-methyl modified nucleosides into siRNA's they showed that these modifications were tolerated in smaller numbers and that there was a loss of activity with increased numbers in wings. They also showed that siRNA's with 2'-O-methyl modified nucleosides showed an increased duration of activity relative to unmodified siRNA.

Another group of researchers compared asRNA and siRNA and found almost identical target position effects, appearance of mRNA cleavage fragments and tolerance for mutational and chemical backbone modifications (Holen et al., et al., *Nucleic Acids Research,* 2003, 31(9), 2401-2407). They found that small numbers of 2'-O-methyl modified nucleosides gave good activity compared to wild type but that the activity lessened as the numbers of 2'-O-methyl modified nucleosides was increased.

In another recent report researchers looked at the effects of a variety of chemical modifications, including 2'-O-methyl, had on the activity and biological properties of siRNA (Ya-Lin Chiu and Tariq M. Rana, *RNA,* 2003, (9), 1034-1048). They showed that incorporation of 2'-O-methyl in the sense or antisense strand (fully modified strands) severely reduced their activity in siRNA's relative to unmodified siRNA. Incorporation into both strands uniformly completely abolished activity.

One group of researchers looked at the effects of 2'-O-methyl groups and other chemically modified siRNA's in mammalian cells (Braasch et al., *Biochemistry,* 2003, (42), 7967-7975). They showed that fully modified 2'-O—$CH_3$ siRNA did not inhibit gene expression in one or both strands.

In another study the placement of a 2'-O-methyl group at the 5'-terminus on the antisense strand was reported to severely limit activity whereas the 3'-terminus of the antisense and the 3' and 5'-termini of the sense strand were tolerated (Czauderna et al., *Nucleic Acids Research,* 2003, 31(11), 2705-2716). They also reported that internal 2'-O-methyls provide nuclease stability and when placed at particular positions internally they show good activity but less than unmodified siRNA. They also disclose siRNA constructs having alternating 2'-O-methyl nucleosides in both strands.

Like the RNAse H pathway, the RNA interference pathway of antisense modulation of gene expression is an effective means for modulating the levels of specific gene products and may therefore prove to be uniquely useful in a number of therapeutic, diagnostic, and research applications involving gene silencing. The present invention therefore further provides compositions useful for modulating gene expression pathways, including those relying on an antisense mechanism of action such as RNA interference and dsRNA enzymes as well as non-antisense mechanisms. One having skill in the art, once armed with this disclosure will be able, without undue experimentation, to identify preferred compositions for these uses.

SUMMARY OF THE INVENTION

In one embodiment the present invention provides oligomeric compounds wherein each one comprises a plurality of nucleosides linked together in a sequence. The sequence comprises nucleosides of at least a first type (F) and nucleosides of a second type (S). The nucleosides can be similar or dissimilar in chemical makeup e.g., different nucleobases and different in other aspects but the two types of nucleosides have different 2'-substituent groups. When the 2'-substituent groups of the first and second types of nucleosides are other than H or OH then the oligomeric compound includes at least two nucleosides of the first type and at least one nucleoside of the second type wherein the nucleosides of the first type and the nucleosides of the second type are located with respect to one another such that the sequence includes at least one FSF motif. Alternatively when the 2'-substituent group of one of the first or the second types of nucleosides is H or OH then the oligomeric compound includes at least three nucleosides of the first type and at least three nucleosides of the second type and the nucleosides of the first type and the nucleosides of the second type are located with respect to one another such that the sequence includes at least one FSFSFS motif.

In one embodiment the oligomeric compound has at least one portion that is complementary to and capable of hybridizing to a selected nucleic acid target.

In another embodiment the oligomeric compound 1 further includes at least one nucleoside of a third type (T), where the third type of nucleoside has a different 2'-substituent group when compared to either of the first or second type of nucleoside.

In one embodiment the 2'-substituent groups of the first type of nucleosides and the second type nucleosides are, independently, —F, —O—$CH_2CH_2$—O—$CH_3$, —$OC_1$-$C_{12}$ alkyl, —O—$CH_2$—$CH_2$—$CH_2$—$NH_2$, —O—$(CH_2)_2$—O—$N(R_1)_2$, —O—$CH_2C(=O)$—$N(R_1)_2$, —O—$(CH_2)_2$—O—$(CH_2)_2$—$N(R_1)_2$, —O—$CH_2$—$CH_2$—$CH_2$—$NHR_1$, —$N_3$, —O—$CH_2$—CH=$CH_2$, —$NHCOR_1$, —$NH_2$, —$NHR_1$, —$N(R_1)_2$, —SH, —$SR_1$, —N(H)OH, —N(H)$OR_1$, —$N(R_1)OH$, —$N(R_1)OR_1$ or —O—$CH_2$—N(H)—C(=$NR_1$)[$N(R_1)_2$];

wherein each $R_1$ is, independently, H, $C_1$-$C_{12}$ alkyl, a protecting group or substituted or unsubstituted $C_1$-$C_{12}$ alkyl, $C_2$-$C_{12}$ alkenyl, or $C_2$-$C_{12}$ alkynyl wherein the substituent groups are selected from halogen, hydroxyl, amino, azido, cyano, haloalkyl, alkenyl, alkoxy, thioalkoxy, haloalkoxy or aryl; and wherein the oligomeric compound includes the FSF motif.

A more preferred list of 2'-substituent groups amenable to the first and second type of nucleosides includes —F, —O—$CH_3$, —O—$CH_2CH_2$—O—$CH_3$, —O—$CH_2$—CH=$CH_2$, $N_3$, $NH_2$, NHOH, —O—$(CH_2)_2$—O—$N(R_1)_2$, —O—$CH_2C(O)$—$N(R_1)_2$, —O—$CH_2$—$CH_2$—$CH_2$—$NH_2$, —O—$(CH_2)_2$—O—$(CH_2)_2$—$N(R_1)_2$ or —O—$CH_2$—N(H)—C(=$NR_1$)[$N(R_1)_2$];

wherein each $R_1$ is, independently, H, $C_1$-$C_{12}$ alkyl, a protecting group or substituted or unsubstituted $C_1$-$C_{12}$ alkyl, $C_2$-$C_{12}$ alkenyl, or $C_2$-$C_{12}$ alkynyl wherein the substituent groups are selected from halogen, hydroxyl, amino, azido, cyano, haloalkyl, alkenyl, alkoxy, thioalkoxy, haloalkoxy or aryl; and wherein the oligomeric compound includes the FSF motif.

An even more preferred list of 2'-substituent groups amenable to the first and second type of nucleosides includes —F, —O—$CH_2CH_2$—O—$CH_3$, —O—$CH_3$, —O—$CH_2$—CH=$CH_2$ or —O—$CH_2$—CH—$CH_2$—$NH(R_j)$ where $R_j$ is H or $C_1$-$C_{10}$ alkyl.

In an even more preferred embodiment the 2'-substituent groups of the first type of nucleosides and the second type nucleosides are, independently, —F, —O—$CH_3$ or —O—$CH_2CH_2$—O—$CH_3$.

In one embodiment, oligomeric compounds of the present invention include a nucleoside of a third type (T), the third type of nucleoside including a 2'-substituent group that is different from the 2'-substituent groups of either of the first or the second type of nucleosides. A preferred 2'-substituent group of the third type of nucleoside is H or OH.

In one embodiment of oligomeric compounds of the present invention include H or OH as one of the first or second types of nucleosides. In this case the minimum number of first and second type nucleosides is 3 each having at least one FSFSFS motif in the resulting oligomeric compound.

In one embodiment oligomeric compounds of the present invention include a plurality of linked nucleosides linked by a phosphodiester internucleoside linking groups. In another embodiment the internucleoside linking groups are phosphorothioate internucleoside linking groups. In another embodiment the internucleoside linking groups, independently, phophosphodiester or phosphorothioate internucleoside linking groups.

In one embodiment oligomeric compounds of the present invention comprise a plurality of nucleosides linked by linking groups independently selected from the group consisting of phosphodiester, phosphorothioate, chiral phosphorothioate, phosphorodithioate, phosphotriester, aminoalkylphosphotriester, methyl phosphonate, alkyl phosphonate, 5'-alkylene phosphonate, chiral phosphonate, phosphinate, phosphoramidate, 3'-amino phosphoramidate, aminoalkylphosphoramidate, thionophosphoramidate, thionoalkylphosphonate, thionoalkylphosphotriester, selenophosphate and boranophosphate, phosphodiester and phosphorothioate.

In one embodiment the oligomeric compounds of the present invention comprise at least one motif selected from $F(SF)_n(S)_{nn}$ where n is from 2 to about 20 and nn is 0 or 1. In a further embodiment oligomeric compounds of the present invention comprise at least two motifs independently selected from $F(SF)_n(S)_{nn}$ where n is from 1 to about 20 and nn is 0 or 1. In a preferred embodiment oligomeric compounds comprise 2 motifs selected from $F(SF)_n(S)_{nn}$ where n is from 1 to about 20 and nn is 0 or 1, and the two motifs are further separated by a region comprising a sequence of nucleosides. In an even more preferred embodiment the sequence of nucleosides is joined together such that one of the motifs is located at the 5'-end of the sequence of nucleosides and the other of the motifs is located at the 3'-end of the sequence of nucleosides and the motifs being separated by from about 6 to about 20 nucleosides.

In one embodiment the oligomeric compounds of the present invention have the formula $X_1$—Y—$X_2$:
wherein
Y is a region of from about 6 to about 18 linked nucleosides; and
each of $X_1$ and $X_2$ is, independently, a plurality of linked nucleosides having the formula $F(SF)_n(S)_{nn}$ where n is from 1 to about 20 and nn is 0 or 1.

In a preferred embodiment each of $X_1$ and $X_2$ is, independently, FSFS, FSFSF, FSFSFS, FSFSFSF or FSFSFSFS. In a further preferred embodiment Y is from about 5 to about 12 linked nucleosides. In another embodiment each of the linked nucleosides is linked by a phosphodiester internucleoside linkage. In another embodiment each of the linked nucleosides is linked by a phosphorothioate internucleoside linkage. And in an even further embodiment each of the linked nucleosides is, independently, linked by a phophosphodiester or a phosphorothioate internucleoside linkage. In another embodiment the linked nucleosides selected from $F(SF)_n(S)_{nn}$ are linked by phosphodiester internucleoside linkages, the linked nucleosides comprising the Y region are linked by phosphorothioate internucleoside linkages and each of the $F(SF)_n(S)_{nn}$ motifs are independently linked to the ends of the Y region by a phosphodiester or phosphorothioate internucleoside linkage. In an even further embodiment the linked nucleosides selected from $F(SF)_n(S)_{nn}$ are linked by phosphorothioate internucleoside linkages, the linked nucleosides comprising the Y region are linked by phosphodiester internucleoside linkages and each of the $F(SF)_n(S)_{nn}$ motifs are independently linked to the ends of the Y region by a phosphodiester or phosphorothioate internucleoside linkage.

In one embodiment the oligomeric compounds of the present invention comprise from about 10 to about 40 nucleotides. In a more preferred embodiment the oligomeric compounds of the present invention comprise from about 18 to about 30 nucleotides. In an even more preferred embodiment the oligomeric compounds of the present invention comprise from 21 to about 24 nucleotides.

In one embodiment the oligomeric compounds of the present invention comprise at least one conjugate group. In a preferred embodiment the conjugate group is a terminal cap moiety. In another preferred embodiment the conjugate group is attached to one or both of the 3'-terminal and 5'-terminal ends of the oligomeric compound. In an even more preferred embodiment the terminal cap moiety is an inverted deoxy abasic moiety.

In one embodiment of the present invention compositions are provided comprising a first oligomeric compound and a second oligomeric compound where at least a portion of the first oligomeric compound is capable of hybridizing with at least a portion of the second oligomeric compound and at least a portion of the first oligomeric compound is complementary to and capable of hybridizing to a selected nucleic acid target. At least one of the first and the second oligomeric compounds comprise at least nucleosides of a first type (F) and nucleosides of a second type (S). The first and the second types of nucleosides differing in at least one aspect from one another in that they have different 2'-substituent groups. When the 2'-substituent groups of the first and the second types of nucleosides are other than H or OH then at least one of the first and the second oligomeric compounds includes at least two nucleosides of the first type and at least one nucleoside of the second type wherein the nucleosides of the first type and the nucleosides of the second type are located with respect to one another such that the first or second oligomeric compound includes at least one FSF motif. When the 2'-substituent group of one of the first or the second type of nucleoside is H or OH then at least one of the first and the second oligomeric compounds includes at least three nucleosides of the first type and at least three nucleosides of the second type and the nucleosides of the first type and the nucleosides of the second type are located with respect to one another such that at least one of the first and the second oligomeric compounds includes at least one FSFSFS motif.

In one embodiment of the present invention compositions comprise at least one of said first and second oligomeric compounds having at least two nucleosides of a first type and at least two nucleosides of a second type and wherein the 2'-substituent groups are other 2'-H and 2'-OH thereby providing a composition having at least one of said first and said second oligomeric compound having at least one FSFS motif. In a further embodiment there are at least three nucleosides of said first type and at least two nucleosides of said second type to give a t least one of said first and said second oligomeric compound having at least one FSFSF motif In one embodiment the compositions of the present invention at least one of the first and the second oligomeric compounds comprise only nucleosides of the first type and nucleosides of the second type and wherein the nucleosides of the first and the second types are alternating throughout the entire sequence of the oligomeric compound. In a further embodiment both of the first and the second oligomeric compounds comprise only nucleosides of the first type and nucleosides of the second type and wherein the nucleosides of the first and the second types are alternating throughout the entire sequence of both of the oligomeric compounds.

In one embodiment the compositions of the present invention comprise a third type of nucleoside (T) that is different than said first and said second type of nucleosides. In a preferred embodiment the 2'-substituent group of the third type nucleoside is 2'-H or 2'-OH.

In one embodiment the 2'-substituent groups of the first and the second types of nucleosides are, independently, —F, —O—CH$_2$CH$_2$—O—CH$_3$, —OC$_1$-C$_{12}$ alkyl, —O—CH$_2$—CH$_2$—CH$_2$—NH$_2$, —O—(CH$_2$)$_2$—O—N(R$_1$)$_2$, —O—CH$_2$C(=O)—N(R$_1$)$_2$, —O—(CH$_2$)$_2$—O—(CH$_2$)$_2$—N(R$_1$)$_2$, —O—CH$_2$—CH$_2$—CH$_2$—NHR$_1$, —N$_3$, —O—CH$_2$—CH=CH$_2$, —NHCOR$_1$, —NH$_2$, —NHR$_1$, —N(R$_1$)$_2$, —SH, —SR$_1$, —N(H)OH, —N(H)OR$_1$, —N(R$_1$)OH, —N(R$_1$)OR$_1$ or —O—CH$_2$—N(H)—C(=NR$_1$)[N(R$_1$)$_2$]; wherein each R$_1$ is, independently, H, C$_1$-C$_{12}$ alkyl, a protecting group or substituted or unsubstituted C$_1$-C$_{12}$ alkyl, C$_2$-C$_{12}$ alkenyl, or C$_2$-C$_{12}$ alkynyl wherein the substituent groups are selected from halogen, hydroxyl, amino, azido, cyano, haloalkyl, alkenyl, alkoxy, thioalkoxy, haloalkoxy or aryl. A more preferred list of 2'-substituent groups of the first and the second types of nucleosides are, independently, —F, —O—CH$_3$, —O—CH$_2$CH$_2$—O—CH$_3$, —O—CH$_2$—CH=CH$_2$, N$_3$, NH$_2$, NHOH, —O—(CH$_2$)$_2$—O—N(R$_1$)$_2$, —O—CH$_2$C(O)—N(R$_1$)$_2$, —O—CH$_2$—CH$_2$—CH$_2$—NH$_2$, —O—(CH$_2$)$_2$—O—(CH$_2$)$_2$—N(R$_1$)$_2$ or —O—CH$_2$—N(H)—C(=NR$_1$)[N(R$_1$)$_2$];

wherein each R$_1$ is, independently, H, C$_1$-C$_{12}$ alkyl, a protecting group or substituted or unsubstituted C$_1$-C$_{12}$ alkyl, C$_2$-C$_{12}$ alkenyl, or C$_2$-C$_{12}$ alkynyl wherein the substituent groups are selected from halogen, hydroxyl, amino, azido, cyano, haloalkyl, alkenyl, alkoxy, thioalkoxy, haloalkoxy or aryl wherein the oligomeric compound includes the FSF motif.

An even more preferred list of 2'-substituent groups of the first and the second types of nucleosides includes —F, —O—CH$_2$CH$_2$—O—CH$_3$, —O—CH$_3$, —O—CH$_2$—CH=CH$_2$ or —O—CH$_2$—CH—CH$_2$—NH(R$_j$) where R$_j$ is H or C$_1$-C$_{10}$ alkyl.

A preferred list of 2'-substituent groups of the first and the second types of nucleosides includes —F, —O—CH$_3$ or —O—CH$_2$CH$_2$—O—CH$_3$. With —F or —O—CH$_3$ being an even more preferred list.

In one embodiment each of the first and the second type of nucleosides have 3'-endo conformational geometry.

In one embodiment, the compositions of the present invention include first type of nucleosides that are 2'-OH nucleosides. In another embodiment the first type nucleoside is 2'-H nucleoside. In another embodiment the second type nucleoside is a 2'-F nucleoside. In even another embodiment the second type nucleoside is a 2'-O—CH$_3$ nucleoside. In another embodiment the first type of nucleosides are 2'-fluoro nucleosides and the second type of nucleosides are 2'-O—CH$_3$ nucleosides.

In one embodiment of the present invention the first oligomeric compound further comprises a 5'-phosphate group. In another embodiment the second oligomeric compound further comprises a 5'-phosphate group. In even a further embodiment each of the first and the second oligomeric compounds independently, comprise a 5'-phosphate group. In an even further embodiment the first oligomeric compound comprises a 3'-terminal OH group.

In one embodiment of the present invention compositions the nucleosides of each of the first and the second oligomeric compounds are linked by phosphodiester internucleoside linking groups. In another embodiment the nucleosides of each of the first and the second oligomeric compounds are linked by phosphorothioate internucleoside linking groups.

In an even further embodiment the nucleosides of one the first and the second oligomeric compound are linked by phosphorothioate internucleoside linking groups and the nucleosides of the other of the first and the second oligomeric compound are linked by phosphodiester internucleoside linking groups. In a further embodiment the nucleosides of the first oligomeric compound are linked by phosphorothioate internucleoside linking groups and the nucleosides of the second oligomeric compound are linked by phosphodiester internucleoside linking groups. In an even further embodiment each of the nucleosides of the first and the second oligomeric compound are independently linked by phosphorothioate or phosphodiester internucleoside linking groups.

In one embodiment of the present invention each of the nucleosides of the first and the second oligomeric compound are independently linked by an internucleoside linking group selected from the group consisting of phosphodiester, phosphorothioate, chiral phosphorothioate, phosphorodithioate, phosphotriester, aminoalkylphosphotriester, methyl phosphonate, alkyl phosphonate, 5'-alkylene phosphonate, chiral phosphonate, phosphinate, phosphoramidate, 3'-amino phosphoramidate, aminoalkylphosphoramidate, thionophosphoramidate, thionoalkylphosphonate, thionoalkylphosphotriester, selenophosphate and boranophosphate.

In one embodiment each of the first and the second oligomeric compounds comprise only the first and the second type nucleosides and wherein the first and the second type nucleosides are alternating in both of the first and the second oligomeric compounds wherein preferred first type nucleosides comprise 2'-F or 2'-O—CH$_3$ groups. In a preferred embodiment the first type nucleosides comprises one of 2'-F or 2'-O—CH$_3$ groups and the second type nucleosides comprise the other of 2'-F or 2'-O—CH$_3$ groups with 2'-F or 2'-O—CH$_3$ groups preferred for the first type nucleosides. In a preferred embodiment the first oligomeric compound has first type nucleosides starting at its 5'-terminus and wherein the first type nucleosides of the first and the second oligomeric compounds align with each other when the first and second oligomeric compounds are hybridized. In another preferred embodiment the first oligomeric compound has first type nucleosides starting at its 5'-terminus wherein the first type nucleosides of the first oligomeric compound and the second type nucleosides of the second oligomeric compound align with each other when the first and the second oligomeric compounds are hybridized.

In one embodiment of the present invention when the first and second oligomeric compounds comprise only the first and second type nucleosides and where the first and second type nucleosides are alternating in both of the first and the second oligomeric compounds the first type nucleosides comprises one of 2'-F or 2'-O—CH$_3$ groups and the second type nucleosides comprise the other of 2'-F or 2'-O—CH$_3$ groups. In a preferred embodiment the nucleosides of the first oligomeric compound are linked with phosphorothioate internucleoside linking groups. In another preferred embodiment the nucleosides of the second oligomeric compound are linked with phosphodiester internucleoside linking groups.

In one embodiment compositions of the present invention comprise at least one conjugate group. In a preferred embodiment the conjugate group is attached at the 3'-end, the 5'-end or both the 3'-end and the 5'-end of one of the first and second oligomeric compounds. In a more preferred embodiment the conjugate group comprises a terminal cap moiety. In an even more preferred embodiment the terminal cap moiety is an inverted deoxy abasic moiety. In a more preferred embodiment one of the first and second oligomeric compounds is a sense strand and wherein the sense strand comprises a terminal cap moiety at one or both of the 3'-terminal and the 5'-terminal ends wherein a preferred terminal cap moiety is an inverted deoxy abasic moiety.

In one embodiment of the present invention the first and the second oligomeric compounds are a complementary pair of siRNA oligonucleotides.

In one embodiment at least one of the first or second oligomeric compounds comprise at least one motif selected from $F(SF)_n(S)_{nn}$ where n is from 2 to about 20 and nn is 0 or 1. In a preferred embodiment at least one of the first or second oligomeric compounds comprises at least two motifs independently selected from $F(SF)_n(S)_{nn}$ where n is from 2 to about 20 and nn is 0 or 1. In an even more preferred embodiment the two motifs are separated by a region comprising a sequence of nucleosides. In another preferred embodiment one of the two motifs are located at the 5'-end of one of the first or second oligomeric compounds and the second of the two motifs is located at the 3'-end of the same oligomeric compound and wherein from about 6 to about 20 nucleosides are located between the motifs. In a preferred embodiment the first or second oligomeric compound having the motifs has the formula: $X_3$—$Y_2$—$X_4$:

wherein $Y_2$ is a region of from about 6 to about 18 linked nucleosides and each of $X_3$ and $X_4$ is, independently, a plurality of linked nucleosides having the formula $(SF)_n$ $(S)_{nn}$ where n is from 2 to about 20 and nn is 0 or 1; and nn is from 1 to about 3.

In a preferred embodiment each of $X_3$ and $X_4$ is, independently, FSFS, FSFSF, FSFSFS, FSFSFSF or FSFSFSFS. In another preferred embodiment Y2 is from about 5 to about 12 linked nucleosides. In a preferred embodiment each of the linked nucleosides is linked by a phosphodiester internucleoside linkage. In a further preferred each of the linked nucleosides is linked by a phosphorothioate internucleoside linkage and in another preferred embodiment each of the linked nucleosides is, independently, linked by a phosphodiester or a phosphorothioate internucleoside linkage.

In a further embodiment the linked nucleosides selected from $F(SF)_n(S)_{nn}$ are linked by phosphodiester internucleoside linkages, the linked nucleosides comprising the Y region are linked by phosphorothioate internucleoside linkages and each of the $F(SF)_n(S)_{nn}$ motifs are independently linked to the ends of the Y region by a phosphodiester or phosphorothioate internucleoside linkage. In a further embodiment the linked nucleosides selected from $F(SF)_n$ $(S)_{nn}$ are linked by phosphorothioate internucleoside linkages, the linked nucleosides comprising the Y region are linked by phosphodiester internucleoside linkages and each of the $F(SF)_n(S)_{nn}$ motifs are independently linked to the ends of the Y region by a phosphodiester or phosphorothioate internucleoside linkage.

In one embodiment compositions of the present invention comprise first and the second oligomeric compounds that are an antisense/sense pair of oligonucleotides.

In one embodiment compositions are provided wherein each of the first and second oligomeric compounds has from about 8 to about 80 nucleotides. In other embodiments, the oligomeric compounds have from about 12 to about 30 nucleotides. In yet other embodiments, the oligomeric compounds have from about 12 to about 24 nucleotides. In certain preferred embodiments, the oligomeric compounds have from about 19 to about 23 nucleotides.

In one embodiment compositions are provided wherein the first oligomeric compound is an antisense oligonucleotide.

In one embodiment compositions are provided wherein the second oligomeric compound is a sense oligonucleotide.

In one embodiment methods are provided inhibiting gene expression comprising contacting one or more cells, a tissue or an animal with a composition of the invention.

In one embodiment methods are provided inhibiting gene expression comprising contacting one or more cells, a tissue or an animal with an oligomeric compound of the invention.

DETAILED DESCRIPTION OF THE INVENTION

The present invention provides single and double stranded compositions comprising at least one alternating motif Alternating motifs of the present invention have the formula $F(SF)_n(S)_{nn}$ where F is a nucleoside of a first type, S is a nucleoside of a second type, n is from 1 to about 20 and nn is 0 or 1. Each of the types of nucleosides have identical 2'-substituent groups with the two types being differentiated from each other in that at least the 2'-substituent groups are different. H and OH are not used in the alternating motif until there are at least 3 of each type of nucleosides present thereby forming a FSFSFS or larger run of alternating nucleosides in which case one of the first and second types of nucleosides can be H or OH. The alternating motifs can be present in one more regions of a single stranded oligomeric compound or can be found in one or more regions in two oligomeric compounds forming a double stranded composition of the invention.

In one aspect of the present invention the compositions comprise a region of complementarity to a nucleic acid target. The complementary region can comprise a continuous sequence of nucleosides bound by internucleoside linkages or can comprise multiple regions that are interrupted by secondary structures such as a loops thereby forming a complementary region from two or more non-continuous regions of the same oligomeric compound. Double stranded regions of the compositions of the present invention can be formed from two oligomeric compounds hybridized together or from a single oligomeric compound that has a region of self complementarity.

In another aspect of the present invention oligomeric compounds are provided comprising at least one alternating motif. These oligomeric compounds are useful as asRNAs in the RNAi pathway. In the context of the present invention an "asRNA" is an antisense RNA oligomeric compound that is not duplexed with another separate oligonucleotide such as a sense strand but may contain duplexed regions formed between adjacent complementary regions. In one aspect the compositions comprising alternating motifs of the present invention mimic RNA by incorporating regions of nucleosides having 3'-endo conformational geometry and enhance desired properties such as but not limited to modulation of pharmacokinetic properties through modification of protein binding, protein off-rate, absorption and clearance; modulation of nuclease stability as well as chemical stability; modulation of the binding affinity and specificity of the oligomer (affinity and specificity for enzymes as well as for complementary sequences); and increasing efficacy of RNA cleavage.

In one aspect of the present invention compositions are provided comprising a first and a second oligomeric compound that are at least partially hybridized to form a duplex region and further comprising a region that is complementary to and hybridizes to a nucleic acid target. Each of the compositions of the invention comprise at least one alternating motif. In one aspect the compositions include a first oligomeric compound that is an antisense strand having a complementary region to a nucleic acid target and a second oligomeric compound that is a sense strand having one or more regions of complementarity to and forming at least one duplex region with the first oligomeric compound. At least one alternating motif is located on either the first or second oligomeric compound.

Compositions of the present invention also include single and double stranded constructs that comprise at least two regions of alternating nucleosides in one or both of the strands. These alternating regions can comprise up to about 40 nucleosides but preferable comprise from about 3 to about 9 nucleosides. In a preferred embodiment the regions of alternating nucleosides are located at the termini of one or both oligomeric compounds in an oligomeric compound or composition of the invention. In an even more preferred embodiment an oligomeric compound of the invention comprises from 4 to about 8 nucleosides of alternating nucleosides at each termini (3' and 5') and these regions are separated by from about 5 to about 12 linked nucleosides.

Some representative duplexed constructs amenable to the present invention are shown below:

```
                                                 (SEQ ID NO.: 53)
5'-NN NNN NNN N(N)n NNN NNN NNN-3' as (SEQ ID NO.: 53)
3'-NN NNN NNN N(N)n NNN NNN NNN-5' s (SEQ ID NO.: 53)
5'-NN NNN NNN N(N)n NNN NNN NNN-3' as (SEQ ID NO.: 53)
3'-NN NNN NNN N(N)n NNN NNN NNN-5' s (SEQ ID NO.: 53)
5'-NN NNN NNN N(N)n NNN NNN NNN-3' as (SEQ ID NO.: 53)
3'-NN NNN NNN N(N)n NNN NNN NNN-5' s (SEQ ID NO.: 53)
5'-N NNN NNN N(N)n NNN NNN NNN-3' as (SEQ ID NO.: 53)
3'-N NNN NNN N(N)n NNN NNN NNN-5' s (SEQ ID NO.: 53)
5'-N NNN NNN N(N)n NNN NNN NNN-3' as (SEQ ID NO.: 53)
3'-N NNN NNN N(N)n NNN NNN NNN-5' s (SEQ ID NO.: 53)
5'-N NNN NNN N(N)n NNN NNN NNN-3' as (SEQ ID NO.: 53)
3'-N NNN NNN N(N)n NNN NNN NNN-5' s
```

The underlined regions represent linked nucleosides that can be uniform or modified. Essentially the underlined region can be described as being the gap and is shown being variable with n being generally from about 1 to about 40 but from 1 to about 4 being preferred. The alternating regions are shown in bold. These examples are meant to be representative and not limiting. The alternating nucleosides can be aligned on the two strands such as for example all the modifications in the alternating regions of the sense strand are paired with identical modifications in the antisense strand or alternatively the registers can be offset with the like modifications in the alternating regions of one strand pairing with unlike modifications in the other strand. Another option is to have dissimilar modifications in each of the strands which would not lead to an aligned or misaligned register.

Preferred 2'-modifications for the alternating regions comprise all possible orientations of OMe, MOE, OH, F, deoxy, ara OH, ara F with backbone either full PO or Full PS throughout or PO/PS either in wings or gap and the other of PO/PS in the other of the wings or the gap.

Compositions of the present invention are useful for the modulation of gene expression. In one aspect of the present invention a targeted cell, group of cells, a tissue or an animal is contacted with a composition of the invention to effect reduction of mRNA that can directly inhibit gene expression. In another embodiment the reduction of mRNA indirectly upregulates a non-targeted gene through a pathway that relates the targeted gene to a non-targeted gene. Numerous methods and models for the regulation of genes using compositions of the invention are illustrated in the examples.

Compositions of the invention modulate gene expression by hybridizing to a nucleic acid target resulting in loss of its normal function. As used herein, the term "target nucleic acid" or "nucleic acid target" is used for convenience to encompass any nucleic acid capable of being targeted including without limitation DNA, RNA (including pre-mRNA and mRNA or portions thereof) transcribed from such DNA, and also cDNA derived from such RNA. In a preferred embodiment of the invention the target nucleic acid is a messenger RNA. In a further preferred embodiment the degradation of the targeted messenger RNA is facilitated by a RISC complex that is formed with compositions of the invention. In another preferred embodiment the degradation of the targeted messenger RNA is facilitated by a nuclease such as RNaseH.

The hybridization of a composition of the invention with its target nucleic acid is generally referred to as "antisense". Consequently, the preferred mechanism in the practice of some preferred embodiments of the invention is referred to herein as "antisense inhibition." Such antisense inhibition is typically based upon hydrogen bonding-based hybridization of oligonucleotide strands or segments such that at least one strand or segment is cleaved, degraded, or otherwise rendered inoperable. In this regard, it is presently preferred to target specific nucleic acid molecules and their functions for such antisense inhibition.

The functions of DNA to be interfered with can include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA. In the context of the present invention, "modulation" and "modulation of expression" mean either an increase (stimulation) or a decrease (inhibition) in the amount or levels of a nucleic acid molecule encoding the gene, e.g., DNA or RNA. Inhibition is often the preferred form of modulation of expression and mRNA is often a preferred target nucleic acid.

The compositions and methods of the present invention are also useful in the study, characterization, validation and modulation of small non-coding RNAs. These include, but are not limited to, microRNAs (miRNA), small nuclear RNAs (snRNA), small nucleolar RNAs (snoRNA), small temporal RNAs (stRNA) and tiny non-coding RNAs (tncRNA) or their precursors or processed transcripts or their association with other cellular components.

Small non-coding RNAs have been shown to function in various developmental and regulatory pathways in a wide range of organisms, including plants, nematodes and mammals. MicroRNAs are small non-coding RNAs that are processed from larger precursors by enzymatic cleavage and inhibit translation of mRNAs. stRNAs, while processed from precursors much like miRNAs, have been shown to be involved in developmental timing regulation. Other non-coding small RNAs are involved in events as diverse as cellular splicing of transcripts, translation, transport, and chromosome organization.

As modulators of small non-coding RNA function, the compositions of the present invention find utility in the control and manipulation of cellular functions or processes such as regulation of splicing, chromosome packaging or methylation, control of developmental timing events, increase or decrease of target RNA expression levels depending on the timing of delivery into the specific biological pathway and translational or transcriptional control. In addition, the compositions of the present invention can be modified in order to optimize their effects in certain cellular compartments, such as the cytoplasm, nucleus, nucleolus or mitochondria.

The compositions of the present invention can further be used to identify components of regulatory pathways of RNA processing or metabolism as well as in screening assays or devices.

Oligomeric Compounds

In the context of this invention, the term "oligomeric compound" refers to a plurality of naturally-occurring and or non-naturally-occurring monomeric units joined together in a specific sequence. This term includes oligonucleotides, oligonucleosides, oligonucleotide analogs, oligonucleotide mimetics and combinations of these. Oligomeric compounds are typically structurally distinguishable from, yet functionally interchangeable with, naturally-occurring or synthetic wild-type oligonucleotides. Thus, oligomeric compounds include all such structures that function effectively to mimic the structure and/or function of a desired RNA or DNA strand, for example, by hybridizing to a target.

Oligomeric compounds are routinely prepared linearly but can be joined or otherwise prepared to be circular and may also include branching. Oligomeric compounds can included double stranded constructs such as for example two strands hybridized to form double stranded compounds. The double stranded compounds can be linked or separate and can include overhangs on the ends. In general an oligomeric compound comprises a backbone of linked momeric subunits where each linked momeric subunit is directly or indirectly attached to a heterocyclic base moiety. Oligomeric compounds may also include monomeric subunits that are not linked to a heterocyclic base moiety thereby providing abasic sites. The linkages joining the monomeric subunits, the sugar moieties or surrogates and the heterocyclic base moieties can be independently modified giving rise to a plurality of motifs for the resulting oligomeric compounds including hemimers, gapmers and chimeras.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions that function similarly. Such modified or substituted oligonucleotides are often preferred over native forms because of desirable properties such as, for example, enhanced cellular uptake, enhanced affinity for nucleic acid target and increased stability in the presence of nucleases.

Included in preferred oligomeric compounds are oligonucleotides such as antisense oligonucleotides, antisense oligonucleotides, ribozymes, external guide sequence (EGS) oligonucleotides, alternate splicers, primers, probes, and other oligonucleotides which hybridize to at least a portion of the target nucleic acid. As such, these oligonucleotides may be introduced in the form of single-stranded, double-stranded, circular or hairpin oligonucleotides and may contain structural elements such as internal or terminal bulges or loops. Once introduced to a system, the compositions of the invention may elicit the action of one or more enzymes or structural proteins to effect modification of the target nucleic acid.

One non-limiting example of such an enzyme is RNAse H, a cellular endonuclease which cleaves the RNA strand of an RNA:DNA duplex. It is known in the art that single-stranded antisense oligonucleotides which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While the preferred form of antisense oligonucleotide is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

In the context of this invention, the term "oligonucleotide" refers to a sequence of nucleosides that are joined by internucleoside linkages that do not have phosphorus atoms. Internucleoside linkages of this type include short chain alkyl, cycloalkyl, mixed heteroatom alkyl, mixed heteroatom cycloalkyl, one or more short chain heteroatomic and one or more short chain heterocyclic. These internucleoside linkages include but are not limited to siloxane, sulfide, sulfoxide, sulfone, acetyl, formacetyl, thioformacetyl, methylene formacetyl, thioformacetyl, alkeneyl, sulfamate; methyleneimino, methylenehydrazino, sulfonate, sulfonamide, amide and others having mixed N, O, S and $CH_2$ component parts.

Representative United States patents that teach the preparation of the above oligonucleosides include, but are not limited to, U.S. Pat. No. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

In addition to the modifications described above, the nucleosides of the compositions of the invention can have a variety of other modification so long as these other modifications either alone or in combination with other nucleosides enhance one or more of the desired properties described above. Thus, for nucleotides that are incorporated into compositions of the invention, these nucleotides can have sugar portions that correspond to naturally-occurring sugars or modified sugars. Representative modified sugars include carbocyclic or acyclic sugars, sugars having substituent groups at one or more of their 2', 3' or 4' positions and sugars having substituents in place of one or more hydrogen atoms of the sugar. Additional nucleosides amenable to the present invention having altered base moieties and or altered sugar moieties are disclosed in U.S. Pat. No. 3,687,808 and PCT application PCT/US89/02323.

Oligomeric compounds having altered base moieties or altered sugar moieties are also included in the present invention. All such modified oligomeric compounds are comprehended by this invention so long as they function effectively to mimic the structure of a desired RNA or DNA strand. A class of representative base modifications include a tricyclic cytosine analog, termed "G clamp" (Lin, et al., *J. Am. Chem. Soc.* 1998, 120, 8531). This analog makes four hydrogen bonds to a complementary guanine (G) within a helix by simultaneously recognizing the Watson-Crick and Hoogsteen faces of the targeted G. This G clamp modification when incorporated into phosphorothioate oligonucleotides, dramatically enhances antisense potencies in cell culture. The compositions of the invention also can include phenoxazine-substituted bases of the type disclosed by Flanagan, et al., *Nat. Biotechnol.* 1999, 17(1), 48-52.

The oligomeric compounds in accordance with this invention preferably comprise from about 8 to about 80 nucleobases (i.e. from about 8 to about 80 linked nucleosides and/or monomeric subunits). One of ordinary skill in the art will appreciate that the invention embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases in length.

In one preferred embodiment, the oligomeric compounds of the invention are 10 to 50 nucleobases in length. One having ordinary skill in the art will appreciate that this embodies oligomeric compounds of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases in length.

In another preferred embodiment, the oligomeric compounds of the invention are 12 to 30 nucleobases in length. One having ordinary skill in the art will appreciate that this embodies oligomeric compounds of 12, 13, 14, 15, 16, 17, 18, 19, 20, 21, 22, 23, 24, 25, 26, 27, 28, 29, or 30 nucleobases in length.

In a further preferred embodiment, the oligomeric compounds of the invention are 12 to 24 nucleobases in length. One having ordinary skill in the art will appreciate that this embodies oligomeric compounds of 12, 13, 14, 15, 16, 17, 18, 19, 20, 21, 22, 23 or 24 nucleobases in length.

In another preferred embodiment, the oligomeric compounds of the invention are 19 to 23 nucleobases in length. One having ordinary skill in the art will appreciate that this embodies oligomeric compounds of 19, 20, 21, 22 or 23 nucleobases in length.

One particularly preferred length for oligomeric compounds is from about 12 to about 30 nucleobases. Another particularly preferred length is from about 12 to about 24 nucleobases. A further particularly preferred length is from about 19 to about 23 nucleobases.

Chimeric Oligomeric Compounds

It is not necessary for all positions in an oligomeric compound to be uniformly modified, and in fact more than one of the aforementioned modifications may be incorporated in a single oligomeric compound or even at a single monomeric subunit such as a nucleoside within a oligonucleotide. The present invention also includes chimeric oligomeric compounds such as chimeric oligonucleotides. "Chimeric" oligomeric compounds or "chimeras," in the context of this invention, are oligomeric compounds such as oligonucleotides containing two or more chemically distinct regions, each made up of at least one monomer unit, i.e., a nucleotide in the case of a nucleic acid based oligomer.

Chimeric oligonucleotides typically contain at least one region modified so as to confer increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of inhibition of gene expression. Consequently, comparable results can often be obtained with shorter oligonucleotides when chimeras are used, compared to for example phosphorothioate deoxyoligonucleotides hybridizing to the same target region. Cleavage of the RNA target can be routinely detected by gel electrophoresis and, if necessary, associated nucleic acid hybridization techniques known in the art.

Chimeric compositions of the invention may be formed as composite structures of two or more oligomeric compounds such as oligonucleotides, oligonucleotide analogs, oligonucleosides and/or oligonucleotide mimetics as described above. Such oligomeric compounds have also been referred to in the art as hybrids hemimers, gapmers or inverted gapmers. Representative United States patents that teach the preparation of such hybrid structures include, but are not limited to, U.S. Pat. No. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

Oligomer Mimetics

Another preferred group of oligomeric compounds amenable to the present invention includes oligonucleotide mimetics. The term mimetic as it is applied to oligonucleotides is intended to include oligonucleotides wherein only the furanose ring or both the furanose ring and the internucleotide linkage are replaced with novel groups, replacement of only the furanose ring is also referred to in the art as being a sugar surrogate. The heterocyclic base moiety or a modified heterocyclic base moiety is maintained for hybridization with an appropriate target nucleic acid. One such oligonucleotide, an oligonucleotide mimetic that has been shown to have excellent hybridization properties, is referred to as a peptide nucleic acid (PNA). In PNA oligonucleotides, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA oligonucleotides include, but are not limited to, U.S. Pat. Nos. 5,539,082; 5,714,331; and 5,719,262, each of which is herein incorporated by reference. Further teaching of PNA oligonucleotides can be found in Nielsen et al., *Science*, 1991, 254, 1497-1500.

One oligonucleotide mimetic that has been reported to have excellent hybridization properties, is peptide nucleic acids (PNA). The backbone in PNA compounds is two or more linked aminoethylglycine units which gives PNA an amide containing backbone. The heterocyclic base moieties are bound directly or indirectly to aza nitrogen atoms of the amide portion of the backbone. Representative United States patents that teach the preparation of PNA compounds include, but are not limited to, U.S. Pat. No. 5,539,082; 5,714,331; and 5,719,262, each of which is herein incorporated by reference. Further teaching of PNA compounds can be found in Nielsen et al., Science, 1991, 254, 1497-1500.

Numerous modifications have been made to the structure of PNA since the basic PNA structure was first prepared. The basic structure is shown below:

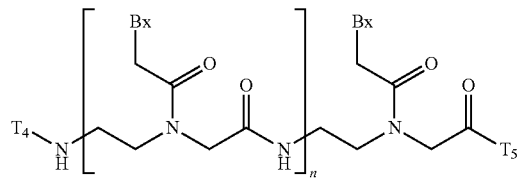

wherein

Bx is a heterocyclic base moiety;

$T_4$ is hydrogen, an amino protecting group, —C(O)$R_5$, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, alkylsulfonyl, arylsulfonyl, a chemical functional group, a reporter group, a conjugate group, a D or L α-amino acid linked via the α-carboxyl group or optionally through the ω-carboxyl group when the amino acid is aspartic acid or glutamic acid or a peptide derived from D, L or mixed D and L amino acids linked through a carboxyl group, wherein the substituent groups are selected from hydroxyl, amino, alkoxy, carboxy, benzyl, phenyl, nitro, thiol, thioalkoxy, halogen, alkyl, aryl, alkenyl and alkynyl;

$T_5$ is —OH, —N($Z_1$)$Z_2$, $R_5$, D or L α-amino acid linked via the α-amino group or optionally through the ω-amino group when the amino acid is lysine or ornithine or a peptide derived from D, L or mixed D and L amino acids linked through an amino group, a chemical functional group, a reporter group or a conjugate group;

$Z_1$ is hydrogen, $C_1$-$C_6$ alkyl, or an amino protecting group;

$Z_2$ is hydrogen, $C_1$-$C_6$ alkyl, an amino protecting group, —C(=O)—(CH$_2$)$_n$-J-$Z_3$, a D or L α-amino acid linked via the α-carboxyl group or optionally through the ω-carboxyl group when the amino acid is aspartic acid or glutamic acid or a peptide derived from D, L or mixed D and L amino acids linked through a carboxyl group;

$Z_3$ is hydrogen, an amino protecting group, —$C_1$-$C_6$ alkyl, —C(=O)—CH$_3$, benzyl, benzoyl, or —(CH$_2$)$_n$—N(H)$Z_1$;

each J is O, S or NH;

$R_5$ is a carbonyl protecting group; and n is from 2 to about 50.

Another class of oligonucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. A preferred class of linking groups that have been used to link morpholino monomeric units have also been used to give a non-ionic oligonucleotide. The non-ionic morpholino-based oligonucleotides are less likely to have undesired interactions with cellular proteins. Morpholino-based oligonucleotides are non-ionic mimics of oligonucleotides and are less likely to form undesired interactions with cellular proteins (Dwaine A. Braasch and David R. Corey, *Biochemistry*, 2002, 41(14), 4503-4510). Morpholino-based oligonucleotides are disclosed in U.S. Pat. No. 5,034,506, issued Jul. 23, 1991. The morpholino class of oligonucleotides have been prepared having a variety of different linking groups joining the monomeric subunits.

Morpholino nucleic acids have been prepared having a variety of different linking groups ($L_2$) joining the monomeric subunits. The basic formula is shown below:

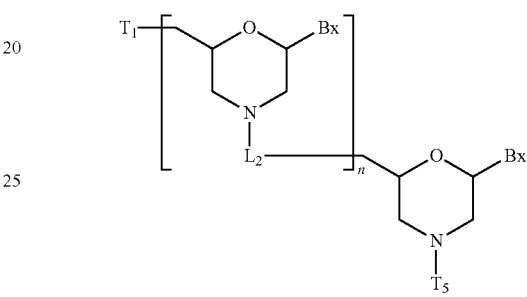

wherein $T_1$ is hydroxyl or a protected hydroxyl;

$T_5$ is hydrogen or a phosphate or phosphate derivative;

$L_2$ is a linking group; and n is from 2 to about 50.

A further class of oligonucleotide mimetic is referred to as cyclohexenyl nucleic acids (CeNA). The furanose ring normally present in an DNA/RNA molecule is replaced with a cyclophenyl ring. CeNA DMT protected phosphoramidite monomers have been prepared and used for oligonucleotide synthesis following classical phosphoramidite chemistry. Fully modified CeNA oligonucleotides and oligonucleotides having specific positions modified with CeNA have been prepared and studied (see Wang et al., *J. Am. Chem. Soc.*, 2000, 122, 8595-8602). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation. Furthermore the incorporation of CeNA into a sequence targeting RNA was stable to serum and able to activate *E. Coli* RNase resulting in cleavage of the target RNA strand.

The general formula of CeNA is shown below:

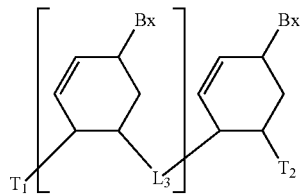

wherein
each Bx is a heterocyclic base moiety;
$T_1$ is hydroxyl or a protected hydroxyl; and
T2 is hydroxyl or a protected hydroxyl.

Another class of oligonucleotide mimetic (anhydrohexitol nucleic acid) can be prepared from one or more anhydrohexitol nucleosides (see, Wouters and Herdewijn, Bioorg. Med. Chem. Lett., 1999, 9, 1563-1566) and would have the general formula:

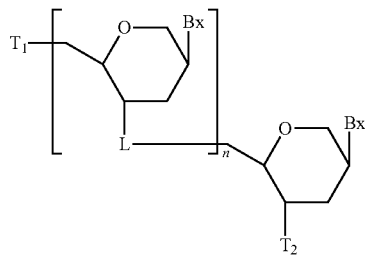

A further preferred modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage is preferably a methylene (—$CH_2$-)$_n$ group bridging the 2' oxygen atom and the 4' carbon atom wherein n is 1 or 2 (Singh et al., Chem. Commun., 1998, 4, 455-456). LNA and LNA analogs display very high duplex thermal stabilities with complementary DNA and RNA (Tm=+3 to +10 C), stability towards 3'-exonucleolytic degradation and good solubility properties. The basic structure of LNA showing the bicyclic ring system is shown below:

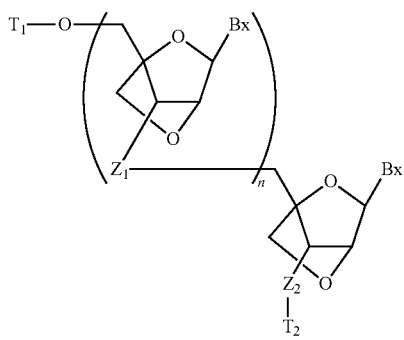

The conformations of LNAs determined by 2D NMR spectroscopy have shown that the locked orientation of the LNA nucleotides, both in single-stranded LNA and in duplexes, constrains the phosphate backbone in such a way as to introduce a higher population of the N-type conformation (Petersen et al., J. Mol. Recognit., 2000, 13, 44-53). These conformations are associated with improved stacking of the nucleobases (Wengel et al., Nucleosides Nucleotides, 1999, 18, 1365-1370).

LNA has been shown to form exceedingly stable LNA: LNA duplexes (Koshkin et al., J. Am. Chem. Soc., 1998, 120, 13252-13253). LNA:LNA hybridization was shown to be the most thermally stable nucleic acid type duplex system, and the RNA-mimicking character of LNA was established at the duplex level. Introduction of 3 LNA monomers (T or A) significantly increased melting points (Tm=+15/+11) toward DNA complements. The universality of LNA-mediated hybridization has been stressed by the formation of exceedingly stable LNA:LNA duplexes. The RNA-mimicking of LNA was reflected with regard to the N-type conformational restriction of the monomers and to the secondary structure of the LNA:RNA duplex.

LNAs also form duplexes with complementary DNA, RNA or LNA with high thermal affinities. Circular dichroism (CD) spectra show that duplexes involving fully modified LNA (esp. LNA:RNA) structurally resemble an A-form RNA:RNA duplex. Nuclear magnetic resonance (NMR) examination of an LNA:DNA duplex confirmed the 3'-endo conformation of an LNA monomer. Recognition of double-stranded DNA has also been demonstrated suggesting strand invasion by LNA. Studies of mismatched sequences show that LNAs obey the Watson-Crick base pairing rules with generally improved selectivity compared to the corresponding unmodified reference strands.

Novel types of LNA-oligonucleotides, as well as the LNAs, are useful in a wide range of diagnostic and therapeutic applications. Among these are antisense applications, PCR applications, strand-displacement oligomers, substrates for nucleic acid polymerases and generally as nucleotide based drugs.

Potent and nontoxic antisense oligonucleotides containing LNAs have been described (Wahlestedt et al., Proc. Natl. Acad. Sci. U.S.A, 2000, 97, 5633-5638.) The authors have demonstrated that LNAs confer several desired properties to antisense agents. LNA/DNA copolymers were not degraded readily in blood serum and cell extracts. LNA/DNA copolymers exhibited potent antisense activity in assay systems as disparate as G-protein-coupled receptor signaling in living rat brain and detection of reporter genes in Escherichia coli. Lipofectin-mediated efficient delivery of LNA into living human breast cancer cells has also been accomplished.

The synthesis and preparation of the LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). LNAs and preparation thereof are also described in WO 98/39352 and WO 99/14226.

The first analogs of LNA, phosphorothioate-LNA and 2'-thio-LNAs, have also been prepared (Kumar et al., Bioorg. Med. Chem. Lett., 1998, 8, 2219-2222). Preparation of locked nucleoside analogs containing oligodeoxyribonucleotide duplexes as substrates for nucleic acid polymerases has also been described (Wengel et al., PCT International Application WO 98-DK393 19980914). Furthermore, synthesis of 2'-amino-LNA, a novel conformationally restricted high-affinity oligonucleotide analog with a handle has been described in the art (Singh et al., J. Org. Chem., 1998, 63, 10035-10039). In addition, 2'-Amino- and 2'-methylamino-LNA's have been prepared and the thermal stability of their duplexes with complementary RNA and DNA strands has been previously reported.

Further oligonucleotide mimetics have been prepared to include bicyclic and tricyclic nucleoside analogs having the formulas (amidite monomers shown):

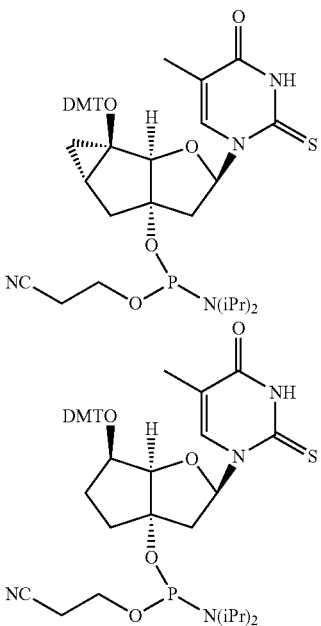

(see Steffens et al., *Helv. Chim. Acta,* 1997, 80, 2426-2439; Steffens et al., *J. Am. Chem. Soc.,* 1999, 121, 3249-3255; and Renneberg et al., *J. Am. Chem. Soc.,* 2002, 124, 5993-6002). These modified nucleoside analogs have been oligomerized using the phosphoramidite approach and the resulting oligonucleotides containing tricyclic nucleoside analogs have shown increased thermal stabilities (Tm's) when hybridized to DNA, RNA and itself. Oligonucleotides containing bicyclic nucleoside analogs have shown thermal stabilities approaching that of DNA duplexes.

Another class of oligonucleotide mimetic is referred to as phosphonomonoester nucleic acids incorporate a phosphorus group in a backbone the backbone. This class of oligonucleotide mimetic is reported to have useful physical and biological and pharmacological properties in the areas of inhibiting gene expression (antisense oligonucleotides, ribozymes, sense oligonucleotides and triplex-forming oligonucleotides), as probes for the detection of nucleic acids and as auxiliaries for use in molecular biology.

The general formula (for definitions of Markush variables see: U.S. Pat. Nos. 5,874,553 and 6,127,346 herein incorporated by reference in their entirety) is shown below.

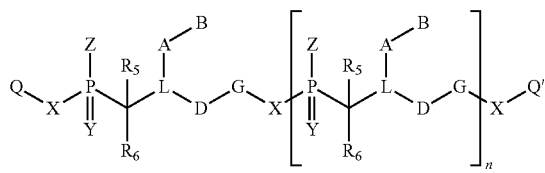

Another oligonucleotide mimetic has been reported wherein the furanosyl ring has been replaced by a cyclobutyl moiety.

Modified Internucleoside Linkages

Specific examples of preferred oligomeric compounds useful in this invention include oligonucleotides containing modified e.g. non-naturally occurring internucleoside linkages. As defined in this specification, oligonucleotides having modified internucleoside linkages include internucleoside linkages that retain a phosphorus atom and internucleoside linkages that do not have a phosphorus atom. For the purposes of this specification, and as sometimes referenced in the art, modified oligonucleotides that do not have a phosphorus atom in their internucleoside backbone can also be considered to be oligonucleosides.

In the *C. elegans* system, modification of the internucleotide linkage (phosphorothioate) did not significantly interfere with RNAi activity. Based on this observation, it is suggested that certain preferred compositions of the invention can also have one or more modified internucleoside linkages. A preferred phosphorus containing modified internucleoside linkage is the phosphorothioate internucleoside linkage.

Preferred modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

In more preferred embodiments of the invention, oligonucleotides have one or more phosphorothioate and/or heteroatom internucleoside linkages, in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester internucleotide linkage is represented as —O—P(=O)(OH)—O—$CH_2$—]. The MMI type internucleoside linkages are disclosed in the above referenced U.S. Pat. No. 5,489,677. Preferred amide internucleoside linkages are disclosed in the above referenced U.S. Pat. No. 5,602,240.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH$_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

Modified Sugars

In addition to having at least one alternating motif the compositions of the present invention may also contain additional modified sugar moieties. Preferred modified sugar moieties comprise a sugar substituent group, which is normally attached to the 2'-position but alternatively can be attached to the 3', 4' or 5'-position, selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C$_1$ to C$_{10}$ alkyl or C$_2$ to C$_{10}$ alkenyl and alkynyl. Particularly preferred are O[(CH$_2$)$_n$O]$_m$CH$_3$, O(CH$_2$)$_n$OCH$_3$, O(CH$_2$)$_n$NH$_2$, O(CH$_2$)$_n$CH$_3$, O(CH$_2$)$_n$ONH$_2$, and O(CH$_2$)$_n$ON—[(CH$_2$)$_n$CH$_3$]$_2$, where n and m are from 1 to about 10. Other preferred sugar substituent groups include: C$_1$ to C$_{10}$ lower alkyl, substituted lower alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—CH$_2$CH$_2$OCH$_3$, also known as 2'-O-(2-methoxyethyl) or 2'-MOE) (Martin et al., Helv. Chim. Acta, 1995, 78, 486-504) i.e., an alkoxyalkoxy group. A further preferred modification includes 2'-dimethylaminooxyethoxy, i.e., a O(CH$_2$)$_2$ON(CH$_3$)$_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—CH2OCH$_2$N(CH$_3$)$_2$.

Other preferred sugar substituent groups include methoxy (—O—CH$_3$), aminopropoxy (—OCH$_2$CH$_2$CH$_2$NH$_2$), allyl (—CH$_2$—CH=CH$_2$), —O-allyl (—O—CH$_2$—CH=CH$_2$) and fluoro (F). 2'-Sugar substituent groups may be in the arabino (up) position or ribo (down) position. A preferred 2'-arabino modification is 2'-F. Similar modifications may also be made at other positions on the oligomeric compound, particularly the 3' position of the sugar on the 3' terminal nucleoside or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

Further representative sugar substituent groups include groups of formula I$_a$ or II$_a$:

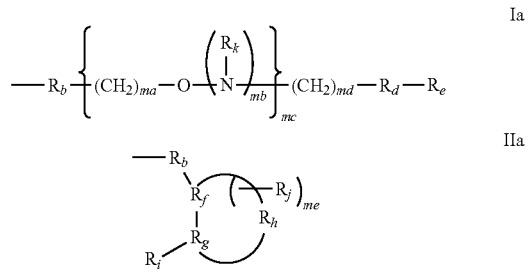

wherein:

R$_b$ is O, S or NH;

R$_d$ is a single bond, O, S or C(=O);

R$_e$ is C$_1$-C$_{10}$ alkyl, N(R$_k$)(R$_m$), N(R$_k$)(R$_n$), N=C(R$_p$)(R$_q$), N=C(R$_p$)(R$_r$) or has formula III$_a$;

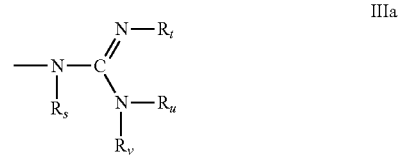

R$_p$ and R$_q$ are each independently hydrogen or C$_1$-C$_{10}$ alkyl;

R$_r$ is —R$_x$—R$_y$;

each R$_s$, R$_t$, R$_u$ and R$_v$ is, independently, hydrogen, C(O)R$_w$, substituted or unsubstituted C$_1$-C$_{10}$ alkyl, substituted or unsubstituted C$_2$-C$_{10}$ to alkenyl, substituted or unsubstituted C$_2$-C$_{10}$ alkynyl, alkylsulfonyl, arylsulfonyl, a chemical functional group or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl;

or optionally, R$_u$ and R$_v$, together form a phthalimido moiety with the nitrogen atom to which they are attached;

each R$_w$ is, independently, substituted or unsubstituted C$_1$-C$_{10}$ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, iso-butyryl, phenyl or aryl;

R$_k$ is hydrogen, a nitrogen protecting group or —R$_x$—R$_y$;

R$_p$ is hydrogen, a nitrogen protecting group or —R$_x$—R$_y$;

R$_x$ is a bond or a linking moiety;

R$_y$ is a chemical functional group, a conjugate group or a solid support medium;

each R$_m$ and R$_n$ is, independently, H, a nitrogen protecting group, substituted or unsubstituted C$_1$-C$_{10}$ alkyl, substituted or unsubstituted C$_2$-C$_{10}$ alkenyl, substituted or unsubstituted C$_2$-C$_{10}$ alkynyl, wherein the substituent groups are selected from hydroxyl, amino, alkoxy, carboxy, benzyl, phenyl, nitro, thiol, thioalkoxy, halogen, alkyl, aryl, alkenyl, alkynyl; NH$_3$$^+$, N(R$_u$)(R$_v$), guanidino and acyl where said acyl is an acid amide or an ester;

or $R_m$ and $R_n$, together, are a nitrogen protecting group, are joined in a ring structure that optionally includes an additional heteroatom selected from N and O or are a chemical functional group;

$R_t$ is $OR_z$, $SR_z$, or $N(R_z)_2$;

each $R_z$ is, independently, H, $C_1$-$C_8$ alkyl, $C_1$-$C_8$ haloalkyl, C(=NH)N(H)$R_u$, C(=O)N(H)$R_u$ or OC(=O)N(H)$R_u$;

$R_f$, $R_g$ and $R_h$ comprise a ring system having from about 4 to about 7 carbon atoms or having from about 3 to about 6 carbon atoms and 1 or 2 heteroatoms wherein said heteroatoms are selected from oxygen, nitrogen and sulfur and wherein said ring system is aliphatic, unsaturated aliphatic, aromatic, or saturated or unsaturated heterocyclic;

$R_j$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(R_k)(R_m)OR_k$, halo, $SR_k$ or CN;

$m_a$ is 1 to about 10;

each mb is, independently, 0 or 1;

mc is 0 or an integer from 1 to 10;

md is an integer from 1 to 10;

me is from 0, 1 or 2; and provided that when mc is 0, md is greater than 1.

Representative substituents groups of Formula I are disclosed in U.S. patent application Ser. No. 09/130,973, filed Aug. 7, 1998, entitled "Capped 2'-Oxyethoxy Oligonucleotides," hereby incorporated by reference in its entirety.

Representative cyclic substituent groups of Formula II are disclosed in U.S. patent application Ser. No. 09/123,108, filed Jul. 27, 1998, entitled "RNA Targeted 2'-Oligonucleotides that are Conformationally Preorganized," hereby incorporated by reference in its entirety.

Particularly preferred sugar substituent groups include O[(CH$_2$)$_n$O]$_m$CH$_3$, O(CH$_2$)$_n$OCH$_3$, O(CH$_2$)$_n$NH$_2$, O(CH$_2$)$_n$CH$_3$, O(CH$_2$)$_n$ONH$_2$, and O(CH$_2$)$_n$ON[(CH$_2$)$_n$CH$_3$)]$_2$, where n and m are from 1 to about 10.

Representative guanidino substituent groups that are shown in formula III and IV are disclosed in co-owned U.S. patent application Ser. No. 09/349,040, entitled "Functionalized Oligomers", filed Jul. 7, 1999, hereby incorporated by reference in its entirety.

Representative acetamido substituent groups are disclosed in U.S. Pat. No. 6,147,200 which is hereby incorporated by reference in its entirety.

Representative dimethylaminoethyloxyethyl substituent groups are disclosed in International Patent Application PCT/US99/17895, entitled "2'-O-Dimethyl aminoethyloxyethyl-Oligonucleotides", filed Aug. 6, 1999, hereby incorporated by reference in its entirety.

Modified Nucleobases/Naturally Occurring Nucleobases

Oligomeric compounds may also include nucleosides or other surrogate or mimetic monomeric subunits that include a nucleobase (often referred to in the art simply as "base" or "heterocyclic base moiety"). The nucleobase is another moiety that has been extensively modified or substituted and such modified and or substituted nucleobases are amenable to the present invention. As used herein, "unmodified" or "natural" nucleobases include the purine bases adenine (A) and guanine (G), and the pyrimidine bases thymine (T), cytosine (C) and uracil (U). Modified nucleobases also referred herein as heterocyclic base moieties include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are particularly useful for increasing the binding affinity of the compositions of the invention. These include 5-substituted pyrimidines, 6-azapyrimidines and N-2, N-6 and O-6 substituted purines, including 2 aminopropyladenine, 5-propynyluracil and 5-propynylcytosine. 5 methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278) and are presently preferred base substitutions, even more particularly when combined with 2'-O-methoxyethyl sugar modifications.

Oligomeric compounds of the present invention can also include polycyclic heterocyclic compounds in place of one or more heterocyclic base moieties. A number of tricyclic heterocyclic compounds have been previously reported. These compounds are routinely used in antisense applications to increase the binding properties of the modified strand to a target strand. The most studied modifications are targeted to guanosines hence they have been termed G-clamps or cytidine analogs. Many of these polycyclic heterocyclic compounds have the general formula:

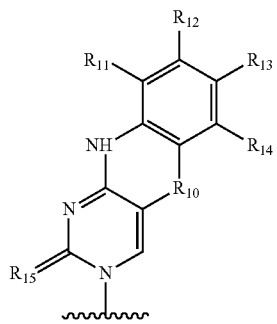

Representative cytosine analogs that make 3 hydrogen bonds with a guanosine in a second strand include 1,3-diazaphenoxazine-2-one ($R_{10}$=O, $R_{11}$-$R_{14}$=H) [Kurchavov, et al., *Nucleosides and Nucleotides*, 1997, 16, 1837-1846], 1,3-diazaphenothiazine-2-one ($R_{10}$=S, $R_{11}$-$R_{14}$=H), [Lin, K.-Y.; Jones, R. J.; Matteucci, M. J. Am. Chem. Soc. 1995, 117, 3873-3874] and 6,7,8,9-tetrafluoro-1,3-diazaphenoxazine-2-one ($R_{10}$=O, $R_{11}$-$R_{14}$=F) [Wang, J.; Lin, K.-Y., Matteucci, M. Tetrahedron Lett. 1998, 39, 8385-8388]. Incorporated into oligonucleotides these base modifications were shown to hybridize with complementary guanine and the latter was also shown to hybridize with adenine and to enhance helical thermal stability by extended stacking interactions (also see U.S. patent application entitled "Modified Peptide Nucleic Acids" filed May 24, 2002, Ser. No. 10/155,920; and U.S. patent application entitled "Nuclease Resistant Chimeric Oligonucleotides" filed May 24, 2002, Ser. No. 10/013,295, both of which are commonly owned with this application and are herein incorporated by reference in their entirety).

Further helix-stabilizing properties have been observed when a cytosine analog/substitute has an aminoethoxy moiety attached to the rigid 1,3-diazaphenoxazine-2-one scaffold ($R_{10}$=O, $R_{11}$=—O—$(CH_2)_2$—$NH_2$, $R_{12\text{-}14}$=H) [Lin, K.-Y.; Matteucci, M. J. Am. Chem. Soc. 1998, 120, 8531-8532]. Binding studies demonstrated that a single incorporation could enhance the binding affinity of a model oligonucleotide to its complementary target DNA or RNA with a $\Delta T_m$ of up to 18° relative to 5-methyl cytosine ($dC5^{me}$), which is the highest known affinity enhancement for a single modification, yet. On the other hand, the gain in helical stability does not compromise the specificity of the oligonucleotides. The $T_m$ data indicate an even greater discrimination between the perfect match and mismatched sequences compared to $dC5^{me}$. It was suggested that the tethered amino group serves as an additional hydrogen bond donor to interact with the Hoogsteen face, namely the O6, of a complementary guanine thereby forming 4 hydrogen bonds. This means that the increased affinity of G-clamp is mediated by the combination of extended base stacking and additional specific hydrogen bonding.

Further tricyclic heterocyclic compounds and methods of using them that are amenable to the present invention are disclosed in U.S. Pat. No. 6,028,183, which issued on May 22, 2000, and U.S. Pat. No. 6,007,992, which issued on Dec. 28, 1999, the contents of both are commonly assigned with this application and are incorporated herein in their entirety.

The enhanced binding affinity of the phenoxazine derivatives together with their uncompromised sequence specificity makes them valuable nucleobase analogs for the development of more potent antisense-based drugs. In fact, promising data have been derived from in vitro experiments demonstrating that heptanucleotides containing phenoxazine substitutions are capable to activate RNaseH, enhance cellular uptake and exhibit an increased antisense activity [Lin, K-Y; Matteucci, M. J. Am. Chem. Soc. 1998, 120, 8531-8532]. The activity enhancement was even more pronounced in case of G-clamp, as a single substitution was shown to significantly improve the in vitro potency of a 20mer 2'-deoxyphosphorothioate oligonucleotides [Flanagan, W. M.; Wolf, J. J.; Olson, P.; Grant, D.; Lin, K.-Y.; Wagner, R. W.; Matteucci, M. Proc. Natl. Acad. Sci. USA, 1999, 96, 3513-3518]. Nevertheless, to optimize oligonucleotide design and to better understand the impact of these heterocyclic modifications on the biological activity, it is important to evaluate their effect on the nuclease stability of the oligomers.

Further modified polycyclic heterocyclic compounds useful as nucleobases are disclosed in but not limited to, the above noted U.S. Pat. No. 3,687,808, as well as U.S. Pat. Nos. 4,845,205; 5,130,302; 5,134,066; 5,175,273; 5,367,066; 5,432,272; 5,434,257; 5,457,187; 5,459,255; 5,484,908; 5,502,177; 5,525,711; 5,552,540; 5,587,469; 5,594,121; 5,596,091; 5,614,617; 5,645,985; 5,646,269; 5,750,692; 5,830,653; 5,763,588; 6,005,096; and 5,681,941, and U.S. patent application Ser. No. 09/996,292 filed Nov. 28, 2001, certain of which are commonly owned with the instant application, and each of which is herein incorporated by reference.

Conjugates

Oligomeric compounds used in the compositions of the present invention can also be modified to have one or more moieties or conjugates which enhance their activity, cellular distribution or cellular uptake. In one embodiment such modified oligomeric compounds are prepared by covalently attaching conjugate groups to functional groups such as hydroxyl or amino groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference. Conjugate moieties include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylaminocarbonyl-oxycholesterol moiety (Crooke et al., J. Pharmacol. Exp. Ther., 1996, 277, 923-937.

The compositions of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999), incorporated herein by reference in its entirety.

Representative United States patents that teach the preparation of such oligonucleotide conjugates include, but are not limited to, U.S. Pat. Nos. 4,828,979; 4,948,882; 5,218, 105; 5,525,465; 5,541,313; 5,545,730; 5,552,538; 5,578, 717, 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,214,136; 5,245,022; 5,254,469; 5,258, 506; 5,262,536; 5,272,250; 5,292,873; 5,317,098; 5,371, 241, 5,391,723; 5,416,203, 5,451,463; 5,510,475; 5,512, 667; 5,514,785; 5,565,552; 5,567,810; 5,574,142; 5,585, 481; 5,587,371; 5,595,726; 5,597,696; 5,599,923; 5,599,928 and 5,688,941, certain of which are commonly owned with the instant application, and each of which is herein incorporated by reference.

Oligomeric compounds used in the compositions of the present invention can also be modified to have one or more stabilizing groups that are generally attached to one or both termini of oligomeric compounds to enhance properties such as for example nuclease stability. Included in stabilizing groups are cap structures. By "cap structure or terminal cap moiety" is meant chemical modifications, which have been incorporated at either terminus of oligonucleotides (see for example Wincott et al., WO 97/26270, incorporated by reference herein). These terminal modifications protect the oligomeric compounds having terminal nucleic acid molecules from exonuclease degradation, and can help in delivery and/or localization within a cell. The cap can be present at the 5'-terminus (5'-cap) or at the 3'-terminus (3'-cap) or can be present on both termini. In non-limiting examples, the 5'-cap includes inverted abasic residue (moiety), 4',5'-methylene nucleotide; 1-(beta-D-erythrofuranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (for more details see Wincott et al., International PCT publication No. WO 97/26270, incorporated by reference herein).

Particularly preferred 3'-cap structures of the present invention include, for example 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Tyer, 1993, Tetrahedron 49, 1925; incorporated by reference herein).

3'-Endo Modifications

In one aspect of the present invention oligomeric compounds include nucleosides that are chemically modified to induce a 3'-endo sugar conformation. A nucleoside can have a chemical modification of the nucleobase, the sugar moiety or both to induce a 3'-endo sugar conformation. These modified nucleosides are used to mimic RNA like nucleosides so that particular properties of an oligomeric compound especially an oligonucleotide can be enhanced while maintaining the desirable 3'-endo conformational geometry. There is an apparent preference for an RNA type duplex (A form helix, predominantly 3'-endo) as a requirement of RNA interference which is supported in part by the fact that duplexes composed of 2'-deoxy-2'-F-nucleosides appear efficient in triggering RNAi response in the C. elegans system. Properties that are enhanced by using more stable 3'-endo nucleosides include but aren't limited to modulation of pharmacokinetic properties through modification of protein binding, protein off-rate, absorption and clearance; modulation of nuclease stability as well as chemical stability; modulation of the binding affinity and specificity of the oligomer (affinity and specificity for enzymes as well as for complementary sequences); and increasing efficacy of RNA cleavage. The present invention includes oligomeric compounds having at least one 2'-O-methyl modified nucleoside and further comprising additional nucleosides that are modified in such a way as to favor a C3'-endo type conformation.

Scheme 1

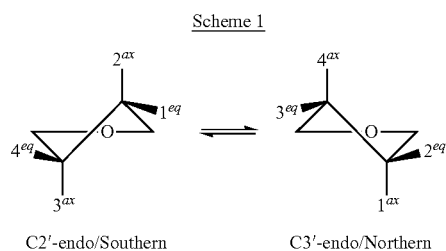

C2'-endo/Southern    C3'-endo/Northern

Nucleoside conformation is influenced by various factors including substitution at the 2', 3' or 4'-positions of the pentofuranosyl sugar. Electronegative substituents generally prefer the axial positions, while sterically demanding substituents generally prefer the equatorial positions (Principles of Nucleic Acid Structure, Wolfgang Sanger, 1984, Springer-Verlag.) Modification of the 2' position to favor the 3'-endo conformation can be achieved while maintaining the 2'-OH as a recognition element, as illustrated in FIG. 2, below (Gallo et al., Tetrahedron (2001), 57, 5707-5713. Harry-O'kuru et al., J. Org. Chem., (1997), 62(6), 1754-1759 and Tang et al., J. Org. Chem. (1999), 64, 747-754.) Alternatively, preference for the 3'-endo conformation can be achieved by deletion of the 2'-OH as exemplified by 2'deoxy-2'F-nucleosides (Kawasaki et al., J. Med. Chem. (1993), 36, 831-841), which adopts the 3'-endo conformation positioning the electronegative fluorine atom in the axial position. Other modifications of the ribose ring, for example substitution at the 4'-position to give 4'-F modified nucleosides (Guillerm et al., Bioorganic and Medicinal Chemistry Letters (1995), 5, 1455-1460 and Owen et al., J. Org. Chem. (1976), 41, 3010-3017), or for example modification to yield methanocarba nucleoside analogs (Jacobson et al., J. Med. Chem. Lett. (2000), 43, 2196-2203 and Lee et al., Bioorganic and Medicinal Chemistry Letters (2001), 11, 1333-1337) also induce preference for the 3'-endo conformation. Some modifications actually lock the conformational geometry by formation of a bicyclic sugar moiety e.g. locked nucleic acid (LNA, Singh et al, Chem. Commun.

(1998), 4, 455-456), and ethylene bridged nucleic acids (ENA, Morita et al, Bioorganic & Medicinal Chemistry Letters (2002), 12, 73-76.)

Examples of modified nucleosides amenable to the present invention are shown below in Table I. These examples are meant to be representative and not exhaustive.

TABLE I

[Chemical structures of modified nucleosides]

TABLE I-continued

[Chemical structures of modified nucleosides]

The preferred conformation of modified nucleosides and their oligomers can be estimated by various methods such as molecular dynamics calculations, nuclear magnetic resonance spectroscopy and CD measurements. Hence, modifications predicted to induce RNA like conformations, A-form duplex geometry in an oligomeric context, are selected for use in one or more of the oligonucleotides of the present invention. The synthesis of numerous of the modified nucleosides amenable to the present invention are known in the art (see for example, Chemistry of Nucleosides and Nucleotides Vol 1-3, ed. Leroy B. Townsend, 1988, Plenum press., and the examples section below.) Nucleosides known to be inhibitors/substrates for RNA dependent RNA polymerases (for example HCV NS5B In one aspect, the present invention is directed to oligonucleotides that are prepared having enhanced properties compared to native RNA against nucleic acid targets. A target is identified and an oligonucleotide is selected having an effective length and sequence that is complementary to a portion of the target sequence. Each nucleoside of the selected sequence is scrutinized for possible enhancing modifications. A preferred modification would be the replacement of one or more RNA nucleosides with nucleosides that have the same 3'-endo conformational geometry. Such modifications can enhance chemical and nuclease stability relative to native RNA while at the same time being much cheaper and easier to synthesize and/or incorporate into an oligonucleotide. The selected sequence can be further divided into regions and the nucleosides of each region evaluated for enhancing modifications that can be the result of a chimeric configuration. Consideration is also given to the termini (e.g. 5' and 3'-termini) as there are often advantageous modifications that can be made to one or more of the terminal monomeric subunits. In one aspect of the invention, desired properties and or activity of oligonucleotides are enhanced by the inclusion of a 5'-phosphate or modified phosphate moiety.

The terms used to describe the conformational geometry of homoduplex nucleic acids are "A Form" for RNA and "B Form" for DNA. The respective conformational geometry for RNA and DNA duplexes was determined from X-ray diffraction analysis of nucleic acid fibers (Arnott and Hukins, *Biochem. Biophys. Res. Comm.,* 1970, 47, 1504.) In general, RNA:RNA duplexes are more stable and have higher melting temperatures (Tm's) than DNA:DNA duplexes (Sanger et al., Principles of Nucleic Acid Structure, 1984, Springer-Verlag; New York, N.Y.; Lesnik et al., Biochemistry, 1995, 34, 10807-10815; Conte et al., Nucleic Acids Res., 1997, 25, 2627-2634). The increased stability of RNA has been attributed to several structural features, most notably the improved base stacking interactions that result from an A-form geometry (Searle et al., Nucleic Acids Res., 1993, 21, 2051-2056). The presence of the 2' hydroxyl in RNA biases the sugar toward a C3' endo pucker, i.e., also designated as Northern pucker, which causes the duplex to favor the A-form geometry. In addition, the 2' hydroxyl groups of RNA can form a network of water mediated hydrogen bonds that help stabilize the RNA duplex (Egli et al., Biochemistry, 1996, 35, 8489-8494). On the other hand, deoxy nucleic acids prefer a C2' endo sugar pucker, i.e., also known as Southern pucker, which is thought to impart a less stable B-form geometry (Sanger, W. (1984) Principles of Nucleic Acid Structure, Springer-Verlag, New York, N.Y.). As used herein, B-form geometry is inclusive of both C2'-endo pucker and O4'-endo pucker. This is consistent with Berger, et. al., *Nucleic Acids Research,* 1998, 26, 2473-2480, who pointed out that in considering the furanose conformations which give rise to B-form duplexes consideration should also be given to a 04'-endo pucker contribution.

DNA:RNA hybrid duplexes, however, are usually less stable than pure RNA:RNA duplexes, and depending on their sequence may be either more or less stable than DNA:DNA duplexes (Searle et al., *Nucleic Acids Res.,* 1993, 21, 2051-2056). The structure of a hybrid duplex is intermediate between A- and B-form geometries, which may result in poor stacking interactions (Lane et al., *Eur. J. Biochem.,* 1993, 215, 297-306; Fedoroff et al., *J. Mol. Biol.,* 1993, 233, 509-523; Gonzalez et al., *Biochemistry,* 1995, 34, 4969-4982; Horton et al., *J. Mol. Biol.,* 1996, 264, 521-533).

The stability of the duplex formed between a target RNA and a synthetic sequence is central to therapies such as but not limited to antisense and RNA interference as these mechanisms require the binding of a synthetic strand of oligonucleotide to an RNA target strand. In the case of antisense, effective inhibition of the mRNA requires that the antisense DNA have a very high binding affinity with the mRNA. Otherwise the desired interaction between the synthetic strand and target mRNA strand will occur infrequently, resulting in decreased efficacy.

One routinely used method of modifying the sugar puckering is the substitution of the sugar at the 2'-position with a substituent group that influences the sugar geometry. The influence on ring conformation is dependant on the nature of the substituent at the 2'-position. A number of different substituents have been studied to determine their sugar puckering effect. For example, 2'-halogens have been studied showing that the 2'-fluoro derivative exhibits the largest population (65%) of the C3'-endo form, and the 2'-iodo exhibits the lowest population (7%). The populations of adenosine (2'-OH) versus deoxyadenosine (2'-H) are 36% and 19%, respectively. Furthermore, the effect of the 2'-fluoro group of adenosine dimers (2'-deoxy-2'-fluoroadenosine-2'-deoxy-2'-fluoro-adenosine) is further correlated to the stabilization of the stacked conformation.

As expected, the relative duplex stability can be enhanced by replacement of 2'-OH groups with 2'-F groups thereby increasing the C3'-endo population. It is assumed that the highly polar nature of the 2'-F bond and the extreme preference for C3'-endo puckering may stabilize the stacked conformation in an A-form duplex. Data from UV hypochromicity, circular dichroism, and $^1$H NMR also indicate that the degree of stacking decreases as the electronegativity of the halo substituent decreases. Furthermore, steric bulk at the 2'-position of the sugar moiety is better accommodated in an A-form duplex than a B-form duplex. Thus, a 2'-substituent on the 3'-terminus of a dinucleoside monophosphate is thought to exert a number of effects on the stacking conformation: steric repulsion, furanose puckering preference, electrostatic repulsion, hydrophobic attraction, and hydrogen bonding capabilities. These substituent effects are thought to be determined by the molecular size, electronegativity, and hydrophobicity of the substituent. Melting temperatures of complementary strands is also increased with the 2'-substituted adenosine diphosphates. It is not clear whether the 3'-endo preference of the conformation or the presence of the substituent is responsible for the increased binding. However, greater overlap of adjacent bases (stacking) can be achieved with the 3'-endo conformation.

One synthetic 2'-modification that imparts increased nuclease resistance and a very high binding affinity to nucleotides is the 2-methoxyethoxy (2'-MOE, 2'-OCH$_2$CH$_2$OCH$_3$) side chain (Baker et al., *J. Biol. Chem.,* 1997, 272, 11944-12000). One of the immediate advantages of the 2'-MOE substitution is the improvement in binding affinity, which is greater than many similar 2' modifications such as O-methyl, O-propyl, and O-aminopropyl. Oligonucleotides having the 2'-O-methoxyethyl substituent also have been shown to be antisense inhibitors of gene expression with promising features for in vivo use (Martin, P., *Helv. Chim. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926). Relative to DNA, the oligonucleotides having the 2'-MOE modification displayed improved RNA affinity and higher nuclease resistance. Chimeric oligonucleotides having 2'-MOE substituents in the wing nucleosides and an internal region of deoxy-phosphorothioate nucleotides (also termed a gapped oligonucleotide or gapmer) have shown effective reduction in the growth of tumors in animal models at low doses. 2'-MOE substituted oligonucleotides have also shown outstanding promise as antisense agents in several disease states. One such MOE substituted oligonucleotide is presently being investigated in clinical trials for the treatment of CMV retinitis.

To better understand the higher RNA affinity of 2'-O-methoxyethyl substituted RNA and to examine the conformational properties of the 2'-O-methoxyethyl substituent, two dodecamer oligonucleotides were synthesized having SEQ ID NO: 54 (CGC GAA UUC GCG) and SEQ ID NO: 55 (GCG CUU AAG CGC). These self-complementary strands have every 2'-position modified with a 2'-O-methoxyethyl. The duplex was crystallized at a resolution of 1.7 Angstrom and the crystal structure was determined. The conditions used for the crystallization were 2 mM oligonucleotide, 50 mM Na Hepes pH 6.2-7.5, 10.50 mM MgCl$_2$, 15% PEG 400. The crystal data showed: space group C$_2$, cell constants a=41.2 Å, b=34.4 Å, c=46.6 Å, □=92.4°. The resolution was 1.7 Å at −170° C. The current R=factor was 20% (R$_{free}$ 26%).

This crystal structure is believed to be the first crystal structure of a fully modified RNA oligonucleotide analogue. The duplex adopts an overall A-form conformation and all modified sugars display C3'-endo pucker. In most of the 2'-O-substituents, the torsion angle around the A'-B' bond, as depicted in Structure II below, of the ethylene glycol linker has a gauche conformation. For 2'-O-MOE, A' and B' of Structure II below are methylene moieties of the ethyl portion of the MOE and R' is the methoxy portion.

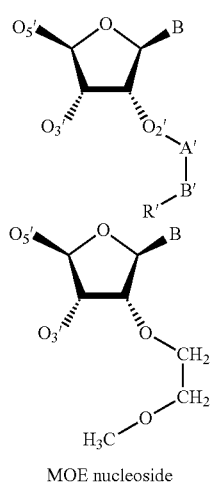

II

MOE nucleoside

In the crystal, the 2'-O-MOE RNA duplex adopts a general orientation such that the crystallographic 2-fold rotation axis does not coincide with the molecular 2-fold rotation axis. The duplex adopts the expected A-type geometry and all of the 24 2'-O-MOE substituents were visible in the electron density maps at full resolution. The electron density maps as well as the temperature factors of substituent atoms indicate flexibility of the 2'-O-MOE substituent in some cases.

Most of the 2'-O-MOE substituents display a gauche conformation around the C—C bond of the ethyl linker. However, in two cases, a trans conformation around the C—C bond is observed. The lattice interactions in the crystal include packing of duplexes against each other via their minor grooves. Therefore, for some residues, the conformation of the 2'-O-substituent is affected by contacts to an adjacent duplex. In general, variations in the conformation of the substituents (e.g. g$^+$ or g$^-$ around the C—C bonds) create a range of interactions between substituents, both inter-strand, across the minor groove, and intra-strand. At one location, atoms of substituents from two residues are in van der Waals contact across the minor groove. Similarly, a close contact occurs between atoms of substituents from two adjacent intra-strand residues.

Previously determined crystal structures of A-DNA duplexes were for those that incorporated isolated 2'-O-methyl T residues. In the crystal structure noted above for the 2'-O-MOE substituents, a conserved hydration pattern has been observed for the 2'-O-MOE residues. A single water molecule is seen located between O2', O3' and the methoxy oxygen atom of the substituent, forming contacts to all three of between 2.9 and 3.4 Å. In addition, oxygen atoms of substituents are involved in several other hydrogen bonding contacts. For example, the methoxy oxygen atom of a particular 2'-O-substituent forms a hydrogen bond to N3 of an adenosine from the opposite strand via a bridging water molecule.

In several cases a water molecule is trapped between the oxygen atoms O2', O3' and OC' of modified nucleosides. 2'-O-MOE substituents with trans conformation around the C—C bond of the ethylene glycol linker are associated with close contacts between OC' and N2 of a guanosine from the opposite strand, and, water-mediated, between OC' and N3(G). When combined with the available thermodynamic data for duplexes containing 2'-O-MOE modified strands, this crystal structure allows for further detailed structure-stability analysis of other modifications.

In extending the crystallographic structure studies, molecular modeling experiments were performed to study further enhanced binding affinity of oligonucleotides having 2'-O-modifications. The computer simulations were conducted on compounds of SEQ ID NO: 7, above, having 2'-O-modifications located at each of the nucleosides of the oligonucleotide. The simulations were performed with the oligonucleotide in aqueous solution using the AMBER force field method (Cornell et al., *J. Am. Chem. Soc.*, 1995, 117, 5179-5197)(modeling software package from UCSF, San Francisco, Calif.). The calculations were performed on an Indigo2 SGI machine (Silicon Graphics, Mountain View, Calif.).

Further 2'-O-modifications that will have a 3'-endo sugar influence include those having a ring structure that incorporates a two atom portion corresponding to the A' and B' atoms of Structure II. The ring structure is attached at the 2' position of a sugar moiety of one or more nucleosides that are incorporated into an oligonucleotide. The 2'-oxygen of the nucleoside links to a carbon atom corresponding to the A' atom of Structure II. These ring structures can be aliphatic, unsaturated aliphatic, aromatic or heterocyclic. A further atom of the ring (corresponding to the B' atom of Structure II), bears a further oxygen atom, or a sulfur or nitrogen atom. This oxygen, sulfur or nitrogen atom is bonded to one or more hydrogen atoms, alkyl moieties, or haloalkyl moieties, or is part of a further chemical moiety such as a ureido, carbamate, amide or amidine moiety. The remainder of the ring structure restricts rotation about the bond joining these two ring atoms. This assists in positioning the "further oxygen, sulfur or nitrogen atom" (part of the R position as described above) such that the further atom can be located in close proximity to the 3'-oxygen atom (O3') of the nucleoside.

Another preferred 2'-sugar substituent group that gives a 3'-endo sugar conformational geometry is the 2'-OMe group. 2'-Substitution of guanosine, cytidine, and uridine dinucleoside phosphates with the 2'-OMe group showed enhanced stacking effects with respect to the corresponding native (2'-OH) species leading to the conclusion that the sugar is adopting a C3'-endo conformation. In this case, it is believed that the hydrophobic attractive forces of the methyl group tend to overcome the destabilizing effects of its steric bulk.

The ability of oligonucleotides to bind to their complementary target strands is compared by determining the melting temperature ($T_m$) of the hybridization complex of the oligonucleotide and its complementary strand. The melting temperature ($T_m$), a characteristic physical property of double helices, denotes the temperature (in degrees centigrade) at which 50% helical (hybridized) versus coil (unhybridized) forms are present. $T_m$ is measured by using the UV spectrum to determine the formation and breakdown (melting) of the hybridization complex. Base stacking, which occurs during hybridization, is accompanied by a reduction in UV absorption (hypochromicity). Consequently, a reduction in UV absorption indicates a higher $T_m$. The higher the $T_m$, the greater the strength of the bonds between the strands.

Freier and Altmann, Nucleic Acids Research, (1997) 25:4429-4443, have previously published a study on the influence of structural modifications of oligonucleotides on the stability of their duplexes with target RNA. In this study, the authors reviewed a series of oligonucleotides containing more than 200 different modifications that had been synthesized and assessed for their hybridization affinity and Tm. Sugar modifications studied included substitutions on the 2'-position of the sugar, 3'-substitution, replacement of the 4'-oxygen, the use of bicyclic sugars, and four member ring replacements. Several nucleobase modifications were also studied including substitutions at the 5, or 6 position of thymine, modifications of pyrimidine heterocycle and modifications of the purine heterocycle. Modified internucleoside linkages were also studied including neutral, phosphorus and non-phosphorus containing internucleoside linkages.

Increasing the percentage of C3'-endo sugars in a modified oligonucleotide targeted to an RNA target strand should preorganize this strand for binding to RNA. Of the several sugar modifications that have been reported and studied in the literature, the incorporation of electronegative substituents such as 2'-fluoro or 2'-alkoxy shift the sugar conformation towards the 3' endo (northern) pucker conformation. This preorganizes an oligonucleotide that incorporates such modifications to have an A-form conformational geometry. This A-form conformation results in increased binding affinity of the oligonucleotide to a target RNA strand.

Molecular modeling experiments were performed to study further enhanced binding affinity of oligonucleotides having 2'-O-modifications. Computer simulations were conducted on compounds having SEQ ID NO: 54, r(CGC GAA UUC GCG), having 2'-O-modifications of the invention located at each of the nucleoside of the oligonucleotide. The simulations were performed with the oligonucleotide in aqueous solution using the AMBER force field method (Cornell et al., J. Am. Chem. Soc., 1995, 117, 5179-5197) (modeling software package from UCSF, San Francisco, Calif.). The calculations were performed on an Indigo2 SGI machine (Silicon Graphics, Mountain View, Calif.).

In addition, for 2'-substituents containing an ethylene glycol motif, a gauche interaction between the oxygen atoms around the O—C—C—O torsion of the side chain may have a stabilizing effect on the duplex (Freier ibid.). Such gauche interactions have been observed experimentally for a number of years (Wolfe et al., Acc. Chem. Res., 1972, 5, 102; Abe et al., J. Am. Chem. Soc., 1976, 98, 468). This gauche effect may result in a configuration of the side chain that is favorable for duplex formation. The exact nature of this stabilizing configuration has not yet been explained. While we do not want to be bound by theory, it may be that holding the O—C—C—O torsion in a single gauche configuration, rather than a more random distribution seen in an alkyl side chain, provides an entropic advantage for duplex formation.

Representative 2'-substituent groups amenable to the present invention that give A-form conformational properties (3'-endo) to the resultant duplexes include 2'-O-alkyl, 2'-O-substituted alkyl and 2'-fluoro substituent groups. Preferred for the substituent groups are various alkyl and aryl ethers and thioethers, amines and monoalkyl and dialkyl substituted amines. It is further intended that multiple modifications can be made to one or more of the compositions of the invention at multiple sites of one or more monomeric subunits (nucleosides are preferred) and or internucleoside linkages to enhance properties such as but not limited to activity in a selected application. Tables I through VII list nucleoside and internucleotide linkage modifications/replacements that have been shown to give a positive ∈Tm per modification when the modification/replacement was made to a DNA strand that was hybridized to an RNA complement.

TABLE I

Modified DNA strand having 2'-substituent groups that gave an overall increase in Tm against an RNA complement:

Positive ∈Tm/mod

| 2'-substituents | 2'-OH |
|---|---|
| | 2'-O—$C_1$-$C_4$ alkyl |
| | 2'-O—$(CH_2)_2CH_3$ |
| | 2'-O—$CH_2CH=CH_2$ |
| | 2'-F |
| | 2'-O—$(CH_2)_2$—O—$CH_3$ |
| | 2'-[O—$(CH_2)_2]_2$—O—$CH_3$ |
| | 2'-[O—$(CH_2)_2]_3$—O—$CH_3$ |
| | 2'-[O—$(CH_2)_2]_4$—O—$CH_3$ |
| | 2'-[O—$(CH_2)_2]_3$—O—$(CH_2)_8CH_3$ |
| | 2'-O—$(CH_2)_2CF_3$ |
| | 2'-O—$(CH_2)_2$OH |
| | 2'-O—$(CH_2)_2$F |
| | 2'-O—$CH_2CH(CH_3)F$ |
| | 2'-O—$CH_2CH(CH_2OH)OH$ |
| | 2'-O—$CH_2CH(CH_2OCH_3)OCH_3$ |
| | 2'-O—$CH_2CH(CH_3)OCH_3$ |
| | 2'-O—$CH_2$—$C_{14}H_7O_2$(—$C_{14}H_7O_2$ = Anthraquinone) |
| | 2'-O—$(CH_2)_3$—$NH_2$* |
| | 2'-O—$(CH_2)_4$—$NH_2$* |

*These modifications can increase the Tm of oligonucleotides but can also decrease the Tm depending on positioning and number (motiff dependant).

TABLE II

Modified DNA strand having modified sugar ring (see structure x) that gave an overall increase in Tm against an RNA complement:

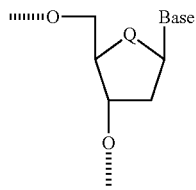

Positive εTm/mod

| Q | |
|---|---|
| | —S— |
| | —CH₂— |

Note: In general ring oxygen substitution with sulfur or methylene had only a minor effect on Tm for the specific motiffs studied. Substitution at the 2'-position with groups shown to stabilize the duplex were destabilizing when CH₂ replaced the ring O. This is thought to be due to the necessary gauche interaction between the ring O with particular 2'-substituents (for example —O—CH₃ and —(O—CH₂CH₂)₃—O—CH₃.

TABLE III

Modified DNA strand having modified sugar ring that give an overall increase in Tm against an RNA complement:

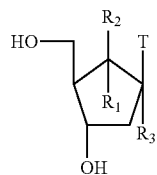

| | Positive εTm/mod |
|---|---|
| —C(H)R₁ effects (R₂, R₃ both = H) | OH |
| | CH₃* |
| | CH₂OH* |
| | OCH₃* |

*These modifications can increase the Tm of oligonucleotides but can also decrease the Tm depending on positioning and number (motiff dependant).

TABLE IV

Modified DNA strand having bicyclic substitute sugar modifications that give an overall increase in Tm against an RNA complement:

| Formula | Positive εTm/mod |
|---|---|
| I | + |
| II | + |

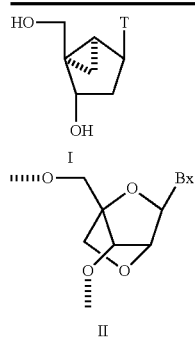

TABLE V

Modified DNA strand having modified heterocyclic base moieties that give an overall increase in Tm against an RNA complement:

| Modification/Formula | Positive εTm/mod |
|---|---|
| Heterocyclic base modifications | 2-thioT |
| | 2'-O-methylpseudoU |
| | 7-halo-7-deaza purines |
| | 7-propyne-7-deaza purines |
| | 2-aminoA(2,6-diaminopurine) |

| Modification/Formula | Positive εTm/mod |
|---|---|
| 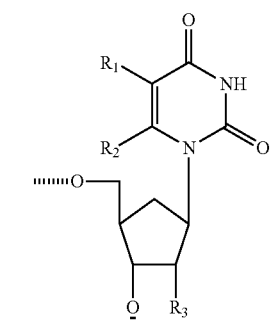 | Br |
| | C/C—CH₃ |
| | (CH₂)₃NH₂ |
| | CH₃ |
| (R₂, R₃ = H), R₁ = | |

Motiffs-disubstitution

| | |
|---|---|
| R₁ = C/C—CH₃, R₂ = H, R₃ = | F |
| R₁ = C/C—CH₃, R₂ = H | R₃ = O—(CH₂)₂—O—CH₃ |
| R₁ = O—CH₃, R₂ = H, | R₃ = O—(CH₂)₂—O—CH₃* |

*This modification can increase the Tm of oligonucleotides but can also decrease the Tm depending on positioning and number (motiff dependant).

Substitution at R₁ can be stabilizing, substitution at R₂ is generally greatly destabilizing (unable to form anti conformation), motiffs with stabilizing 5 and 2'-substituent groups are generally additive e.g. increase stability.

Substitution of the O4 and O2 positions of 2'-O-methyl uridine was greatly duplex destabilizing as these modifications remove hydrogen binding sites that would be an expected result. 6-Aza T also showed extreme destabilization as this substitution reduces the $pK_a$ and shifts the nucleoside toward the enol tautomer resulting in reduced hydrogen bonding.

TABLE VI

DNA strand having at least one modified phosphorus containing internucleoside linkage and the effect on the Tm against an RNA complement:

| εTm/mod+ | εTm/mod− |
|---|---|
| phosphoramidate (the 3'-bridging atom replaced with an N(H)R group, stabilization effect enhanced when also have 2'-F) | phosphorothioate[1] |
| | phosphoramidate[1] |
| | methyl phosphonates[1] |
| | ([1]one of the non-bridging oxygen atoms replaced with S, N(H)R or —CH₃) |

TABLE VII

DNA strand having at least one non-phosphorus
containing internucleoside linkage and the effect
on the Tm against an RNA complement:
Positive ∈Tm/mod —$CH_2C(=O)NHCH_2$—*
—$CH_2C(=O)N(CH_3)CH_2$—*
—$CH_3C(=O)N(CH_2CH_2CH_3)CH_2$—*
—$CH_2C(=O)N(H)CH_2$— (motiff with 5'-propyne on T's)
—$CH_2N(H)C(=O)CH_2$—*
—$CH_2N(CH_3)OCH_2$—*
—$CH_2N(CH_3)N(CH_3)CH_2$—*

*This modification can increase the Tm of oligonucleotides but can also decrease the Tm depending on positioning and number (motiff dependant).
Notes:
In general carbon chain internucleotide linkages were destabilizing to duplex formation. This destabilization was not as severe when double and tripple bonds were utilized. The use of glycol and flexible ether linkages were also destabilizing.

Preferred ring structures of the invention for inclusion as a 2'-O modification include cyclohexyl, cyclopentyl and phenyl rings as well as heterocyclic rings having spacial footprints similar to cyclohexyl, cyclopentyl and phenyl rings. Particularly preferred 2'-O-substituent groups of the invention are listed below including an abbreviation for each:
2'-O-(trans 2-methoxy cyclohexyl)—2'-O-(TMCHL)
2'-O-(trans 2-methoxy cyclopentyl)—2'-O-(TMCPL)
2'-O-(trans 2-ureido cyclohexyl)—2'-O-(TUCHL)
2'-O-(trans 2-methoxyphenyl)—2'-O-(2MP)

Structural details for duplexes incorporating such 2-O-substituents were analyzed using the described AMBER force field program on the Indigo2 SGI machine. The simulated structure maintained a stable A-form geometry throughout the duration of the simulation. The presence of the 2' substitutions locked the sugars in the C3'-endo conformation.

The simulation for the TMCHL modification revealed that the 2'-O-(TMCHL) side chains have a direct interaction with water molecules solvating the duplex. The oxygen atoms in the 2'-O-(TMCHL) side chain are capable of forming a water-mediated interaction with the 3' oxygen of the phosphate backbone. The presence of the two oxygen atoms in the 2'-O-(TMCHL) side chain gives rise to favorable gauche interactions. The barrier for rotation around the O—C—C—O torsion is made even larger by this novel modification. The preferential preorganization in an A-type geometry increases the binding affinity of the 2'-O-(TMCHL) to the target RNA. The locked side chain conformation in the 2'-O-(TMCHL) group created a more favorable pocket for binding water molecules. The presence of these water molecules played a key role in holding the side chains in the preferable gauche conformation. While not wishing to be bound by theory, the bulk of the substituent, the diequatorial orientation of the substituents in the cyclohexane ring, the water of hydration and the potential for trapping of metal ions in the conformation generated will additionally contribute to improved binding affinity and nuclease resistance of oligonucleotides incorporating nucleosides having this 2'-O-modification.

As described for the TMCHL modification above, identical computer simulations of the 2'-O-(TMCPL), the 2'-O-(2MP) and 2'-O-(TUCHL) modified oligonucleotides in aqueous solution also illustrate that stable A-form geometry will be maintained throughout the duration of the simulation. The presence of the 2' substitution will lock the sugars in the C3'-endo conformation and the side chains will have direct interaction with water molecules solvating the duplex. The oxygen atoms in the respective side chains are capable of forming a water-mediated interaction with the 3' oxygen of the phosphate backbone. The presence of the two oxygen atoms in the respective side chains give rise to the favorable gauche interactions. The barrier for rotation around the respective O—C—C—O torsions will be made even larger by respective modification. The preferential preorganization in A-type geometry will increase the binding affinity of the respective 2'-O-modified oligonucleotides to the target RNA. The locked side chain conformation in the respective modifications will create a more favorable pocket for binding water molecules. The presence of these water molecules plays a key role in holding the side chains in the preferable gauche conformation. The bulk of the substituent, the diequatorial orientation of the substituents in their respective rings, the water of hydration and the potential trapping of metal ions in the conformation generated will all contribute to improved binding affinity and nuclease resistance of oligonucleotides incorporating nucleosides having these respective 2'-O-modification.

Ribose conformations in C2'-modified nucleosides containing S-methyl groups were examined. To understand the influence of 2'-O-methyl and 2'-S-methyl groups on the conformation of nucleosides, we evaluated the relative energies of the 2'-O- and 2'-S-methylguanosine, along with normal deoxyguanosine and riboguanosine, starting from both C2'-endo and C3'-endo conformations using ab initio quantum mechanical calculations. All the structures were fully optimized at HF/6-31G* level and single point energies with electron-correlation were obtained at the MP2/6-31G*//HF/6-31G* level. As shown in Table 1, the C2'-endo conformation of deoxyguanosine is estimated to be 0.6 kcal/mol more stable than the C3'-endo conformation in the gas-phase. The conformational preference of the C2'-endo over the C3'-endo conformation appears to be less dependent upon electron correlation as revealed by the MP2/6-31G*//HF/6-31G* values which also predict the same difference in energy. The opposite trend is noted for riboguanosine. At the HF/6-31G* and MP2/6-31G*//HF/6-31G* levels, the C3'-endo form of riboguanosine is shown to be about 0.65 and 1.41 kcal/mol more stable than the C2' endo form, respectively.

TABLE 1

Relative energies* of the C3'-endo and C2'-endo
conformations of representative nucleosides.

| | HF/6-31G | MP2/6-31-G | CONTINUUM MODEL | AMBER |
|---|---|---|---|---|
| dG | 0.60 | 0.56 | 0.88 | 0.65 |
| rG | −0.65 | −1.41 | −0.28 | −2.09 |
| 2'-O-MeG | −0.89 | −1.79 | −0.36 | −0.86 |
| 2'-S-MeG | 2.55 | 1.41 | 3.16 | 2.43 |

*energies are in kcal/mol relative to the C2'-endo conformation

Table 1 also includes the relative energies of 2'-O-methylguanosine and 2'-S-methylguanosine in C2'-endo and C3'-endo conformation. This data indicates the electronic nature of C2'-substitution has a significant impact on the relative stability of these conformations. Substitution of the 2'-O-methyl group increases the preference for the C3'-endo conformation (when compared to riboguanosine) by about 0.4 kcal/mol at both the HF/6-31G* and MP2/6-31G*//HF/6-31G* levels. In contrast, the 2'-S-methyl group reverses the trend. The C2'-endo conformation is favored by about 2.6 kcal/mol at the HF/6-31G* level, while the same difference is reduced to 1.41 kcal/mol at the MP2/6-31G*//HF/6-31G* level. For comparison, and also to evaluate the accuracy of the molecular mechanical force-field parameters used for the 2'-O-methyl and 2'-S-methyl substituted nucleosides, we have calculated the gas phase energies of the nucleosides. The results reported in Table 1 indicate that the calculated relative energies of these nucleosides compare qualitatively well with the ab initio calculations.

Additional calculations were also performed to gauge the effect of solvation on the relative stability of nucleoside conformations. The estimated solvation effect using HF/6-31G* geometries confirms that the relative energetic preference of the four nucleosides in the gas-phase is maintained in the aqueous phase as well (Table 1). Solvation effects were also examined using molecular dynamics simulations of the nucleosides in explicit water. From these trajectories, one can observe the predominance of C2'-endo conformation for deoxyriboguanosine and 2'-S-methylriboguanosine while riboguanosine and 2'-O-methylriboguanosine prefer the C3'-endo conformation. These results are in much accord with the available NMR results on 2'-S-methylribonucleosides. NMR studies of sugar puckering equilibrium using vicinal spin-coupling constants have indicated that the conformation of the sugar ring in 2'-S-methylpyrimidine nucleosides show an average of >75% S-character, whereas the corresponding purine analogs exhibit an average of >90% S-pucker [Fraser, A., Wheeler, P., Cook, P. D. and Sanghvi, Y. S., *J. Heterocycl. Chem.*, 1993, 30, 1277-1287]. It was observed that the 2'-S-methyl substitution in deoxynucleoside confers more conformational rigidity to the sugar conformation when compared with deoxyribonucleosides.

Structural features of DNA:RNA, OMe-DNA:RNA and SMe-DNA:RNA hybrids were also observed. The average RMS deviation of the DNA:RNA structure from the starting hybrid coordinates indicate the structure is stabilized over the length of the simulation with an approximate average RMS deviation of 1.0 Å. This deviation is due, in part, to inherent differences in averaged structures (i.e. the starting conformation) and structures at thermal equilibrium. The changes in sugar pucker conformation for three of the central base pairs of this hybrid are in good agreement with the observations made in previous NMR studies. The sugars in the RNA strand maintain very stable geometries in the C3'-endo conformation with ring pucker values near 0°. In contrast, the sugars of the DNA strand show significant variability.

The average RMS deviation of the OMe-DNA:RNA is approximately 1.2 Å from the starting A-form conformation; while the SMe-DNA:RNA shows a slightly higher deviation (approximately 1.8 Å) from the starting hybrid conformation. The SMe-DNA strand also shows a greater variance in RMS deviation, suggesting the S-methyl group may induce some structural fluctuations. The sugar puckers of the RNA complements maintain C3'-endo puckering throughout the simulation. As expected from the nucleoside calculations, however, significant differences are noted in the puckering of the OMe-DNA and SMe-DNA strands, with the former adopting C3'-endo, and the latter, $C_1'$-exo/C2'-endo conformations.

An analysis of the helicoidal parameters for all three hybrid structures has also been performed to further characterize the duplex conformation. Three of the more important axis-basepair parameters that distinguish the different forms of the duplexes, X-displacement, propeller twist, and inclination, are reported in Table 2. Usually, an X-displacement near zero represents a B-form duplex; while a negative displacement, which is a direct measure of deviation of the helix from the helical axis, makes the structure appear more A-like in conformation. In A-form duplexes, these values typically vary from −4 Å to −5 Å. In comparing these values for all three hybrids, the SMe_DNA:RNA hybrid shows the most deviation from the A-form value, the OMe_DNA:RNA shows the least, and the DNA:RNA is intermediate. A similar trend is also evident when comparing the inclination and propeller twist values with ideal A-form parameters. These results are further supported by an analysis of the backbone and glycosidic torsion angles of the hybrid structures. Glycosidic angles (X) of A-form geometries, for example, are typically near −159° while B form values are near −102°. These angles are found to be −162°, −133°, and −108° for the OMe-DNA, DNA, and SMe-DNA strands, respectively. All RNA complements adopt an X angle close to −160°. In addition, "crankshaft" transitions were also noted in the backbone torsions of the central UpU steps of the RNA strand in the SMe-DNA:RNA and DNA;RNA hybrids. Such transitions suggest some local conformational changes may occur to relieve a less favorable global conformation. Taken overall, the results indicate the amount of A-character decreases as OMe-DNA:RNA>DNA:RNA>SMe-DNA:RNA, with the latter two adopting more intermediate conformations when compared to A- and B-form geometries.

TABLE 2

Average helical parameters derived from the last 500 ps of simulation time.
(canonical A-and B-form values are given for comparison)

| Helicoidal Parameter | B-DNA (x-ray) | B-DNA (fibre) | A-DNA (fibre) | DNA:RNA | OMe_DNA:RNA | SMe_DNA:RNA |
|---|---|---|---|---|---|---|
| X-disp | 1.2 | 0.0 | −5.3 | −4.5 | −5.4 | −3.5 |
| Inclination | −2.3 | 1.5 | 20.7 | 11.6 | 15.1 | 0.7 |
| Propeller | −16.4 | −13.3 | −7.5 | −12.7 | −15.8 | −10.3 |

Stability of C2'-modified DNA:RNA hybrids was determined. Although the overall stability of the DNA:RNA hybrids depends on several factors including sequence-dependencies and the purine content in the DNA or RNA strands DNA:RNA hybrids are usually less stable than RNA:RNA duplexes and, in some cases, even less stable than DNA:DNA duplexes. Available experimental data attributes the relatively lowered stability of DNA:RNA hybrids largely to its intermediate conformational nature between DNA:DNA (B-family) and RNA:RNA (A-family) duplexes. The overall thermodynamic stability of nucleic acid duplexes may originate from several factors including the conformation of backbone, base-pairing and stacking interactions. While it is difficult to ascertain the individual thermodynamic contributions to the overall stabilization of the duplex, it is reasonable to argue that the major factors that promote increased stability of hybrid duplexes are better stacking interactions (electrostatic π-π interactions) and more favorable groove dimensions for hydration. The C2'-

S-methyl substitution has been shown to destabilize the hybrid duplex. The notable differences in the rise values among the three hybrids may offer some explanation. While the 2'-S-methyl group has a strong influence on decreasing the base-stacking through high rise values (~3.2 Å), the 2'-O-methyl group makes the overall structure more compact with a rise value that is equal to that of A-form duplexes (~2.6 Å). Despite its overall A-like structural features, the SMe DNA:RNA hybrid structure possesses an average rise value of 3.2 Å which is quite close to that of B-family duplexes. In fact, some local base-steps (CG steps) may be observed to have unusually high rise values (as high as 4.5 Å). Thus, the greater destabilization of 2'-S-methyl substituted DNA:RNA hybrids may be partly attributed to poor stacking interactions.

It has been postulated that RNase H binds to the minor groove of RNA:DNA hybrid complexes, requiring an intermediate minor groove width between ideal A- and B-form geometries to optimize interactions between the sugar phosphate backbone atoms and RNase H. A close inspection of the averaged structures for the hybrid duplexes using computer simulations reveals significant variation in the minor groove width dimensions as shown in Table 3. Whereas the O-methyl substitution leads to a slight expansion of the minor groove width when compared to the standard DNA:RNA complex, the S-methyl substitution leads to a general contraction (approximately 0.9 Å). These changes are most likely due to the preferred sugar puckering noted for the antisense strands which induce either A- or B-like single strand conformations. In addition to minor groove variations, the results also point to potential differences in the steric makeup of the minor groove. The O-methyl group points into the minor groove while the S-methyl is directed away towards the major groove. Essentially, the S-methyl group has flipped through the bases into the major groove as a consequence of C2'-endo puckering.

may be straight or (where possible) branched hydrocarbyl moiety, which contains at least one carbon-carbon double bond.

Unless otherwise defined herein, alkynyl means $C_2$-$C_{12}$, preferably $C_2$-$C_8$, and more preferably $C_2$-$C_6$ alkynyl, which may be straight or (where possible) branched hydrocarbyl moiety, which contains at least one carbon-carbon triple bond.

Unless otherwise defined herein, heterocycloalkyl means a ring moiety containing at least three ring members, at least one of which is carbon, and of which 1, 2 or three ring members are other than carbon. Preferably the number of carbon atoms varies from 1 to about 12, preferably 1 to about 6, and the total number of ring members varies from three to about 15, preferably from about 3 to about 8. Preferred ring heteroatoms are N, O and S. Preferred heterocycloalkyl groups include morpholino, thiomorpholino, piperidinyl, piperazinyl, homopiperidinyl, homopiperazinyl, homomorpholino, homothiomorpholino, pyrrolodinyl, tetrahydrooxazolyl, tetrahydroimidazolyl, tetrahydrothiazolyl, tetrahydroisoxazolyl, tetrahydropyrrazolyl, furanyl, pyranyl, and tetrahydroisothiazolyl.

Unless otherwise defined herein, aryl means any hydrocarbon ring structure containing at least one aryl ring. Preferred aryl rings have about 6 to about 20 ring carbons. Especially preferred aryl rings include phenyl, napthyl, anthracenyl, and phenanthrenyl.

Unless otherwise defined herein, hetaryl means a ring moiety containing at least one fully unsaturated ring, the ring consisting of carbon and non-carbon atoms. Preferably the ring system contains about 1 to about 4 rings. Preferably the number of carbon atoms varies from 1 to about 12, preferably 1 to about 6, and the total number of ring members varies from three to about 15, preferably from about 3 to about 8. Preferred ring heteroatoms are N, O and S. Preferred hetaryl moieties include pyrazolyl, thiophenyl, pyridyl, imidazolyl, tetrazolyl, pyridyl, pyrimidinyl, purinyl, quinazolinyl, quinoxalinyl, benzimidazolyl, benzothiophenyl, etc.

TABLE 3

Minor groove widths averaged over the last 500 ps of simulation time

| Phosphate Distance | DNA:RNA | OMe_DNA:RNA | SMe_DNA:RNA | DNA:RNA (B-form) | RNA:RNA (A-form) |
|---|---|---|---|---|---|
| P5-P20 | 15.27 | 16.82 | 13.73 | 14.19 | 17.32 |
| P6-P19 | 15.52 | 16.79 | 15.73 | 12.66 | 17.12 |
| P7-P18 | 15.19 | 16.40 | 14.08 | 11.10 | 16.60 |
| P8-P17 | 15.07 | 16.12 | 14.00 | 10.98 | 16.14 |
| P9-P16 | 15.29 | 16.25 | 14.98 | 11.65 | 16.93 |
| P10-P15 | 15.37 | 16.57 | 13.92 | 14.05 | 17.69 |

Chemistries Defined

Unless otherwise defined herein, alkyl means $C_1$-$C_{12}$, preferably $C_1$-$C_8$, and more preferably $C_1$-$C_6$, straight or (where possible) branched chain aliphatic hydrocarbyl.

Unless otherwise defined herein, heteroalkyl means $C_1$-$C_{12}$, preferably $C_1$-$C_8$, and more preferably $C_1$-$C_6$, straight or (where possible) branched chain aliphatic hydrocarbyl containing at least one, and preferably about 1 to about 3, hetero atoms in the chain, including the terminal portion of the chain. Preferred heteroatoms include N, O and S.

Unless otherwise defined herein, cycloalkyl means $C_3$-$C_{12}$, preferably $C_3$-$C_8$, and more preferably $C_3$-$C_6$, aliphatic hydrocarbyl ring.

Unless otherwise defined herein, alkenyl means $C_2$-$C_{12}$, preferably $C_2$-$C_8$, and more preferably $C_2$-$C_6$ alkenyl, which Unless otherwise defined herein, where a moiety is defined as a compound moiety, such as hetarylalkyl (hetaryl and alkyl), aralkyl (aryl and alkyl), etc., each of the sub-moieties is as defined herein.

Unless otherwise defined herein, an electron withdrawing group is a group, such as the cyano or isocyanato group that draws electronic charge away from the carbon to which it is attached. Other electron withdrawing groups of note include those whose electronegativities exceed that of carbon, for example halogen, nitro, or phenyl substituted in the ortho- or para-position with one or more cyano, isothiocyanato, nitro or halo groups.

Unless otherwise defined herein, the terms halogen and halo have their ordinary meanings. Preferred halo (halogen) substituents are Cl, Br, and I.

The aforementioned optional substituents are, unless otherwise herein defined, suitable substituents depending upon desired properties. Included are halogens (Cl, Br, I), alkyl, alkenyl, and alkynyl moieties, $NO_2$, $NH_3$ (substituted and unsubstituted), acid moieties (e.g. —$CO_2H$, —$OSO_3H_2$, etc.), heterocycloalkyl moieties, hetaryl moieties, aryl moieties, etc.

In all the preceding formulae, the squiggle (~) indicates a bond to an oxygen or sulfur of the 5'-phosphate. Phosphate protecting groups include those described in U.S. Pat. Nos. 5,760,209, 5,614,621, 6,051,699, 6,020,475, 6,326,478, 6,169,177, 6,121,437, 6,465,628 each of which is expressly incorporated herein by reference in its entirety.

Oligomer Synthesis

Oligomerization of modified and unmodified nucleosides is performed according to literature procedures for DNA (Protocols for Oligonucleotides and Analogs, Ed. Agrawal (1993), Humana Press) and/or RNA (Scaringe, Methods (2001), 23, 206-217. Gait et al., Applications of Chemically synthesized RNA in RNA:Protein Interactions, Ed. Smith (1998), 1-36. Gallo et al., Tetrahedron (2001), 57, 5707-5713) synthesis as appropriate. In addition specific protocols for the synthesis of compositions of the invention are illustrated in the examples below.

The oligonucleotides used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The present invention is also useful for the preparation of oligonucleotides incorporating at least one 2'-O-protected nucleoside. After incorporation and appropriate deprotection the 2'-O-protected nucleoside will be converted to a ribonucleoside at the position of incorporation. The number and position of the 2-ribonucleoside units in the final oligonucleotide can vary from one at any site or the strategy can be used to prepare up to a full 2'-OH modified oligonucleotide. All 2'-O-protecting groups amenable to the synthesis of oligonucleotides are included in the present invention. In general a protected nucleoside is attached to a solid support by for example a succinate linker. Then the oligonucleotide is elongated by repeated cycles of deprotecting the 5'-terminal hydroxyl group, coupling of a further nucleoside unit, capping and oxidation (alternatively sulfurization). In a more frequently used method of synthesis the completed oligonucleotide is cleaved from the solid support with the removal of phosphate protecting groups and exocyclic amino protecting groups by treatment with an ammonia solution. Then a further deprotection step is normally required for removal of the more specialized protecting groups used for the protection of 2'-hydroxyl groups thereby affording the fully deprotected oligonucleotide.

A large number of 2'-O-protecting groups have been used for the synthesis of oligoribonucleotides but over the years more effective groups have been discovered. The key to an effective 2'-O-protecting group is that it is capable of selectively being introduced at the 2'-O-position and that it can be removed easily after synthesis without the formation of unwanted side products. The protecting group also needs to be inert to the normal deprotecting, coupling, and capping steps required for oligoribonucleotide synthesis. Some of the protecting groups used initially for oligoribonucleotide synthesis included tetrahydropyran-1-yl and 4-methoxytetrahydropyran-4-yl. These two groups are not compatible with all 5'-O-protecting groups so modified versions were used with 5'-DMT groups such as 1-(2-fluorophenyl)-4-methoxypiperidin-4-yl (Fpmp). Reese has identified a number of piperidine derivatives (like Fpmp) that are useful in the synthesis of oligoribonucleotides including 1-[(chloro-4-methyl)phenyl]-4'-methoxypiperidin-4-yl (Reese et al., Tetrahedron Lett., 1986, (27), 2291). Another approach was to replace the standard 5'-DMT (dimethoxytrityl) group with protecting groups that were removed under non-acidic conditions such as levulinyl and 9-fluorenylmethoxycarbonyl. Such groups enable the use of acid labile 2'-protecting groups for oligoribonucleotide synthesis. Another more widely used protecting group initially used for the synthesis of oligoribonucleotides was the t-butyldimethylsilyl group (Ogilvie et al., Tetrahedron Lett., 1974, 2861; Hakimelahi et al., Tetrahedron Lett., 1981, (22), 2543; and Jones et al., J. Chem. Soc. Perkin I., 2762). The 2'-O-protecting groups can require special reagents for their removal such as for example the t-butyldimethylsilyl group is normally removed after all other cleaving/deprotecting steps by treatment of the oligonucleotide with tetrabutylammonium fluoride (TBAF).

One group of researchers examined a number of 2'-O-protecting groups (Pitsch, S., Chimia, 2001, (55), 320-324.) The group examined fluoride labile and photolabile protecting groups that are removed using moderate conditions. One photolabile group that was examined was the [2-(nitrobenzyl)oxy]methyl (nbm) protecting group (Schwartz et al., Bioorg. Med. Chem. Lett., 1992, (2), 1019.) Other groups examined included a number structurally related formaldehyde acetal-derived, 2'-O-protecting groups. Also prepared were a number of related protecting groups for preparing 2'-O-alkylated nucleoside phosphoramidites including 2'-O-[(triisopropylsilyl)oxy]methyl (2'-O—$CH_2$—O—$Si(iPr)_3$, TOM). One 2'-O-protecting group that was prepared to be used orthogonally to the TOM group was 2'-O-[(R)-1-(2-nitrophenyl)ethyloxy)methyl] ((R)-mnbm).

Another strategy using a fluoride labile 5'-O-protecting group (non-acid labile) and an acid labile 2'-O-protecting group has been reported (Scaringe, Stephen A., Methods, 2001, (23) 206-217). A number of possible silyl ethers were examined for 5'-O-protection and a number of acetals and orthoesters were examined for 2'-O-protection. The protection scheme that gave the best results was 5'-O-silyl ether-2'-ACE (5'-O-bis(trimethylsiloxy)cyclododecyloxysilyl ether (DOD)-2'-O-bis(2-acetoxyethoxy)methyl (ACE). This approach uses a modified phosphoramidite synthesis approach in that some different reagents are required that are not routinely used for RNA/DNA synthesis.

Although a lot of research has focused on the synthesis of oligoribonucleotides the main RNA synthesis strategies that are presently being used commercially include 5'-O-DMT-2'-O-t-butyldimethylsilyl (TBDMS), 5'-O-DMT-2'-O-[1(2-fluorophenyl)-4-methoxypiperidin-4-yl] (FPMP), 2'-O-[(triisopropylsilyl)oxy]methyl (2'-O—$CH_2$—O—$Si(iPr)_3$ (TOM), and the 5'-O-silyl ether-2'-ACE (5'-O-bis(trimethylsiloxy)cyclododecyloxysilyl ether (DOD)-2'-O-bis(2-acetoxyethoxy)methyl (ACE). A current list of some of the major companies currently offering RNA products include Pierce Nucleic Acid Technologies, Dharmacon Research Inc., Ameri Biotechnologies Inc., and Integrated DNA Technologies, Inc. One company, Princeton Separations, is marketing an RNA synthesis activator advertised to reduce coupling times especially with TOM and TBDMS chemistries. Such an activator would also be amenable to the present invention.

The primary groups being used for commercial RNA synthesis are:
TBDMS=5'-O-DMT-2'-O-t-butyldimethylsilyl;
TOM=2'-O-[(triisopropylsilyl)oxy]methyl;
DOD/ACE=(5'-O-bis(trimethylsiloxy)cyclododecyloxysilyl ether-2'-O-bis(2-acetoxyethoxy)methyl
FPMP=5'-O-DMT-2'-O-[1(2-fluorophenyl)-4-methoxypiperidin-4-yl].

All of the aforementioned RNA synthesis strategies are amenable to the present invention. Strategies that would be a hybrid of the above e.g. using a 5'-protecting group from one strategy with a 2'-O-protecting from another strategy is also amenable to the present invention.

The preparation of ribonucleotides and oligonucleotides having at least one ribonucleoside incorporated and all the possible configurations falling in between these two extremes are encompassed by the present invention. The corresponding oligomeric comounds can be hybridized to further oligonucleotides including oligoribonucleotides having regions of complementarity to form double-stranded (duplexed) oligonucleotides. Such double stranded oligonucleotide moieties have been shown in the art to modulate target expression and regulate translation as well as RNA processsing via an antisense mechanism. Moreover, the double-stranded moieties may be subject to chemical modifications (Fire et al., Nature, 1998, 391, 806-811; Timmons and Fire, Nature 1998, 395, 854; Timmons et al., Gene, 2001, 263, 103-112; Tabara et al., Science, 1998, 282, 430-431; Montgomery et al., Proc. Natl. Acad. Sci. USA, 1998, 95, 15502-15507; Tuschl et al., Genes Dev., 1999, 13, 3191-3197; Elbashir et al., Nature, 2001, 411, 494-498; Elbashir et al., Genes Dev. 2001, 15, 188-200). For example, such double-stranded moieties have been shown to inhibit the target by the classical hybridization of antisense strand of the duplex to the target, thereby triggering enzymatic degradation of the target (Tijsterman et al., Science, 2002, 295, 694-697).

The methods of preparing oligonucleotides of the present invention can also be applied in the areas of drug discovery and target validation. The present invention comprehends the use of the oligonucleotides and preferred targets identified herein in drug discovery efforts to elucidate relationships that exist between proteins and a disease state, phenotype, or condition. These methods include detecting or modulating a target peptide comprising contacting a sample, tissue, cell, or organism with the oligonucleotides of the present invention, measuring the nucleic acid or protein level of the target and/or a related phenotypic or chemical endpoint at some time after treatment, and optionally comparing the measured value to a non-treated sample or sample treated with a further oligonucleotide of the invention. These methods can also be performed in parallel or in combination with other experiments to determine the function of unknown genes for the process of target validation or to determine the validity of a particular gene product as a target for treatment or prevention of a particular disease, condition, or phenotype.

Effect of nucleoside modifications on RNAi activity is evaluated according to existing literature (Elbashir et al., Nature (2001), 411, 494-498; Nishikura et al., Cell (2001), 107, 415-416; and Bass et al., Cell (2000), 101, 235-238.)

Targets of the Invention

"Targeting" a composition of the present invention to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent.

The targeting process usually also includes determination of at least one target region, segment, or site within the target nucleic acid for the antisense interaction to occur such that the desired effect, e.g., modulation of expression, will result. Within the context of the present invention, the term "region" as applied to targets is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid. The terms region, segment, and site can also be used to describe an oligomeric compound such as an oligonucleotide of the invention such as for example a gapped oligonucleotide having 3 separate segments.

Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding a nucleic acid target, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions which may be targeted effectively with the compositions of the present invention.

The open reading frame (ORF) or "coding region," which is known in the art to refer to the region between the translation initiation codon and the translation termination codon, is also a region which may be targeted effectively. Within the context of the present invention, a preferred region is the intragenic region encompassing the translation initiation or termination codon of the open reading frame (ORF) of a gene.

Other target regions include the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene), and the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. It is also preferred to target the 5' cap region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. Targeting splice sites, i.e., intron-exon junctions or exon-intron junctions, may also be particularly useful in situations where aberrant splicing is implicated in disease, or where an overproduction of a particular splice product is implicated in disease. Aberrant fusion junctions due to rearrangements or deletions are also preferred target sites. mRNA transcripts produced via the process of splicing of two (or more) mRNAs from different gene sources are known as "fusion transcripts". It is also known that introns can be effectively targeted using antisense oligonucleotides targeted to, for example, DNA or pre-mRNA.

It is also known in the art that alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequences.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also preferred target nucleic acids.

The locations on the target nucleic acid to which the preferred compositions of the present invention hybridize are hereinbelow referred to as "preferred target segments." As used herein the term "preferred target segment" is defined as at least an 8-nucleobase portion of a target region that is targeted by the compositions of the invention. While not wishing to be bound by theory, it is presently believed that these target segments represent accessible portions of the target nucleic acid for hybridization.

Exemplary preferred compositions of the invention include oligonucleotides that comprise at least the 8 consecutive nucleobases from the 5'-terminus of a targeted nucleic acid e.g. a cellular gene or mRNA transcribed from the gene (the remaining nucleobases being a consecutive stretch of the same oligonucleotide beginning immediately upstream of the 5'-terminus of the antisense compound which is specifically hybridizable to the target nucleic acid and continuing until the oligonucleotide contains from about 8 to about 80 nucleobases). Similarly preferred compositions of the invention are represented by oligonucleotide sequences that comprise at least the 8 consecutive nucleobases from the 3'-terminus of one of the illustrative preferred antisense compounds (the remaining nucleobases being a consecutive stretch of the same oligonucleotide beginning immediately downstream of the 3'-terminus of the antisense compound which is specifically hybridizable to the target nucleic acid and continuing until the oligonucleotide contains from about 8 to about 80 nucleobases). One having skill in the art armed with the preferred compositions of the invention illustrated herein will be able, without undue experimentation, to identify further preferred antisense compounds.

Once one or more target regions, segments or sites have been identified, compositions of the invention are chosen which are sufficiently complementary to the target, i.e., hybridize sufficiently well and with sufficient specificity, to give the desired effect.

In accordance with one embodiment of the present invention, a series of preferred compositions of the invention can be designed for a specific target or targets. The ends of the strands may be blunt or modified by the addition of one or more natural or modified nucleobases to form an overhang. The sense strand of the duplex is then designed and synthesized as the complement of the antisense strand and may also contain modifications or additions to either terminus. For example, in one embodiment, both strands of the duplex would be complementary over the central nucleobases, each optionally having overhangs at one or both termini.

For example, a duplex comprising an antisense oligonucleotide having the sequence CGAGAGGCGGACGGGACCG (SEQ ID NO.: 1) and having a two-nucleobase overhang of deoxythymidine(dT) would have the following structure:

|  |  | SEQ ID NO. |
|---|---|---|
| cgagaggcggacgggaccgdTdT<br>\|\|\|\|\|\|\|\|\|\|\|\|\|\|\|\|\|\|\|<br>dTdTgctctccgcctgccctggc<br>or could be blunt ended excluding the deoxythymidine (dT's): | Antisense Strand<br><br>Complement Strand | 2<br><br>3 |
| cgagaggcggacgggaccg<br>\|\|\|\|\|\|\|\|\|\|\|\|\|\|\|\|\|\|\|<br>gctctccgcctgccctggc | Antisense Strand<br><br>Complement Strand | 1<br><br>4 |

RNA strands of the duplex can be synthesized by methods disclosed herein or purchased from various RNA synthesis companies such as for example Dharmacon Research Inc., (Lafayette, Colo.). Once synthesized, the complementary strands are annealed. The single strands are aliquoted and diluted to a concentration of 50 uM. Once diluted, 30 uL of each strand is combined with 15 uL of a 5× solution of annealing buffer. The final concentration of the buffer is 100 mM potassium acetate, 30 mM HEPES-KOH pH 7.4, and 2 mM magnesium acetate. The final volume is 75 uL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA compound is 20 uM. This solution can be stored frozen (−20° C.) and freeze-thawed up to 5 times.

Once prepared, the desired synthetic complexes of duplexes are evaluated for their ability to modulate target expression. When cells reach 80% confluency, they are treated with synthetic duplexs comprising at least one oligonucleotide of the invention. For cells grown in 96-well plates, wells are washed once with 200 μL OPTI-MEM-1 reduced-serum medium (Gibco BRL) and then treated with 130 μL of OPTI-MEM-1 containing 12 μg/mL LIPOFECTIN (Gibco BRL) and the desired dsRNA compound at a final concentration of 200 nM. After 5 hours of treatment, the medium is replaced with fresh medium. Cells are harvested 16 hours after treatment, at which time RNA is isolated and target reduction measured by RT-PCR.

In a further embodiment, the "preferred target segments" identified herein may be employed in a screen for additional oligomeric compounds that modulate the expression of a target. "Modulators" are those oligomeric compounds that decrease or increase the expression of a nucleic acid molecule encoding a target and which comprise at least an 8-nucleobase portion which is complementary to a preferred target segment. The screening method comprises the steps of contacting a preferred target segment of a nucleic acid molecule encoding a target with one or more candidate modulators, and selecting for one or more candidate modulators which decrease or increase the expression of a nucleic acid molecule encoding a target. Once it is shown that the candidate modulator or modulators are capable of modulating (e.g. either decreasing or increasing) the expression of a nucleic acid molecule encoding a target, the modulator may then be employed in further investigative studies of the function of a target, or for use as a research, diagnostic, or therapeutic agent in accordance with the present invention.

Hybridization

In the context of this invention, "hybridization" occurs when two sequences come together with enough base complementarity to form a double stranded region. The source of the two sequences can be synthetic or native and can occur in a single strand when the strand has regions of self complementarity. In the present invention, the preferred mechanism of pairing involves hydrogen bonding, which may be Watson-Crick, Hoogsteen or reversed Hoogsteen hydrogen bonding, between complementary nucleoside or nucleotide bases (nucleobases) of the strands of oligonucleotides or between an oligonucleotide and a target nucleic acid. For example, adenine and thymine are complementary nucleobases which pair through the formation of hydrogen bonds. Hybridization can occur under varying circumstances.

Compositions of the present invention are specifically hybridizable when binding to a target nucleic acid interferes with the normal function of the target nucleic acid and causes a loss of activity, and there is a sufficient degree of complementarity to avoid non-specific binding to non-target nucleic acid sequences under conditions in which specific binding is desired, i.e., under physiological conditions in the case of in vivo assays or therapeutic treatment, and under conditions in which assays are performed in the case of in vitro assays.

In the present invention the phrase "stringent hybridization conditions" or "stringent conditions" refers to conditions under which compositions of the invention will hybridize to its target sequence, but to a minimal number of other sequences. Stringent conditions are sequence-dependent and will vary with different circumstances and in the context of this invention, "stringent conditions" under which oligomeric compounds hybridize to a target sequence are determined by the nature and composition of the oligomeric compounds and the assays in which they are being investigated.

"Complementary," as used herein, refers to the capacity for precise pairing of two nucleobases regardless of where the two are located. For example, if a nucleobase at a certain position of an oligonucleotide is capable of hydrogen bonding with a nucleobase at a certain position of a target nucleic acid, the target nucleic acid being a DNA, RNA, or oligonucleotide molecule, then the position of hydrogen bonding between the oligonucleotide and the target nucleic acid is considered to be a complementary position. The oligonucleotide and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid.

It is understood in the art that the sequence of an oligomeric compound need not be 100% complementary to that of its target nucleic acid to be specifically hybridizable. Moreover, an oligmeric compound may hybridize over one or more segments such that intervening or adjacent segments are not involved in the hybridization event (e.g., a loop structure or hairpin structure). It is preferred that the oligmeric compounds of the present invention comprise at least 70% sequence complementarity to a target region within the target nucleic acid, more preferably that they comprise 90% sequence complementarity and even more preferably comprise 95% sequence complementarity to the target region within the target nucleic acid sequence to which they are targeted. For example, an oligmeric compound in which 18 of 20 nucleobases are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an oligmeric compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an oligmeric compound with a region of a target nucleic acid can be determined routinely using BLAST programs (basic local alignment search tools) and PowerBLAST programs known in the art (Altschul et al., J.

Mol. Biol., 1990, 215, 403-410; Zhang and Madden, Genome Res., 1997, 7, 649-656).

Screening and Target Validation

In a further embodiment, "preferred target segments" may be employed in a screen for additional oligmeric compounds that modulate the expression of a selected protein. "Modulators" are those oligmeric compounds that decrease or increase the expression of a nucleic acid molecule encoding a protein and which comprise at least an 8-nucleobase portion which is complementary to a preferred target segment. The screening method comprises the steps of contacting a preferred target segment of a nucleic acid molecule encoding a protein with one or more candidate modulators, and selecting for one or more candidate modulators which decrease or increase the expression of a nucleic acid molecule encoding a protein. Once it is shown that the candidate modulator or modulators are capable of modulating (e.g. either decreasing or increasing) the expression of a nucleic acid molecule encoding a peptide, the modulator may then be employed in further investigative studies of the function of the peptide, or for use as a research, diagnostic, or therapeutic agent in accordance with the present invention.

The preferred target segments of the present invention may also be combined with their respective complementary oligomeric compounds of the present invention to form stabilized double-stranded (duplexed) oligmeric compound with oligonucleotides being preferred. Such double stranded oligonucleotide moieties have been shown in the art to modulate target expression and regulate translation as well as RNA processsing via an antisense mechanism. Moreover, the double-stranded moieties may be subject to chemical modifications (Fire et al., Nature, 1998, 391, 806-811; Timmons and Fire, Nature 1998, 395, 854; Timmons et al., Gene, 2001, 263, 103-112; Tabara et al., Science, 1998, 282, 430-431; Montgomery et al., Proc. Natl. Acad. Sci. USA, 1998, 95, 15502-15507; Tuschl et al., Genes Dev., 1999, 13, 3191-3197; Elbashir et al., Nature, 2001, 411, 494-498; Elbashir et al., Genes Dev. 2001, 15, 188-200). For example, such double-stranded moieties have been shown to inhibit the target by the classical hybridization of antisense strand of the duplex to the target, thereby triggering enzymatic degradation of the target (Tijsterman et al., Science, 2002, 295, 694-697).

The compositions of the present invention can also be applied in the areas of drug discovery and target validation. The present invention comprehends the use of the compositions and preferred targets identified herein in drug discovery efforts to elucidate relationships that exist between proteins and a disease state, phenotype, or condition. These methods include detecting or modulating a target peptide comprising contacting a sample, tissue, cell, or organism with the compositions of the present invention, measuring the nucleic acid or protein level of the target and/or a related phenotypic or chemical endpoint at some time after treatment, and optionally comparing the measured value to a non-treated sample or sample treated with a further oligonucleotide of the invention. These methods can also be performed in parallel or in combination with other experiments to determine the function of unknown genes for the process of target validation or to determine the validity of a particular gene product as a target for treatment or prevention of a particular disease, condition, or phenotype.

Effect of nucleoside modifications on RNAi activity is evaluated according to existing literature (Elbashir et al., Nature (2001), 411, 494-498; Nishikura et al., Cell (2001), 107, 415-416; and Bass et al., Cell (2000), 101, 235-238.)

Kits, Research Reagents, Diagnostics, and Therapeutics

The compositions of the present invention can be utilized for diagnostics, therapeutics, prophylaxis and as research reagents and kits. Furthermore, compositions of the present invention, which are able to inhibit gene expression with exquisite specificity, can be used by those of ordinary skill to elucidate the function of particular genes or to distinguish between functions of various members of a biological pathway.

For use in kits and diagnostics, the compositions of the present invention, either alone or in combination with other oligonucleotides or therapeutics, can be used as tools in differential and/or combinatorial analyses to elucidate expression patterns of a portion or the entire complement of genes expressed within cells and tissues.

As one nonlimiting example, expression patterns within cells or tissues treated with one or more compositions of the present invention are compared to untreated control cells or tissues and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds and or oligonucleotides that affect expression patterns.

Examples of methods of gene expression analysis known in the art include DNA arrays or microarrays (Brazma and Vilo, FEBS Lett., 2000, 480, 17-24; Celis, et al., FEBS Lett., 2000, 480, 2-16), SAGE (serial analysis of gene expression) (Madden, et al., Drug Discov. Today, 2000, 5, 415-425), READS (restriction enzyme amplification of digested cDNAs) (Prashar and Weissman, Methods Enzymol., 1999, 303, 258-72), TOGA (total gene expression analysis) (Sutcliffe, et al., Proc. Natl. Acad. Sci. U.S.A, 2000, 97, 1976-81), protein arrays and proteomics (Celis, et al., FEBS Lett., 2000, 480, 2-16; Jungblut, et al., Electrophoresis, 1999, 20, 2100-10), expressed sequence tag (EST) sequencing (Celis, et al., FEBS Lett., 2000, 480, 2-16; Larsson, et al., J. Biotechnol., 2000, 80, 143-57), subtractive RNA fingerprinting (SuRF) (Fuchs, et al., Anal. Biochem., 2000, 286, 91-98; Larson, et al., Cytometry, 2000, 41, 203-208), subtractive cloning, differential display (DD) (Jurecic and Belmont, Curr. Opin. Microbiol., 2000, 3, 316-21), comparative genomic hybridization (Carulli, et al., J. Cell Biochem. Suppl., 1998, 31, 286-96), FISH (fluorescent in situ hybridization) techniques (Going and Gusterson, Eur. J. Cancer, 1999, 35, 1895-904) and mass spectrometry methods (To, Comb. Chem. High Throughput Screen, 2000, 3, 235-41).

The compositions of the present invention are useful for research and diagnostic applications. In one aspect of the present invention the compositions are useful for research and diagnostics in applications that involve the hybridization of compositions to nucleic acids encoding proteins. For example, oligomeric compounds that are shown to hybridize with such efficiency and under such conditions as disclosed herein as to be effective protein inhibitors will also be effective primers or probes under conditions favoring gene amplification or detection, respectively. These primers and probes are useful in methods requiring the specific detection of nucleic acid molecules encoding proteins and in the amplification of the nucleic acid molecules for detection or for use in further studies. Hybridization of the antisense oligonucleotides, particularly the primers and probes, of the invention with a nucleic acid can be detected by means known in the art. Such means may include conjugation of an enzyme to the oligonucleotide, radiolabelling of the oligonucleotide or any other suitable detection means. Kits using such detection means for detecting the level of selected proteins in a sample may also be prepared.

The specificity and sensitivity of antisense methodologies is also harnessed by those of skill in the art for therapeutic uses. Antisense oligonucleotides have been employed as therapeutic moieties in the treatment of disease states in animals, including humans. Antisense oligonucleotide drugs, including ribozymes, have been safely and effectively administered to humans and numerous clinical trials are presently underway. It is thus established that antisense oligonucleotides can be useful therapeutic modalities that can be configured to be useful in treatment regimes for the treatment of cells, tissues and animals, especially humans.

For therapeutics, an animal, preferably a human, suspected of having a disease or disorder which can be treated by modulating the expression of a selected protein is treated by administering compositions in accordance with this invention. For example, in one non-limiting embodiment, the methods comprise the step of administering to the animal in need of treatment, a therapeutically effective amount of a protein inhibitor. The protein inhibitors of the present invention effectively inhibit the activity of the protein or inhibit the expression of the protein. In one embodiment, the activity or expression of a protein in an animal is inhibited by about 10%. Preferably, the activity or expression of a protein in an animal is inhibited by about 30%. More preferably, the activity or expression of a protein in an animal is inhibited by 50% or more.

For example, the reduction of the expression of a protein may be measured in serum, adipose tissue, liver or any other body fluid, tissue or organ of the animal. Preferably, the cells contained within the fluids, tissues or organs being analyzed contain a nucleic acid molecule encoding a protein and/or the protein itself.

The compositions of the present invention can be utilized in pharmaceutical compositions by adding an effective amount to a suitable pharmaceutically acceptable diluent or carrier. Use of the compositions and methods of the invention may also be useful prophylactically.

Formulations

The compositions of the present invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption.

Representative United States patents that teach the preparation of such uptake, distribution and/or absorption-assisting formulations include, but are not limited to, U.S. Pat. No. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The compositions of the present invention encompass any pharmaceutically acceptable salts, esters, or salts of such esters, or any other compound which, upon administration to an animal, including a human, is capable of providing (directly or indirectly) the biologically active metabolite or residue thereof. Accordingly, for example, the disclosure is also drawn to prodrugs and pharmaceutically acceptable salts of the compositions of the invention, pharmaceutically acceptable salts of such prodrugs, and other bioequivalents. The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the compositions of the invention are prepared as SATE [(S-acetyl-2-thioethyl) phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compositions of the invention: i.e., salts that retain the desired biological activity of the parent compound and do not impart undesired toxicological effects thereto. For oligonucleotides, preferred examples of pharmaceutically acceptable salts and their uses are further described in U.S. Pat. No. 6,287,860, which is incorporated herein in its entirety.

The present invention also includes pharmaceutical compositions and formulations which include the compositions of the present invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

Emulsions are typically heterogenous systems of one liquid dispersed in another in the form of droplets usually exceeding 0.1 µm in diameter. Emulsions may contain additional components in addition to the dispersed phases, and the active drug which may be present as a solution in either the aqueous phase, oily phase or itself as a separate phase. Microemulsions are included as an embodiment of the present invention. Emulsions and their uses are well known in the art and are further described in U.S. Pat. No. 6,287,860, which is incorporated herein in its entirety.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes which are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein in its entirety.

The pharmaceutical formulations and compositions of the present invention may also include surfactants. The use of surfactants in drug products, formulations and in emulsions is well known in the art. Surfactants and their uses are further described in U.S. Pat. No. 6,287,860, which is incorporated herein in its entirety.

In one embodiment, the present invention employs various penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein in its entirety.

One of skill in the art will recognize that formulations are routinely designed according to their intended use, i.e. route of administration.

Preferred formulations for topical administration include those in which the compositions of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, di stearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

For topical or other administration, compositions of the present invention may be encapsulated within liposomes or may form complexes thereto, in particular to cationic liposomes. Alternatively, compositions of the present invention may be complexed to lipids, in particular to cationic lipids. Preferred fatty acids and esters, pharmaceutically acceptable salts thereof, and their uses are further described in U.S. Pat. No. 6,287,860, which is incorporated herein in its entirety. Topical formulations are described in detail in U.S. patent application Ser. No. 09/315,298 filed on May 20, 1999, which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which compositions of the invention are administered in conjunction with one or more penetration enhancers surfactants and chelators. Preferred surfactants include fatty acids and/or esters or salts thereof, bile acids and/or salts thereof. Preferred bile acids/salts and fatty acids and their uses are further described in U.S. Pat. No. 6,287,860, which is incorporated herein in its entirety. Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Compositions of the present invention may be delivered orally, in granular form including sprayed dried particles, or complexed to form micro or nanoparticles. Oligonucleotide complexing agents and their uses are further described in U.S. Pat. No. 6,287,860, which is incorporated herein in its entirety. Oral formulations for oligonucleotides and their preparation are described in detail in U.S. application Ser. No. 09/108,673 (filed Jul. 1, 1998), Ser. No. 09/315,298 (filed May 20, 1999) and Ser. No. 10/071,822, filed Feb. 8, 2002, each of which is incorporated herein by reference in their entirety.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Certain embodiments of the invention provide pharmaceutical compositions containing one or more of the compositions of the present invention and one or more other chemotherapeutic agents which function by a non-antisense mechanism. Examples of such chemo-therapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the compositions of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to non-steroidal anti-inflammatory drugs and corticosteroids, and antiviral drugs, including but not limited to ribivirin, vidarabine, acyclovir and ganciclovir, may also be combined in compositions of the invention. Combinations of compositions of the invention and other non-antisense drugs are also within the scope of this invention. One or more compositions of the invention can be used in combination with other therapeutic agents to create a cocktail as is currently the strategy for certain viral infections.

In another related embodiment, therapeutically effective combination therapies may comprise the use of two or more oligonucleotides and or compositions of the present invention wherein the multiple compositions are targeted to a single or multiple nucleic acid targets. Numerous examples of antisense oligonucleotides are known in the art. Two or more combined compounds may be used together or sequentially Dosing The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}s$ found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate the invention and are not intended to limit the same.

Example 1

Alternating 2'-O-Methyl siRNA's Targeting PTEN

A dose response was performed in the PTEN system to look at positional effects of alternating 2'-O-methyl constructs in asRNA and siRNA constructs.

| SEQ ID NO/ISIS NO | SEQUENCES 5'-3' |
|---|---|
| 8/335454 | 5'-P-<u>UUU</u>GU<u>C</u>U<u>C</u>UGGU<u>CC</u>UU<u>A</u>CUU (P = S, antisense) |
| 9/335455 | 5'-P-U<u>UU</u>GUC<u>UC</u>UGG<u>UCC</u>UUA<u>CUU</u> (P = S, antisense) |
| 10/335456 | 5'-P-<u>UUU</u>GU<u>C</u>U<u>C</u>UGGU<u>CC</u>UU<u>A</u>CUU (P = O, antisense) |
| 11/335457 | 5'-P-U<u>UU</u>GUC<u>UC</u>UGG<u>UCC</u>UUA<u>CUU</u> (P = O, antisense) |
| 12/303912 | 5'-P-UUUGUCUCUGGUCCUUACUU (P = S, antisense) |
| 13/308746 | AAGUAAGGACCAGAGACAAA (P = O, sense) |
| 14/335452 | <u>A</u>AGU<u>A</u>AGG<u>A</u>CC<u>A</u>GAG<u>A</u>C<u>A</u>A (P = O, sense) |
| 15/335453 | A<u>A</u>G<u>UA</u>AGG<u>A</u>C<u>C</u>AG<u>AGA</u>C<u>A</u>AA (P = O, sense) |

Underlined = 2'-O-methyl and 5'-P- is a 5'-phosphate group.

| siRNA duplexes (5',3'-sense and 3',5'-antisense) | Activity (150 nm) |
|---|---|
| 13/308746 (S, P = O) 5'-AAGUAAGGACCAGAGACAAA-3' | 14.8 |
| 12/303912 (AS, P = S) 3'-UUCAUUCCUGGUCUCUGUUU-P-5' (unmodified standard) | |

| siRNA duplexes (5',3'-sense and 3',5'-antisense) | Activity (150 nm) |
|---|---|
| 14/335452 (S, P +32 O) 5'-<u>A</u>AGU<u>A</u>AGG<u>A</u>CC<u>A</u>GAG<u>A</u>C<u>A</u>AA-3' | |
| 8/335454 (AS, P = S) 3'-<u>UU</u>C<u>AUU</u>CC<u>UGG</u>UC<u>UC</u>UG<u>UUU</u>-P-5' | 43.8 |
| 10/335456 (AS, P = O) 3'-<u>UU</u>C<u>AUU</u>CC<u>UGG</u>UC<u>UC</u>UG<u>UUU</u>-P-5' | 41.0 |
| 9/335455 (AS, P = S) 3'-<u>UUCAUUCCUGGUCUCUGUUU</u>-P-5' | 53.1 |
| 11/335457 (AS, P = O) 3'-<u>UUCAUUCCUGGUCUCUGUUU</u>-P-5' | 49.7 |
| 15/335453 (S, P = O) 5'-A<u>A</u>G<u>UA</u>AGG<u>A</u>C<u>C</u>AG<u>AGA</u>C<u>A</u>AA-3' | |
| 8/335454 (AS, P = S) 3'-<u>UU</u>C<u>AUU</u>CC<u>UGG</u>UC<u>UC</u>UG<u>UUU</u>-P-5' | 54.3 |

| | |
|---|---|
| 10/335456 (AS, P = O)  3'-UUCAUUCCUGGUCUCUGUUU-P-5' | 50.3 |
| 9/335455 (AS, P = S)  3'-UUCAUUCCUGGUCUCUGUUU-P-5' | 52.2 |
| 11/335457 (AS, P = O)  3'-UUCAUUCCUGGUCUCUGUUU-P-5' | 52.8 |
| 13/308746 (S, P = O)  5'-AAGUAAGGACCAGAGACAAA-3' | |
| 8/335454 (AS, P = S)  3'-UUCAUUCCUGGUCUCUGUUU-P-5' | 40.0 |
| 10/335456 (AS, P = O)  3'-UUCAUUCCUGGUCUCUGUUU-P-5' | 26.3 |
| 9/335455 (AS, P = S)  3'-UUCAUUCCUGGUCUCUGUUU-P-5' | 56.6 |
| 11/335457 (AS, P = O)  3'-UUCAUUCCUGGUCUCUGUUU-P-5' | 74.4 |

| asRNA single stranded (5',3'-sense and 3',5'-antisense) | Activity (200 nm) |
|---|---|
| 12/303912 (AS, P = S)  3'-UUCAUUCCUGGUCUCUGUUU-P-5' | 27.9 |
| 8/335454 (AS, P = S)  3'-UUCAUUCCUGGUCUCUGUUU-P-5' | 53.5 |
| 10/335456 (AS, P = O)  3'-UUCAUUCCUGGUCUCUGUUU-P-5' | 93.2 |
| 9/335455 (AS, P = S)  3'-UUCAUUCCUGGUCUCUGUUU-P-5' | 48.3 |
| 11/335457 (AS, P = O)  3'-UUCAUUCCUGGUCUCUGUUU-P-5' | 89.6 |

| SEQ ID NO: | Sequence (5'-3') |
|---|---|
| 12 | UUUGUCUCUGGUCCUUACUU |
| 13 | AAGUAAGGACCAGAGACAAA |

The asRNA assay was run as a dose response with only the 200 nm dose shown (0, 50, 100 and 200 nm). The siRNA assay was also performed as a dose response with only the 150 nm dose shown (20, 40 80, 150 nm).

Example 2

Alternating 2'-F siRNA's Targeting PTEN in T-24 Cells

A dose response was performed in the PTEN system to look at positional effects of alternating 2'-F constructs in asRNA constructs.

| SEQ ID NO/ ISIS NO | SEQUENCE |
|---|---|
| 13/308746 | 5'-P-AAG UAA GGA CCA GAG AC AAA-3' (PO, S, RNA) |
| 12/303912 | 3'-OH-UUC AUU CCU GGU CUC UGU UU-P-5' (PS, AS, RNA) |
| 16/339927 | 5'-PO-AAG UAA GGA CCA GAG ACA AA-3' (PO, S, deoxy) |
| 17/339923 | 3'-OH-UTC AUT C^mCU GGT CTC TGT UT-5'-P (PO, AS, deoxy) |
| 18/339928 | 5'-PO-AAG UAA GGA ^mCCA GAG ACA AA-3' (PO, S, deoxy) |
| 17/339923 | 3'-OH-UTC AUT C^mCU GGT CTC TGT UT-5'-P (PO, AS, deoxy) |
| 13/308746 | 5'-PO-AAG UAA GGA CCA GAG ACA AA-3' (PO, S, RNA) |
| 17/339923 | 3'-OH-UTC AUT C^mCU GGT CTC TGT UT-5'-P (PO, AS, deoxy) |
| 16/339927 | 5'-PO-AAG UAA GGA CCA GAG ACA AA-3' (PO, S, deoxy) |
| 17/339924 | 3'-OH-UTC AUT C^mCU GGT CTC TGT UT-5'-P (PS, AS, deoxy) |
| 18/339928 | 5'-PO-AAG UAA GGA ^mCCA GAG ACA AA-3' (PO, S, deoxy) |
| 19/339924 | 3'-OH-UTC AUT C^mCU GGT CTC TGT UT-5'-P (PS, AS, deoxy) |

| SEQ ID NO/ ISIS NO | SEQUENCE |
|---|---|
| 13/308746 | 5'-PO-AAG UAA GGA CCA GAG ACA AA-3' (PO, S, RNA) |
| 19/339924 | 3'-OH-<u>UTC</u> <u>A</u>U<u>T</u> <u>C</u>'''C<u>U</u> G<u>GT</u> <u>CTC</u> T<u>GT</u> <u>UT</u>-5'-P (PS, AS, deoxy) |

Underlined nucleosides are 2'-F modified nucleosides, all other nucleosides are ribonucleosides (RNA) or 2'-deoxyribonucleosides (deoxy) as annotated, PO and PS are phosphodiester and phosphorothioate respectively, 5'-P is 5'-phosphate, and '''C's are 5-methyl cytidines.

| SEQ ID NO: | Sequence (5'-3') |
|---|---|
| 20 | TUTGTCTCTGGUCCTUACTU |

The above siRNA constructs were assayed to determine the effects of the full alternating 2'-F/2'-deoxy antisense strands (PO or PS) as compared to sense strands having full alternating 2'-F/2'-deoxy (PO). The siRNA construct having PO sense and PS antisense strands that are full RNA was prepared for comparison.

The activities are listed below:

| siRNA Construct | Activity (% untreated control 150 nM) | | |
|---|---|---|---|
| | | Sense | Antisense |
| 308746/303912 | 16% | PO unmodified RNA | /PS unmodified RNA |
| 339927/339923 | 81% | PO deoxy alternating 3'-1 | /PO deoxy alternating 5'-1 |
| 339927/339924 | 39% | PO deoxy alternating 3'-1 | /PS deoxy alternating 5'-1 |
| 339928/339923 | 81% | PO deoxy alternating 3'-0 | /PO deoxy alternating 5'-1 |
| 339928/339924 | 39% | PO deoxy alternating 3'-0 | /PS deoxy alternating 5'-1 |
| 308746/339923 | 43% | PO unmodified RNA | /PO deoxy alternating 5'-1 |
| 308746/339924 | 37% | PO unmodified RNA | /PS deoxy alternating 5'-1 |

The alternating 3'-1 (sense strand) means that the alternating 2'-F groups start adjacent to the 3'-nucleoside and 3'-0 means the 2'-F starts alternating at the 3'-terminal nucleoside, alternating 5'-1 (antisense strand) means that the alternating 2'-F groups start adjacent to the 5'-nucleoside.

Example 3

Alternating 2'-F siRNA's Targeting PTEN in T-24 Cells

A dose response was performed in the PTEN system to look at positional effects of alternating 2'-F constructs in asRNA constructs.

| SEQ ID NO/ ISIS NO | SEQUENCE |
|---|---|
| 13/308746 | 5'-P-AAG UAA GGA CCA GAG AC AAA-3' (PO, S, RNA) |
| 12/303912 | 3'-OH-UUC AUU CCU GGU CUC UGU UU-P-5' (PS, AS, RNA) |
| 16/339927 | 5'-PO-<u>AAG</u> <u>UAA</u> <u>GGA</u> <u>CCA</u> <u>GAG</u> <u>ACA</u> <u>AA</u>-3' (PO, S, deoxy) |
| 21/339925 | 3'-OH-T<u>U</u>'''C <u>A</u>T<u>U</u> '''C<u>CT</u> G<u>GU</u> '''C<u>U</u>'''C <u>UGU</u> T<u>U</u>-5'-P (PO, AS, deoxy) |
| 18/339928 | 5'-PO-<u>AAG</u> <u>UAA</u> <u>GGA</u> '''<u>CCA</u> <u>GAG</u> <u>ACA</u> <u>AA</u>-3' (PO, S, deoxy) |
| 21/339925 | 3'-OH-T<u>U</u>'''C <u>A</u>T<u>U</u> '''C<u>CT</u> G<u>GU</u> '''C<u>U</u>'''C <u>UGU</u> T<u>U</u>-5'-P (PO, AS, deoxy) |
| 13/308746 | 5'-PO-AAG UAA GGA CCA GAG ACA AA-3' (PO, S, RNA) |
| 21/339925 | 3'-OH-T<u>U</u>'''C <u>A</u>T<u>U</u> '''C<u>CT</u> G<u>GU</u> '''C<u>U</u>'''C <u>UGU</u> T<u>U</u>-5'-P (PO, AS, deoxy) |
| 16/339927 | 5'-PO-<u>AAG</u> <u>UAA</u> <u>GGA</u> <u>CCA</u> <u>GAG</u> <u>ACA</u> <u>AA</u>-3' (PO, S, deoxy) |
| 21/339926 | 3'-OH-T<u>U</u>'''C <u>A</u>T<u>U</u> '''C<u>CT</u> G<u>GU</u> '''C<u>U</u>'''C <u>UGU</u> T<u>U</u>-5'-P (PS, AS, deoxy) |
| 18/339928 | 5'-PO-<u>AAG</u> <u>UAA</u> <u>GGA</u> '''<u>CCA</u> <u>GAG</u> <u>ACA</u> <u>AA</u>-3' (PO, S, deoxy) |

| SEQ ID NO/ ISIS NO | SEQUENCE |
|---|---|
| 21/339926 | 3'-OH-T<u>U</u><sup>m</sup>C A<u>TU</u> <sup>m</sup>C<u>C</u>T <u>GGU</u> <sup>m</sup>C<u>U</u><sup>m</sup>C <u>UGU</u> T<u>U</u>-5'-P (PO, S, deoxy) |
| 13/308746 | 5'-PO-AAG UAA GGA CCA GAG ACA AA-3' (PO, S, RNA) |
| 22/339926 | 3'-OH-T<u>U</u><sup>m</sup>C A<u>TU</u> <sup>m</sup>C<u>C</u>T <u>GGU</u> <sup>m</sup>C<u>U</u><sup>m</sup>C <u>UGU</u> T<u>U</u>-5'-P (PS, AS, deoxy) |

Underlined nucleosides are 2'-F modified nucleosides, all other nucleosides are ribonucleosides (RNA) or 2'-deoxyribonucleosides (deoxy) as annotated, PO and PS are phosphodiester and phosphorothioate respectively, 5'-P is 5'-phosphate, and <sup>m</sup>C's are 5-methyl cytidines.

| SEQ ID NO: | Sequence (5'-3') |
|---|---|
| 23 | UTUGUCUCUGGTCCUTACUT |

The above siRNA constructs were assayed to determine the effects of the full alternating 2'-F/2'-deoxy antisense strands (PO or PS) as compared to sense strands having full alternating 2'-F/2'-deoxy (PO). The siRNA construct having PO sense and PS antisense strands that are full RNA was prepared for comparison. The register of the antisense strand has been shifted relative to Example 2 (2'-F is at 5'-0 as opposed to 5'-1).

The activities are listed below:

| siRNA Construct | Activity (% untreated control 150 nM) | Sense | Antisense |
|---|---|---|---|
| 308746/303912 | 16% | PO unmodified RNA | /PS unmodified RNA |
| 339927/339925 | 86% | PO deoxy alternating 3'-1 | /PO deoxy alternating 5'-0 |
| 339927/339926 | 79% | PO deoxy alternating 3'-1 | /PS deoxy alternating 5'-0 |
| 339928/339925 | 51% | PO deoxy alternating 3'-0 | /PO deoxy alternating 5'-0 |
| 339928/339926 | 69% | PO deoxy alternating 3'-0 | /PS deoxy alternating 5'-0 |
| 308746/339925 | 73% | PO unmodified RNA | /PO deoxy alternating 5'-0 |
| 308746/339926 | 52% | PO unmodified RNA | /PS deoxy alternating 5'-0 |

The alternating 3'-1 (sense strand) means that the alternating 2'-F groups start adjacent to the 3'-nucleoside and 3'-0 means the 2'-F starts alternating at the 3'-terminal nucleoside, alternating 5'-1 (antisense strand) means that the alternating 2'-F groups start adjacent to the 5'-nucleoside.

Example 4

Alternating 2'-O-Methyl/2'-F siRNA's Targeting PTEN in T-24 Cells

A dose response was performed in the PTEN system to look at positional effects of alternating 2'-O-Methyl/2'-F siRNA's.

| SEQ ID NO/ ISIS NO | SEQUENCE (Bold = 2'-F, Underlined = 2'-OCH4) |
|---|---|
| 13/308746 | 5'-P-AAG UAA GGA CCA GAG AC AAA-3' (PO, S, RNA) |
| 12/303912 | 3'-OH-UUC AUU CCU GGU CUC UGU UU-P-5' (PS, AS, RNA) |
| 24/340573 | 5'-PO-A<u>AG</u> U<u>AA</u> G<u>GA</u> C<u>CA</u> G<u>AG</u> A<u>CA</u> A<u>A</u>-3' (PO, S) |
| 25/340569 | 3'-OH-<u>UU</u>C <u>AU</u>U <u>CC</u>U <u>GG</u>U <u>CU</u>C <u>UG</u>U <u>UU</u>-5'-P (PO, AS) |
| 26/340574 | 5'-PO-<u>A</u>AG <u>U</u>AA <u>G</u>GA <u>C</u>CA <u>G</u>AG <u>A</u>CA <u>A</u>A-3' (PO, S) |
| 25/340569 | 3'-OH-<u>UU</u>C <u>AU</u>U <u>CC</u>U <u>GG</u>U <u>CU</u>C <u>UG</u>U <u>UU</u>-5'-P (PO, AS) |
| 13/308746 | 5'-PO-AAG UAA GGA CCA GAG ACA AA-3' (PO, AS, RNA) |
| 25/340569 | 3'-OH-<u>UU</u>C <u>AU</u>U <u>CC</u>U <u>GG</u>U <u>CU</u>C <u>UG</u>U <u>UU</u>-5'-P (PO, AS) |
| 24/340573 | 5'-PO-A<u>AG</u> U<u>AA</u> G<u>GA</u> C<u>CA</u> G<u>AG</u> A<u>CA</u> A<u>A</u>-3' (PO, S) |
| 27/340570 | 3'-OH-<u>UU</u>C <u>AU</u>U <u>CC</u>U <u>GG</u>U <u>CU</u>C <u>UG</u>U <u>UU</u>-5'-P (PS, AS) |

| SEQ ID NO/ ISIS NO | SEQUENCE (Bold = 2'-F, Underlined = 2'-OCH4) |
|---|---|
| 26/340574 | 5'-PO-<u>AA</u>G U<u>AA</u> <u>GG</u>A C<u>C</u>A <u>GA</u>G A<u>C</u>A <u>AA</u>-3' (PO, S) |
| 27/340570 | 3'-OH-<u>UU</u>C A<u>UU</u> <u>CC</u>U GGU CUC UGU <u>UU</u>-5'-P (PS, AS) |
| 13/308746 | 5'-PO-AAG UAA GGA CCA GAG ACA AA-3' (PO, AS, RNA) |
| 27/340570 | 3'-OH-<u>UU</u>C A<u>UU</u> <u>CC</u>U GGU CUC UGU <u>UU</u>-5'-P (PS, AS) |

Underlined nucleosides are 2'-OCH₃ modified nucleosides, bold are 2'-F modified nucleosides, PO and PS are phosphodiester and phosphorothioate respectively, 5'-P is 5'-phosphate, and ᵐC's are 5-methyl cytidines.

The above siRNA constructs were assayed to determine the effects of the full alternating 2'-O-methyl/2'-F antisense strands (PO or PS) where the 5'-terminus of the antisense strands are 2'-F modified nucleosides with the remaining positions alternating. The sense strands were prepared with the positioning of the modified nucleosides in both orientations such that for each siRNA tested with 2'-O-methyl modified nucleosides beginning at the 3'-terminus of the sense strand another identical siRNA was prepared with 2'-F modified nucleosides beginning at the the 3'-terminus of the sense strand. Another way to describe the differences between these two siRNA's is that the register of the sense strand is in both possible orientations with the register of the antisense strand being held constant in one orientation.

The activities are listed below:

| siRNA Construct | Activity (% untreated control 150 nM) | |
|---|---|---|
| | Sense | Antisense |
| 308746/303912 | 28% PO unmodified RNA | PS unmodified RNA |
| 340574/340569 | 46% PO (2'-F, 3'-0) | PO (2'-F, 5'-0) |
| 340574/340570 | 62% PO (2'-F, 3'-0) | PS (2'-F, 5'-0) |

| siRNA Construct | Activity (% untreated control 150 nM) | |
|---|---|---|
| | Sense | Antisense |
| 340573/340569 | 84% PO (2'-O-methyl, 3'-0) | PO (2'-F, 5'-0) |
| 340573/340570 | 23% PO (2'-O-methyl, 3'-0) | PS (2'-F, 5'-0) |
| 308746/340569 | 23% PO unmodified RNA | PO (2'-F, 5'-0) |
| 308746/340570 | 38% PO unmodified RNA | PS (2'-F, 5'-0) |

Within the alternating motif for this assay the antisense strands were prepared beginning with a 2'-F group at the 5'-terminal nucleoside. The sense strands were prepared with the alternating motif beginning at the 3'-terminal nucleoside with either the 2'-F (2'-F, 3'-0) or the 2'-O-methyl (2'-O-methyl, 3'-0). The siRNA constructs were prepared with the internucleoside linkages for the sense strand as full phosphodiester and the internucleoside linkages for the antisense strands as either full phosphodiester or phosphorothioate.

Example 5

Alternating 2'-O-Methyl/2'-F siRNA's Targeting PTEN in T-24 Cells

A dose response was performed in the PTEN system to look at positional effects of alternating 2'-O-Methyl/2'-F siRNA's.

| SEQ ID NO/ ISIS NO | SEQUENCE (Bold = 2'-F, Underlined = 2'-OCH4) |
|---|---|
| 13/308746 | 5'-P-AAG UAA GGA CCA GAG AC AAA-3' (PO, S, RNA) |
| 12/303912 | 3'-OH-UUC AUU CCU GGU CUC UGU UU-P-5' (PS, AS, RNA) |
| 24/340573 | 5'-PO-<u>A</u>AG <u>U</u>AA <u>G</u>GA <u>C</u>CA <u>G</u>AG <u>A</u>CA <u>A</u>A-3' (PO, S) |
| 28/340571 | 3'-OH-U<u>U</u>C A<u>UU</u> C<u>C</u>U GGUC U<u>G</u>U U<u>U</u>-5'-P (PO, AS) |
| 26/340574 | 5'-PO-<u>AA</u>G U<u>AA</u> <u>GG</u>A C<u>C</u>A <u>GA</u>G A<u>C</u>A <u>AA</u>-3' (PO, S) |
| 28/340571 | 3'-OH-U<u>U</u>C A<u>UU</u> C<u>C</u>U GGUC U<u>G</u>U U<u>U</u>-5'-P (PO, AS) |
| 13/308746 | 5'-PO-AAG UAA GGA CCA GAG ACA AA-3' (PO, AS, RNA) |
| 28/340571 | 3'-OH-U<u>U</u>C A<u>UU</u> C<u>C</u>U GGUC U<u>G</u>U U<u>U</u>-5'-P (PO, AS) |
| 24/340573 | 5'-PO-<u>A</u>AG <u>U</u>AA <u>G</u>GA <u>C</u>CA <u>G</u>AG <u>A</u>CA <u>A</u>A-3' (PO, S) |
| 29/340572 | 3'-OH-U<u>U</u>C A<u>UU</u> C<u>C</u>U GGUC U<u>G</u>U U<u>U</u>-5'-P (PS, AS) |
| 26/340574 | 5'-PO-<u>AA</u>G U<u>AA</u> <u>GG</u>A C<u>C</u>A <u>GA</u>G A<u>C</u>A <u>AA</u>-3' (PO, S) |
| 29/340572 | 3'-OH-U<u>U</u>C A<u>UU</u> C<u>C</u>U GGUC U<u>G</u>U U<u>U</u>-5'-P (PS, AS) |
| 13/308746 | 5'-PO-AAG UAA GGA CCA GAG ACA AA-3' (PO, AS, RNA) |
| 29/340572 | 3'-OH-U<u>U</u>C A<u>UU</u> C<u>C</u>U GGUC U<u>G</u>U U<u>U</u>-5'-P (PS, AS) |

Underlined nucleosides are 2'-F modified nucleosides, bold are 2'-F modified nucleosides, PO and PS are phosphodiester and phosphorothioate respectively, 5'-P is 5'-phosphate, and $^m$C's are 5-methyl cytidines.

The above siRNA constructs were assayed to determine the effects of the full alternating 2'-O-methyl/2'-F antisense strands (PO or PS) where the 5'-terminus of the antisense strands are 2'-O-methyl modified nucleosides with the remaining positions alternating. The sense strands were prepared with the positioning of the modified nucleosides in both orientations such that for each siRNA tested with 2'-O-methyl modified nucleosides beginning at the the 3'-terminus of the sense strand another identical siRNA was prepared with 2'-F modified nucleosides beginning at the the 3'-terminus of the sense strand. Another way to describe the differences between these two siRNA's is that the register of the sense strand is in both possible orientations with the register of the antisense strand being held constant in one orientation.

The activities are listed below:

| siRNA Construct | Activity (% untreated control 150 nM) | Sense | Antisense |
|---|---|---|---|
| 308746/303912 | 27% | PO unmodified RNA | PS unmodified RNA |
| 340574/340571 | 112% | PO (2'-F, 3'-0) | PO (2'-O-methyl, 5'-0) |
| 340574/340572 | 81% | PO (2'-F, 3'-0) | PS (2'-O-methyl, 5'-0) |
| 340573/340571 | 40% | PO (2'-O-methyl, 3'-0) | PO (2'-O-methyl, 5'-0) |
| 340573/340572 | 71% | PO (2'-O-methyl, 3'-0) | PS (2'-O-methyl, 5'-0) |
| 308746/340571 | 46% | PO unmodified RNA | PO (2'-O-methyl, 5'-0) |
| 308746/340572 | 44% | PO unmodified RNA | PS (2'-O-methyl, 5'-0) |

Within the alternating motif for this assay the antisense strands were prepared beginning with a 2'-F group at the 5'-terminal nucleoside. The sense strands were prepared with the alternating motif beginning at the 3'-terminal nucleoside with either the 2'-F (2'-F, 3'-0) or the 2'-O-methyl (2'-O-methyl, 3'-0). The siRNA constructs were prepared with the internucleoside linkages for the sense strand as full phosphodiester and the internucleoside linkages for the antisense strands as either full phosphodiester or phosphorothioate.

Example 6

Double Stranded Alternating Constructs

A number of double stranded constructs were also assayed in HeLa cells. The constructs and activities are shown below:

| SEQ ID NO/ ISIS NO | SEQUENCES 5'-3' |
|---|---|
| 12/303912 | 5'-PO-UU UGU CUC UGG UCC UUA CUU-3' (AS, PS) |
| 124/308746 | 5'-PO-AAG TAA GGA CCA GAG ACA AA-3' (S, PO) |
| 125/335452 | 5'-PO-<u>AA</u>G T<u>AA</u> <u>GG</u>A C<u>CA</u> <u>GA</u>G <u>AC</u>A <u>AA</u>-3' (PO, 2'-OMe) |
| 15/335453 | 5'-PO-<u>AA</u>G U<u>AA</u> <u>GG</u>A <u>CC</u>A <u>GA</u>G <u>AC</u>A <u>AA</u>-3' (PO, 2'-OMe) |
| 8/335454 | 5'-PO-<u>UU</u> <u>UGU</u> <u>CU</u>C <u>UGG</u> <u>UC</u>C <u>UUA</u> <u>CU</u>U-3' (PS, 2'-OMe) |
| 9/335455 | 5'-PO-<u>UU</u> UGU C<u>UC</u> <u>UGG</u> U<u>CC</u> UU<u>A</u> <u>CU</u>U-3' (PS, 2'-OMe) |
| 10/335456 | 5'-PO-<u>UU</u> UGU C<u>UC</u> <u>UGG</u> UCC <u>UUA</u> <u>CU</u>U-3' (PO, 2'-OMe) |
| 11/335457 | 5'-PO-<u>UU</u> <u>UGU</u> <u>CU</u>C <u>UGG</u> <u>UC</u>C <u>UU</u>A <u>CU</u>U-3'3' (PO, 2'-OMe) |
| 17/339923 | 5'-PO-<u>TU</u> <u>TGT</u> <u>CTC</u> <u>TGG</u> <u>U</u>$^m$CC <u>TUA</u> <u>CTU</u>-3' (PO, T-F/2'-H) |
| 19/339924 | 5'-PO-<u>TU</u> <u>TGT</u> <u>CTC</u> <u>TGG</u> <u>U</u>$^m$CC <u>TUA</u> <u>CTU</u>-3' (PS, T-F/2'-H) |
| 21/339925 | 5'-PO-<u>UT</u> <u>UGU</u> $^m$C<u>U</u>$^m$C <u>UGG</u> T<u>C</u>$^m$C <u>UTA</u> $^m$C<u>UT</u>-3' (PO, T-F/2'-H) |
| 22/339926 | 5'-PO-<u>UT</u> <u>UGU</u> $^m$C<u>U</u>$^m$C <u>UGG</u> T<u>C</u>$^m$C <u>UTA</u> $^m$C<u>UT</u>-3' (PS, T-F/2'-H) |
| 126/339927 | 5'-PO-<u>AA</u>G T<u>AA</u> <u>GG</u>A $^m$C<u>CA</u> <u>GA</u>G <u>AC</u>A <u>AA</u>-3' (PS, T-F/2'-H) |
| 127/339928 | 5'-PO-<u>AA</u>G U<u>AA</u> <u>GG</u>A <u>C</u>$^m$CA <u>GA</u>G A$^m$<u>CA</u> <u>AA</u>-3' (PO, T-F/2'-H) |
| 25/340569 | 5'-PO-<u>UU</u>U <u>GU</u>C <u>UC</u>U <u>GG</u>U <u>CC</u>U <u>UA</u>C <u>UU</u>-3' (PO, T-F/2'-OMe) |
| 27/340570 | 5'-PO-<u>UU</u>U <u>GU</u>C <u>UC</u>U <u>GG</u>U <u>CC</u>U <u>UA</u>C <u>UU</u>-3' (PS, T-F/2'-OMe) |
| 128/340571 | 5'-PO-<u>UU</u>U <u>GU</u>C <u>UC</u>U <u>GG</u>U <u>CC</u>U <u>UA</u>C <u>UU</u>-3' (PO, T-F/2'-OMe) |
| 129/340572 | 5'-PO-<u>UU</u>U <u>GU</u>C <u>UC</u>U <u>GG</u>U <u>CC</u>U <u>UA</u>C <u>UU</u>-3' (PS, T-F/2'-OMe) |
| 130/340573 | 5'-PO-<u>AA</u>G <u>UA</u>A <u>GG</u>A <u>CC</u>A <u>GA</u>G <u>AC</u>A <u>AA</u>-3' (PO, T-F/2'-OMe) |
| 131/340574 | 5'-PO-<u>AA</u>G <u>UA</u>A <u>GG</u>A <u>CC</u>A <u>GA</u>G <u>AC</u>A <u>AA</u>-3' (PO, 2'-F/2'-OMe) |
| 30/344217 | 5'-PO-<u>UU</u>U <u>GU</u>C <u>UC</u>U <u>GG</u>U <u>CC</u>U <u>UA</u>C <u>UU</u>-3' (PO, T-F) |
| 31/344218 | 5'-PO-<u>UU</u>U <u>GU</u>C <u>UC</u>U <u>GG</u>U <u>CC</u>U <u>UA</u>C <u>UU</u>-3' (PS, T-F) |

| SEQ ID NO/ ISIS NO | SEQUENCES 5'-3' |
|---|---|
| 32/344219 | 5'-PO-UUU GUC UCU GGU CCU UAC UU-3' (PO, T-F) |
| 33/344220 | 5'-PO-UUU GUC UCU GGU CCU UAC UU-3' (PS, T-F) |
| 34/344221 | 5'-PO-AAG UAA GGA CCA GAG ACA AA-3' (PO, T-F) |
| 35/344222 | 5'-PO-AAG UAA GGA CCA GAG ACA AA-3' (PO, 2'-F) |

The particular constructs and their activities are shown below:

| Double stranded construct | | Activity | |
|---|---|---|---|
| Antisense | Sense | % UTC (dose; nM) | IC50 (nM) |
| 303912 | 308746 | 24 (100) | 2 |
| 339923 | 339927 | 52 (100) | |
| 339923 | 339928 | 51 (100) | 100 |
| 339923 | 308746 | 41 (100) | 12 |
| 339924 | 339927 | 43 (100) | 56 |
| 339924 | 339928 | 34 (100) | 51 |
| 339924 | 308746 | 46 (100) | 77 |
| 339925 | 339927 | 78 (100) | |
| 339925 | 339928 | 91 (100) | |
| 339925 | 308746 | 65 (100) | |
| 339926 | 339927 | 53 (100) | |
| 339926 | 339928 | 47 (100) | |
| 339926 | 308746 | 34 (100) | 67 |
| 335454 | 335452 | 52 (11) | 19 |
| 335454 | 335453 | 58 (11) | 67 |
| 335454 | 308746 | 63 (11) | 34 |
| 335455 | 335452 | 59 (11) | 30 |
| 335455 | 335453 | 54 (11) | 15 |
| 335455 | 308746 | 69 (100) | |
| 335456 | 335452 | 45 (11) | 3 |
| 335456 | 335453 | 51 (11) | 21 |
| 335456 | 308746 | 38 (11) | 1 |
| 335457 | 335452 | 56 (100) | |
| 335457 | 335453 | 52 (11) | 14 |
| 335457 | 308746 | 52 (100) | |
| 340569 | 340573 | 67 (15) | |
| 340569 | 340574 | 35 (15) | 4 |
| 340569 | 308746 | 19 (15) | 0.2 |
| 340570 | 340573 | 25 (15) | 3 |
| 340570 | 340574 | 77 (15) | 92 |
| 340570 | 308746 | 52 (15) | 23 |
| 340571 | 340573 | 32 (15) | 4 |
| 340571 | 340574 | 84 (15) | |
| 340571 | 308746 | 38 (15) | 4 |
| 340572 | 340573 | 64 (15) | |
| 340572 | 340574 | 71 (15) | |
| 340572 | 308746 | 51 (15) | 0.7 |
| 344217 | 344222 | 23 (15) | 0.7 |
| 344217 | 308746 | 22 (15) | 0.8 |
| 344218 | 344221 | 28 (15) | 3 |
| 344218 | 344222 | 28 (15) | 5 |
| 344218 | 308746 | 28 (15) | 3 |
| 344219 | 344221 | 44 (15) | 6 |
| 344219 | 344222 | 40 (15) | 6 |
| 344219 | 308746 | 31 (15) | 2 |
| 344220 | 344221 | 47 (15) | 33 |
| 344220 | 344222 | 52 (15) | 55 |
| 344220 | 308746 | 44 (15) | 23 |

A wide variety of additional alternating constructs have been prepared and screening in various assays is ongoing. Some representative constructs that have been made are shown below:

| SEQ ID NO/ ISIS NO | ANTISENSE SEQUENCES 5'-3' |
|---|---|
| 36/335197 | 5'-P-TTTGTCTCTGGTCCTTACTT-OH (AS, PS) |
| 37/335198 | 5'-P-TTTGTCTCTGGTCCTTACTT-OH (AS, PS) |
| 38/335201 | 5'-P-TTTGTCTCTGGTCCTTACTT-OH (AS, PO) |
| 39/335202 | 5'-P-TTTGTCTCTGGTCCTTACTT-OH (AS, PO) |
| 40/335215 | 5'-P-UTUGUCUCUGGTCCUTACUT-OH (AS, PS) |
| 413/335216 | 5'-P-TUTGTCTCTGGUCCUUACTU-OH (AS, PS) |
| 42/335219 | 5'-P-UTUGUCUCUGGTCCUTACUT-OH (AS, PO) |
| 43/335220 | 5'-P-TUTGTCTCTGGUCCUUACTU-OH (AS, PO) |
| 44/xxxxx | 5'-P-AAGUAAGGACCAGAGACAAA-3' (S, PO) |
| 45/xxxxx | 5'-P-AAGUAAGGACCAGAGACAAA-3' (S, PO) |

For the above sequences, underlined is 2'-O-methoxyethyl, for the antisense strands (AS) the bold is 2'-H, for the sense strands (S) the bold is 2'-OH, PS indicates full phosphorothioate, PO indicates full phosphodiester, 5'-P- is a 5'-phosphate group and all C nucleosides are 5'-methyl C's.

Each of the antisense strands were duplexed with each of the sense strands to give 16 different siRNA constructs.

| 46/335211 | 5'-P-UTUGUCUCUGGTCCUTACUT-OH (PS) |
|---|---|
| 47/335212 | 5'-P-TUTGTCTCTGGUCCUUACTU-OH (PS) |
| 48/335213 | 5'-P-UTUGUCUCUGGTCCUTACUT-OH (PO) |
| 49/335214 | 5'-P-TUTGTCTCTGGUCCUUACTU-OH (PO) |
| 44/xxxxx | 5'-P-AAGUAAGGACCAGAGACAAA-3' (S, PO) |
| 45/xxxxx | 5'-P-AAGUAAGGACCAGAGACAAA-3' (S, PO) |

For the above sequences, underlined is 2'-O-methoxyethyl, for the antisense and the sense strands the bold is 2'-OH, PS indicates full phosphorothioate, PO indicates full phosphodiester, 5'-P- is a 5'-phosphate group and all C nucleosides are 5'-methyl C's.

Each of the antisense strands were duplexed with each of the sense strands to give 8 different siRNA constructs.

| 50/335217 | 5'-P-UUUGUCUCUGGUCCUUACUU-OH (PS) |
|---|---|
| 50/335218 | 5'-P-UUUGUCUCUGGUCCUUACUU-OH (PS) |
| 51/335221 | 5'-P-UUUGUCUCUGGUCCUUACUU-OH (PO) |

-continued

```
51/335222   5'-P-UUUGUCUCUGGUCCUUACUU-OH (PO)

36/335199   5'-P-TTTGTCTCTGGTCCTTACTT-OH (PS)

37/335200   5'-P-TTTGTCTCTGGTCCTTACTT-OH (PS)

38/335203   5'-P-TTTGTCTCTGGTCCTTACTT-OH (PO)

39/335204   5'-P-TTTGTCTCTGGTCCTTACTT--OH (PO)

44/xxxxx    5'-P-AAGUAAGGACCAGAGACAAA-3' (S, PO)

45/xxxxx    5'-P-AAGUAAGGACCAGAGACAAA-3' (S, PO)
```

For the above sequences, underlined is 2'-O-methyl, for the antisense strands (AS) the bold is 2'-H, for the sense strands (S) the bold is 2'-OH, PS indicates full phosphorothioate, PO indicates full phosphodiester, 5'-P- is a 5'-phosphate group and all C nucleosides are 5'-methyl C's.

Each of the antisense strands were duplexed with each of the sense strands to give 16 different siRNA constructs.

| SEQ ID NO: | Sequence (5'-3') |
|---|---|
| 52 | TTTGTCTCTGGTCCTTACTT |
| 23 | UTUGUCUCUGGTCCUTACUT |
| 20 | TUTGTCTCTGGUCCUUACTU |
| 12 | UUUGUCUCUGGUCCUUACUU |
| 13 | AAGUAAGGACCAGAGACAAA. |

Example 7

Reduction of endogenous PTEN mRNA in HeLa cells by 19- and 20-basepair siRNA is shown in this example. HeLa cells were transfected with siRNA in the presence of lipofectin and treated for 16 hours prior to lysis and analysis by RT-PCR. Maximum % reduction (Max Red) is the amount of mRNA reduction compared to untreated control cells at the highest concentration (150 nM), with IC50 indicating the interpolated concentration at which 50% reduction is achieved. The notation "5'-P—" indicates the presence of a 5'-phosphate. Bold nucleosides have 2'-OMe substituents. Otherwise the nucleosides have a 2'-OH substituent. The constructs have phosphodiester linkages unless underlined. Underlined nucleosides have phosphorthioate linkages.

| SEQ ID No. | siRNA | IC50 (nM) | Max Red |
|---|---|---|---|
| 13 | 5'-AAG UAA GGA CCA GAG ACA AA-3' | 2.4 | 83 |
| 12 | 3'-UUC AUU CCU GGU CUC UGU UU-P-5' | | |
| 13 | 5'-AAG UAA GGA CCA GAG ACA AA-3' | 1.7 | 94 |
| 56 | 3'-UUC AUU CCU GGU CUC UGU UU-P-5' | | |
| 14 | 5'-P-AAG UAA GGA CCA GAG ACA AA-3' | 2.8 | 60 |
| 10 | 3'-UUC AUU CCU GGU CUC UGU UU-P-5' | | |
| 57 | 5'-AAG UAA GGA CCA GAG ACA A-3' | 0.55 | 90 |
| 58 | 3'-UUC AUU CCU GGU CUC UGU U-5' | | |
| 59 | 5'-AAG UAA GGA CCA GAG ACA A-3' | 1.2 | 95 |
| 60 | 3'-UUC AUU CCU GGU CUC UGU U-5' | | |
| 61 | 5'-GGG UAA AUA CAU UCU ACA U-3' | 1.7 | 83 |
| 62 | 3'-CCC AUU UAU GUA AGA UGU A-5' | | |
| 63 | 5'-GGG UAA AUA CAU UCU ACA U-3' | 0.63 | 92 |
| 64 | 3'-CCC AUU UAU GUA AGA UGU A-5' | | |
| 65 | 5'-UCA AAU CCA GAG GCU AGC A-3' | 13.6 | 71 |
| 66 | 3'-AGU UUA GGU CUC CGA UCG U-5' | | |
| 67 | 5'-UCA AAU CCA GAG GCU AGC A-3' | n.d. | 20 |
| 68 | 3'-AGU UUA GGU CUC CGA UCG U-5' | | |

Example 8

Reduction of endogenous PTEN mRNA in HeLa cells by 20-basepair siRNA containing 2'-OMe modifications is shown in this example. HeLa cells were transfected with siRNA in the presence of lipofectin and treated for 16 hours prior to lysis and analysis by RT-PCR. Maximum % reduction is the amount of mRNA reduction compared to untreated control cells at the highest concentration (150 nM), with IC50 indicating the interpolated concentration at which 50% reduction is achieved. The notation "5'-P—" indicates the presence of a 5'-phosphate. Bold nucleosides have 2'-OMe substituents. Otherwise the nucleosides have a 2'-OH substituent. The constructs have phosphodiester linkages unless underlined. Underlined nucleosides have phosphorthioate linkages.

| SEQ ID No. | siRNA | IC50 (nM) | Max Red |
|---|---|---|---|
| 13 | 5'-AAG UAA GGA CCA GAG ACA AA-3' | 1.1 | 79 |
| 12 | 3'-*UUC AUU CCU GGU CUC UGU UU*-P-5' | | |
| 13 | 5'-AAG UAA GGA CCA GAG ACA AA-3' | 1.2 | 71 |
| 10 | 3'-UUC AUU CCU GGU CUC UGU UU-P-5' | | |
| 13 | 5'-AAG UAA GGA CCA GAG ACA AA-3' | 37.4 | 48 |
| 69 | 3'-UUCAUU CCUGGU CUCUGU UU-P-5' | | |
| 14 | 5'-P-AAG UAA GGA CCA GAG ACA AA-3' | 2.6 | 60 |
| 10 | 3'-UUC AUU CCU GGU CUC UGU UU-P-5' | | |
| 14 | 5'-P-AAG UAA GGA CCA GAG ACA AA-3' | 19.2 | 47 |
| 69 | 3'-UUCAUU CCUGGU CUCUGU UU-P-5' | | |
| 70 | 5'-P-AAG UAA GGA CCA GAG ACA AA-3' | 21.1 | 59 |
| 10 | 3'-UUC AUU CCU GGU CUC UGU UU-5' | | |
| 70 | 5'-P-AAG UAA GGA CCA GAG ACA AA-3' | 66.6 | 4 |
| 69 | 3'-UUCAUU CCUGGU CUCUGU UU-P-5' | | |
| 13 | 5'-AAG UAA GGA CCA GAG ACA AA-3' | 136 | 47 |
| 71 | 3'-UUC AUU CCU GGU CUC UGU UU-P-5' | | |
| 13 | 5'-AAG UAA GGA CCA GAG ACA AA-3' | 440 | 31 |
| 72 | 3'-UUC AUUCCU GGUCUC UGUUU-P-5' | | |
| 70 | 5'-P-AAG UAA GGA CCA GAG ACA AA-3' | 14.2 | 62 |
| 71 | 3'-UUC AUU CCU GGU CUC UGU UU-P-5' | | |
| 70 | 5'-AAG UAA GGA CCA GAG ACA AA-3' | 14.7 | 57 |
| 72 | 3'-UUC AUUCCU GGUCUC UGUUU-P-5' | | |
| 14 | 5'-P-AAG UAA GGA CCA GAG ACA AA-3' | 179 | 36 |
| 71 | 3'-UUC AUU CCU GGU CUC UGU UU-P-5' | | |
| 14 | 5'-P-AAG UAA GGA CCA GAG ACA AA-3' | 29.5 | 51 |
| 72 | 3'-UUC AUUCCU GGUCUC UGUUU-P-5' | | |

Example 9

Reduction of endogenous PTEN mRNA in HeLa cells by 20-basepair siRNA containing 2'-F modifications is shown in this example. HeLa cells were transfected with siRNA in the presence of lipofectin and treated for 16 hours prior to lysis and analysis by RT-PCR. Maximum % reduction is the amount of mRNA reduction compared to untreated control cells at the highest concentration (150 nM), with IC50 indicating the interpolated concentration at which 50% reduction is achieved. The notation "5'-P—" indicates the presence of a 5'-phosphate. Bold nucleosides have 2'-F substituents. Otherwise the nucleosides have a 2'-OH substituent. The constructs have phosphodiester linkages unless underlined. Underlined nucleosides have phosphorthioate linkages.

| SEQ ID No. | siRNA | IC50 (nM) | Max Red |
|---|---|---|---|
| 13 | 5'-AAG UAA GGA CCA GAG ACA AA-3' | 2.5 | 83 |
| 12 | 3'-UUC AUU CCU GGU CUC UGU UU-P-5' | | |
| 13 | 5'-AAG UAA GGA CCA GAG ACA AA-3' | 0.77 | 87 |
| 73 | 3'-UUC AUU CCU GGU CUC UGU UU-P-5' | | |
| 13 | 5'-AAG UAA GGA CCA GAG ACA AA-3' | 2.6 | 78 |
| 74 | 3'-UUC AUU CCU GGU CUC UGU UU-P-5' | | |
| 75 | 5'-P-AAG UAA GGA CCA GAG ACA AA-3' | 0.67 | 86 |
| 73 | 3'-UUC AUU CCU GGU CUC UGU UU-P-5' | | |
| 75 | 5'-AAG UAA GGA CCA GAG ACA AA-3' | 4.7 | 76 |
| 74 | 3'-UUC AUU CCU GGU CUC UGU UU-P-5' | | |
| 76 | 5'-P-AAG UAA GGA CCA GAG ACA AA-3' | 0.71 | 86 |
| 73 | 3'-UUC AUU CCU GGU CUC UGU UU-P-5' | | |
| 76 | 5'-P-AAG UAA GGA CCA GAG ACA AA-3' | 2.8 | 77 |
| 74 | 3'-UUC AUU CCU GGU CUC UGU UU-P-5' | | |
| 13 | 5'-AAG UAA GGA CCA GAG ACA AA-3' | 1.5 | 76 |
| 77 | 3'-UUC AUU CCU GGU CUC UGU UU-P-5' | | |
| 13 | 5'-AAG UAA GGA CCA GAG ACA AA-3' | 22.9 | 77 |
| 78 | 3'-UUC AUU CCU GGU CUC UGU UU-P-5' | | |
| 76 | 5'-P-AAG UAA GGA CCA GAG ACA AA-3' | 6.1 | 71 |
| 77 | 3'-UUC AUU CCU GGU CUC UGU UU-P-5' | | |
| 76 | 5'-P-AAG UAA GGA CCA GAG ACA AA-3' | 33.3 | 57 |
| 78 | 3'-UUC AUU CCU GGU CUC UGU UU-P-5' | | |
| 75 | 5'-P-AAG UAA GGA CCA GAG ACA AA-3' | 5.7 | 75 |
| 77 | 3'-UUC AUU CCU GGU CUC UGU UU-P-5' | | |
| 75 | 5'-P-AAG UAA GGA CCA GAG ACA AA-3' | 54.7 | 54 |
| 78 | 3'-UUC AUU CCU GGU CUC UGU UU-P-5' | | |

Example 10

Reduction of endogenous PTEN mRNA in HeLa cells by 20-basepair siRNA containing 2'-F and 2'-deoxy (2'-H) modifications is shown in this example. HeLa cells were transfected with siRNA in the presence of lipofectin and treated for 16 hours prior to lysis and analysis by RT-PCR. Maximum % reduction is the amount of mRNA reduction compared to untreated control cells at the highest concentration (150 nM), with IC50 indicating the interpolated concentration at which 50% reduction is achieved. The notation "5'-P—" indicates the presence of a 5'-phosphate. Bold nucleosides have 2'-F substituents. Nucleosides with a "d" subscript have a deoxy sugar. Otherwise the nucleosides have a 2'-OH substituent. The constructs have phosphodiester linkages unless underlined. Underlined nucleosides have phosphorthioate linkages.

| SEQ ID No. | siRNA | IC50 (nM) | Max Red |
|---|---|---|---|
| 13 | 5'-AAG UAA GGA CCA GAG ACA AA-3' | 2.6 | 76 |
| 12 | 3'-UUC AUU CCU GGU CUC UGU UU-P-5' | | |
| 13 | 5'-AAG UAA GGA CCA GAG ACA AA-3' | 11.7 | 60 |
| 79 | 3'-UT$_d$C A$_d$UT$_d$ CC$_d$U G$_d$GT$_d$ CT$_d$C T$_d$GT$_d$ UT$_d$-P-5' | | |
| 13 | 5'-AAG UAA GGA CCA GAG ACA AA-3' | 76.7 | 54 |
| 80 | 3'-UT$_d$C A$_d$UT$_d$ CC$_d$U G$_d$GT$_d$ CT$_d$C T$_d$GT$_d$ UT$_d$-P-5' | | |
| 81 | 5'-A$_d$AG$_d$ UA$_d$A G$_d$GA$_d$ CC$_d$A G$_d$AG$_d$ AC$_d$A A$_d$A-3' | 100 | 49 |
| 79 | 3'-UT$_d$C A$_d$UT$_d$ CC$_d$U G$_d$GT$_d$ CT$_d$C T$_d$GT$_d$ UT$_d$-P-5' | | |
| 81 | 5'-A$_d$AG$_d$ UA$_d$A G$_d$GA$_d$ CC$_d$A G$_d$AG$_d$ AC$_d$A A$_d$A-3' | 50.7 | 66 |
| 80 | 3'-UT$_d$C A$_d$UT$_d$ CC$_d$U G$_d$GT$_d$ CT$_d$C T$_d$GT$_d$ UT$_d$-P-5' | | |
| 82 | 5'-AA$_d$G T$_d$AA$_d$ GG$_d$A C$_d$CA$_d$ GA$_d$G A$_d$CA$_d$ AA$_d$-3' | 122 | 48 |
| 79 | 3'-UT$_d$C A$_d$UT$_d$ CC$_d$U G$_d$GT$_d$ CT$_d$C T$_d$GT$_d$ UT$_d$-P-5' | | |
| 82 | 5'-AA$_d$G T$_d$AA$_d$ GG$_d$A C$_d$CA$_d$ GA$_d$G A$_d$CA$_d$ AA$_d$-3' | 55.7 | 57 |
| 80 | 3'-UT$_d$C A$_d$UT$_d$ CC$_d$U G$_d$GT$_d$ CT$_d$C T$_d$GT$_d$ UT$_d$-P-5' | | |
| 13 | 5'-AAG UAA GGA CCA GAG ACA AA-3' | n.d. | 35 |
| 83 | 3'-TU$_d$C A$_d$TU$_d$ CC$_d$T G$_d$GU$_d$ CU$_d$C U$_d$GU$_d$ TU$_d$-P-5' | | |
| 13 | 5'-AAG UAA GGA CCA GAG ACA AA-3' | 66.8 | 48 |
| 84 | 3'-TU$_d$C A$_d$TU$_d$ CC$_d$T G$_d$GU$_d$ CU$_d$C U$_d$GU$_d$ TU$_d$-P-5' | | |
| 82 | 5'-AA$_d$G T$_d$AA$_d$ GG$_d$A C$_d$CA$_d$ GA$_d$G A$_d$CA$_d$AA$_d$-3' | n.d. | 22 |
| 83 | 3'-TU$_d$C A$_d$TU$_d$ CC$_d$T G$_d$GU$_d$ CU$_d$C U$_d$GU$_d$ TU$_d$-P-5' | | |

| SEQ ID No. | siRNA | IC50 (nM) | Max Red |
|---|---|---|---|
| 82 | 5'-AA$_d$G T$_d$AA$_d$ GG$_d$A C$_d$CA$_d$ GA$_d$G A$_d$CA$_d$ AA$_d$-3' | 145 | 66 |
| 84 | 3'-<u>T</u>U$_d$<u>C</u> <u>A</u>$_d$<u>T</u><u>U</u>$_d$ <u>CC</u>$_d$<u>T</u> <u>G</u>$_d$GU$_d$ <u>C</u>U$_d$C U$_d$GU$_d$ <u>T</u>U$_d$-P-5' | | |
| 81 | 5'-A$_d$AG$_d$ UA$_d$A G$_d$GA$_d$ CC$_d$A G$_d$AG$_d$ AC$_d$A A$_d$A-3' | n.d. | 9 |
| 83 | 3'-TU$_d$C A$_d$TU$_d$ CC$_d$T G$_d$GU$_d$ CU$_d$C U$_d$GU$_d$ TU$_d$-P-5' | | |
| 81 | 5'-A$_d$AG$_d$ UA$_d$A G$_d$GA$_d$ CC$_d$A G$_d$AG$_d$ AC$_d$A A$_d$A-3' | 158 | 58 |
| 84 | 3'-<u>T</u>U$_d$<u>C</u> <u>A</u>$_d$<u>T</u><u>U</u>$_d$ <u>CC</u>$_d$<u>T</u> <u>G</u>$_d$GU$_d$ <u>C</u>U$_d$C U$_d$GU$_d$ <u>T</u>U$_d$-P-5' | | |

Example 11

Reduction of endogenous PTEN mRNA in HeLa cells by 20-basepair siRNA containing 2'-F and 2'-OMe modifications is shown in this example. HeLa cells were transfected with siRNA in the presence of lipofectin and treated for 16 hours prior to lysis and analysis by RT-PCR. Maximum % reduction is the amount of mRNA reduction compared to untreated control cells at the highest concentration (150 nM), with IC50 indicating the interpolated concentration at which 50% reduction is achieved. The notation "5'-P—" indicates the presence of a 5'-phosphate. Bold nucleosides have 2'-F substituents. Nucleosides with a "m" subscript have 2'-OMe substituents. Otherwise the nucleosides have a 2'-OH substituent. The constructs have phosphodiester linkages unless underlined. Underlined nucleosides have phosphorthioate linkages.

Example 12

Reduction of endogenous PTEN mRNA in HeLa cells by 19-basepair siRNAs containing 2'-F and 2'-OMe modifications is shown in this example. HeLa cells were transfected with siRNA in the presence of lipofectin and treated for 16 hours prior to lysis and analysis by RT-PCR. Maximum % reduction is the amount of mRNA reduction compared to untreated control cells at the highest concentration (150 nM), with IC50 indicating the interpolated concentration at which 50% reduction is achieved. The notation "5'-P—" indicates the presence of a 5'-phosphate. Bold nucleosides have 2'-F substituents. Nucleosides with a "m" subscript have 2'-OMe substituents. Otherwise the nucleosides have a 2'-OH substituent. The constructs have phosphodiester linkages unless underlined. Underlined nucleosides have phosphorthioate linkages.

| SEQ ID No. | siRNA | IC50 (nM) | Max Red |
|---|---|---|---|
| 13 | 5'-AAG UAA GGA CCA GAG ACA AA-3' | 1.5 | 86 |
| 12 | 3'-<u>UUC AUU CCU GGU CUC UGU UU</u>-P-5' | | |
| 13 | 5'-AAG UAA GGA CCA GAG ACA AA-3' | 0.18 | 87 |
| 85 | 3'-UU$_m$C A$_m$UU$_m$ CC$_m$U G$_m$GU$_m$ CU$_m$C U$_m$GU$_m$ UU$_m$-P-5' | | |
| 13 | 5'-AAG UAA GGA CCA GAG ACA AA-3' | 23.4 | 66 |
| 86 | 3'-UU$_m$C A$_m$UU$_m$ CC$_m$U G$_m$GU$_m$ CU$_m$C U$_m$GU$_m$ UU$_m$-P-5' | | |
| 132 | 5'-A$_m$AG$_m$ UA$_m$A G$_m$GA$_m$ CC$_m$A G$_m$AG$_m$ AC$_m$A A$_m$A-3' | 3.8 | 80 |
| 86 | 3'-UU$_m$C A$_m$UU$_m$ CC$_m$U G$_m$GU$_m$ CU$_m$C U$_m$GU$_m$ UU$_m$-P-5' | | |
| 132 | 5'-A$_m$AG$_m$ UA$_m$A G$_m$GA$_m$ CC$_m$A G$_m$AG$_m$ AC$_m$A A$_m$A-3' | 92 | 59 |
| 85 | 3'-UU$_m$C A$_m$UU$_m$ CC$_m$U G$_m$GU$_m$ CU$_m$C U$_m$GU$_m$ UU$_m$-P-5' | | |
| 133 | 5'-AA$_m$G U$_m$AA$_m$ GG$_m$A C$_m$CA$_m$ GA$_m$G A$_m$CA$_m$ AA$_m$-3' | 192 | 48 |
| 87 | 3'-UU$_m$C A$_m$UU$_m$ CC$_m$U G$_m$GU$_m$ CU$_m$C U$_m$GU$_m$ UU$_m$-P-5' | | |
| 133 | 5'-AA$_m$G U$_m$AA$_m$ GG$_m$A C$_m$CA$_m$ GA$_m$G A$_m$CA$_m$ AA$_m$-3' | 3.4 | 84 |
| 85 | 3'-UU$_m$C A$_m$UU$_m$ CC$_m$U G$_m$GU$_m$ CU$_m$C U$_m$GU$_m$ UU$_m$-P-5' | | |
| 13 | 5'-AAG UAA GGA CCA GAG ACA AA-3' | 3.8 | 70 |
| 134 | 3'-U$_m$UC$_m$ AU$_m$U C$_m$CU$_m$ GG$_m$U C$_m$UC$_m$ UG$_m$U U$_m$U-P-5' | | |
| 13 | 5'-AAG UAA GGA CCA GAG ACA AA-3' | 53.2 | 52 |
| 135 | 3'-U$_m$UC$_m$ AU$_m$U C$_m$CU$_m$ GG$_m$U C$_m$UC$_m$ UG$_m$U U$_m$U-P-5' | | |
| 133 | 5'-AA$_m$G U$_m$AA$_m$ GG$_m$A C$_m$CA$_m$ GA$_m$G A$_m$CA$_m$ AA$_m$-3' | 3.5 | 82 |
| 134 | 3'-U$_m$UC$_m$ AU$_m$U C$_m$CU$_m$ GG$_m$U C$_m$UC$_m$ UG$_m$U U$_m$U-P-5' | | |
| 133 | 5'-AA$_m$G U$_m$AA$_m$ GG$_m$A C$_m$CA$_m$ GA$_m$G A$_m$CA$_m$ AA$_m$-3' | n.d. | 13 |
| 135 | 3'-U$_m$UC$_m$ AU$_m$U C$_m$CU$_m$ GG$_m$U C$_m$UC$_m$ UG$_m$U U$_m$U-P-5' | | |
| 132 | 5'-A$_m$AG$_m$ UA$_m$A G$_m$GA$_m$ CC$_m$A G$_m$AG$_m$ AC$_m$A A$_m$A-3' | n.d. | 27 |
| 134 | 3'-U$_m$UC$_m$ AU$_m$U C$_m$CU$_m$ GG$_m$U C$_m$UC$_m$ UG$_m$U U$_m$U-P-5' | | |
| 132 | 5'-A$_m$AG$_m$ UA$_m$A G$_m$GA$_m$ CC$_m$A G$_m$AG$_m$ AC$_m$A A$_m$A-3' | n.d. | 32 |
| 132 | 3'-U$_m$UC$_m$ AU$_m$U C$_m$CU$_m$ GG$_m$U C$_m$UC$_m$ UG$_m$U U$_m$U-P-5' | | |

| SEQ ID No. | siRNA | IC50 (nM) | Max Red |
|---|---|---|---|
| 57 | 5'-AAG UAA GGA CCA GAG ACA AA-3' | 0.55 | 74 |
| 58 | 3'-UUC AUU CCU GGU CUC UGU UU-P-5' | | |
| 57 | 5'-AAG UAA GGA CCA GAG ACA AA-3' | 0.66 | 74 |
| 88 | 3'-U$_m$UC$_m$ AU$_m$U C$_m$CU$_m$ GG$_m$U C$_m$UC$_m$ UG$_m$U U$_m$U-P-5' | | |
| 89 | 5'-AA$_m$G U$_m$AA$_m$ GG$_m$A C$_m$CA$_m$ GA$_m$G A$_m$CA$_m$ AA$_m$-3' | 0.38 | 81 |
| 88 | 3'-U$_m$UC$_m$ AU$_m$U C$_m$CU$_m$ GG$_m$U C$_m$UC$_m$ UG$_m$U U$_m$U-P-5' | | |
| 61 | 5'-GGG UAA AUA CAU UCU ACA U-3' | 7.4 | 58 |
| 62 | 3'-CCC AUU UAU GUA AGA UGU A-5' | | |
| 61 | 5'-GGG UAA AUA CAU UCU ACA U-3' | 0.29 | 80 |
| 90 | 3'-C$_m$CC$_m$ AU$_m$U U$_m$AU$_m$ GU$_m$A A$_m$GA$_m$ UG$_m$U A$_m$-5' | | |
| 91 | 5'-GG$_m$G U$_m$AA$_m$ AU$_m$A C$_m$AU$_m$ UC$_m$U A$_m$CA$_m$ U-3' | 0.03 | 88 |
| 90 | 3'-C$_m$CC$_m$ AU$_m$U U$_m$AU$_m$ GU$_m$A A$_m$GA$_m$ UG$_m$U A$_m$-5' | | |

Example 13

Additional Alternating Sequences

The following sequences were prepared. Subscripts denote structural modifications. These codes are consistent with IUPAC rules on biochemical nomenclature. As used herein, any first lower case letter following the base code represents a sugar feature. In particular, "m" is 2'-O-methyl; "r" is ribo; "e" is 2'-O-methoxyethyl (MOE); "f" is 2'-deoxy-2'-fluoro; and "s" is 4'-thioribose. Any second lower case letter after the base code represents a linkage feature. In particular, "s" is a phosphorothioate linkage; and "o" is a phosphodiester linkage. For example Ums is has a uracil base, a 2'-O-methoxy group on the sugar and a phosphorthioate linkage to the sugar of the nucleoside that follows.

| SEQ ID NO/ISIS NO | SEQUENCES (5'-3') |
|---|---|
| *Alternating 2'-OCH$_3$/2'-OH full P = S as/s RNA* | |
| 136 (as)/335454 | UmsUrsUmsGrsUmsCrsUmsCrsUmsGrsGmsUrsCmsCrsUmsUrsAmsCrsUmsU |
| 13 (s)/308746 | AAGUAAGGACCAGAGACAAA |
| *Alternating 2'-OCH$_3$/2'-OH as/s RNA* | |
| 10 (as)/335456 | UmoUUmoGUmoCUmoCUmoGGmoUCmoCUmoUAmoCUmoU |
| 13 (s)/308746 | AAGUAAGGACCAGAGACAAA |
| 137 (as)/344217 | UUfoUGfoUCfoUCfoUGfoGUfoCCfoUUfoACfoUUf |
| 13 (s)/308746 | AAGUAAGGACCAGAGACAAA |
| 92 (as)/352507 | UmoUUmoGAmoAAmoAUmoGUmoUGmoAUmoCUmoCCm |
| 93 (s)/343868 | GGAGAUCAACAUUUUCAAA |
| *Alternating 2'-OCH$_3$/2'-OH as/s 2'-OCH$_3$/2'-OH* | |
| 10 (as)/335456 | UmoUUmoGUmoCUmoCUmoGGmoUCmoCUmoUAmoCUmoU |
| 14 (s)/335452 | AmoAGmoUAmoAGmoGAmoCCmoAGmoAGmoACmoAAmoA |
| 94 (as)/341396 | UmoUGmoUCmoUCmoUGmoGUmoCCmoUUmoACmoUUm |
| 59 (s)/341406 | AAmoGUmoAAmoGGmoACmoCAmoGAmoGAmoCAmoA |
| 95 (as)/345847 | UmoCUmoUAmoUCmoACmoCUmoUUmoAGmoCUmoCUm |
| 96 (s)/345849 | AGmoAGmoCUmoAAmoAGmoGUmoGAmoUAmoAGmoA |
| 92 (as)/352507 | UmoUUmoGAmoAAmoAUmoGUmoUGmoAUmoCUmoCCm |
| 97 (s)/352511 | GGmoAGmoAUmoCAmoACmoAUmoUUmoUCmoAAmoA |
| 92 (as)/352507 | UmoUUmoGAmoAAmoAUmoGUmoUGmoAUmoCUmoCCm |

-continued

| SEQ ID NO/ISIS NO | SEQUENCES (5'-3') |
|---|---|
| 98 (s)/352512 | GmoGmoAmoGmoAmoUmoCmoAmoAmoCmoAmoUmoUmo UmoUmoCmoAmoAmoAm |
| 92 (as)/352507 | UmoUUmoGAmoAAmoAUmoGUmoUGmoAUmoCUmoCCm |
| 99 (s)/352513 | GGmoAmoGmoAmoUmoCmoAmoAmoCmoAmoUmoUmoUmo UmoCmoAmoAmoA |

Alternating 2'-F/2'-OH as/s 2'-F/2'-OH

| 138 (as)/344217 | UUfoUGfoUCfoUCfoUGfoGUfoCCfoUUfoACfoUUf |
|---|---|
| 139 (s)/344221 | AfoAGfoUAfoAGfoGAfoCCfoAGfoAGfoACfoAAfoA |
| 138 (as)/344217 | UUfoUGfoUCfoUCfoUGfoGUfoCCfoUUfoACfoUUf |
| 140 (s)/344222 | AAfoGUfoAAfoGGfoACfoCAfoGAfoGAfoCAfoAAf |

Alternating 2'-H (d = deoxy)/2'-F as/s RNA

| 17 (as)/339923 | TdoUfoTdoGfoTdoCfoTdoCfoTdoGfoGdoUfomCdoCfoTdoUfo AdoCfoTdoUf |
|---|---|
| 13 (s)/308746 | AAGUAAGGACCAGAGACAAA |

Alternating 2'-OCH$_3$/2'-F as/s RNA

| 141 (as)/340569 | UmoUfoUmoGfoUmoCfoUmoCfoUmoGfoGmoUfoCmoCfoUmo UfoAmoCfoUmoUf |
|---|---|
| 13 (s)/308746 | AAGUAAGGACCAGAGACAAA |
| 142 (as)/340571 | UfoUmoUfoGmoUfoCmoUfoCmoUfoGmoGfoUmoCfoCmoUfo UmoAfoCmoUfoUm |
| 13 (s)/308746 | AAGUAAGGACCAGAGACAAA |
| 100 (as)/352820 | UmoUfoGmoUfoCmoUfoCmoUfoGmoGfoUmoCfoCmoUfoUmo AfoCmoUfoUm |
| 57 (s)/341401 | AAGUAAGGACCAGAGACAA |

Alternating 2'-OCH$_3$/2'-F as/s 2'-OCH$_3$/2'-F

| 141 (as)/340569 | UmoUfoUmoGfoUmoCfoUmoCfoUmoGfoGmoUfoCmoCfoUmo UfoAmoCfoUmoUf |
|---|---|
| 143 (s)/340574 | AmoAfoGmoUfoAmoAfoGmoGfoAmoCfoCmoAfoGmoAfoGmo AfoCmoAfoAmoAf |
| 144 (as)/340571 | UfoUmoUfoGmoUfoCmoUfoCmoUfoGmoGfoUmoCfoCmoUfo UmoAfoCmoUfoUm |
| 145 (s)/340573 | AfoAmoGfoUmoAfoAmoGfoGmoAfoCmoCfoAmoGfoAmoGfo AmoCfoAmoAfoAm |
| 100 (as)/352820 | UmoUfoGmoUfoCmoUfoCmoUfoGmoGfoUmoCfoCmoUfoUmo AfoCmoUfoUm |
| 146 (s)/352821 | AfoAmoGfoUmoAfoAmoGfoGmoAfoCmoCfoAmoGfoAmoGfo AmoCfoAmoAf |
| 101 (as)/351827 | UmoGfoUmoCfoAmoUfoAmoUfoUmoCfoCmoUfoGmoGfoAmo |
| 102(s)/351828 | AfoGmoGfoAmoUfoCmoCfoAmoGfoGmoAfoAmoUfoAmoUfo GmoAfoCmoAf |
| 103 (as)/351829 | UmoCfoCmoUfoGmoGfoAmoUfoCmoCfoUmoUfoCmoAfoCmo CfoAmoAfoUm |
| 104 (s)/351830 | AfoUmoUfoGmoGfoUmoGfoAmoAfoGmoGfoAmoUfoCmoCfo AmoGfoGmoAf |
| 105 (as)/351831 | UmoCfoUmoUfoAmoUfoCmoAfoCmoCfoUmoUfoUmoAfoGmo CfoUmoCfoUm |

| SEQ ID NO/ISIS NO | SEQUENCES (5'-3') |
|---|---|
| 106 (s)/351832 | AfoGmoAfoGmoCfoUmoAfoAmoAfoGmoGfoUmoGfoAmoUfo AmoAfoGmoAf |
| 107 (as)/351833 | AmoUfoAmoCfoUmoCfoAmoGfoAmoAfoGmoGfoUmoGfoUmo CfoUmoUfoCm |
| 108 (s)/351834 | GfoAmoAfoGmoAfoCmoAfoCmoCfoUmoUfoCmoUfoGmoAfo GmoUfoAmoUf |
| 109 (as)/355713 | UmoUfoUmoGfoAmoAfoAmoAfoUmoGfoUmoUfoGmoAfoUmo CfoUmoCfoCm |
| 110 (s)/355714 | GfoGmoAfoGmoAfoUmoCfoAmoAfoCmoAfoUmoUfoUmoUfo CmoAfoAmoAf |

Alternating 2'-OCH$_3$/2'-F full P = S as/s 2'-OCH$_3$/2'-F

| 147 (as)/340570 | UmsUfsUmsGfsUmsCfsUmsCfsUmsGfsGmsUfsCmsCfsUmsUfs AmsCfsUmsUf |
|---|---|
| 145 (s)/340573 | AfoAmoGfoUmoAfoAmoGfoGmoAfoCmoCfoAmoGfoAmoGfo AmoCfoAmoAfoAm |

Alternating 2'-F/2'-OH as/s RNA

| 148 (as)/344219 | UfoUUfoGUfoCUfoCUfoGGfoUCfoCUfoUAfoCUfoU |
|---|---|
| 13 (s)/308746 | AAGUAAGGACCAGAGACAAA |

Alternating 2'-OCH$_3$/2'-OH as/s alternating 2'-MOE/2'-OH

| 92 (as)/352507 | UmoUUmoGAmoAAmoAUmoGUmoUGmoAUmoCUmoCCm |
|---|---|
| 111 (s)/352514 | GGeoAGeoAUeoCAeoACeoAUeoUUeoUCeoAAeoA |

Full P = S RNA as/s alternating 2'-MOE/2'-OH

| 149 (as)/346280 | UrsUrsUrsGrsArsArsArsArsUrsGrsUrsUrsGrsArsUrsCrsUrs CrsCrsU |
|---|---|
| 111 (s)/352514 | GGeoAGeoAUeoCAeoACeoAUeoUUeoUCeoAAeoA |

Full P = S as/s alternating 2'-OH/2'-OCH$_3$ alternating P = O/P = S

| 112 (as)/346280 | UrsUrsUrsGrsArsArsArsArsUrsGrsUrsUrsGrsArsUrsCrs UrsCrsCrsU |
|---|---|
| 97 (s)/352511 | GGmoAGmoAUmoCAmoACmoAUmoUUmoUCmoAAmoA |

Alternating 2'-OCH$_3$/2'-OH as/s full P = S RNA

| 92 (as)/352507 | UmoUUmoGAmoAAmoAUmoGUmoUGmoAUmoCUmoCCm |
|---|---|
| 113 (s)/346287 | GrsGrsArsGrsArsUrsCrsArsArsCrsArsUrsUrsUrsCrsArsArsA |

Gapmers having alternating wing motifs in one or both strands
2'-OCH$_3$/2'-OH wing/RNA gap/2'-OCH$_3$/2'-OH wing
as/s full alternating 2'-OCH$_3$/2'-OH

| 114 (as-P)/353563 | UmoUGmoUCmoUCUGGUCCUUmoACmoUUm |
|---|---|
| 59 (s)/341406 | AAmoGUmoAAmoGGmoACmoCAmoGAmoGAmoCAmoA |
| 115 (as-P)/353565 | UmoGCmoUAmoGCCUCUGGAUmoUUmoGAm |
| 116 (s)/341405 | UCmoAAmoAUmoCCmoAGmoAGmoCmoUAmoGCmoA |

2'-OCH$_3$/2'-OH wing/RNA gap/2'-OCH$_3$/2'-OH wing both as and s

| 114 (as-P)/353563 | UmoUGmoUCmoUCUGGUCCUUmoACmoUUm |
|---|---|
| 117 (s)/353564 | AAmoGUmoAAGGACCAGAGAmoCAmoA |

| SEQ ID NO/ISIS NO | SEQUENCES (5'-3') |
|---|---|
| 115 (as-P)/353565 | UmoGCmoUAmoGCCUCUGGAUmoUUmoGAm |
| 118 (s)/353566 | UCmoAAmoAUCCAGAGGCUAmoGCmoA |

Example 14

Assays of Example 13 Constructs

The constructs of example 13 were tested in accordance with the assays described herein. Cell line 20 is HeLa. Cell line 160 is U-87 MG. Cell line 243 is MH-S. Cells are available from commercial sources. For example, HeLa cells can be obtained from American Type Culture Collection, Manassas Va. Culture methods used for HeLa cells are available from the ATCC and may be found, for example, at http://www.atcc.org. For cells grown in 96-well plates, wells were washed once with 200 µL OPTI-MEM-1 reduced-serum medium (Gibco BRL) and then treated with 130 µL of OPTI-MEM-1 containing 12 µg/mL LIPOFECTIN™ (Gibco BRL) and the dsRNA at the desired concentration. After 5 hours of treatment, the medium was replaced with fresh medium. Cells were harvested 16 hours after dsRNA treatment, at which time RNA was isolated and target reduction measured by RT-PCR as described in previous examples.

| Construct | Assay/Species | Target | Cell Line | IC50 (nM) |
|---|---|---|---|---|
| 335454:308746 | Dose Response/Human | PTEN | 20 | 3.31 |
| 335456:308746 | Dose Response/Human | PTEN | 20 | 0.449 |
| 344217:308746 | Dose Response/Human | PTEN | 20 | 0.597 |
| 352507:343868 | Dose Response/Human | Survivin | 20 | 1.0171 |
| 335456:335452 | Dose Response/Human | PTEN | 20 | 0.248 |
| 341396:341406 | Dose Response/Human | PTEN | 20 | 1.0316 |
| 345847:345849 | RTPCR EIF4E MH-S/Mouse | eIF4E | 243 | 0.27303 |
| 352507:352511 | Dose Response/Human | Survivin | 20 | 0.23734 |
| 352507:352511 | Dose Response/Human | Survivin | 160 | 0.37 |
| 352507:352511 | Dose Response/Human | Survivin | 20 | 0.47 |
| 352507:352512 | Dose Response/Human | Survivin | 20 | 0.039396 |
| 352507:352512 | Dose Response/Human | Survivin | 20 | 0.6 |
| 352507:352513 | Dose Response/Human | Survivin | 20 | 0.34906 |
| 344217:344221 | Dose Response/Human | PTEN | 20 | 0.674 |
| 344217:344222 | Dose Response/Human | PTEN | 20 | 0.345 |
| 339923:308746 | Dose Response/Human | PTEN | 20 | 0.466 |
| 340569:308746 | Dose Response/Human | PTEN | 20 | 0.263 |
| 340571:308746 | Dose Response/Human | PTEN | 20 | 3.32 |
| 352820:341401 | Dose Response/Human | PTEN | 20 | 1.0348 |
| 340569:340574 | Dose Response/Human | PTEN | 20 | 0.496 |
| 340571:340573 | Dose Response/Human | PTEN | 20 | 1.36 |
| 352820:352821 | Dose Response/Human | PTEN | 20 | 0.28988 |
| 351827:351828 | RTPCR EIF4E MH-S/Mouse | eIF4E | 243 | 0.054034 |
| 351829:351830 | RTPCR EIF4E MH-S/Mouse | eIF4E | 243 | 0.50058 |
| 351831:351832 | RTPCR EIF4E MH-S/Mouse | eIF4E | 243 | 0.051497 |
| 351833:351834 | RTPCR EIF4E MH-S/Mouse | eIF4E | 243 | 0.092224 |
| 355713:355714 | Dose Response/Human | Survivin | 20 | 0.064756 |
| 355713:355714 | Dose Response/Human | Survivin | 20 | 0.064756 |
| 355713:355714 | Dose Response/Human | Survivin | 20 | 078878 |
| 355713:355714 | Dose Response/Human | Survivin | 160 | 0.107 |
| 355713:355714 | Dose Response/Human | Survivin | 20 | 0.151 |
| 340570:340573 | Dose Response/Human | PTEN | 20 | 1.83 |
| 344219:308746 | Dose Response/Human | PTEN | 20 | 0.886 |
| 352507:352514 | Dose Response/Human | Survivin | 20 | 0.21038 |
| 352507:352514 | Dose Response/Human | Survivin | 160 | 0.538 |
| 352507:352514 | Dose Response/Human | Survivin | 20 | 0.547 |
| 346280:352514 | Dose Response/Human | Survivin | 20 | 1.0094 |
| 346280:352511 | Dose Response/Human | Survivin | 20 | 1.4662 |
| 352507:346287 | Dose Response/Human | Survivin | 20 | 0.42207 |
| 353563:341406 | Dose Response/Human | PTEN | 20 | 0.78421 |
| 353563:341406 | Dose Response/Human | PTEN | 20 | 0.88581 |
| 353565:341405 | Dose Response/Human | PTEN | 20 | 17.275 |
| 353563:353564 | Dose Response/Human | PTEN | 20 | 0.27194 |
| 353563:353564 | Dose Response/Human | PTEN | 20 | 5.2523 |
| 353565:353566 | Dose Response/Human | PTEN | 20 | 5.7721 |

Example 15

Synthesis of Nucleoside Phosphoramidites

The following compounds, including amidites and their intermediates were prepared as described in U.S. Pat. No. 6,426,220 and published PCT WO 02/36743; 5'-O-Dimethoxytrityl-thymidine intermediate for 5-methyl dC amidite, 5'-O-Dimethoxytrityl-2'-deoxy-5-methylcytidine intermediate for 5-methyl-dC amidite, 5'-O-Dimethoxytrityl-2'-deoxy-N4-benzoyl-5-methylcytidine penultimate intermediate for 5-methyl dC amidite, [5'-O-(4,4'-Dimethoxytriphenylmethyl)-2'-deoxy-N$^4$-benzoyl-5-methylcytidin-3'-O-yl]-2-cyanoethyl-N,N-diisopropylphosphoramidite (5-methyl dC amidite), 2'-Fluorodeoxyadenosine, 2'-Fluorodeoxyguanosine, 2'-Fluorouridine, 2'-Fluorodeoxycytidine, 2'-O-(2-Methoxyethyl) modified amidites, 2'-O-(2-methoxyethyl)-5-methyluridine intermediate, 5'-O-DMT-2'-O-(2-methoxyethyl)-5-methyluridine penultimate intermediate, [5'-O-(4,4'-Dimethoxytriphenylmethyl)-2'-O-(2-methoxyethyl)-5-methyluridin-3'-O-yl]-2-cyanoethyl-N,N-diisopropylphosphoramidite (MOE T amidite), 5'-O-Dimethoxytrityl-2'-O-(2-methoxyethyl)-5-methylcytidine intermediate, 5'-O-dimethoxytrityl-2'-O-(2-methoxyethyl)-N$^4$-benzoyl-5-methyl-cytidine penultimate intermediate, [5'-O-(4,4'-Dimethoxytriphenylmethyl)-2'-O-(2-methoxyethyl)-N$^4$-benzoyl-5-methylcytidin-3'-O-yl]-2-cyanoethyl-N,N-diisopropylphosphoramidite (MOE 5-Me-C amidite), [5'-O-(4,4'-Dimethoxytriphenylmethyl)-2'-O-(2-methoxyethyl)-N$^6$-benzoyladenosin-3'-O-yl]-2-cyanoethyl-N,N-diisopropylphosphoramidite (MOE A amdite), [5'-O-(4,4'-Dimethoxytriphenylmethyl)-2'-O-(2-methoxyethyl)-N$^4$-isobutyrylguanosin-3'-O-yl]-2-cyanoethyl-N,N-diisopropylphosphoramidite (MOE G amidite), 2'-O-(Aminooxyethyl) nucleoside amidites and 2'-O-(dimethylaminooxyethyl) nucleoside amidites, 2'-(Dimethylaminooxyethoxy) nucleoside amidites, 5'-O-tert-Butyldiphenylsilyl-O$^2$-2'-anhydro-5-methyluridine, 5'-O-tert-Butyldiphenylsilyl-2'-O-(2-hydroxyethyl)-5-methyluridine, 2'-O-([2-phthalimidoxy)ethyl]-5'-t-butyldiphenylsilyl-5-methyluridine, 5'-O-tert-butyldiphenylsilyl-2'-O-[(2-formadoximinooxy)ethyl]-5-methyluridine, 5'-O-tert-Butyldiphenylsilyl-2'-O—[N,N dimethylaminooxyethyl]-5-methyluridine, 2'-O-(dimethylaminooxyethyl)-5-methyluridine, 5'-O-DMT-2'-O-(dimethylaminooxyethyl)-5-methyluridine, 5'-O-DMT-2'-O-(2-N,N-dimethylaminooxyethyl)-5-methyluridine-3'-[(2-cyanoethyl)-N,N-diisopropylphosphoramidite], 2'-(Aminooxyethoxy) nucleoside amidites, N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite], 2'-dimethylaminoethoxyethoxy (2'-DMAEOE) nucleoside amidites, 2'-O[2(2-N,N-dimethylaminoethoxy)ethyl]-5-methyl uridine, 5'-O-dimethoxytrityl-2'-O-[2(2-N,N-dimethylaminoethoxy)-ethyl)]-5-methyl uridine and 5'-O-Dimethoxytrityl-2'-O-[2(2-N,N-dimethylaminoethoxy)-ethyl)]-5-methyl uridine-3'-O-(cyanoethyl-N,N-diisopropyl) phosphoramidite.

Example 16

Oligonucleotide and Oligonucleoside Synthesis

The oligonucleotides used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Oligonucleotides: Unsubstituted and substituted phosphodiester (P=O) oligonucleotides are synthesized on an automated DNA synthesizer (Applied Biosystems model 394) using standard phosphoramidite chemistry with oxidation by iodine.

Phosphorothioates (P=S) are synthesized similar to phosphodiester oligonucleotides with the following exceptions: thiation was effected by utilizing a 10% w/v solution of 3,H-1,2-benzodithiole-3-one 1,1-dioxide in acetonitrile for the oxidation of the phosphite linkages. The thiation reaction step time was increased to 180 sec and preceded by the normal capping step. After cleavage from the CPG column and deblocking in concentrated ammonium hydroxide at 55° C. (12-16 hr), the oligonucleotides were recovered by precipitating with >3 volumes of ethanol from a 1 M NH$_4$OAc solution. Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. No. 5,610,289 or 5,625,050, herein incorporated by reference.

Phosphoramidite oligonucleotides are prepared as described in U.S. Pat. No. 5,256,775 or 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Oligonucleosides: Methylenemethylimino linked oligonucleosides, also identified as MMI linked oligonucleosides, methyl enedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligo-nucleosides, also identified as amide-4 linked oligonucleosides, as well as mixed backbone oligonucleotides having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 17

RNA Synthesis

In general, RNA synthesis chemistry is based on the selective incorporation of various protecting groups at strategic intermediary reactions. Although one of ordinary skill in the art will understand the use of protecting groups in organic synthesis, a useful class of protecting groups includes silyl ethers. In particular bulky silyl ethers are used to protect the 5"-hydroxyl in combination with an acid-labile orthoester protecting group on the 2'-hydroxyl. This set of protecting groups is then used with standard solid-phase synthesis technology. It is important to lastly remove the acid labile orthoester protecting group after all other synthetic steps. Moreover, the early use of the silyl protecting groups during synthesis ensures facile removal when desired, without undesired deprotection of 2' hydroxyl.

Following this procedure for the sequential protection of the 5'-hydroxyl in combination with protection of the 2'-hydroxyl by protecting groups that are differentially removed and are differentially chemically labile, RNA oligonucleotides were synthesized.

RNA oligonucleotides are synthesized in a stepwise fashion. Each nucleotide is added sequentially (3'- to 5'-direction) to a solid support-bound oligonucleotide. The first nucleoside at the 3'-end of the chain is covalently attached to a solid support. The nucleotide precursor, a ribonucleoside phosphoramidite, and activator are added, coupling the second base onto the 5'-end of the first nucleoside. The support is washed and any unreacted 5'-hydroxyl groups are capped with acetic anhydride to yield 5'-acetyl moieties. The linkage is then oxidized to the more stable and ultimately desired P(V) linkage. At the end of the nucleotide addition cycle, the 5'-silyl group is cleaved with fluoride. The cycle is repeated for each subsequent nucleotide.

Following synthesis, the methyl protecting groups on the phosphates are cleaved in 30 minutes utilizing 1 M disodium-2-carbamoyl-2-cyanoethylene-1,1-dithiolate trihydrate ($S_2Na_2$) in DMF. The deprotection solution is washed from the solid support-bound oligonucleotide using water. The support is then treated with 40% methylamine in water for 10 minutes at 55° C. This releases the RNA oligonucleotides into solution, deprotects the exocyclic amines, and modifies the 2'-groups. The oligonucleotides can be analyzed by anion exchange HPLC at this stage.

The 2'-orthoester groups are the last protecting groups to be removed. The ethylene glycol monoacetate orthoester protecting group developed by Dharmacon Research, Inc. (Lafayette, Colo.), is one example of a useful orthoester protecting group which, has the following important properties. It is stable to the conditions of nucleoside phosphoramidite synthesis and oligonucleotide synthesis. However, after oligonucleotide synthesis the oligonucleotide is treated with methylamine which not only cleaves the oligonucleotide from the solid support but also removes the acetyl groups from the orthoesters. The resulting 2-ethyl-hydroxyl substituents on the orthoester are less electron withdrawing than the acetylated precursor. As a result, the modified orthoester becomes more labile to acid-catalyzed hydrolysis. Specifically, the rate of cleavage is approximately 10 times faster after the acetyl groups are removed. Therefore, this orthoester possesses sufficient stability in order to be compatible with oligonucleotide synthesis and yet, when subsequently modified, permits deprotection to be carried out under relatively mild aqueous conditions compatible with the final RNA oligonucleotide product.

Additionally, methods of RNA synthesis are well known in the art (Scaringe, S. A. Ph.D. Thesis, University of Colorado, 1996; Scaringe, S. A., et al., *J. Am. Chem. Soc.,* 1998, 120, 11820-11821; Matteucci, M. D. and Caruthers, M. H. *J. Am. Chem. Soc.,* 1981, 103, 3185-3191; Beaucage, S. L. and Caruthers, M. H. *Tetrahedron Lett.,* 1981, 22, 1859-1862; Dahl, B. J., et al., *Acta Chem. Scand.,* 1990, 44, 639-641; Reddy, M. P., et al., *Tetrahedrom Lett.,* 1994, 25, 4311-4314; Wincott, F. et al., *Nucleic Acids Res.,* 1995, 23, 2677-2684; Griffin, B. E., et al., *Tetrahedron,* 1967, 23, 2301-2313; Griffin, B. E., et al., *Tetrahedron,* 1967, 23, 2315-2331).

RNA antisense oligonucleotides (RNA oligonucleotides) of the present invention can be synthesized by the methods herein or purchased from Dharmacon Research, Inc (Lafayette, Colo.). Once synthesized, complementary RNA antisense oligonucleotides can then be annealed by methods known in the art to form double stranded (duplexed) antisense oligonucleotides. For example, duplexes can be formed by combining 30 μl of each of the complementary strands of RNA oligonucleotides (50 uM RNA oligonucleotide solution) and 15 μl of 5× annealing buffer (100 mM potassium acetate, 30 mM HEPES-KOH pH 7.4, 2 mM magnesium acetate) followed by heating for 1 minute at 90° C., then 1 hour at 37° C. The resulting duplexed antisense oligonucleotides can be used in kits, assays, screens, or other methods to investigate the role of a target nucleic acid.

Example 18

Synthesis of Chimeric Oligonucleotides

Chimeric oligonucleotides, oligonucleosides or mixed oligonucleotides/oligo-nucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligonucleotide. Oligonucleotides of the first type are also known in the art as "gapmers" or gapped oligonucleotides. Oligonucleotides of the second type are also known in the art as "hemimers" or "wingmers".

[2'-O-Me]-[2'-deoxy]-[2'-O-Me] Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 394, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by incorporating coupling steps with increased reaction times for the 5'-dimethoxytrityl-2'-O-methyl-3'-O-phosphoramidite. The fully protected oligonucleotide is cleaved from the support and deprotected in concentrated ammonia ($NH_4OH$) for 12-16 hr at 55° C. The deprotected oligo is then recovered by an appropriate method (precipitation, column chromatography, volume reduced in vacuo and analyzed spetrophotometrically for yield and for purity by capillary electrophoresis and by mass spectrometry.

[2'-O-(2-Methoxyethyl)]-[2'-deoxy]-[2'-O-(Methoxyethyl)] Chimeric Phosphorothioate Oligonucleotides

[2'-O-(2-methoxyethyl)]-[2'-deoxy]-[2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]-[2'-deoxy Phosphorothioate]-[2'-O-(2-Methoxyethyl) Phosphodiester] Chimeric Oligonucleotides

[2'-O-(2-methoxyethyl phosphodiester]-[2'-deoxy phosphorothioate]-[2'-O-(methoxyethyl) phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidation with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 19

Design and Screening of Duplexed Antisense Oligonucleotides Directed to a Selected Target In one aspect of the present invention, compositions comprising a series of nucleic acid duplexes and their complements can be designed to a particular nucleic acid target. The ends of the strands may be modified by the addition of one or more natural or modified nucleobases to form an overhang. The sense strand of these compositions is then designed and synthesized as the complement of the antisense strand and may also contain modifications or additions to either terminus. For example, in one embodiment, both strands of the complexes would be complementary over the central nucleobases, each having overhangs at one or both termini.

For example, a duplex comprising an antisense oligonucleotide having the sequence CGAGAGGCGGACGGGACCG (SEQ ID NO.: 1) and having a two-nucleobase overhang of deoxythymidine(dT) would have the following structure:

| | | SEQ ID NO. |
|---|---|---|
| cgagaggcggacgggaccgdTdT<br>\|\|\|\|\|\|\|\|\|\|\|\|\|\|\|\|\|\|\|<br>dTdTgctctccgcctgccctggc | Antisense Strand<br><br>Complement Strand | 2<br><br>3 |

RNA strands of the duplex can be synthesized by methods disclosed herein or purchased from Dharmacon Research Inc., (Lafayette, Colo.). Once synthesized, the complementary strands are annealed. The single strands are aliquoted and diluted to a concentration of 50 uM. Once diluted, 30 uL of each strand is combined with 15 uL of a 5× solution of annealing buffer. The final concentration of said buffer is 100 mM potassium acetate, 30 mM HEPES-KOH pH 7.4, and 2 mM magnesium acetate. The final volume is 75 uL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 uM. This solution can be stored frozen (−20° C.) and freeze-thawed up to 5 times.

Once prepared, the duplexed antisense oligonucleotides are evaluated for their ability to modulate a target expression.

When cells reached 80% confluency, they are treated with duplexed antisense compositions of the invention. For cells grown in 96-well plates, wells are washed once with 200 μL OPTI-MEM-1 reduced-serum medium (Gibco BRL) and then treated with 130 μL of OPTI-MEM-1 containing 12 μg/mL LIPOFECTIN (Gibco BRL) and the desired duplex antisense oligonucleotide at a final concentration of 200 nM. After 5 hours of treatment, the medium is replaced with fresh medium. Cells are harvested 16 hours after treatment, at which time RNA is isolated and target reduction measured by RT-PCR.

Example 20

Oligonucleotide Isolation

After cleavage from the controlled pore glass solid support and deblocking in concentrated ammonium hydroxide at 55° C. for 12-16 hours, the oligonucleotides or oligonucleosides are recovered by precipitation out of 1 M NH$_4$OAc with >3 volumes of ethanol. Synthesized oligonucleotides were analyzed by electrospray mass spectroscopy (molecular weight determination) and by capillary gel electrophoresis and judged to be at least 70% full length material. The relative amounts of phosphorothioate and phosphodiester linkages obtained in the synthesis was determined by the ratio of correct molecular weight relative to the −16 amu product (+/−32+/−48). For some studies oligonucleotides were purified by HPLC, as described by Chiang et al., *J. Biol. Chem.* 1991, 266, 18162-18171. Results obtained with HPLC-purified material were similar to those obtained with non-HPLC purified material.

Example 21

Oligonucleotide Synthesis—96 Well Plate Format

Oligonucleotides were synthesized via solid phase P(III) phosphoramidite chemistry on an automated synthesizer capable of assembling 96 sequences simultaneously in a 96-well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites were purchased from commercial vendors (e.g. PE-Applied Biosystems, Foster City, Calif., or Pharmacia, Piscataway, N.J.). Non-standard nucleosides are synthesized as per standard or patented methods. They are utilized as base protected beta-cyanoethyldiisopropyl phosphoramidites.

Oligonucleotides were cleaved from support and deprotected with concentrated NH$_4$OH at elevated temperature (55-60° C.) for 12-16 hours and the released product then dried in vacuo. The dried product was then re-suspended in sterile water to afford a master plate from which all analytical and test plate samples are then diluted utilizing robotic pipettors.

Example 22

Oligonucleotide Analysis Using 96-Well Plate Format

The concentration of oligonucleotide in each well was assessed by dilution of samples and UV absorption spectroscopy. The full-length integrity of the individual products was evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition was confirmed by mass analysis of the oligonucleotides utilizing electrospray-mass spectroscopy. All assay test plates were diluted from the master plate using single and multi-channel robotic pipettors. Plates were judged to be acceptable if at least 85% of the oligonucleotides on the plate were at least 85% full length.

Example 23

Cell Culture and Oligonucleotide Treatment

The effect of oligonucleotides on target nucleic acid expression can be tested in any of a variety of cell types provided that the target nucleic acid is present at measurable levels. This can be routinely determined using, for example, PCR or Northern blot analysis. The following cell types are provided for illustrative purposes, but other cell types can be routinely used, provided that the target is expressed in the cell type chosen. This can be readily determined by methods routine in the art, for example Northern blot analysis, ribonuclease protection assays, or RT-PCR.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media (Invitrogen Corporation, Carlsbad, Calif. or Gibco/Life Technologies, Gaithersburg, Md.) supplemented with 10% fetal calf serum (Invitrogen Corporation, Carlsbad, Calif. or Gibco/Life Technologies, Gaithersburg, Md.), penicillin 100 units per mL, and streptomycin 100 micrograms per mL (Invitrogen Corporation, Carlsbad, Calif. or Gibco/Life Technologies, Gaithersburg, Md.). Cells were routinely passaged by trypsinization and dilution when they reached 90% confluence. Cells were seeded into 96-well plates (Falcon-Primaria #353872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells:

The human lung carcinoma cell line A549 was obtained from the American Type Culture Collection (ATCC) (Manassas, Va.). A549 cells were routinely cultured in DMEM basal media (Invitrogen Corporation, Carlsbad, Calif. or Gibco/Life Technologies, Gaithersburg, Md.) supplemented with 10% fetal calf serum (Invitrogen Corporation, Carlsbad, Calif. or Gibco/Life Technologies, Gaithersburg, Md.), penicillin 100 units per mL, and streptomycin 100 micrograms per mL (Invitrogen Corporation, Carlsbad, Calif. or Gibco/Life Technologies, Gaithersburg, Md.). Cells were routinely passaged by trypsinization and dilution when they reached 90% confluence.

NHDF Cells:

Human neonatal dermal fibroblast (NHDF) were obtained from the Clonetics Corporation (Walkersville, Md.). NHDFs were routinely maintained in Fibroblast Growth Medium (Clonetics Corporation, Walkersville, Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville, Md.). HEKs were routinely maintained in Keratinocyte Growth Medium (Clonetics Corporation, Walkersville, Md.) formulated as recommended by the supplier. Cells were routinely maintained for up to 10 passages as recommended by the supplier.

3T3-L1 Cells:

The mouse embryonic adipocyte-like cell line 3T3-L1 was obtained from the American Type Culture Collection (Manassas, Va.). 3T3-L1 cells were routinely cultured in DMEM, high glucose (Gibco/Life Technologies, Gaithersburg, Md.) supplemented with 10% fetal calf serum (Gibco/Life Technologies, Gaithersburg, Md.). Cells were routinely passaged by trypsinization and dilution when they reached 80% confluence. Cells were seeded into 96-well plates (Falcon-Primaria #3872) at a density of 4000 cells/well for use in RT-PCR analysis.

For Northern blotting or other analyses, cells may be seeded onto 100 mm or other standard tissue culture plates and treated similarly, using appropriate volumes of medium and oligonucleotide.

Treatment with Oligonucleotides:

When cells reached 65-80% confluency, they were treated with oligonucleotide. For cells grown in 96-well plates, wells were washed once with 100 μL OPTI-MEM™-1 reduced-serum medium (Invitrogen Corporation, Carlsbad, Calif.) and then treated with 130 μL of OPTI-MEM™-1 containing 3.75 μg/mL LIPOFECTIN™ (Invitrogen Corporation, Carlsbad, Calif.) and the desired concentration of oligonucleotide. Cells are treated and data are obtained in triplicate. After 4-7 hours of treatment at 37° C., the medium was replaced with fresh medium. Cells were harvested 16-24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is selected from either ISIS 13920 (TCCGT-CATCGCTCCTCAGGG, SEQ ID NO: 150) which is targeted to human H-ras, or ISIS 18078, (GTGCGCGCGAGCCCGAAATC, SEQ ID NO: 151) which is targeted to human Jun-N-terminal kinase-2 (JNK2). Both controls are 2'-O-methoxyethyl gapmers (2'-O-methoxyethyls shown in bold) with a phosphorothioate backbone. For mouse or rat cells the positive control oligonucleotide is ISIS 15770, ATGCATTCTGC-CCC-CAAGGA, SEQ ID NO: 152, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-H-ras (for ISIS 13920), JNK2 (for ISIS 18078) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of c-H-ras, JNK2 or c-raf mRNA is then utilized as the oligonucleotide screening concentration in subsequent experiments for that cell line. If 60% inhibition is not achieved, that particular cell line is deemed as unsuitable for oligonucleotide transfection experiments. The concentrations of antisense oligonucleotides used herein are from 50 nM to 300 nM.

Example 24

Analysis of Oligonucleotide Inhibition of a Target Expression

Antisense modulation of a target expression can be assayed in a variety of ways known in the art. For example, a target mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. The preferred method of RNA analysis of the present invention is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of a target can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. See, for example, Ausubel, F. M. et al., *Current Protocols in Molecular Biology*, Volume 2, pp. 11.12.1-11.12.9, John Wiley & Sons, Inc., 1997. Preparation of monoclonal antibodies is taught in, for example, Ausubel, F. M. et al., *Current Protocols in Molecular Biology*, Volume 2, pp. 11.4.1-11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1-10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1-10.8.21, John Wiley & Sons, Inc., 1997. Enzyme-linked immunosorbent assays (ELISA) are standard in the art and can be found at, for example, Ausubel, F. M. et al., *Current Protocols in Molecular Biology*, Volume 2, pp. 11.2.1-11.2.22, John Wiley & Sons, Inc., 1991.

Example 25

Design of Phenotypic Assays and In Vivo Studies for the Use of Target Inhibitors Phenotypic Assays Once a target inhibitors have been identified by the methods disclosed herein, the oligonucleotides are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of a target in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with a target inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Analysis of the geneotype of the cell (measurement of the expression of one or more of the genes of the cell) after treatment is also used as an indicator of the efficacy or potency of the a target inhibitors. Hallmark genes, or those genes suspected to be associated with a specific disease state, condition, or phenotype, are measured in both treated and untreated cells.

In Vivo Studies

The individual subjects of the in vivo studies described herein are warm-blooded vertebrate animals, which includes humans.

The clinical trial is subjected to rigorous controls to ensure that individuals are not unnecessarily put at risk and that they are fully informed about their role in the study.

To account for the psychological effects of receiving treatments, volunteers are randomly given placebo or a target inhibitor. Furthermore, to prevent the doctors from being biased in treatments, they are not informed as to whether the medication they are administering is a a target inhibitor or a placebo. Using this randomization approach, each volunteer has the same chance of being given either the new treatment or the placebo.

Volunteers receive either the a target inhibitor or placebo for eight week period with biological parameters associated with the indicated disease state or condition being measured at the beginning (baseline measurements before any treatment), end (after the final treatment), and at regular intervals during the study period. Such measurements include the levels of nucleic acid molecules encoding a target or a target protein levels in body fluids, tissues or organs compared to pre-treatment levels. Other measurements include, but are not limited to, indices of the disease state or condition being treated, body weight, blood pressure, serum titers of pharmacologic indicators of disease or toxicity as well as ADME (absorption, distribution, metabolism and excretion) measurements. Information recorded for each patient includes age (years), gender, height (cm), family history of disease state or condition (yes/no), motivation rating (some/moderate/great) and number and type of previous treatment regimens for the indicated disease or condition.

Volunteers taking part in this study are healthy adults (age 18 to 65 years) and roughly an equal number of males and females participate in the study. Volunteers with certain characteristics are equally distributed for placebo and a target inhibitor treatment. In general, the volunteers treated with placebo have little or no response to treatment, whereas the volunteers treated with the a target inhibitor show positive trends in their disease state or condition index at the conclusion of the study.

Example 26

RNA Isolation
Poly(A)+ mRNA Isolation

Poly(A)+ mRNA was isolated according to Miura et al., (*Clin. Chem.*, 1996, 42, 1758-1764). Other methods for poly(A)+ mRNA isolation are routine in the art. Briefly, for cells grown on 96-well plates, growth medium was removed from the cells and each well was washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 µL of lysate was transferred to Oligo d(T) coated 96-well plates (AGCT Inc., Irvine Calif.). Plates were incubated for 60 minutes at room temperature, washed 3 times with 200 µL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 µL of elution buffer (5 mM Tris-HCl pH 7.6), preheated to 70° C., was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Total RNA Isolation

Total RNA was isolated using an RNEASY 96™ kit and buffers purchased from Qiagen Inc. (Valencia, Calif.) following the manufacturer's recommended procedures. Briefly, for cells grown on 96-well plates, growth medium was removed from the cells and each well was washed with 200 µL cold PBS. 150 µL Buffer RLT was added to each well and the plate vigorously agitated for 20 seconds. 150 µL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 1 minute. 500 µL of Buffer RW1 was added to each well of the RNEASY 96™ plate and incubated for 15 minutes and the vacuum was again applied for 1 minute. An additional 500 µL of Buffer RW1 was added to each well of the RNEASY 96™ plate and the vacuum was applied for 2 minutes. 1 mL of Buffer RPE was then added to each well of the RNEASY 96™ plate and the vacuum applied for a period of 90 seconds. The Buffer RPE wash was then repeated and the vacuum was applied for an additional 3 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 140 µL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 27

Real-Time Quantitative PCR Analysis of a Target mRNA Levels

Quantitation of a target mRNA levels was accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from Invitrogen Corporation, (Carlsbad, Calif.). RT-PCR reactions were carried out by adding 20 µl PCR cocktail (2.5×PCR buffer minus $MgCl_2$, 6.6 mM $MgCl_2$, 375 µM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30 µl total RNA solution (20-200 ng). The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen (Molecular Probes, Inc. Eugene, Oreg.). GAPDH expression is quantified by real time RT-PCR, by being run simultaneously with the target, multiplexing, or separately. Total RNA is quantified using RiboGreen RNA quantification reagent (Molecular Probes, Inc. Eugene, Oreg.). Methods of RNA quantification by RiboGreen are taught in Jones, L. J., et al, (Analytical Biochemistry, 1998, 265, 368-374).

In this assay, 170 μL of RiboGreen™ working reagent (RiboGreen™ reagent diluted 1:350 in 10 mM Tris-HCl, 1 mM EDTA, pH 7.5) is pipetted into a 96-well plate containing 30 μL purified, cellular RNA. The plate is read in a CytoFluor 4000 (PE Applied Biosystems) with excitation at 485 nm and emission at 530 nm.

Probes and are designed to hybridize to a human a target sequence, using published sequence information.

Concerning Survivin as the target, PCR reagents were obtained from PE-Applied Biosystems, Foster City, Calif. RT-PCR reactions were carried out by adding 25 μL PCR cocktail (1×TAQMAN buffer A, 5.5 mM MgCl$_2$, 300 μM each of dATP, dCTP and dGTP, 600 μM of dUTP, 100 nM each of forward primer, reverse primer, and probe, 20 Units RNAse inhibitor, 1.25 Units AMPLITAQ GOLD, and 12.5 Units MuLV reverse transcriptase) to 96 well plates containing 25 μl, poly(A) mRNA solution. The RT reaction was carried out by incubation for 30 minutes at 48° C. Following a 10 minute incubation at 95° C. to activate the AMPLITAQ GOLD, 40 cycles of a two-step PCR protocol were carried out: 95° C. for 15 seconds (denaturation) followed by 60° C. for 1.5 minutes (annealing/extension). Probes and primers to human Survivin were designed to hybridize to a human Survivin sequence, using published sequence information (GenBank accession number U75285, incorporated herein as SEQ ID NO: 153). For human Survivin the PCR primers were:
forward primer: AAGGACCACCGCATCTCTACA (SEQ ID NO: 154)
reverse primer: CCAAGTCTGGCTCGTTCTCAGT (SEQ ID NO: 5) and the PCR probe was: FAM-CGAGGCTGGCTTCATCCACTGCC-TAMRA (SEQ ID NO: 6) where FAM (PE-Applied Biosystems, Foster City, Calif.) is the fluorescent reporter dye and TAMRA (PE-Applied Biosystems, Foster City, Calif.) is the quencher dye. For human GAPDH the PCR primers were:
forward primer: GAAGGTGAAGGTCGGAGTC (SEQ ID NO: 7)
reverse primer: GAAGATGGTGATGGGATTTC (SEQ ID NO: 155) and the PCR probe was: 5' JOE-CAAGCTTCCCGTTCTCAGCC-TAMRA 3' (SEQ ID NO: 156) where JOE (PE-Applied Biosystems, Foster City, Calif.) is the fluorescent reporter dye and TAMRA (PE-Applied Biosystems, Foster City, Calif.) is the quencher dye.

Example 28

Northern Blot Analysis of a Target mRNA Levels

Eighteen hours after antisense treatment, cell monolayers were washed twice with cold PBS and lysed in 1 mL RNAZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then probed using QUICKHYB™ hybridization solution (Stratagene, La Jolla, Calif.) using manufacturer's recommendations for stringent conditions.

To detect human a target, a human a target specific primer probe set is prepared by PCR To normalize for variations in loading and transfer efficiency membranes are stripped and probed for human glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

To detect human Survivin, for example, a human Survivin specific probe was prepared by PCR using the forward primer AAGGACCACCGCATCTCTACA (SEQ ID NO: 157) and the reverse primer CCAAGTCTGGCTCGTTCTCAGT (SEQ ID NO: 5). To normalize for variations in loading and transfer efficiency membranes were stripped and probed for human glyceraldehyde-3-phosphate dehydrogenase (GAPDH) RNA (Clontech, Palo Alto, Calif.).

Example 29

Inhibition of Human a Target Expression by Oligonucleotides

In accordance with the present invention, a series of compositions are designed to target different regions of the human target RNA. The oligonucleotides are analyzed for their effect on human target mRNA levels by quantitative real-time PCR as described in other examples herein. Data are averages from three experiments. The target regions to which these preferred sequences are complementary are herein referred to as "preferred target segments" and are therefore preferred for targeting by compositions of the present invention. The sequences represent the reverse complement of the preferred compositions.

As these "preferred target segments" have been found by experimentation to be open to, and accessible for, hybridization with the compositions of the present invention, one of skill in the art will recognize or be able to ascertain, using no more than routine experimentation, further embodiments of the invention that encompass other compositions that specifically hybridize to these preferred target segments and consequently inhibit the expression of a target.

According to the present invention, compositions include antisense oligonucleotides, antisense oligonucleotides, asRNA's (single strand that may include a double stranded region), siRNA's (double stranded or single stranded with a double stranded region), ribozymes, external guide sequence (EGS) oligonucleotides, alternate splicers, primers, probes, and other short oligonucleotides which hybridize to at least a portion of the target nucleic acid.

Example 30

Modulation of Human Survivin Expression by Double Stranded RNA (dsRNA)

In accordance with the present invention, a series of double stranded oligomeric compounds comprising the antisense compounds of the present invention and their complements thereof, were designed to target survivin mRNA. The oligomeric compounds were evaluated in HeLa cells. Culture methods used for HeLa cells are found, for example, at http://www.atcc.org.

For cells grown in 96-well plates, wells were washed once with 200 µL OPTI-MEM-1™ reduced-serum medium (Gibco BRL) and then treated with 130 µL of OPTI-MEM-1™ containing 12 µg/mL LIPOFECTIN™ (Gibco BRL) and the desired dsRNA at a final concentration of 25 nM. After 5 hours of treatment, the medium was replaced with fresh medium. Cells were harvested 16 hours after dsRNA treatment, at which time RNA was isolated and target reduction measured by RT-PCR.

Prior to treatment of the HeLa cells, the dsRNA oligomers were generated by annealing the antisense and sense strands according to the method outlined herein and known to those skilled in the art.

Example 31

Western Blot Analysis of Target Protein Levels

Western blot analysis (immunoblot analysis) is carried out using standard methods. Cells are harvested 16-20 h after treatment with oligomeric compounds or compositions of the invention, washed once with PBS, suspended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to a target is used, with a radiolabeled or fluorescently labeled secondary antibody directed against the primary antibody species. Bands are visualized using a PHOSPHORIMAGER™ (Molecular Dynamics, Sunnyvale Calif.).

Example 32

Design and Screening of Duplexed Antisense Compounds Targeting Survivin

In accordance with the present invention, a series of nucleic acid duplexes comprising the antisense compounds of the present invention and their complements can be designed to target survivin. The nucleobase sequence of the antisense strand of the duplex comprises at least a portion of an oligonucleotide to survivin as described herein. The ends of the strands may be modified by the addition of one or more natural or modified nucleobases to form an overhang. The sense strand of the dsRNA is then designed and synthesized as the complement of the antisense strand and may also contain modifications or additions to either terminus. For example, in one embodiment, both strands of the dsRNA duplex would be complementary over the central nucleobases, each having overhangs at one or both termini.

For example, a duplex comprising an antisense strand having the sequence CGAGAGGCGGACGGGACCG (SEQ ID NO: 1) and having a two-nucleobase overhang of deoxythymidine(dT) would have the following structure:

```
                                         SEQ
                                         ID NO.
cgagaggcggacgggaccgdTdT  Antisense Strand  2
|||||||||||||||||||
dTdTgctctccgcctgccctggc  Complement        3
                         Strand
```

In another embodiment, a duplex comprising an antisense strand having the same sequence CGAGAGGCGGACGGGACCG (SEQ ID NO: 10) may be prepared with blunt ends (no single stranded overhang) as shown:

```
cgagaggcggacgggaccg  Antisense Strand 1
|||||||||||||||||||
gctctccgcctgccctggc  Complement Strand 4
```

RNA strands of the duplex can be synthesized by methods disclosed herein or purchased from Dharmacon Research Inc., (Lafayette, Colo.). Once synthesized, the complementary strands are annealed. The single strands are aliquoted and diluted to a concentration of 50 uM. Once diluted, 30 uL of each strand is combined with 15 uL of a 5x solution of annealing buffer. The final concentration of said buffer is 100 mM potassium acetate, 30 mM HEPES-KOH pH 7.4, and 2 mM magnesium acetate. The final volume is 75 uL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 uM. This solution can be stored frozen (−20° C.) and freeze-thawed up to 5 times.

Once prepared, the duplexed antisense compounds are evaluated for their ability to modulate survivin expression according to the protocols described herein.

Example 33

Representative Cell Lines

MCF-7 Cells

The human breast carcinoma cell line MCF-7 is obtained from the American Type Culture Collection (Manassas, Va.). These cells contain a wild-type p53 gene. MCF-7 cells are routinely cultured in DMEM low glucose (Gibco/Life Technologies, Gaithersburg, Md.) supplemented with 10% fetal calf serum (Gibco/Life Technologies, Gaithersburg, Md.). Cells are routinely passaged by trypsinization and dilution when they reach 90% confluence. Cells are seeded into 96-well plates (Falcon-Primaria #3872) at a density of 7000 cells/well for treatment with the compositions of the invention.

HepB3 Cells

The human hepatoma cell line HepB3 (Hep3B2.1-7) is obtained from the American Type Culture Collection (ATCC-ATCC Catalog # HB-8064) (Manassas, Va.). This cell line was initially derived from a hepatocellular carcinoma of an 8-yr-old black male. The cells are epithelial in morphology and are tumorigenic in nude mice. HepB3 cells are routinely cultured in Minimum Essential Medium (MEM) with Earle's Balanced Salt Solution, 2 mM L-glutamine, 1.5 g/L sodium bicarbonate, 0.1 mM nonessential amino acids, 1.0 mM sodium pyruvate (ATCC #20-2003, Manassas, Va.) and with 10% heat-inactivated fetal bovine serum (Gibco/Life Technologies, Gaithersburg, Md.). Cells are routinely passaged by trypsinization and dilution when they reach 90% confluence.

T-24 Cells

The transitional cell bladder carcinoma cell line T-24 is obtained from the American Type Culture Collection (ATCC) (Manassas, Va.). T-24 cells are routinely cultured in complete McCoy's 5A basal media (Gibco/Life Technologies, Gaithersburg, Md.) supplemented with 10% fetal calf serum (Gibco/Life Technologies, Gaithersburg, Md.), penicillin 100 units per mL, and streptomycin 100 µg/mL (Gibco/Life Technologies, Gaithersburg, Md.). Cells are routinely passaged by trypsinization and dilution when they reach 90% confluence. Cells are seeded into 96-well plates (Falcon-Primaria #3872) at a density of 7000 cells/well for treatment with the compound of the invention.

A549 Cells

The human lung carcinoma cell line A549 is obtained from the American Type Culture Collection (ATCC) (Manassas, Va.). A549 cells are routinely cultured in DMEM basal media (Gibco/Life Technologies, Gaithersburg, Md.) supplemented with 10% fetal calf serum (Gibco/Life Technologies, Gaithersburg, Md.), penicillin 100 units per mL, and streptomycin 100 µg/mL (Gibco/Life Technologies, Gaithersburg, Md.). Cells are routinely passaged by trysinization and dilution when they reach 90% confluence. Cells are seeded into 96-well plates (Falcon-Primaria #3872) at a density of 7000 cells/well for treatment with the compound of the invention.

Primary Mouse Hepatocytes

Primary mouse hepatocytes are prepared from CD-1 mice purchased from Charles River Labs. Primary mouse hepatocytes are routinely cultured in Hepatocyte Attachment Media (Invitrogen Life Technologies, Carlsbad, Calif.) supplemented with 10% Fetal Bovine Serum (Invitrogen Life Technologies, Carlsbad, Calif.), 250 nM dexamethasone (Sigma-Aldrich Corporation, St. Louis, Mo.), 10 nM bovine insulin (Sigma-Aldrich Corporation, St. Louis, Mo.). Cells are seeded into 96-well plates (Falcon-Primaria #353872, BD Biosciences, Bedford, Mass.) at a density of 4000-6000 cells/well for treatment with the compositions of the invention.

Example 34

Liposome-Mediated Treatment with Compositions of the Invention

When cells reach the desired confluency, they can be treated with the compositions of the invention by liposome-mediated transfection. For cells grown in 96-well plates, wells are washed once with 200 µL OPTI-MEM™-1 reduced-serum medium (Gibco BRL) and then treated with 100 µL of OPTI-MEM™-1 containing 2.5 µg/mL LIPOFECTIN™ (Gibco BRL) and the compositions of the invention at the desired final concentration. After 4 hours of treatment, the medium is replaced with fresh medium. Cells are harvested 16 hours after treatment with the compositions of the invention for target mRNA expression analysis by real-time PCR.

Example 35

Electroporation-Mediated Treatment with Compositions of the Invention

When the cells reach the desired confluency, they can be treated with the compositions of the invention by electorporation. Cells are electroporated in the presence of the desired concentration of an oligonucleotide of the invention in 1 mm cuvettes at a density of $1 \times 10^7$ cells/mL, a voltage of 75V and a pulse length of 6 ms. Following the delivery of the electrical pulse, cells are replated for 16 to 24 hours. Cells are then harvested for target mRNA expression analysis by real-time PCR.

Example 36

Apoptosis Assay

Caspase-3 activity is evaluated with an fluorometric HTS Caspase-3 assay (Oncogene Research Products, San Diego, Calif.) that detects cleavage after aspartate residues in the peptide sequence (DEVD). The DEVD substrate is labeled with a fluorescent molecule, which exhibits a blue to green shift in fluorescence upon cleavage. Active caspase-3 in treated cells is measured by this assay according to the manufacturer's instructions. Following treatment with the compositions of the invention, 50 µL of assay buffer is added to each well, followed by addition 20 µL of the caspase-3 fluorescent substrate conjugate. Data are obtained in triplicate. Fluorescence in wells is immediately detected (excitation/emission 400/505 nm) using a fluorescent plate reader (SpectraMAX GeminiXS, Molecular Devices, Sunnyvale, Calif.). The plate is covered and incubated at 37° C. for an additional three hours, after which the fluorescence is again measured (excitation/emission 400/505 nm). The value at time zero is subtracted from the measurement obtained at 3 hours. The measurement obtained from the untreated control cells is designated as 100% activity.

Example 37

Cell Proliferation and Viability Assay

Cell viability and proliferation are measured using the CyQuant Cell Proliferation Assay Kit (Molecular Probes, Eugene, Oreg.) utilizing the CyQuant GR green fluorescent dye which exhibits strong fluorescence enhancement when bound to cellular nucleic acids. The assay is performed according to the manufacturer's instructions. After the treatment with one or more compositions of the invention, the microplate is gently inverted to remove the medium from the wells, which are each washed once with 200 µL of phosphate-buffered saline. Plates are frozen at −70° C. and then thawed. A volume of 200 µL of the CyQUANT GR dye/cell-lysis buffer is added to each well. The microplate is incubated for 5 minutes at room temperature, protected from light. Data are obtained in triplicate. Fluorescence in wells is immediately detected (excitation/emission 480/520 nm) using a fluorescent plate reader (SpectraMAX GeminiXS, Molecular Devices, Sunnyvale, Calif.). The measurement obtained from the untreated control cells is designated as 100% activity.

Example 38

Leptin-Deficient Mice: A Model of Obesity and Diabetes (Ob/Ob Mice)

Leptin is a hormone produced by fat that regulates appetite. Deficiencies in this hormone in both humans and non-human animals leads to obesity. ob/ob mice have a mutation in the leptin gene which results in obesity and hyperglycemia. As such, these mice are a useful model for the investigation of obesity and diabetes and treatments designed to treat these conditions. ob/ob mice have higher circulating levels of insulin and are less hyperglycemic than db/db mice, which harbor a mutation in the leptin receptor. In accordance with the present invention, the compositions of the invention are tested in the ob/ob model of obesity and diabetes.

Seven-week old male C57Bl/6J-Lepr ob/ob mice (Jackson Laboratory, Bar Harbor, Me.) are fed a diet with a fat content of 10-15% and are subcutaneously injected with the compositions of the invention or a control compound at a dose of 25 mg/kg two times per week for 4 weeks. Saline-injected animals, leptin wildtype littermates (i.e. lean littermates) and ob/ob mice fed a standard rodent diet serve as controls. After the treatment period, mice are sacrificed and target levels are evaluated in liver, brown adipose tissue (BAT) and white adipose tissue (WAT). RNA isolation and target mRNA expression level quantitation are performed as described by other examples herein.

To assess the physiological effects resulting from inhibition of target mRNA, the ob/ob mice are further evaluated at the end of the treatment period for serum lipids, serum free fatty acids, serum cholesterol (CHOL), liver triglycerides, fat tissue triglycerides and liver enzyme levels. Hepatic steatosis, or clearing of lipids from the liver, is assessed by measuring the liver triglyceride content. Hepatic steatosis is assessed by routine histological analysis of frozen liver tissue sections stained with oil red O stain, which is commonly used to visualize lipid deposits, and counterstained with hematoxylin and eosin, to visualize nuclei and cytoplasm, respectively.

The effects of target inhibition on glucose and insulin metabolism are evaluated in the ob/ob mice treated with the compositions of the invention. Plasma glucose is measured at the start of the treatment and after 2 weeks and 4 weeks of treatment. Plasma insulin is similarly measured at the beginning of the treatment, and following at 2 weeks and at 4 weeks of treatment. Glucose and insulin tolerance tests are also administered in fed and fasted mice. Mice receive intraperitoneal injections of either glucose or insulin, and the blood glucose and insulin levels are measured before the insulin or glucose challenge and at 15, 20 or 30 minute intervals for up to 3 hours.

To assess the metabolic rate of ob/ob mice treated with the compositions of the invention, the respiratory quotient and oxygen consumption of the mice are also measured.

The ob/ob mice that received treatment are further evaluated at the end of the treatment period for the effects of target inhibition on the expression genes that participate in lipid metabolism, cholesterol biosynthesis, fatty acid oxidation, fatty acid storage, gluconeogenesis and glucose metabolism. These genes include, but are not limited to, HMG-CoA reductase, acetyl-CoA carboxylase 1 and acetyl-CoA carboxylase 2, carnitine palmitoyltransferase I and glycogen phosphorylase, glucose-6-phosphatase and phosphoenolpyruvate carboxykinase 1, lipoprotein lipase and hormone sensitive lipase. mRNA levels in liver and white and brown adipose tissue are quantitated by real-time PCR as described in other examples herein, employing primer-probe sets that are generated using published sequences of each gene of interest.

Example 39

Leptin Receptor-Deficient Mice: A Model of Obesity and Diabetes (Db/Db Mice)

Leptin is a hormone produced by fat that regulates appetite. Deficiencies in this hormone in both humans and non-human animals leads to obesity. db/db mice have a mutation in the leptin receptor gene which results in obesity and hyperglycemia. As such, these mice are a useful model for the investigation of obesity and diabetes and treatments designed to treat these conditions. db/db mice, which have lower circulating levels of insulin and are more hyperglycemic than ob/ob mice which harbor a mutation in the leptin gene, are often used as a rodent model of type 2 diabetes. In accordance with the present invention, oligonucleotides of the present invention are tested in the db/db model of obesity and diabetes.

Seven-week old male C57Bl/6J-Lepr db/db mice (Jackson Laboratory, Bar Harbor, Me.) are fed a diet with a fat content of 15-20% and are subcutaneously injected with one or more of the compositions of the invention or a control compound at a dose of 25 mg/kg two times per week for 4 weeks. Saline-injected animals, leptin receptor wildtype littermates (i.e. lean littermates) and db/db mice fed a standard rodent diet serve as controls. After the treatment period, mice are sacrificed and target levels are evaluated in liver, brown adipose tissue (BAT) and white adipose tissue (WAT). RNA isolation and target mRNA expression level quantitation are performed as described by other examples herein.

After the treatment period, mice are sacrificed and target levels are evaluated in liver, brown adipose tissue (BAT) and white adipose tissue (WAT). RNA isolation and target mRNA expression level quantitation are performed as described by other examples herein.

To assess the physiological effects resulting from inhibition of target mRNA, the db/db mice that receive treatment are further evaluated at the end of the treatment period for serum lipids, serum free fatty acids, serum cholesterol (CHOL), liver triglycerides, fat tissue triglycerides and liver enzyme levels. Hepatic steatosis, or clearing of lipids from the liver, is assessed by measuring the liver triglyceride content. Hepatic steatosis is also assessed by routine histological analysis of frozen liver tissue sections stained with oil red O stain, which is commonly used to visualize lipid deposits, and counterstained with hematoxylin and eosin, to visualize nuclei and cytoplasm, respectively.

The effects of target inhibition on glucose and insulin metabolism are also evaluated in the db/db mice treated with the compositions of the invention. Plasma glucose is measured at the start of the treatment and after 2 weeks and 4 weeks of treatment. Plasma insulin is similarly measured at the beginning of the treatment, and following 2 weeks and 4 weeks of treatment. Glucose and insulin tolerance tests are also administered in fed and fasted mice. Mice receive intraperitoneal injections of either glucose or insulin, and the blood glucose levels are measured before the insulin or glucose challenge and 15, 30, 60, 90 and 120 minutes following the injection.

To assess the metabolic rate of db/db mice treated with the compositions of the invention, the respiratory quotient and oxygen consumption of the mice is also measured.

The db/db mice that receive treatment are further evaluated at the end of the treatment period for the effects of target inhibition on the expression genes that participate in lipid metabolism, cholesterol biosynthesis, fatty acid oxidation, fatty acid storage, gluconeogenesis and glucose metabolism. These genes include, but are not limited to, HMG-CoA reductase, acetyl-CoA carboxylase 1 and acetyl-CoA carboxylase 2, carnitine palmitoyltransferase I and glycogen phosphorylase, glucose-6-phosphatase and phosphoenolpyruvate carboxykinase 1, lipoprotein lipase and hormone sensitive lipase. mRNA levels in liver and white and brown adipose tissue are quantitated by real-time PCR as described in other examples herein, employing primer-probe sets that are generated using published sequences of each gene of interest.

Example 40

Lean Mice on a Standard Rodent Diet

C57Bl/6 mice are maintained on a standard rodent diet and are used as control (lean) animals. In a further embodiment of the present invention, the compositions of the invention are tested in normal, lean animals.

Seven-week old male C57Bl/6 mice are fed a diet with a fat content of 4% and are subcutaneously injected with one or more of the compositions of the invention or control compounds at a dose of 25 mg/kg two times per week for 4 weeks. Saline-injected animals serve as a control. After the treatment period, mice are sacrificed and target levels are evaluated in liver, brown adipose tissue (BAT) and white adipose tissue (WAT). RNA isolation and target mRNA expression level quantitation are performed as described by other examples herein.

After the treatment period, mice are sacrificed and target levels are evaluated in liver, brown adipose tissue (BAT) and white adipose tissue (WAT). RNA isolation and target mRNA expression level quantitation are performed as described by other examples herein.

To assess the physiological effects resulting from inhibition of target mRNA, the lean mice that receive treatment are further evaluated at the end of the treatment period for serum lipids, serum free fatty acids, serum cholesterol (CHOL), liver triglycerides, fat tissue triglycerides and liver enzyme levels. Hepatic steatosis, or clearing of lipids from the liver, is assessed by measuring the liver triglyceride content. Hepatic steatosis is also assessed by routine histological analysis of frozen liver tissue sections stained with oil red O stain, which is commonly used to visualize lipid deposits, and counterstained with hematoxylin and eosin, to visualize nuclei and cytoplasm, respectively.

The effects of target inhibition on glucose and insulin metabolism are also evaluated in the lean mice treated with the compositions of the invention. Plasma glucose is measured at the start of the treatment and after 2 weeks and 4 weeks of treatment. Plasma insulin is similarly measured at the beginning of the treatment, and following 2 weeks and 4 weeks of treatment. Glucose and insulin tolerance tests are also administered in fed and fasted mice. Mice receive intraperitoneal injections of either glucose or insulin, and the blood glucose levels are measured before the insulin or glucose challenge and 15, 30, 60, 90 and 120 minutes following the injection.

To assess the metabolic rate of lean mice treated with the compositions of the invention, the respiratory quotient and oxygen consumption of the mice is also measured.

The lean mice that received treatment are further evaluated at the end of the treatment period for the effects of target inhibition on the expression genes that participate in lipid metabolism, cholesterol biosynthesis, fatty acid oxidation, fatty acid storage, gluconeogenesis and glucose metabolism. These genes include, but are not limited to, HMG-CoA reductase, acetyl-CoA carboxylase 1 and acetyl-CoA carboxylase 2, carnitine palmitoyltransferase I and glycogen phosphorylase, glucose-6-phosphatase and phosphoenolpyruvate carboxykinase 1, lipoprotein lipase and hormone sensitive lipase. mRNA levels in liver and white and brown adipose tissue are quantitated by real-time PCR as described in other examples herein, employing primer-probe sets that are generated using published sequences of each gene of interest.

Example 41

Chemically Modified siRNA Targeted to PTEN: In Vivo Study

Six- to seven-week old Balb/c mice (Jackson Laboratory, Bar Harbor, Me.) were injected with compounds targeted to PTEN. Each treatment group was comprised of four animals. Animals were dosed via intraperitoneal injection twice per day for 4.5 days, for a total of 9 doses per animal. Saline-injected animals served as negative controls. Animals were sacrificed 6 hours after the last dose of oligonucleotide was administered, and plasma samples and tissues were harvested. Target reduction in liver was also measured at the conclusion of the study.

Two doses of each treatment were tested. Treatment with ISIS 116847 (5'-CTGCTAGCCTCTGGATTTGA-3', SEQ ID NO: 119), a 5-10-5 gapmer was administered at doses of 12.5 mg/kg twice daily or at 6.25 mg/kg twice daily. The siRNA compounds described below were administered at doses of 25 mg/kg twice daily or 6.25 mg/kg twice daily. Each siRNA is composed of an antisense and complement strand as described in previous examples, with the antisense strand targeted to mouse PTEN. ISIS 116847 and all of the siRNAs of this experiment also have perfect complementarity with human PTEN.

An siRNA duplex targeted to PTEN 15 comprised of antisense strand ISIS 341391 (5'-UUGUCUCUGGUCC-UUACUU-3', SEQ ID NO: 120) and the sense strand ISIS 341401 (5'-AAGUAAGGACCAGAGACAA-3', SEQ ID NO: 121). Both strands of the ISIS 341391/341401 duplex are comprised of ribonucleosides with phosphodiester internucleoside linkages.

Another siRNA duplex targeted to PTEN is comprised of antisense strand ISIS 359995 (5'-UUGUCUCUGGUCC-UUACUU-3', SEQ ID NO: 122) and the sense strand ISIS 359996 (5'-AAGUAAGGACCAGAGACAA-3', SEQ ID NO: 123). Both strands of the ISIS 359995/359996 duplex are comprised of alternating 2'-O—CH$_3$ modified and 2'-F modified nucleosides with a phosphodiester backbone. 2'-F nucleosides are indicated with bold type.

PTEN mRNA levels in liver were measured at the end of the study using real-time PCR and RiboGreen™ RNA quantification reagent (Molecular Probes, Inc. Eugene, Oreg.) as taught in previous examples above. PTEN mRNA levels were determined relative to total RNA (using Ribogreen) or GAPDH expression, prior to normalization to saline-treated control. Results are presented in Table 4 as the average % inhibition of mRNA expression for each treatment group, normalized to saline-injected control.

TABLE 4

Target reduction by chemically modified siRNAs targeted to PTEN in mouse liver

| Treatment | Dose (mg/kg, administered 2x/day) | % Inhibition Ribogreen | GAPDH |
|---|---|---|---|
| ISIS 116847 | 12.5 | 92 | 95 |
|  | 6.25 | 92 | 95 |
| ISIS 341391/341401 | 25 | 12 | 21 |
|  | 6.25 | 2 | 9 |
| ISIS 359995/359996 | 25 | 6 | 13 |
|  | 6.25 | 5 | 13 |

As shown in Table 4, all oligonucleotides targeted to PTEN caused a reduction in mRNA levels in liver as compared to saline-treated control. The mRNA levels measured for the ISIS 341391/341401 duplex are also suggestive of dose-dependent inhibition.

The effects of treatment with the RNA duplexes on plasma glucose levels were evaluated in the mice treated as described above. Approximate average plasma glucose is presented in Table 5 for each treatment group.

TABLE 5

Effects of chemically modified siRNAs targeted to PTEN on plasma glucose levels in normal mice

| Treatment | Dose (mg/kg, administered 2x/day) | Plasma glucose (mg/dL) |
|---|---|---|
| Saline | N/A | 186 |
| ISIS 116847 | 12.5 | 169 |
|  | 6.25 | 166 |
| ISIS 341391/341401 | 25 | 159 |
|  | 6.25 | 182 |
| ISIS 359996/359995 | 25 | 182 |
|  | 6.25 | 169 |

To assess the physiological effects resulting from in vivo siRNA targeted to PTEN mRNA, the mice were evaluated at the end of the treatment period for plasma triglycerides, plasma cholesterol, and plasma transaminase levels. Plasma cholesterol levels from animals treated with either dose of ISIS 116847 were increased about 20% over levels measured for saline-treated animals. Conversely, the cholesterol levels measured for animals treated with either the 25 mg/kg or the 6.25 mg/kg doses of the ISIS 341391/341401 duplex were decreased about 12% as compared to saline-treated controls. The ISIS 359996/359995 duplex did not cause significant alterations in cholesterol levels. All of the treatment groups showed decreased plasma triglycerides as compared to saline-treated control, regardless of treatment dose.

Increases in the transaminases ALT and AST can indicate hepatotoxicity. The transaminase levels measured for mice treated with the siRNA duplexes were not elevated to a level indicative of hepatotoxicity with respect to saline treated control. Treatment with 12.5 mg/kg doses of ISIS 116847 caused approximately 7-fold and 3-fold increases in ALT and AST levels, respectively. Treatment with the lower doses (6.25 mg/kg) of ISIS 116847 caused approximately 4-fold and 2-fold increases in ALT and AST levels, respectively.

At the end of the study, liver, white adipose tissue (WAT), spleen, and kidney were harvested from animals treated with the oligomeric compounds and were weighed to assess gross organ alterations. Approximate average tissue weights for each treatment group are presented in Table 6.

TABLE 6

Effects of chemically modified siRNAs targeted to PTEN on tissue weight in normal mice

| Treatment | Dose (mg/kg, administered 2x/day) | Liver | WAT | Spleen | Kidney |
|---|---|---|---|---|---|
|  |  |  | Tissue weight (g) |  |  |
| Saline | N/A | 1.0 | 0.5 | 0.1 | 0.3 |
| ISIS 116847 | 12.5 | 1.1 | 0.4 | 0.1 | 0.3 |
|  | 6.25 | 1.1 | 0.4 | 0.1 | 0.3 |
| ISIS 341391/341401 | 25 | 1.0 | 0.3 | 0.1 | 0.3 |
|  | 6.25 | 0.9 | 0.4 | 0.1 | 0.3 |
| ISIS 359996/359995 | 25 | 1.1 | 0.4 | 0.1 | 0.3 |
|  | 6.25 | 1.0 | 0.3 | 0.1 | 0.4 |

As shown in Table 6, treatment with antisense oligonucleotides or siRNA duplexes targeted to PTEN did not substantially alter liver, WAT, spleen, or kidney weights in normal mice as compared to the organ weights of mice treated with saline alone.

Example 42

Stability of Alternating 2'-O-Methyl/2'-Fluoro siRNA Constructs in Mouse Plasma

Intact duplex RNA was analyzed from diluted mouse-plasma using an extraction and capillary electrophoresis method similar to those previously described (Leeds, J. M., et al., 1996, Anal. Biochem., 235, 36-43; Geary, R. S., et al., 1999, *Anal. Biochem.*, 274, 241-248. Heparin-treated mouse plasma, from 3-6 month old female Balb/c mice (Charles River Labs) was thawed from −80° C. and diluted to 25% (v/v) with phosphate buffered saline (140 mM NaCl, 3 mM KCl, 2 mM potassium phosphate, 10 mM sodium phosphate). Approximately 10 nmol of pre-annealed siRNA, at a concentration of 100 µM, was added to the 25% plasma and incubated at 37° C. for 0, 15, 30, 45, 60, 120, 180, 240, 360, and 420 minutes. Aliquots were removed at the indicated time, treated with EDTA to a final concentration of 2 mM, and placed on ice at 0° C. until analyzed by capillary gel electrophoresis (Beckman P/ACE MDQ-UV with eCap DNA Capillary tube). The area of the siRNA duplex peak was measured and used to calculate the percent of intact siRNA remaining. Adenosine triphosphate (ATP) was added at a concentration of 2.5 mM to each injection as an internal calibration standard. A zero time point was taken by diluting siRNA in phosphate buffered saline followed by capillary electrophoresis. Percent intact siRNA was plotted against time, allowing the calculation of a pseudo first-order half-life. Results are shown in Table 7.

TABLE 7

Stability of alternating 2'-O-methyl/2'-fluoro siRNA constructs in mouse plasma

| Construct | Time (minutes) | | | | | | | | |
|---|---|---|---|---|---|---|---|---|---|
|  | 0 | 15 | 30 | 45 | 60 | 120 | 180 | 240 | 360 |
| 338918_338943 | 76.98 | 71.33 | 49.77 | 40.85 | 27.86 | 22.53 | 14.86 | 4.18 | 0 |
| 351831_351832 | 82.42 | 81.05 | 79.56 | 77.64 | 75.54 | 75.55 | 75.56 | 75.55 | 75 |

The parent (unmodified) construct is approximately 50% degraded after 30 minutes and nearly gone after 4 hours (completely gone at 6 hours). In contrast, the alternating 2'-O-methyl/2'-fluoro construct remains relatively unchanged and 75% remains even after 6 hours.

What is claimed is:

1. A composition comprising a first oligomeric compound and a second oligomeric compound, wherein:
   said first oligomeric compound is capable of hybridizing with said second oligomeric compound;
   said first oligomeric compound is complementary to and capable of hybridizing to a selected nucleic acid target;
   each of said first and said second oligomeric compounds independently comprises 20-23 linked nucleosides;
   at least one of said first and said second oligomeric compounds comprises a region having the formula $X_1$-Y-$X_2$, wherein Y is a region of from about 5 to about 12 linked nucleosides and each of $X_1$ and $X_2$ is, independently, a plurality of linked nucleosides having the formula FSFS, where one of F and S is a 2'-F modified nucleoside and the other of F and S is a 2'-O-$CH_3$ modified nucleoside; and
   each internucleoside linkage of said first and said second oligomeric compound is, independently, a phosphodiester or a phosphorothioate internucleoside linkage.

2. The composition of claim 1 wherein said first oligomeric compound comprises a 5'-phosphate group.

3. The composition of claim 1 wherein said second oligomeric compound comprises a 5'-phosphate group.

4. The composition of claim 1 wherein each of said first and said second oligomeric compounds comprise a 5'-phosphate group.

5. The composition of claim 1 wherein at least one of said first and said second oligomeric compounds comprises at least one conjugate group.

6. The composition of claim 1 wherein at least one of said first and said second oligomeric compounds comprises at least one terminal cap moiety attached at the 3'-end, the 5'-end or both the 3'-end and the 5'-end of the oligomeric compound.

7. A method of inhibiting gene expression comprising contacting one or more cells, a tissue or an animal with a composition of claim 1.

* * * * *